United States Patent
Zhang et al.

(10) Patent No.: US 11,434,535 B2
(45) Date of Patent: Sep. 6, 2022

(54) CENTROMERE/KINETOCHORE PROTEIN GENES FOR CANCER DIAGNOSIS, PROGNOSIS AND TREATMENT SELECTION

(71) Applicant: The Regents of the University of California, Oakland, CA (US)

(72) Inventors: Weiguo Zhang, Berkeley, CA (US); Gary Karpen, El Cerrito, CA (US); Jian-Hua Mao, Moraga, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/312,138

(22) PCT Filed: May 18, 2015

(86) PCT No.: PCT/US2015/031413
§ 371 (c)(1),
(2) Date: Nov. 17, 2016

(87) PCT Pub. No.: WO2015/179312
PCT Pub. Date: Nov. 26, 2015

(65) Prior Publication Data
US 2017/0175202 A1    Jun. 22, 2017

Related U.S. Application Data

(60) Provisional application No. 61/994,838, filed on May 17, 2014.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57484* (2013.01); *C12Q 2600/106* (2013.01); *C12Q 2600/118* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 5,541,308 A | * | 7/1996 | Hogan | C12Q 1/6811 536/23.1 |
| 6,582,908 B2 | * | 6/2003 | Fodor | B01J 19/0046 435/288.3 |
| 2004/0191783 A1 | * | 9/2004 | Leclercq | C12Q 1/6837 506/16 |
| 2011/0145176 A1 | * | 6/2011 | Perou | C12Q 1/6886 706/12 |
| 2012/0129711 A1 | | 5/2012 | Mosser et al. | |
| 2012/0222139 A1 | | 8/2012 | Hu et al. | |
| 2013/0190312 A1 | * | 7/2013 | Huang | A61K 31/4439 514/236.8 |
| 2013/0288364 A1 | * | 10/2013 | Cheeseman | C07K 14/46 435/349 |
| 2015/0226740 A1 | * | 8/2015 | Perreault | G16B 30/00 424/185.1 |

FOREIGN PATENT DOCUMENTS

| | | |
|---|---|---|
| WO | 2009/039479 A1 | 3/2009 |
| WO | 2009/067611 A1 | 5/2009 |
| WO | 2009/089548 A2 | 7/2009 |

OTHER PUBLICATIONS

International Search report from PCT/US2015/031413 dated Nov. 2, 2015, 4 pages.
Thiru et al., "Kinetochore genes are coordinately up-regulated in human tumors as part of a FoxM1-related cell division program," Mol Bio Cell, vol. 24, Jul. 1, 2014, pp. 1983-1994 (and supplemental material downloaded from (molbiolcell.org/content/suppl/2014/05/12/mbc.E14-03-0837.DC1.html).
European Search Report 15796107.9, dated Oct. 4, 2017 (9 pages).

* cited by examiner

*Primary Examiner* — Katherine D Salmon
(74) *Attorney, Agent, or Firm* — Kilpatrick Townsend & Stockton LLP

(57) ABSTRACT

The invention described in the application relates to a panel of gene expression markers for patient with a tumor. The invention thus provides methods and compositions, e.g., kits, for evaluating gene expression levels of the markers and methods of using such gene expression levels to evaluate the likelihood of disease progression or response to chemotherapy or radiation therapy. Such information can be used in determining prognosis and treatment options for cancer patients.

7 Claims, 13 Drawing Sheets

Specification includes a Sequence Listing.

CENTROMERE/KINETOCHORE PROTEIN GENES FOR CANCER DIAGNOSIS, PROGNOSIS AND TREATMENT SELECTION

CROSS-REFERENCES TO RELATED APPLICATIONS

This application is a U.S. National Stage entry of International Application No. PCT/US2015/031413, filed May 18, 2015, which claims priority to U.S. Provisional No. 61/994,838 filed May 17, 2014, each of which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy, with NIH Grant Nos. R01GM066272 and R01GM119011 awarded by the National Institute of General Medical Sciences, and with NIH Grant No. R01CA116481 awarded by the National Cancer Institute. The government has certain rights in the invention.

REFERENCE TO A "SEQUENCE LISTING" SUBMITTED AS ASCII TEXT FILES VIA EFS-WEB

The Sequence Listing written in file 077429-013210US-1028533_SequenceListing.txt created on Jan. 24, 2017, 194,113 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Chromosomal instability (CIN) is a hallmark of most human cancers and contributes to other cancer properties such as tumor heterogeneity and drug resistance. Centromeres and kinetochores consist of centromeric chromatin, as well as inner and outer kinetochore structures, which are required for attachments to the mitotic spindle and normal chromosome segregation in mitosis. In normal cells, the levels of centromere and kinetochore proteins are tightly regulated to ensure faithful chromosome segregation. However, diverse types of tumor cells display significantly altered levels of centromere/kinetochore proteins. Although the direct impact of centromere and kinetochore (CEN/KT) gene misregulation on cancer progression and outcome remains largely unknown, studies in diverse eukaryotes has demonstrated a direct relationship with both numerical CIN (aneuploidy, or gains and losses of whole chromosomes or fragments) and structural CIN (chromosome rearrangements and local copy number changes). Loss of many centromere and kinetochore proteins by mutation or depletion can result in whole chromosome loss or gain, while increased levels generate chromosomes with two centromeres (dicentrics), resulting in increased frequencies of mutations, chromosome breaks and translocations. In the field of cancer there is a need in the art for effective methods for patient diagnosis, prognosis, and response to therapy that assess the chromosomal instability of the patient's cancer.

BRIEF SUMMARY OF THE INVENTION

In one aspect, provided herein is a method of evaluating the likelihood of disease progression for a patient that has a tumor. The method includes detecting the levels of RNA expression of each member of a panel of 14 genes or a subset of at least 9 genes of the panel in a tumor sample from the patient, wherein the 14 genes are: CENP-A, HJURP, M1S18B, CENP-N, CENP-M, CENP-W, CENP-U, CENP-L, CENP-K, ZWINT, NDC80, NUF2, SPC24, and SPC25; and correlating the levels of expression with the likelihood of disease progression comprising determining a normalized value for the level of expression of each member of the panel compared to a reference level; and adding the normalized value for expression for each gene to generate a risk score, wherein a high risk score indicates that the patient has a likelihood of disease progression. In some instances, the at least 9 genes include CENP-A, HJURP, MIS18B, CENP-N, CENP-M, CENP-U, ZWINT, NDC80, and SPC25.

Also provided herein is a method of evaluating the likelihood of response to chemotherapy or radiotherapy in a patient that has a tumor. The method includes detecting the level of RNA expression of a panel of 9 genes in a tumor sample from the patient; wherein the 9 genes are: CENP-A, HJURP, MIS18B, CENP-N, CENP-M, CENP-U, ZWINT, NDC80, and SPC25; and correlating the levels of expression with the likelihood of response comprising determining a normalized value for the level of expression of each member of the panel compared to a reference level; and adding the normalized values for expression for each biomarker to generate a risk score, wherein a high risk score indicates that the patient has a likelihood of response to chemotherapy or radiotherapy. In other embodiments, the method includes detecting a panel of 14 genes or a subset of at least 9 genes of the panel in a tumor sample from the patient, wherein the 14 genes are: CENP-A, HJURP, M1S18B, CENP-N, CENP-M, CENP-W, CENP-U, CENP-L, CENP-K, ZWINT, NDC80, NUF2, SPC24, and SPC25. The at least 9 genes can be CENP-A, HJURP, MIS18B, CENP-N, CENP-M, CENP-U, ZWINT, NDC80, and SPC25.

In some embodiments, the step of detecting the levels of RNA expression comprises performing an amplification assay, hybridization assay, sequencing assay or microarray.

In some embodiments, the methods described above also include recommending the administration of chemotherapy or radiotherapy to the patient.

In another aspect, provided herein is a method of evaluating the likelihood of disease progression for a patient that has a tumor. The method includes detecting the level of expression of a panel of 14 biomarkers or a subset of at least 9 biomarkers of the panel in a tumor sample from the patient; wherein the 14 biomarkers are: CENP-A, HJURP, M1S18B, CENP-N, CENP-M, CENP-W, CENP-U, CENP-L, CENP-K, ZWINT, NDC80, NUF2, SPC24, and SPC25; and correlating the levels of expression with the likelihood of disease progression comprising determining a normalized value for the level of expression of each member of the panel compared to a reference level; and adding the normalized values for expression for each biomarker to generate a risk score, wherein when the risk score is in the top tertile of a reference scale, the patient has a likelihood of disease progression. In some instances, the at least 9 biomarkers include CENP-A, HJURP, MIS18B, CENP-N, CENP-M, CENP-U, ZWINT, NDC80, and SPC25.

Also provided herein is a method of evaluating a likelihood of response to chemotherapy or radiotherapy in a patient that has a tumor. The method includes detecting the level of expression of a panel of 9 biomarkers in a tumor sample from the patient; wherein the 9 biomarkers are: CENP-A, HJURP, MIS18B, CENP-N, CENP-M, CENP-U, ZWINT, NDC80, and SPC25; and correlating the levels of expression with the response comprising determining a normalized value for the level of expression of each member of the panel compared to a reference level; and adding the normalized values for expression for each biomarker to generate a risk score, wherein when the risk score is in the top tertile of a reference scale, the patient has a likelihood of response to chemotherapy or radiotherapy. In some embodiments, the method also includes recommending the administration of chemotherapy or radiotherapy to the patient. In other embodiments, the method includes detecting a panel of 14 biomarkers or a subset of at least 9 biomarkers of the panel in a tumor sample from the patient, wherein the 14 genes are: CENP-A, HJURP, M1S18B, CENP-N, CENP-M, CENP-W, CENP-U, CENP-L, CENP-K, ZWINT, NDC80, NUF2, SPC24, and SPC25.

In some embodiments, the level of expression is the level of protein expression. The step of detecting the level of protein expression can include performing an immunoassay. In other embodiments, the level of expression is the level of RNA expression. The step of detecting the level of RNA expression comprises performing an amplification assay, hybridization assay, sequencing assay or microarray.

In some embodiments, the reference scale is a plurality of risk scores derived from a population of reference patients that have the same type of tumor as the patient. The risk scores of the reference scale can be of the same type of tumor sample as the patient's tumor sample.

In yet another aspect, provided herein is method of evaluating the likelihood of disease progression for a patient that has a tumor. The method includes detecting the levels of RNA expression of each member of a panel of 14 genes or a subset of at least 9 genes of the panel in a tumor sample from the patient comprising performing a quantitative polymerase chain reaction (qPCR) to detect the levels of expression of each gene in the panel, and wherein the 14 genes are: CENP-A, HJURP, M1S18B, CENP-N, CENP-M, CENP-W, CENP-U, CENP-L, CENP-K, ZWINT, NDC80, NUF2, SPC24, and SPC25; and correlating the levels of RNA expression with the likelihood of disease progression comprising determining a normalized value for the level of expression of each member of the panel compared to a reference level; and adding the normalized value for expression for each gene to generate a risk score ranging from 0 to 1, wherein when the risk score is 0.66 or above, e.g., 0.66, 0.67, 0.70, 0.75, 0.8, 0.85, 0.90, 0.95, 0.99 or 1.0, the patient has a likelihood of disease progression. In some embodiments, the at least 9 genes include CENP-A, HJURP, MIS18B, CENP-N, CENP-M, CENP-U, ZWINT, NDC80, and SPC25.

In another aspect, provided herein is method of evaluating the likelihood of response to chemotherapy or radiotherapy for a patient that has a tumor. The method includes detecting the levels of RNA expression of each member of a panel of 9 genes in a tumor sample from the patient comprising performing a quantitative polymerase chain reaction (qPCR) to detect the levels of expression of each gene in the panel, and wherein the 9 genes are: CENP-A, HJURP, MIS18B, CENP-N, CENP-M, CENP-U, ZWINT, NDC80, and SPC25; and correlating the levels of RNA expression with the likelihood of response comprising determining a normalized value for the level of expression of each member of the panel compared to a reference level; and adding the normalized value for expression for each gene to generate a risk score ranging from 0 to 1, wherein when the risk score is 0.66 or above, e.g., 0.66, 0.67, 0.70, 0.75, 0.8, 0.85, 0.90, 0.95, 0.99 or 1.0, the patient has a likelihood of response to chemotherapy or radiotherapy. In some embodiments, the method also includes recommending the administration of chemotherapy or radiotherapy to the patient. In additional embodiments, the panel of genes include 14 genes such as, CENP-A, HJURP, M1S18B, CENP-N, CENP-M, CENP-W, CENP-U, CENP-L, CENP-K, ZWINT, NDC80, NUF2, SPC24, and SPC25.

In some aspects, the method provided herein is for determining the level of genomic instability of a tumor in a patient. The method includes detecting the levels of RNA expression of each member of a panel of 14 genes or a subset of at least 9 genes of the panel in a tumor sample taken from the patient's tumor to detect the levels of expression of each gene in the panel, and wherein the 14 genes are: CENP-A, HJURP, M1S18B, CENP-N, CENP-M, CENP-W, CENP-U, CENP-L, CENP-K, ZWINT, NDC80, NUF2, SPC24, and SPC25; and correlating the levels of RNA expression with the level of genomic instability comprising determining a normalized value for the level of expression of each member of the panel compared to a reference level; and adding the normalized value for expression for each gene to generate a risk score, wherein when a high risk score indicates that the patient's tumor has a high level of genomic instability. In some embodiments, RNA expression is evaluated using RT-PCR. In some embodiments, the at least 9 gene includes CENP-A, HJURP, MIS18B, CENP-N, CENP-M, CENP-U, ZWINT, NDC80, and SPC25.

In any of the methods described above, the tumor can be early stage breast cancer. In some embodiments, the breast cancer is luminal A. In other embodiments, the breast cancer is luminal B. In some embodiments, the breast cancer is ER positive breast cancer. In some cases, the breast cancer is a ER positive tumor that has undergone adjuvant hormone therapy. In some cases, the tumor is an early stage non-small cell lung cancer. In other cases, the tumor is an early stage ovarian cancer. In yet other cases, the tumor is ovarian cancer at any stage. In some embodiments, the tumor is an early stage cancer. In other embodiments, the tumor is a late stage cancer.

In some embodiments, the tumor sample is a tumor tissue sample or a tumor cell sample. The reference level may be determined from a normal, healthy cell. In some cases, the reference level may be determined from a normal, healthy cell from the same patient.

In one aspect, disclosed herein is a microarray for detecting expression of a gene panel for predicting survival, wherein the gene panel consists of: CENP-A, HJURP, M1S18B, CENP-N, CENP-M, CENP-W, CENP-U, CENP-L, CENP-K, ZWINT, NDC80, NUF2, SPC24, and SPC25, or a subset of at least 9 genes of the gene panel; and optionally contains probes for detecting expression of a reference gene. In some instances, the 9 genes of the gene panel are CENP-A, HJURP, MIS18B, CENP-N, CENP-M, CENP-U, ZWINT, NDC80, and SPC25.

In another aspect, disclosed herein is a kit includes primers and probes for detecting expression of 14 genes or a subset of at least 9 genes of the 14 genes, wherein the 14 genes are: CENP-A, HJURP, M1S18B, CENP-N, CENP-M, CENP-W, CENP-U, CENP-L, CENP-K, ZWINT, NDC80, NUF2, SPC24, and SPC25. In some embodiments, the kit also contains primers and probes for detecting expression of a reference gene. In further embodiments, the kit additionally contains an instruction manual. In some instances, the 9 genes are CENP-A, HJURP, MIS18B, CENP-N, CENP-M, CENP-U, ZWINT, NDC80, and SPC25

The methods presented above can be used in diagnosis or prognosis of solid tumor cancers. Furthermore, the methods are useful for treatment selection by a clinician or other individual in a clinical setting.

Other objects, features, and advantages of the present invention will be apparent to one of skill in the art from the following detailed description and figures.

BRIEF DESCRIPTION OF THE DRAWINGS

FIGS. 1A-1C provides a CEN/KT gene list and their misregulation across cancers.

FIG. 1A shows a schematic overview of the centromere and kinetochore structure on replicated mitotic sister chromatids. The blow-up shows CENP-A nucleosome as the structural basis for centromeric chromatin and kinetochore formation, and the CCAN network (CENP-C, CENP-N, CENP-I, CENP-H, CENP-T, CENP-W, CENP-S, CENP-X, CENP-M, CENP-U, CENP-L, CENP-K, CENP-O, CENP-P, CENP-Q, AND CENP-R) in the inner-kinetochore that connects CENP-A chromatin and the KMN network (KNL1, ZWINT, MIS12, NSL1, PMF1, KNL3, NDC80, SPC24, SPC25 AND NUF2) located in the outer kinetochore. HJURP chaperone (directly binds to CENP-A) and the Mis18 complex are CENP-A assembly factors. FIG. 1B shows the list of 31 CEN/KT genes. Regions are shown including Mis18 (grey) and HJURP (purple), which transiently localize to centromeres for CENP-A assembly. The Affymetrix probes for CENP-P did not pass our qualifier filter and were subsequently removed from all analysis. Fifteen out of thirty-one CEN/KT genes are misexpressed in >50% datasets (fold change >2 fold, FDR p<0.05) across various cancers compared to corresponding normal tissues (FIG. 1C).

FIG. 3D-3F are forest plots where squares denote HR, and left and right limits of the bars indicate 95% CI. Forest plot shows hazard ratios associated with high CES in various cancers with subtype or stage information (FIG. 3D). In particular, high CES predicts poor OS for early stage (stages I and II combined) ovarian cancers, non small cell lung cancers (NSCLCs), stage I lung adenocarcinomas (ADCs), gastric cancers and breast cancer luminal subtypes. Decreased HRs associated with more aggressive breast cancer HER2+ and basal-like. High CES is associated with increased risk for relapse or disease progression for various cancers and subtypes or stages (FIG. 3E). High CES is associated with increased hazard for DMFS for luminal A and B breast cancers (FIG. 3F). The trend is opposite for HER2+ and basal-like subtypes.

(FIG. 4A) Bar graphs of average $IC_{50}$ values show that CCLE (Cancer Cell Line Encyclopedia) cell lines in the top CES quartile are significantly more sensitive to Topo I inhibitors topotecan (left) and irinotecan (right) than those in the bottom CES quartile. Two tailed student-t test p-values are shown. Error bars indicate standard errors. (FIG. 4B-4C) Adjuvant chemotherapy significantly reduces the hazard associated with high CES in early stage NSCLCs. JBR.10 clinical trial early stage NSCLC patients are divided into CES high (top tertile) and low (lower two tertiles) groups (FIG. 4B). Kaplan-Meier curve to the left is for CES high group showing significant improvement of patient overall survival (OS) after adjuvant chemotherapy (ACT) compared to no ACT (OBS). The right graph of FIG. 4B shows that ACT did not significantly improve overall survival for CES low group compared to OBS. (FIG. 4C) Meta-analysis combing JBR.10 and UT SPORE early stage NSCLC patients. Patients are divided into CES high (top tertile) and low (lower two tertiles) groups. Kaplan-Meier curve in FIG. 4C, left is for CES high group showing significant improvement of patient overall survival after adjuvant chemotherapy (ACT) compared to no ACT (OBS). The right graph of FIG. 4C shows that ACT did not improve overall survival for CES low group compared to OBS. (FIG. 4D) Radiotherapy reduces the hazards associated with high CES for breast cancer patients. Breast cancer patients are divided into CES high, intermediate or low groups. Kaplan-Meier survival curves are in FIG. 4D, left for overall survival (OS) and in FIG. 4D, right for disease-free survival (DFS). Patient numbers, Log-rank p-values and treatment information are indicated for each graph. High CES values are associated with significantly better survival after RT compared to no RT, for both disease-free survival and overall survival (FIG. 4D, top row). The benefits associated with RT are not statistically significant for patients with intermediate CES values (FIG. 4D, middle row). No significant benefit was detected between low CES patients, with or without RT, for disease-free survival or overall survival (FIG. 4D, bottom row).

FIG. 7A shows that adjuvant chemotherapy (black bars) negates inferior OS associated with high CES for stage I ADCs and NSCLCs (black bars with an asterisk) by meta-analysis. In addition, adjuvant chemo and radiotherapy (RT) (black bars) improve inferior OS (black bars with an asterisk) associated with high CES for NSCLCs. Adjuvant chemo- and radio-therapies reduce risk of first progression (FP) associated with high CES in NSCLC (FIG. 7B). Adjuvant chemotherapy with or without hormone therapy negates inferior RFS associated with high CES for ER+ breast cancer patients compared to untreated or tamoxifen only treatment (FIG. 7C). Tamoxifen alone does not improve poor RFS associated with high CES ER+ breast cancer patients. Adjuvant chemotherapy including 5-FU does not significantly improve poor OS associated with high CES gastric cancer patients (FIG. 7D). Adjuvant therapy with either platin or topotecan improves overall survival in high CES late stage ovarian cancers and topotecan is superior to platin in reducing hazards. (FIG. 7E).

DETAILED DESCRIPTION OF THE INVENTION

I. Introduction

Figure 1A:
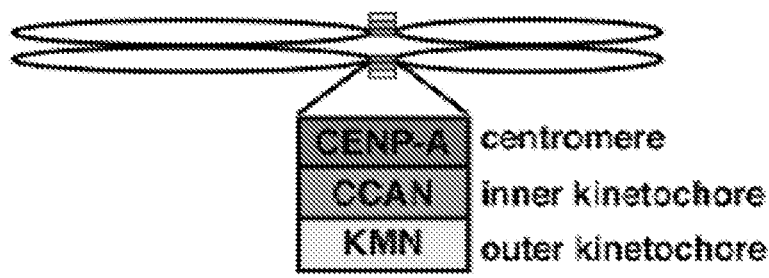
Figure 1A:
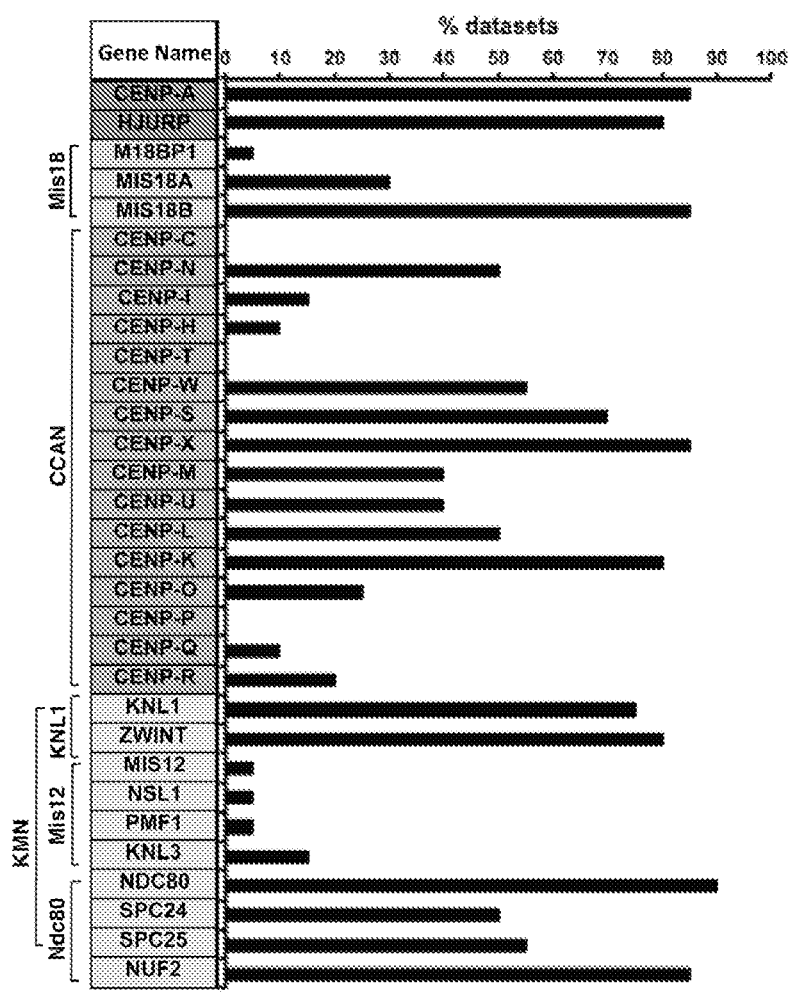

Described herein are methods for predicting the risk of disease recurrence, disease relapse, disease progression, and/or metastatis of a cancer in a subject. The methods also include predicting a likelihood of response to a cancer therapy, such as radiation therapy and/or chemotherapy in a subject with cancer. The method includes determining the expression level, such as the RNA expression level or the protein expression level of 14 CEN/KT genes, transforming the levels into a centromere and kinetochore gene expression score (CES), and determining that the subject has a likelihood of a poor prognosis based having a high CES value compared to a reference range of CES values. In some instances, a high CES value represents any CES value in the top tertile of the reference range of CES values. A high CES value can also predict a likelihood of survival upon receiving adjuvant cancer therapy.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "cancer" refers to any disease involving an abnormal growth of cells and includes all stages and all forms of the disease that affects any tissue, organ or cell in the body. The term includes all known cancers and neoplastic conditions, whether characterized as malignant, benign, soft tissue, or solid, and cancers of all stages and grades including pre- and post-metastatic cancers. Examples of different types of cancer include, but are not limited to, breast cancer, lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; ovarian cancer; prostate cancer, renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancerous cells.

The term "tumor sample" includes a biological sample or a sample from a biological source that contains one or more tumor cells. Biological samples include samples from body fluids, e.g., blood, plasma, serum, or urine, or samples derived, e.g., by biopsy, from cells, tissues or organs, preferably tumor tissue suspected to include or essentially consist of cancer cells.

The terms "determining," "assessing," "assaying," "measuring" and "detecting" can be used interchangeably and refer to both quantitative and semi-quantitative determinations. Where either a quantitative and semi-quantitative determination is intended, the phrase "determining a level" of a polynucleotide or polypeptide of interest or "detecting" a polynucleotide or polypeptide of interest can be used.

The term "amount" or "lever" refers to the quantity of a polynucleotide of interest or a polypeptide of interest present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "nucleic acid" or "polynucleotide" as used herein refers to a deoxyribonucleotide or ribonucleotide in either single- or double-stranded form. The term encompasses nucleic acids containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (Strauss-Soukup (1997) Biochemistry 36: 8692-8698), and benzylphosphonate linkages (Samstag (1996) Antisense Nucleic Acid Drug Dev 6: 153-156).

The term "protein," "peptide" or "polypeptide" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "gene product" or "gene expression product" refers to an RNA or protein encoded by the gene.

The term "hybridizing" refers to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences in a mixed population (e.g., a cell lysate or DNA preparation from a tissue biopsy). A "stringent hybridization" and "stringent hybridization wash conditions" in the context of nucleic acid hybridization (e.g., as in array, microarray, Southern or northern hybridizations) are sequence dependent, and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, Ch. 2, "Overview of principles of hybridization and the strategy of nucleic acid probe assays," Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell (2001) Molecular Cloning: A Laboratory Manual (3rd ed.) Vol. 1-3, Cold Spring Harbor Laboratory, Cold Spring Harbor Press, NY). An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4×SSC to 6×SSC at 40° C. for 15 minutes.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

The term "standard control" as used herein refers to a predetermined amount or concentration of a polynucleotide sequence or polypeptide sequence that is present in an established normal tissue sample, e.g., a healthy, non-cancer tissue sample, or a diploid, non-transformed, non-cancerous, genomically stable healthy human cell line. The standard control value is suitable for the use of a method of the present invention, to serve as a basis for comparing the amount of a specific mRNA or protein that is present in a test sample. An established sample serving as a standard control provides an average amount of a specific mRNA or protein that is typical in a normal tissue sample. A standard control value may vary depending on the nature of the sample as well as other factors such as the gender, age, ethnicity of the subjects based on whom such a control value is established.

The term "treatment," "treat," or "treating" refer to a method of reducing the effects of a cancer (e.g., breast cancer, lung cancer, ovarian cancer or the like) or symptom of cancer. Thus, in the disclosed method, treatment can refer to a 10%, 20%, 30%, 40%, 50%, 60%, 70%, 80%, 90%, or 100% reduction in the severity of an cancer or symptom of the cancer. For example, a method of treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100% or any percent reduction between 10 and 100% as compared to native or control levels. It is understood that treatment does not necessarily refer to a cure or complete ablation of the disease, condition, or symptoms of the disease or condition.

The term "recommending" or "suggesting," in the context of a treatment of a disease, refers to making a suggestion or a recommendation for therapeutic intervention (e.g., drug therapy, adjunctive therapy, etc.) and/or disease management which are specifically applicable to the patient.

The terms "responsive," "clinical response," "positive clinical response," and the like, as used in the context of a patient's response to a cancer therapy, are used interchangeably and refer to a favorable patient response to a treatment as opposed to unfavorable responses, i.e. adverse events. In a patient, beneficial response can be expressed in terms of a number of clinical parameters, including loss of detectable tumor (complete response, CR), decrease in tumor size and/or cancer cell number (partial response, PR), tumor growth arrest (stable disease, SD), enhancement of anti-tumor immune response, possibly resulting in regression or rejection of the tumor; relief, to some extent, of one or more symptoms associated with the tumor; increase in the length of survival following treatment; and/or decreased mortality at a given point of time following treatment. Continued increase in tumor size and/or cancer cell number and/or tumor metastasis is indicative of lack of beneficial response to treatment. In a population the clinical benefit of a drug, i.e., its efficacy can be evaluated on the basis of one or more endpoints. For example, analysis of overall response rate (ORR) classifies as responders those patients who experience CR or PR after treatment with drug. Analysis of disease control (DC) classifies as responders those patients who experience CR, PR or SD after treatment with drug.

A positive clinical response can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition of metastasis; (6) enhancement of anti-tumor immune response, possibly resulting in regression or rejection of the tumor; (7) relief, to some extent, of one or more symptoms associated with the tumor; (8) increase in the length of survival following treatment; and/or (9) decreased mortality at a given point of time following treatment. Positive clinical response may also be expressed in terms of various measures of clinical outcome. Positive clinical outcome can also be considered in the context of an individual's outcome relative to an outcome of a population of patients having a comparable clinical diagnosis, and can be assessed using various endpoints such as an increase in the duration of recurrence-free interval (RFI), an increase in the time of survival as compared to overall survival (OS) in a population, an increase in the time of disease-free survival (DFS), an increase in the duration of distant recurrence-free interval (DRFI), and the like. Additional endpoints include a likelihood of any event (AE)-free survival, a likelihood of metastatic relapse (MR)-free survival (MRFS), a likelihood of disease-free survival (DFS), a likelihood of relapse-free survival (RFS), a likelihood of first progression (FP), and a likelihood of distant metastatis-free survival (DMFS). An increase in the likelihood of positive clinical response corresponds to a decrease in the likelihood of cancer recurrence or relapse.

The term "good prognosis" refers to the prediction of the likelihood of a clinical response, disease-specific survival, overall survival or disease free survival, including partial remission, complete remission, and suppression of cancer cell proliferation and/or metastasis. A good prognosis for a patient with a solid tumor cancer includes a positive response rate in terms of disease remission or tumor shrinkage, or any other form of evaluating reduced tumor burden or growth. A good prognosis can be measured as the length (time) of survival.

The term "poor prognosis" refers to the prediction of the likelihood of cancer-attributable death or progression, including recurrence, relapse and/or metastatic spread.

The term "overall survival" refers to the time interval from either the time of diagnosis or the start of treatment that the patient is still alive.

The term "progression-free survival" refers to the time interval from treatment of the patient until the progression of cancer or death of the patient, whichever occurs first.

The term "responder" or "responsive" refers to a patient who has cancer, and who exhibits a beneficial clinical response following treatment with a cancer therapy.

The term "non-responder" or "non-responsive" refers to a patient who has a cancer, and who does not exhibit a beneficial clinical response following treatment with a cancer therapy.

The term "subject" is intended to include animals. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancers.

The term "risk score" refers to a statistically derived value that can provide physicians and caregivers valuable diagnostic and prognostic insight. In some instances, the score provides a projected risk of disease recurrence/relapse or disease progression, a projected rate of disease progression, and/or a projected response to a particular therapy. An individual's score can be compared to a reference score or a reference score scale to determine risk of disease recurrence/relapse or to assist in the selection of therapeutic intervention or disease management approaches.

The term "high CES score," "high CES value," "high risk score" refers to a centromere and kinetochore expression score (CES) having a numerical value in the top percentile range, such as top tertile (e.g., top 33%), of a range of CES values for a particular subject population. In some embodiments, a cancer patient with a high CES score is also at high risk of a poor prognosis or negative disease outcome. The term "intermediate CES score" or "medium CES score" refers to a CES value in the middle tertile of the range, and the term "low CES score" refers to a CES value in the lower tertile of the range.

III. Detailed Descriptions of Embodiments

A. CEN/KT Genes and Gene Products

The methods described herein are based, in part, on the surprising discovery of that 14 centromere and kinetochore structural protein genes (CEN/KT genes) are overexpressed in various cancers and are predictive of disease progression for specific cancer stages. The centromere and kinetochore gene expression score (CES) described herein can transform the expression levels of the 14 genes or the expression levels of at least 9 genes of the 14 genes into a predictive score. The CES score is also predictive of therapy response and survival after treatment.

The methods described herein can be used to evaluate a patient with cancer. Non-limiting examples of cancer include breast cancer, lung cancer (e.g., non-small cell lung cancer); prostate cancer, ovarian cancer, digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; bladder cancer; prostate cancer; cervical cancer, uterine cancer, renal cancer (e.g., renal cell carcinoma); cancer of the central nervous system, e.g., lower grade brain cancer; skin cancer; lymphomas; head and neck cancers; adrenocortical cancer; and thyroid cancer. The cancer can be a very early stage cancer, early stage cancer, late stage cancer, or metastatic cancer. In some embodiments, the cancer is a very early stage cancer or an early stage cancer. In some embodiments, the breast cancer is a breast cancer subtype such as basal-like breast cancer, HER2-positive (HER2+) breast cancer, luminal B breast cancer, luminal A breast cancer, and normal-like breast cancer. The breast cancer may include an estrogen receptor positive (ER+) tumor or an estrogen receptor negative (ER−) tumor. In some embodiments, the breast cancer is ductal carcinoma in situ. In some embodiments, the cancer is early stage ovarian cancer (stage I or stage II) or an early stage (e.g., stage I), lung cancer.

The present disclosure relates to measuring the gene products of a biomarker panel, e.g., a human CEN/KT gene panel of at least 9 genes including CENP-A, HJURP, MIS18B CENP-N, CENP-M, CENP-U, ZWINT, NDC80, and SPC25, or a 14 human CEN/KT genes panel including CENP-A, CENP-K, CENP-L, CENP-M, CENP-N, CENP-U, CENP-W, MIS18B, HJURP, ZWINT, NDC80, SPC24, SPC25 and NUF2, in a patient with a tumor. In some cases, the measurement is performed prior to the patient undergoing a therapeutic intervention, such as surgery, chemotherapy, radiation therapy, drug therapy, immunotherapy and the like.

The human histone centromeric protein A (CENP-A) polypeptide sequence is set forth in, e.g., Genbank Accession No. AAH02703.1 and NCBI Ref. Seq. Nos. NP_001035891 and NP_001800. The human CENP-A mRNA (coding) sequence is set forth in, e.g., NCBI Ref. Seq. Nos. NM_001042426, and NM_001809.

The human centromere protein K (CENP-K) polypeptide sequence is set forth in, e.g., NCBI Ref. Seq. Nos. NP_001253967 and NP_071428. The human CENP-K mRNA (coding) sequence is set forth in, e.g., NCBI Ref. Seq. Nos. NM_001267038, and NM_022145.

The human centromere protein L (CENP-L) polypeptide sequence is set forth in, e.g., NCBI Ref. Seq. Nos. NP_001120653, NP_001164653 and NP_201576. The human CENP-L mRNA (coding) sequence is set forth in, e.g., NCBI Ref. Seq. Nos. NM_001127181, NM_001171182, and NM_033319.

The human centromere protein M (CENP-M) polypeptide sequence is set forth in, e.g., NCBI Ref. Seq. Nos. NP_001002876, NP_001103685 and NP_076958. The human CENP-M mRNA (coding) sequence is set forth in, e.g., NCBI Ref. Seq. Nos. NM_001002876, NM_001110215, and NM_024053.

The human centromere protein U (CENP-U) polypeptide sequence is set forth in, e.g., NCBI Ref. Seq. No. NP_078905. The human CENP-U mRNA (coding) sequence is set forth in, e.g., NCBI Ref. Seq. No. NM_024629.

The human centromere protein W (CENP-W) polypeptide sequence is set forth in, e.g., NCBI Ref. Seq. Nos. NP_0001012525, NP_001273453 and NP_001273454. The human CENP-W mRNA (coding) sequence is set forth in, e.g., NCBI Ref. Seq. Nos. NM_001012507, NM_001286524, and NM_001286525.

The human Mis18-beta (MIS18B) polypeptide sequence is set forth in, e.g., NCBI Ref Seq. No. NP_009211. The human MIS18B mRNA (coding) sequence is set forth in, e.g., NCBI Ref. Seq. No. NM_007280. The MIS18B polypeptide is also known as cancer/testis antigen 86, CT86, Opa-interacting protein 5 and OIP-5.

The human holiday junction recognition (HJURP) polypeptide sequence is set forth in, e.g., NCBI Ref. Seq. Nos. NP_001269891, NP_001269892, and NP_060880. The human HJURP mRNA (coding) sequence is set forth in, e.g., NCBI Ref. Seq. Nos. NM_001282962, NM_001282963, and NM_018410.

The human holiday junction recognition protein (HJURP) polypeptide sequence is set forth in, e.g., NCBI Ref. Seq. Nos. NP_001269891, NP_001269892, and NP_060880. The human HJURP mRNA (coding) sequence is set forth in, e.g., NCBI Ref. Seq. Nos. NM_001282962, NM_001282963, and NM_018410.

The human ZW10 interactor (ZWINT) polypeptide sequence is set forth in, e.g., NCBI Ref. Seq. Nos. NP_001005413, NP_008988, and NP_127490. The human ZWINT mRNA (coding) sequence is set forth in, e.g., NCBI Ref. Seq. Nos. NM_001005413, NM_007057, and NM_032997.

The human kinetochore protein NDC80 homolog (NDC80) polypeptide sequence is set forth in, e.g., NCBI Ref. Seq. No. NP_006092. The human NDC80mRNA (coding) sequence is set forth in, e.g., NCBI Ref. Seq. No. NM_006101. The NDC80 polypeptide is also known as kinetochore protein Hec1, HsHec1, kinetochore-associated protein 2, KNTC2, and retinoblastoma-associated protein HEC.

The human kinetochore protein Spc24 (SPC24) polypeptide sequence is set forth in, e.g., NCBI Ref. Seq. Nos. NP_872319 and XP_005259810. The human SPC24 (coding) sequence is set forth in, e.g., NCBI Ref. Seq. Nos. NM_182513 and XM_005259753.

The human kinetochore protein Spc25 (SPC25) polypeptide sequence is set forth in, e.g., NCBI Ref. Seq. No. NP_065726. The human SPC25 (coding) sequence is set forth in, e.g., NCBI Ref. Seq. No. NM_020675.

The human kinetochore protein Nuf2 homolog (NUF2) polypeptide sequence is set forth in, e.g., NCBI Ref. Seq. No. NP_113611 and NP_663735. The human NUF2 (coding) sequence is set forth in, e.g., NCBI Ref. Seq. Nos. NM_031423 and NM_145697.

The at least 9 CEN/KT biomarkers or 14 CEN/KT biomarkers are particularly useful in the methods of the present disclosure for diagnosing or prognosing cancer in a patient and for personalized therapeutic management by selecting therapy. As such, in some embodiments, the detection or determination of the expression level, e.g., RNA expression level or protein expression level of the 14 CEN/KT gene products is performed.

B. Methods of Quantifying RNA Levels

The methods of the present disclosure include detecting the level of RNA expression of 14 CEN/KT genes or a subset of the 14 CEN/KT genes, e.g., a subset of at least 9 genes of the 14 genes, in a tumor sample obtained from a patient suspected of having cancer or at risk of having cancer. In some embodiments, the patient has been diagnosed with cancer.

The tumor sample can be a biological sample comprising cancer cells. In some embodiments, the tumor sample is a fresh or archived sample obtained from a tumor, e.g., by a tumor biopsy or fine needle aspirate. The sample also can be any biological fluid containing cancer cells. The tumor sample can be isolated or obtained from any number of primary tumors, including, but not limited to, tumors of the breast, lung, prostate, brain, liver, kidney, intestines, colon, spleen, pancreas, thymus, testis, ovary, uterus, and the like. In some embodiments, the tumor sample is from a tumor cell line. The collection of a tumor sample from a subject is performed in accordance with the standard protocol generally followed by hospital or clinics, such as during a biopsy.

Any method known to those of ordinary skill in the art can be used to detect RNA expression levels. In some embodiments, RNA is isolated from the tumor sample. RNA can be isolated from the tumor sample using a variety of methods. Standard methods for RNA extraction from tissue or cells are described in, for example, Ausubel et al., Current Protocols of Molecular Biology, John Wiley & Sons, 1997 and Sambrook and Russell, *Molecular Cloning: A Laboratory Manual* 3rd ed., 2001. Commercially available kits, e.g., RNeasy® mini columns (Qiagen), PureLink® RNA mini kit (Thermo Fisher Scientific), etc. can also be used to isolate RNA.

The level of RNA (e.g., mRNA) expression of the 14 CEN/KT genes described above can be detected or measured by a variety of methods including, but not limited to, an amplification assay, a hybridization assay, a sequencing assay, or an array. Non-limiting examples of such methods include reverse-transcription polymerase chain reaction (RT-PCR); quantitative real-time PCR (qRT-PCR); quantitative PCR, such as TaqMan®; Northern blotting; in situ hybridization assays; microarray analysis, e.g., microarrays from NanoString Technologies; multiplexed hybridization-based assays, e.g., QuantiGene 2.0 Multiplex Assay from Panomics; serial analysis of gene expression (SAGE); cDNA-mediated annealing, selection, extension, and ligation; direct sequencing or pyrosequencing; massively parallel sequencing; next generation sequencing; high performance liquid chromatography (HPLC) fragment analysis; capillarity electrophoresis; and the like.

Various methods involving amplification reactions and/or reactions in which probes are linked to a solid support and used to quantify RNA may be used. Alternatively, the RNA may be linked to a solid support and quantified using a probe to the sequence of interest.

In some embodiments, the target RNA is first reverse transcribed and the resulting cDNA is quantified. In some embodiments, RT-PCR or other quantitative amplification techniques are used to quantify the target RNA. Amplification of cDNA using PCR is well known (see U.S. Pat. Nos. 4,683,195 and 4,683,202; PCR PROTOCOLS: A GUIDE TO METHODS AND APPLICATIONS (Innis et al., eds, 1990)). Methods of quantitative amplification are disclosed in, e.g., U.S. Pat. Nos. 6,180,349; 6,033,854; and 5,972,602, as well as in, e.g., Gibson et al., Genome Research 6:995-1001 (1996); DeGraves, et al., Biotechniques 34(1):106-10, 112-5 (2003); Deiman B, et al., Mol Biotechnol. 20(2):163-79 (2002). Alternative methods for determining the level of a mRNA of interest in a sample may involve other nucleic acid amplification methods such as ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art.

In general, quantitative amplification is based on the monitoring of the signal (e.g., fluorescence of a probe) representing copies of the template in cycles of an amplification (e.g., PCR) reaction. One method for detection of amplification products is the 5'-3' exonuclease "hydrolysis" PCR assay (also referred to as the TaqMan® assay) (U.S. Pat. Nos. 5,210,015 and 5,487,972; Holland et al., PNAS USA 88: 7276-7280 (1991); Lee et al., Nucleic Acids Res. 21: 3761-3766 (1993)). This assay detects the accumulation of a specific PCR product by hybridization and cleavage of a doubly labeled fluorogenic probe (the "TagMan®" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, Nature Biotech. 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce (Tyagi and Kramer, Nature Biotechnol. 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of nucleic acids are also known. For example, some methodologies employ one or more probe oligonucleotides that are structured such that a change in fluorescence is generated when the oligonucleotide(s) is hybridized to a target nucleic acid. For example, one such method involves a dual fluorophore approach that exploits fluorescence resonance energy transfer (FRET), e.g., LightCycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., Nature Biotechnology 17:804-807, 1999, and U.S. Pat. No. 6,326,145), Sunrise™ (or Amplifluor™) probes (e.g., Nazarenko et al., Nuc. Acids Res. 25:2516-2521, 1997, and U.S. Pat. No. 6,117,635), and probes that form a secondary structure that results in reduced signal without a quencher and that emits increased signal when hybridized to a target (e.g., Lux Probes™).

In other embodiments, intercalating agents that produce a signal when intercalated in double stranded DNA may be used. Exemplary agents include SYBR GREEN™ and SYBR GOLD™. Since these agents are not template-specific, it is assumed that the signal is generated based on template-specific amplification. This can be confirmed by monitoring signal as a function of temperature because melting point of template sequences will generally be much higher than, for example, primer-dimers, etc.

In other embodiments, the mRNA is immobilized on a solid surface and contacted with a probe, e.g., in a dot blot or Northern format. In an alternative embodiment, the probe(s) are immobilized on a solid surface and the mRNA is contacted with the probe(s), for example, in a gene chip array. A skilled artisan can readily adapt known mRNA detection methods for use in detecting the level of mRNA encoding the biomarkers or other proteins of interest.

In some embodiments, microarrays, e.g., are employed. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261. Although a planar array surface is often employed the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992. Arrays may be packaged in such a manner as to allow for diagnostics or other manipulation of an all-inclusive device.

In some embodiments, gene-specific probes and/or primers are used in hybridization assays to detect RNA expression. The probes and/or primers may be labeled with any detectable moiety or compound, such as a radioisotope, fluorophore, chemiluminescent agent, and enzyme.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, Tetrahedron Letts., 22:1859-1862, 1981, using an automated synthesizer, as described in Needham-Van Devanter et al., Nucleic Acids Res. 12:6159-6168, 1984.

In some embodiments, the methods further comprise detecting level of expression of one or more reference genes that can be used as controls to determine expression levels. Such genes are typically expressed constitutively at a high level and can act as a reference for determining accurate gene expression level estimates. Non-limiting examples of control genes include ARPC2, ATF4, ATP5B, B2M, CDH4, CELF1, CLTA, CLTC, COPB1, CTBP1, CYC1, CYFIP1, DAZAP2, DHX15, DIMT1, EEF1A1, FLOT2, GAPDH, GUSB, HADHA, HDLBP, HMBS, HNRNPC, HPRT1, HSP90AB1, MTCH1, MYL12B, NACA, NDUFB8, PGK1, PPIA, PPIB, PTBP1, RPL13A, RPLP0, RPS13, RPS23, RPS3, S100A6, SDHA, SEC31A, SET, SF3B1, SFRS3, SNRNP200, STARD7, SUMO1, TBP, TFRC, TMBIM6, TPT1, TRA2B, TUBA1C, UBB, UBC, UBE2D2, UBE2D3, VAMP3, XPO1, YTHDC1, YWHAZ, and 18S rRNA genes. Accordingly, a determination of RNA expression levels of the genes of interest, e.g., the gene expression levels of the panel of 14 CEN/KT genes may also comprise determining expression levels of one or more reference genes disclosed above.

The level of mRNA expression of each of the 14 CEN/KT genes can be normalized to a reference level for a control gene. The control value can be predetermined, determined concurrently, or determined after a sample is obtained from the subject. The standard can be run in the same assay or can be a known standard from a previous assay. The normalized levels of mRNA expression of the CEN/KT genes can be transformed in to a score, e.g., a CES score.

C. Methods of Quantifying Protein Levels

In some embodiments, the methods disclosed herein include determining the level of 14 polypeptides encoded by 14 CEN/KT genes, such as CENP-A, CENP-K, CENP-L, CENP-M, CENP-N, CENP-U, CENP-W, MIS18B, HJURP, ZWINT, NDC80, SPC24, SPC25 and NUF2 or a subset of at least 9 polypeptides of the 14 polypeptides encoded by the 14 CEN/KT genes. In some embodiments, the level of the CENP-A, HJURP, MIS18B, CENP-N, CENP-M, CENP-U ZWINT, NDC80 and SPC25 polypeptides are detected or measured. These polypeptides can be detected in various tumor samples.

Any method known to those of ordinary skill in the art can be used to detect protein expression levels. A general overview of the applicable technology can be found in Harlow & Lane, *Antibodies: A Laboratory Manual* (1988) and Harlow & Lane, *Using Antibodies* (1999). Methods of producing polyclonal and monoclonal antibodies that react specifically with an allelic variant are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

The level of such polypeptides can be detected by a variety of methods including, but not limited to, Western blotting, immunoassays, e.g., enzyme-linked immunosorbent assay (ELISA), enzyme immunoassay (EIA), radioimmunoassay (RIA), sandwich assays, competitive assays, immunohistochemistry, mass spectrometry, 2-D gel electrophoresis, protein array, antibody array, and the like.

For a review of immunological and immunoassay procedures, see *Basic and Clinical Immunology* (Stites & Terr eds., 7th ed. 1991). Moreover, the immunoassays can be performed in any of several configurations, which are reviewed extensively in *Enzyme Immunoassay* (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991).

Similar to normalizing the mRNA level of the CEN/KT genes, the level of protein expression can also be compared and normalized to a control value for a standard.

D. Establishing CES Scores

After determining the expression of level of the panel of CEN/KT genes, the method presented herein includes calculating a CES score, e.g., a risk score based on the level of the 14 CEN/KT gene expression products. The level of expression of the 14 CEN/KT genes can be equally weighted in the CES score. In some instances, the level of expression of each gene is weighted with a predefined coefficient. The predefined coefficient is the same or different for the genes.

In some embodiments, the CES score is generated using the following formula: CES score=sum of the log 2 (mRNA level) for the 14 CEN/KT genes (e.g., CENP-A, CENP-K, CENP-L, CENP-M, CENP-N, CENP-U, CENP-W, MIS18B, HJURP, ZWINT, NDC80, SPC24, SPC25 and NUF2).

In some embodiments, a patient's CES score is categorized as "high," "intermediate," or "low" relative to a reference scale, e.g., a range of CES scores from a population of reference subjects that have the same cancer as the patient. In some cases, a high score corresponds to a numerical value in the top tertile, (e.g., the highest ⅓) of the reference scale; an intermediate score corresponds to the intermediate tertile (e.g., the middle ⅓) of the reference scale; and a low score corresponds to the bottom tertile (e.g., the lowest ⅓) of the reference scale. In other embodiments, a high score represents a risk score that is 0.66 or above, e.g., 0.66, 0.67, 0.70, 0.75, 0.80, 0.85, 0.90, 0.95, 0.99 or 1.0 based on a normalized, standardized reference scale on a scale of 0 to 1. In yet other embodiments, a patient's CES score is compared to one or more threshold value(s) to provide a likelihood of cancer progression and/or response to chemotherapy or radiation therapy. In some cases, the high risk score corresponds to a numerical value, e.g., risk score in the top 5%, top 10%, top 15%, top 20%, top 25%, top 30%, top 35%, top 40%, top 45%, top 50%, or top 60% of the reference scale.

In order to establish a reference CES scale or a threshold value for practicing the method of this invention, a reference population of subjects can be used. In some embodiments, the reference population has the same type of cancer or tumor as the test patient. The reference population may have the same subtype and/or stage of cancer or tumor as the test patient. The subjects in the reference population can be within the appropriate parameters, if applicable, for the purpose of screening for and/or monitoring cancer using the methods provided herein. Optionally, the reference subjects are of same gender, similar age, or similar ethnic background. The reference subject may be of the same gender, similar age, or similar ethnic background as the test subject.

The status of the reference subjects can be confirmed by well established, routinely employed methods including but not limited to general physical examination of the individuals and general review of their medical history. Furthermore, the group of reference subjects must be of a reasonable size, such that the average levels of the 14 CEN/KT polynucleotides (mRNA) or corresponding polypeptide in samples obtained from the group can be reasonably regarded as representative of the normal or average level among this population of subjects.

To establish a threshold value, an average value is determined based on the individual values found in each subject of the selected reference group. For example, a risk score over the threshold value can indicate a more than average likelihood of cancer progression whereas a risk score below the threshold value can indicate an average or below-average likelihood of cancer progression. In some embodiments, a standard deviation is also determined during the same process. In some cases, separate threshold values may be established for separately defined groups having distinct characteristics such as age, gender, or ethnic background.

According to the methods described herein, the patient's risk score is compared to one or more threshold values. In some embodiments, the risk score is deemed "high" if it is at least 1, 2, 3, 4, 5, 10, 15, 20 or more standard deviations greater than the threshold value. In other embodiments, the risk score is "low" or below the threshold if it is at least 1, 2, 3, 4, 5, 10, 15, 20 or more standard deviations lower than the threshold value.

In some embodiments, a computer-based analysis program is used to translate the raw data generated by the detection methods described herein (e.g., the presence, absence, or amount of a given marker or markers) into a risk score of predictive value to a clinician.

E. Correlating CES Scores with Prognostic Outcomes or Treatment Selection

The CES score, as determined according to the methods above, can predict that the patient has an above-average or statistically significant likelihood of poor prognosis, e.g., tumor progression, overall survival, recurrence, relapse, and/or metastasis. If treated with chemotherapy or radiation therapy, such a patient has a statistically significant likelihood of responding to the therapy, and in some cases have a good prognosis, e.g., long-term overall survival, any-event free survival, metastatic relapse free-survival, distant metastasis-free survival, and/or disease-free survival.

In some embodiments, if the subject has a high CES score, there is a likelihood that the subject will have a poor prognosis, e.g., will experience death, cancer relapse, cancer recurrence, cancer progression, and/or local or distant metastasis. In some cases, a high CES score predicts that the subject will have poor metastatic relapse-free survival (MRFS), such as a short term MRFS, no MRFS, or a below-average probability of MRFS. In other cases, a high CES score predicts that the subject will have poor any event (AE)-free survival, e.g., a short term AE-free survival, no AE-free survival, or a below-average probability of AE-free survival. The subject may have an early stage cancer, such as an early stage breast cancer, lung cancer, gastric cancer, or ovarian cancer.

In some embodiments, it is predicted that a subject with breast cancer and a high CES value will have poor distant metastasis-free survival (DMFS), e.g., a shorter term of DMFS, no DMFS, or a below-average probability of DMFS, compared to a breast cancer subject with a low CES value. A breast cancer patient with a high CES may also have an ER negative tumor and/or an advanced tumor grade. Such a patient may have an aggressive tumor. Patients with ER positive breast cancer and a high CES are predicted to have poor AE-free survival, poor DMFS or poor relapse-free survival In some cases, the patients with ER positive breast cancer have either a normal breast-like tumor, a luminal A tumor, or a luminal B tumor. In some cases, the patients with ER positive breast cancer have been treated with adjuvant tamoxifen therapy. Patients with luminal A tumors and a high CES are predicted to have poor overall survival. Similarly, patients with luminal B tumors and a high CES are expected to have poor overall survival.

In some embodiments, breast cancer patients with either a specific breast cancer subtype, e.g., basal-like subtype, and a high CES value will have overall survival and/or disease-free survival (DFS) after receiving cancer therapy. These patients are also predicted to have good DMFS after receiving treatment. Additionally, these patients are predicted to be responsive to cancer therapy. In some instances, the cancer therapy includes radiation therapy, chemotherapy alone, radiation therapy and chemotherapy, or any of the above in combination with drug therapy, hormone therapy, and/or surgery.

In some embodiments, patients with lung cancer, such as non-small cell lung carcinoma (NSCLC) and a high CES value are predicted to respond to adjuvant cancer therapy and experience improved overall survival and/or improved DFS, compared to not receiving adjuvant therapy. If it is determined that a patient with lung cancer has a high CES value, it is recommended or suggested that the patient receive adjuvant radiation therapy, adjuvant chemotherapy, or any combination thereof.

F. Computer-Implemented Methods, Systems, and Devices

Any of the methods described herein may be totally or partially performed with a computer system including one or more processors, which can be configured to perform the steps. Thus, embodiments are directed to computer systems configured to perform the steps of any of the methods described herein, potentially with different components performing a respective step or a respective group of steps. Although presented as numbered steps, steps of methods herein can be performed at a same time or in a different order. Additionally, portions of these steps may be used with portions of other steps from other methods. Also, all or portions of a step may be optional. Any of the steps of any of the methods can be performed with modules, circuits, or other means for performing these steps.

Figure 9:
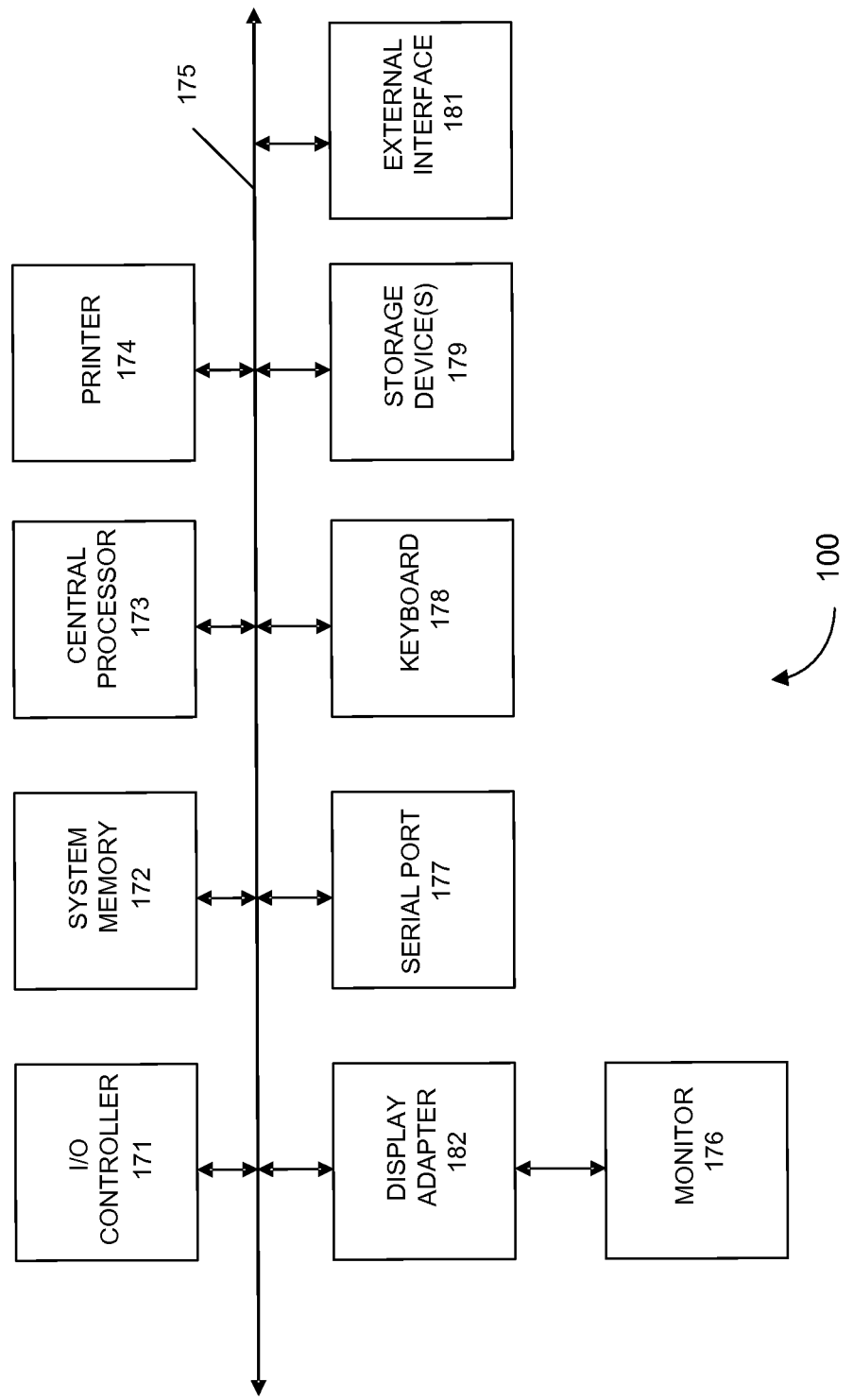
FIG. 9 shows a block diagram of an example computer system 100 usable with system and methods according to embodiments of the present disclosure.

Any of the computer systems mentioned herein may utilize any suitable number of subsystems. Examples of such subsystems are shown in FIG. 9 in computer apparatus 100. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 9 are interconnected via a system bus 175. Additional subsystems such as a printer 174, keyboard 178, storage device(s) 179, monitor 176, which is coupled to display adapter 182, and others are shown. Peripherals and input/output (I/O) devices, which couple to I/O controller 171, can be connected to the computer system by any number of means known in the art, such as serial port 177. For example, serial port 177 or external interface 181 (e.g. Ethernet, Wi-Fi, etc.) can be used to connect computer system 100 to a wide area network such as the Internet, a mouse input device, or a scanner. The interconnection via system bus 175 allows the central processor 173 to communicate with each subsystem and to control the execution of instructions from system memory 172 or the storage device(s) 179 (e.g., a fixed disk, such as a hard drive or optical disk), as well as the exchange of information between subsystems. The system memory 172 and/or the storage device(s) 179 may embody a computer readable medium. Any of the data mentioned herein can be output from one component to another component and can be output to the user.

A computer system can include a plurality of the same components or subsystems, e.g., connected together by external interface 181 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present disclosure can be implemented in the form of control logic using hardware (e.g., an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

G. Selecting Cancer Therapies

In some embodiments, the method of the present disclosure also includes selecting a therapeutic intervention for the subject with cancer having a high CES score or a high likelihood of death, disease relapse, recurrence, progression and/or metastasis. For a cancer subject with a high CES value, radiation therapy, chemotherapy, drug therapy, e.g., hormone therapy, immunotherapy, surgery, or any combination thereof can be selected. In some instances, surgery and an adjuvant therapy, such as radiation therapy, chemotherapy, drug therapy, e.g., hormone therapy, immunotherapy, or any combination thereof are suggested for the subject with a high CES score.

Non-limiting examples of useful chemotherapy agents include alkylating agents, e.g., cyclophosphamide, mechlorethamine, chlorambucil, ifosfamid, melphalan, streptozocin, carmustine, lomustine, busulfan, dacarbazine, temozolomide, thiotepa, and altretamine, antimetabolites, e.g., 5-fluorouracil (5-FU), 6-mercaptopurine (6-MP), capecitabine, cytarabine, floxuridine, gemcitabine, hydroxyurea, methotrexate, and pemetrexed, anthracyclines, e.g., daunorubicin, doxorubicin, epirubicin, and idarubicin, other antitumor antibiotics, e.g., actinomycin-D, bleomycin, mitomycin-c and mitoxantrone, topoisomerase inhibitors, e.g., topotecan, irinotecan, etoposide, teniposide, and metoxantrone, mitotic inhibitors, e.g., paclitaxel, docetaxel, ixabepilone, vinblastine, vincristine, vinrelbine, and estramustine, corticosteroids, e.g., prednisone, methylprednisone, and dexamethasone, L-aspraginase, and the proteasome inhibitor bortezomib. Without limitations, examples of radiation therapy include external beam radiation therapy, internal radiation therapy, or systemic radiation therapy.

The therapeutic intervention can include one or more DNA damaging compounds or agents, such as cisplatin, carboplatin, oxaliplatin, picoplatin, other platinum-based compounds, doxorubicin, daunorubicin, other anthracyclines, variants thereof and derivatives thereof.

In some instances, administration of one or more anthracyclines; cyclophosphamide; one or more taxanes; methotrexate; 5-fluorouracil; one or more anthracyclines and cyclophosphamide; one or more anthracyclines, cyclophosphamide, and one or more taxanes; cyclophosphamide, methotrexate and 5-fluorouracil, or any combination thereof is recommended.

In some embodiments, one or more therapeutic interventions are recommended. Each therapy can be administered simultaneously or sequentially.

H. Kits

For use in diagnostic applications, prognostic applications, and therapy selection applications described above, kits are also disclosed herein. The kits of the invention may comprise any or all of the reagents to perform the methods described herein. In such applications the kits may include any or all of the following: assay reagents, buffers, nucleic acids that bind to at least one of the genes described herein, hybridization probes and/or primers, antibodies or other moieties that specifically bind to at least one of the polypeptides encoded by the genes described herein, etc. In addition, the kit may include reagents such as nucleic acids, hybridization probes, primers, antibodies and the like that specifically bind to a reference gene or a reference polypeptide. The kit may comprise probes to one or more reference genes identified herein, such as, ARPC2, ATF4, ATP5B, B2M, CDH4, CELF1, CLTA, CLTC, COPB1, CTBP1, CYC1, CYFIP1, DAZAP2, DHX15, DIMT1, EEF1A1, FLOT2, CAPDH, GUSB, HADHA, HDLBP, HMBS, HNRNPC, HPRT1, HSP90AB1, MTCH1, MYL12B, NACA, NDUFB8, PGK1, PPIA, PPIB, PTBP1, RPL13A, RPLP0, RPS13, RPS23, RPS3, S100A6, SDHA, SEC31A, SET, SF3B1, SFRS3, SNRNP200, STARD7, SUMO1, TBP, TFRC, TMBIM6, TPT1, TRA2B, TUBA1C, UBB, UBC, UBE2D2, UBE2D3, VAMP3, XPO1, YTHDC1, YWHAZ, and 18S rRNA.

The term "kit" as used herein in the context of detection reagents, are intended to refer to such things as combinations of multiple gene expression product detection reagents, or one or more gene expression product detection reagents in combination with one or more other types of elements or components (e.g., other types of biochemical reagents, containers, packages such as packaging intended for commercial sale, substrates to which gene expression detection product reagents are attached, electronic hardware components, etc.).

In some embodiments, the present disclosure provides oligonucleotide probes attached to a solid support, such as an array slide or chip, e.g., as described in DNA Microarrays: A Molecular Cloning Manual, 2003, Eds. Bowtell and Sambrook, Cold Spring Harbor Laboratory Press. Construction of such devices are well known in the art, for example as described in US Patents and Patent Publications U.S. Pat. No. 5,837,832; PCT application WO95/11995; U.S. Pat. Nos. 5,807,522; 7,157,229, 7,083,975, 6,414,175, 6,375, 903, 6,315,958, 6,295,153, and 5,143,854, 2007/0037274, 2007/0140906, 2004/0126757, 2004/0110212, 2004/ 0110211, 2003/0143550, 2003/0003032, and 2002/ 0041420. Nucleic acid arrays are also reviewed in the following references: *Biotechnol Annu Rev* 8:85-101 (2002); Sosnowski et al, Psychiatr Genet 12(4):181-92 (December 2002); Heller, *Annu Rev Biomed Eng* 4: 129-53 (2002); Kolchinsky et al, *Hum. Mutat* 19(4):343-60 (April 2002); and McGail et al, Adv Biochem Eng Biotechnol 77:21-42 (2002).

A microarray can be composed of a large number of unique, single-stranded polynucleotides, usually either synthetic antisense polynucleotides or fragments of cDNAs, fixed to a solid support. Typical polynucleotides are preferably about 6-60 nucleotides in length, more preferably about 15-30 nucleotides in length, and most preferably about 18-25 nucleotides in length. For certain types of arrays or other detection kits/systems, it may be preferable to use oligonucleotides that are only about 7-20 nucleotides in length. In other types of arrays, such as arrays used in conjunction with chemiluminescent detection technology, preferred probe lengths can be, for example, about 15-80 nucleotides in length, preferably about 50-70 nucleotides in length, more preferably about 55-65 nucleotides in length, and most preferably about 60 nucleotides in length.

In addition, the kits may include instructional materials containing directions (i.e., protocols) for the practice of the methods provided herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

IV. EXAMPLES

The following examples are offered to illustrate, but not to limit, the claimed invention.

Example 1. M is Expression of Specific Centromere and Kinetochore Proteins Predicts Cancer Patient Survival and Response to Radiotherapy and Chemotherapy Chromosomal instability (CIN) is a hallmark of most human cancers and contributes to tumor heterogeneity and drug resistance. Aberrant centromere and kinetochore function causes CIN through chromosome missegregation during mitosis and chromosome rearrangements. However, we previously lacked a systematic understanding of the impact of centromere and kinetochore structural protein genes (CEN/KT genes) in cancer progression in patients. Based on differential gene expression between cancer and normal tissues and prognostic values of gene misexpression using a large number of patient data from many cancer types, we identified a core subset of 14 CEN/KT genes and devised a CES system (for Centromere and kinetochore gene Expression Score) that strongly correlates with copy number alternation (CNA) and mutation frequencies in various types of cancers. The CES score is an effective predictor of overall patient survival and disease progression for a wide spectrum of cancer types, including breast, lung, gastric and early stage ovarian cancers. Most importantly, high CES values are correlated with sensitivity to DNA damaging compounds in cancer cell lines, and effectively predict therapeutic outcomes for cancer patients after chemotherapy and radiotherapy. These results suggest that the CES system provides a novel and effective biomarker for cancer prognosis and for choosing therapeutic options.

INTRODUCTION

Genomic instability is characteristic of most human cancers and is believed to enable acquisition of other cancer hallmarks such as uninhibited cell growth and proliferation, heterogeneity and drug resistance (Hanahan and Weinberg, 2011). The major type of genomic instability is chromosomal instability (CIN), characterized by an increased rate of chromosomal abnormalities including gain/loss of whole chromosomes or large segments (aneuploidy), structural rearrangements and focal aberrations (e.g. amplifications and deletions) (Beroukhim et al., 2010; Geigl et al., 2008). CIN has been observed in pre-cancerous lesions and malignant growth (P than et al., 2003). Aneuploidy has been hypothesized to promote tumorigenesis (Boveri, 1902, 1914; Siegel and Amon, 2012; Weaver et al., 2007). Recent cancer genome sequencing studies suggested that CIN contributes to inter- and intra-tumor heterogeneity (de Bruin et al., 2014; Hiley and Swanton, 2014; Nik-Zainal et al., 2012; Yachida et al., 2010; Zhang et al., 2014). Aberrant chromosome behavior can cause abnormal chromosomal structure, increase mutation frequency or epigenetically modify gene activity.

During cancer development, defective chromosome segregation and integrity pathways could synergize with altered signal transduction pathways, or they could act independently. For example, many oncogenes encode fused or misregulated signaling molecules caused by chromosomal translocations or inversions (Pierotti, 2003). In another example, dynamic amplification of the EGFR locus in glioblastoma cells contributes to resistance to EGFR inhibitors (Nathanson et al., 2014). On the other hand, rare mutations in spindle checkpoint components such as Bub1, BubR1 and Mad1 promote aneuploidy and link to tumorigenesis in mouse and humans (Kops et al., 2005). Thus, continuous modifications of the genomic landscape can allow rapid accumulation of deleterious changes that promote cancer progression and growth (Schvartzman et al., 2010), and confer drug resistance during treatments (Lee et al., 2011; Nathanson et al., 2014; Swanton et al., 2007; Weaver and Cleveland, 2006). One paradoxical phenomenon is that extreme CIN can cause growth disadvantage, presumably due to excess stress from genotoxic effects and proteomic imbalance (Hiley and Swanton, 2014; Siegel and Amon, 2012). These results, and the possibility of selectively killing cancer cells displaying CIN, demonstrate CIN to be both a challenge and a potential opportunity for cancer treatment (Carter et al., 2006; Roschke and Kirsch, 2005).

While the exact cause of CIN in most sporadic cancers remains unclear, proposed mechanisms include oncogene-induced replication stress, the breakage-fusion-bridge cycles induced by telomere dysfunction or translocations, and aberrant mitosis (Artandi and DePinho, 2010; Kops et al., 2005; Negrini et al., 2010). Chromosome missegregation also can be accompanied by DNA damage through chromosome fragmentation (Janssen et al., 2011). Centromeres and associated kinetochores are required for proper chromosome congression, mitotic checkpoint function, and separation of sister chromatids during mitosis in eukaryotic cells (Allshire, 1997; Cleveland et al., 2003; Earnshaw et al., 1991). Thus, another potential cause of CIN is misregulation of centromere and kinetochore functions, which leads to chromosomal abnormalities in cell lines and model organisms.

Centromeres and kinetochores consist of centromeric chromatin, as well as inner and outer kinetochore structures (FIG. 1A). CENP-A, a histone H3 variant enriched at active centromeres, is a key epigenetic mark that determines centromere identity and its faithful propagation (Allshire and Karpen, 2008; Black et al., 2010). All other centromere and kinetochore proteins ultimately require CENP-A for their localization (Allshire and Karpen, 2008). The CCAN (Constitutive Centromere Associated Network) links chromatin to the outer kinetochore and contains several subcomplexes. The CENP-T/-W/-S/-X complex resides within the H3 domains interspersed between CENP-A nucleosomes (Blower et al., 2002; Foltz et al., 2006; Nishino et al., 2012; Sullivan and Karpen, 2004). CENP-N/-L/-M determines the localization of CENP-H/-I/-K, which is in turn required for CENP-O/-P/-Q/-R/-U recruitment. The CCAN ensures the recruitment of the KMN network (KNL1 complex, MIS12 complex and NDC80 complex) to the outer kinetochore (Cheeseman and Desai, 2008; Hori et al., 2008; Perpelescu and Fukagawa, 2011), and the NDC80 complex interacts with spindle microtubules.

CENP-A is incorporated into centromeric chromatin using HJURP as its chaperone and assembly factor (Dunleavy et al., 2009; Foltz et al., 2009; Mellone et al., 2009). HJURP is recruited to the centromere by the MIS18 complex containing MIS18A, MIS18B and M18BP1 subunits (Barnhart et al., 2011; Fujita et al., 2007; Moree et al., 2011). Moreover, several CCAN components such as CENP-C and members of CENP-H/-I/-K and CENP-N/-L/-M are also required for CENP-A assembly (Black and Cleveland, 2011; Cheeseman et al., 2008; Moree et al., 2011; Okada et al., 2006).

The levels of centromere and kinetochore proteins appear to be tightly regulated to ensure faithful chromosome segregation. Loss of many centromere and kinetochore proteins by mutation or depletion result in chromosome segregation defects and cell death, and overexpression of some key proteins can also compromise functions (Allshire and Karpen, 2008). For example, overexpression or ectopic tethering of *Drosophila* CENP-A results in mis-incorporation into normally non-centromeric chromosomal regions, causing neo-centromere formation, dicentric behavior, and chromosomal breakage and abnormalities (Heun et al., 2006; Mendiburo et al., 2011). Elevated levels of human CENP-A or HJURP in cell lines also mislocalize to other regions of the genome and cause chromatin bridges and micronuclei (Mishra et al., 2011). Importantly, overexpression of several centromeric proteins, including CENP-A, HJURP and CENP-H, correlates with poor prognosis for several types of cancers, suggesting potential roles in cancer etiology (Hu et al., 2010; Mcgovern et al., 2012; Tomonaga et al., 2005; Tomonaga et al., 2003).

We hypothesized that misregulation of centromere and kinetochore protein genes cause chromosomal abnormalities that contribute to human cancer progression and/or tumor maintenance. We systematically investigated differential expression of centromere and kinetochore structural protein (CEN/KT) genes between cancerous and normal tissues, and studied the prognostic impact of their gene expression levels. We found that overexpression of 14 CEN/KT genes is consistently observed in many different types of cancers. We derive a CES system (for Centromere and kinetochore gene Expression Score) that summarizes the extent of centromere and kinetochore gene misexpression across several cancer types. We correlated CES values with a significant fraction of genomic instability in a wide spectrum of cancer types. We also show that the tumor CES value predicts patient survival and disease progression. Radiotherapy (RT) and DNA damaging compounds kill cancer cells by damaging DNA beyond repair followed by cell death, yet are associated with potentially severe collateral damage to patients. We hypothesized that tumors with high CES values are already subjected to high levels of genotoxic stress and might be more sensitive to further damage. This idea is supported by sensitivity of high CES cancer cell lines to Topo I inhibitors that cause DNA damage and inhibit replication and transcription (Mathijssen et al., 2002). Using breast cancer and lung cancer clinical datasets, we found that the CES system effectively forecasts patient outcome after RT or adjuvant chemotherapy, and propose that this system may be valuable for optimizing treatment regimens in clinical oncology. The CEN/KT genes identified here are components that determine dynamic centromere and kinetochore structure and play pivotal roles in faithful chromosome segregation. Many of the CES genes are involved in the process of CENP-A nucleosome assembly, suggesting the potential importance of this process in cancer progression. These chromosomal functions are distinct from many existing drug targets that are involved in signal transduction and regulation of oncogenic or tumor suppression pathways. Thus, the CEN/KT proteins identified here may be novel targets for development of cancer therapy drugs, which may be particularly effective when combined with drugs targeted to components of orthogonal pathways, such as signal transduction and cell growth.

Results

A. Misregulation of a Subset of Centromere and Kinetochore Protein Genes in Human Cancers We manually compiled a list of 31 centromere and kinetochore (CEN/KT) protein genes (FIG. 1B) to investigate their potential roles in cancer prognosis. The list was restricted to proteins demonstrated to localize to and determine centromere or kinetochore structures (Black et al., 2010). The list includes CENP-A and downstream CCAN and KMN components, as well as factors required for CENP-A nucleosome assembly and centromere propagation (e.g., HJURP and MIS18) that transiently localize to centromeres (Dunleavy et al., 2009; Foltz et al., 2009; Fujita et al., 2007; Mellone et al., 2009).

Using GEO databases, CEN/KT gene expression analysis was performed for a wide spectrum of human cancer types, specifically breast, lung, liver, nasopharyngeal, gastric, head and neck, cervical, prostate, glioblastoma, colorectal, pancreas and ovarian (Table 1). We consistently observe misregulation of a subset of CEN/KT genes in most types of cancers compared to corresponding normal tissues. In addition, we detected difference between tumors at different disease stages during cancer progression. For example, in breast tissues, CEN/KT misregulation in ductal carcinoma in situ (DCIS) is intermediate between normal tissues and invasive ductal carcinomas (IDCs). In liver, CEN/KT genes show no significant misregulation in cirrhotic or dysplastic tissues, but are significantly misregulated from very early stage to very advanced cancers. In prostate, only metastatic cancers display significant misregulation for CEN/KT genes, while malignant local lesions show limited misregulation. These results suggest a potential role for CEN/KT protein misregulation in initiation or early stages of cancer progression. In addition, the absence of CEN/KT gene misregulation in liver dysplasia suggests that defective CEN/KT regulation is not simply a result of cell overproliferation.

TABLE 1

GEO datasets used for studying CEN/KT gene.

| Cancer types | GEO Series Accession Number |
| --- | --- |
| breast | GSE21422 and GSE3744 |
| lung | GSE19188 |
| ovarian | GSE14407 |
| liver | GSE6764 |
| pancreas | GSE16515 |
| colorectal | GSE8671 |
| nasopharyngeal | GSE12452 |
| gastric | GSE13911 |
| head and neck | GSE6791 |
| cervical | GSE6791 |
| prostate | GSE3325 |
| glioblastoma | GSE4290 |

To address the potential role of CEN/KT genes in cancer progression, we analyzed datasets containing tissue samples representing different stages of disease progression. Specifically, our analyses of 13 Affymetrix gene expression microarray datasets from 9 cancer types revealed that expression of 15 CEN/KT genes is significantly misregulated (FDR p<0.05, at least 2-fold difference) in over 50% of examined cancer datasets comparing cancer to corresponding normal tissues, and early to advanced stage tumor samples (FIG. 1C and Table 2). These results suggest that defective CEN/KT gene regulation is conserved among a wide array of cancers, and may play an important role in disease progression.

TABLE 2

GEO datasets used for studying differentially expressed CEN/KT genes.

| | | Breast | | | Cervical | Head & Neck | | Colon | Gastric | Brain and CNS |
| --- | --- | --- | --- | --- | --- | --- | --- | --- | --- | --- |
| | | GSE17080 | GSE21422 | GSE3744 | GSE6791 | GSE6791 | GSE12452 | GSE8671 | GSE13911 | GSE4290 |
| Gene | Probe ID | IDC vs Normal | DCIS vs Normal | IDC vs Normal | BC vs Normal | Tumor vs Normal | Tumor vs Normal | Tumor vs Normal | adenoma vs Normal | Tumor vs Normal | astrocytomas vs normal |
| CENP-A | 204962_s_at | 30.98 | 2.83 | 5.27 | 8.75 | 6.23 | 4.04 | 5.12 | 17.18 | 7.69 | 4.56 |
| | 210821_x_at | 8.81 | 1.10 | 3.20 | 3.15 | 0.06 | 2.33 | 0.64 | 9.59 | 4.92 | 3.37 |
| HJURP | 218726_at | 37.95 | 2.04 | 2.60 | 9.22 | 5.72 | 1.24 | 4.01 | 18.63 | 7.30 | 5.76 |
| M18BP1 | 206500_s_at | 4.20 | 0.65 | 0.72 | 2.55 | 2.52 | 1.55 | 0.94 | 7.63 | 2.83 | 2.47 |
| | 226630_at | 1.08 | 0.43 | 0.02 | 0.05 | 6.20 | 0.23 | 2.84 | 11.10 | 0.90 | 1.17 |
| | 241816_at | 1.62 | 0.24 | 0.16 | 0.50 | 0.37 | 0.05 | 0.38 | 1.49 | 0.90 | 2.96 |
| | 244173_at | 0.39 | 0.85 | 0.56 | 1.23 | 0.08 | 0.94 | 0.15 | 0.31 | 1.48 | 0.24 |
| MIS18A | 219004_s_at | 12.37 | 0.98 | 1.92 | 2.98 | 7.15 | 4.35 | 4.20 | 13.61 | 4.64 | 0.15 |
| | 228597_at | 13.05 | 1.38 | 1.46 | 2.97 | 9.07 | 1.06 | 4.41 | 16.26 | 2.44 | 2.11 |
| | 229671_s_at | 10.95 | 1.80 | 1.57 | 2.85 | 0.31 | 4.07 | 4.30 | 11.33 | 0.84 | 2.25 |
| MIS18B | 213599_at | 33.63 | 2.57 | 4.22 | 4.46 | 7.61 | 3.43 | 5.05 | 18.04 | 5.22 | 3.65 |
| CENP-T | 218148_at | 1.17 | 1.61 | 0.25 | 0.98 | 1.86 | 0.75 | 0.15 | 1.17 | 0.51 | 1.80 |
| CENP-W | 226936_at | 7.98 | 0.04 | 0.28 | 2.09 | 7.43 | 3.97 | 2.91 | 23.45 | 8.09 | 0.12 |
| CENP-S | 213454_at | 12.06 | 0.28 | 0.95 | 2.80 | 5.74 | 2.06 | 0.29 | 16.29 | 0.47 | 0.17 |
| CENP-X | 209478_at | 14.56 | 2.44 | 4.71 | 0.87 | 0.03 | 0.08 | 0.89 | 4.53 | 1.51 | 0.05 |
| CENP-C | 204739_at | 6.71 | 1.25 | 1.54 | 0.91 | 2.86 | 0.03 | 0.56 | 1.46 | 1.89 | 0.61 |

TABLE 2-continued

GEO datasets used for studying differentially expressed CEN/KT genes.

| Gene | Probe ID | | | | | | | | | |
|---|---|---|---|---|---|---|---|---|---|---|
| CENP-N | 219555_s_at | 21.13 | 1.53 | 3.69 | 5.96 | 3.62 | 3.23 | 3.81 | 18.46 | 6.20 | 0.82 |
| | 222118_at | 5.59 | 0.55 | 2.54 | 2.49 | 3.96 | 5.11 | 3.88 | 10.95 | 3.97 | 0.11 |
| | 228559_at | 21.26 | 2.71 | 2.59 | 5.66 | 4.53 | 2.12 | 2.53 | 13.61 | 4.35 | 0.83 |
| | 234811_at | 2.59 | 0.02 | 0.60 | 0.51 | 0.28 | 0.15 | 0.57 | 1.45 | 0.50 | 0.72 |
| CENP-M | 218741_at | 24.37 | 2.19 | 3.40 | 4.38 | 3.36 | 2.26 | 0.94 | 8.71 | 7.41 | 3.42 |
| CENP-U | 218883_s_at | 37.45 | 3.12 | 3.19 | 7.30 | 5.54 | 0.32 | 7.22 | 11.01 | 4.63 | 8.43 |
| | 229304_s_at | 7.37 | 1.98 | 1.65 | 1.71 | 1.70 | 0.51 | 4.02 | 7.01 | 0.35 | 3.24 |
| | 229305_at | 24.09 | 1.43 | 1.31 | 3.17 | 3.39 | 0.94 | 6.02 | 8.36 | 1.61 | 2.52 |
| CENP-H | 231772_x_at | 17.85 | 1.74 | 2.07 | 2.02 | 3.38 | 3.51 | 5.46 | 11.62 | 6.93 | 5.25 |
| CENP-I | 1555046_at | 1.01 | 0.46 | 0.20 | 1.07 | 0.81 | 0.44 | 0.91 | 1.23 | 0.74 | 0.47 |
| | 1563223_a_at | 0.07 | 0.25 | 0.09 | 0.94 | 1.43 | 1.54 | 0.85 | 1.33 | 2.20 | 0.25 |
| | 207590_s_at | 12.03 | 0.98 | 1.52 | 2.32 | 1.75 | 1.53 | 3.70 | 8.26 | 1.47 | 0.53 |
| | 214804_at | 17.29 | 0.65 | 1.22 | 2.32 | 5.19 | 2.70 | 4.71 | 6.92 | 4.35 | 1.64 |
| CENP-L | 1554271_a_at | 20.53 | 3.57 | 2.99 | 4.54 | 0.91 | 2.43 | 1.92 | 10.63 | 3.93 | 4.22 |
| | 232065_x_at | 9.57 | 4.56 | 2.84 | 3.83 | 4.45 | 3.39 | 4.20 | 8.42 | 9.45 | 4.21 |
| CENP-K | 222848_at | 29.45 | 2.84 | 2.61 | 3.76 | 11.72 | 1.57 | 6.76 | 16.12 | 4.87 | 5.49 |
| CENP-O | 219472_at | 1.89 | 0.24 | 0.35 | 0.12 | 1.49 | 0.20 | 0.01 | 0.50 | 1.38 | 1.45 |
| | 226118_at | 15.16 | 1.81 | 1.98 | 2.75 | 4.76 | 2.79 | 3.05 | 4.28 | 3.02 | 3.50 |
| CENP-Q | 219294_at | 5.36 | 0.10 | 0.27 | 1.77 | 8.13 | 3.39 | 4.03 | 9.66 | 4.18 | 5.63 |
| CENP-R | 205176_s_at | 0.30 | 0.60 | 1.59 | 0.06 | 6.54 | 0.59 | 5.11 | 12.20 | 0.97 | 7.38 |
| KNL1 | 1552680_a_at | 32.52 | 0.58 | 0.12 | 3.16 | 1.62 | 0.47 | 1.31 | 3.15 | 4.37 | 1.78 |
| | 1552682_a_at | 2.97 | 0.84 | 0.64 | 0.98 | 0.32 | 0.04 | 0.82 | 4.67 | 1.57 | 0.03 |
| | 220247_at | 0.14 | 0.45 | 0.37 | 0.73 | 1.52 | 3.81 | 0.25 | 0.17 | 0.56 | 0.25 |
| | 228323_at | 38.73 | 3.05 | 4.18 | 9.34 | 8.85 | 1.10 | 5.12 | 13.74 | 5.34 | 5.67 |
| ZWINT | 204026_s_at | 44.43 | 3.62 | 3.42 | 9.20 | 8.74 | 3.10 | 9.20 | 14.70 | 4.08 | 3.44 |
| MIS12 | 221559_s_at | 0.01 | 0.43 | 0.81 | 0.25 | 8.92 | 1.59 | 1.52 | 1.41 | 0.05 | 3.83 |
| NSL1 | 209483_s_at | 5.65 | 0.40 | 0.15 | 1.81 | 0.98 | 0.12 | 0.09 | 0.42 | 0.70 | 0.51 |
| | 209484_s_at | 4.87 | 0.53 | 0.51 | 1.37 | 4.00 | 1.56 | 1.82 | 0.45 | 1.90 | 3.76 |
| | 230592_at | 0.29 | 0.10 | 0.87 | 0.81 | 3.52 | 0.63 | 0.90 | 0.54 | 0.31 | 1.31 |
| | 235799_at | 0.43 | 0.09 | 0.45 | 0.07 | 2.28 | 2.93 | 0.34 | 0.83 | 2.87 | 0.48 |
| PMF1 | 202337_at | 5.86 | 2.30 | 3.72 | 0.33 | 0.51 | 2.40 | 0.00 | 6.97 | 0.38 | 5.13 |
| KNL3 | 219512_at | 14.65 | 1.43 | 1.28 | 3.67 | 5.02 | 4.92 | 3.76 | 7.22 | 3.94 | 1.89 |
| NDC80 | 204162_at | 28.46 | 3.16 | 3.56 | 5.33 | 6.95 | 2.68 | 6.97 | 15.36 | 8.77 | 10.01 |
| SPC24 | 235572_at | 20.13 | 1.79 | 2.81 | 4.01 | 3.21 | 0.39 | 2.75 | 3.03 | 11.63 | 3.85 |
| SPC25 | 209891_at | 34.65 | 1.93 | 2.94 | 4.58 | 4.22 | 1.90 | 2.87 | 15.78 | 7.47 | 2.78 |
| NUF2 | 223381_at | 31.63 | 2.91 | 6.65 | 10.62 | 8.28 | 1.88 | 6.00 | 17.42 | 11.67 | 6.77 |

| | | Brain and CNS | | GSE6764 | | | Lung | | | | Pancreatic |
|---|---|---|---|---|---|---|---|---|---|---|---|
| | | | | | | | GSE19188 | | | GSE31210 | GSE16515 |
| Gene | Probe ID | Glioblastoma vs normal | oligodendrogliomas vs normal | dysplastic vs normal | early stage vs normal | late stage vs normal | LCC vs normal | ADC vs normal | SCC vs normal | ADC vs Normal | Tumor vs Normal |
| CENP-A | 204962_s_at | 13.34 | 5.07 | 0.16 | 3.35 | 13.65 | 24.32 | 18.91 | 42.27 | 8.51 | 6.41 |
| | 210821_x_at | 5.54 | 5.47 | 0.07 | 0.36 | 0.09 | 19.21 | 14.49 | 23.43 | 2.73 | 0.72 |
| HJURP | 218726_at | 15.26 | 3.21 | 0.10 | 2.56 | 8.02 | 23.64 | 22.57 | 38.31 | 7.84 | 4.19 |
| M18BP1 | 206500_s_at | 5.74 | 1.29 | 0.10 | 1.77 | 2.00 | 3.65 | 5.68 | 6.72 | 0.44 | 1.62 |
| | 226630_at | 4.65 | 0.77 | 0.01 | 1.09 | 2.68 | 2.24 | 3.26 | 3.09 | 0.65 | 0.87 |
| | 241816_at | 5.30 | 0.63 | 0.60 | 1.82 | 1.38 | 3.46 | 3.57 | 6.97 | 0.40 | 1.05 |
| | 244173_at | 0.68 | 0.04 | 0.02 | 0.81 | 1.29 | 0.12 | 0.01 | 0.60 | 0.27 | 3.52 |
| MIS18A | 219004_s_at | 5.88 | 1.37 | 0.64 | 1.42 | 5.19 | 14.42 | 13.88 | 23.43 | 6.17 | 2.35 |
| | 228597_at | 9.17 | 1.42 | 0.22 | 2.54 | 3.82 | 14.46 | 11.80 | 20.73 | 5.47 | 2.27 |
| | 229671_s_at | 6.30 | 2.27 | 0.17 | 0.13 | 1.64 | 10.45 | 9.52 | 16.44 | 5.55 | 0.21 |
| MIS18B | 213599_at | 9.33 | 5.63 | 0.37 | 2.17 | 7.90 | 21.78 | 17.32 | 32.91 | 4.44 | 4.12 |
| CENP-T | 218148_at | 1.77 | 0.90 | 1.76 | 0.74 | 3.15 | 0.03 | 0.63 | 0.40 | 0.02 | 0.61 |
| CENP-W | 226936_at | 4.65 | 0.08 | 0.13 | 4.53 | 9.20 | 10.86 | 10.21 | 31.70 | 3.15 | 3.72 |
| CENP-S | 213454_at | 0.67 | 0.28 | 0.83 | 0.30 | 2.77 | 11.49 | 3.84 | 3.64 | 6.57 | 0.32 |
| CENP-X | 209478_at | 1.68 | 1.92 | 0.20 | 1.80 | 3.87 | 10.68 | 11.88 | 13.76 | 8.85 | 3.24 |
| CENP-C | 204739_at | 1.07 | 0.19 | 0.15 | 0.57 | 1.48 | 2.53 | 4.33 | 2.45 | 0.88 | 2.75 |
| CENP-N | 219555_s_at | 7.90 | 0.57 | 0.26 | 1.35 | 8.56 | 15.33 | 15.21 | 31.04 | 4.06 | 3.18 |
| | 222118_at | 4.82 | 0.30 | 0.03 | 1.08 | 5.35 | 4.85 | 3.00 | 12.01 | 0.74 | 0.46 |
| | 228559_at | 1.27 | 1.52 | 0.23 | 1.32 | 1.61 | 9.43 | 7.21 | 23.60 | 1.94 | 1.46 |
| | 234811_at | 2.54 | 1.41 | 0.47 | 0.51 | 0.73 | 1.68 | 0.21 | 1.06 | 0.16 | 1.78 |
| CENP-M | 218741_at | 6.77 | 3.38 | 0.38 | 2.46 | 5.08 | 10.61 | 13.00 | 22.74 | 8.90 | 4.17 |
| CENP-U | 218883_s_at | 15.47 | 7.14 | 0.12 | 4.37 | 10.03 | 13.16 | 15.13 | 23.22 | 7.44 | 6.89 |
| | 229304_s_at | 7.81 | 3.88 | 1.47 | 0.79 | 3.30 | 6.97 | 5.79 | 12.70 | 2.37 | 2.37 |
| | 229305_at | 8.77 | 3.55 | 1.27 | 0.67 | 2.54 | 12.41 | 8.95 | 19.81 | 4.74 | 2.92 |
| CENP-H | 231772_x_at | 8.20 | 3.13 | 0.07 | 1.69 | 5.11 | 15.83 | 10.18 | 19.21 | 3.95 | 1.23 |
| CENP-I | 1555046_at | 0.12 | 0.22 | 0.00 | 0.70 | 1.82 | 2.48 | 1.23 | 0.75 | 0.96 | 3.30 |
| | 1563223a_at | 1.23 | 0.70 | 0.33 | 1.68 | 1.43 | 1.45 | 0.89 | 0.86 | 0.53 | 2.77 |
| | 207590_s_at | 2.88 | 0.52 | 0.22 | 0.09 | 3.50 | 13.56 | 13.93 | 21.23 | 5.26 | 0.43 |
| | 214804_at | 6.96 | 2.04 | 0.30 | 0.34 | 6.83 | 14.58 | 14.02 | 30.52 | 3.89 | 2.20 |
| CENP-L | 1554271_a_at | 11.16 | 3.79 | 0.47 | 1.31 | 6.83 | 15.96 | 18.96 | 22.31 | 6.30 | 3.26 |
| | 232065_x_at | 12.98 | 2.86 | 0.11 | 3.29 | 8.56 | 14.14 | 13.80 | 22.30 | 6.57 | 3.07 |
| CENP-K | 222848_at | 17.13 | 3.66 | 0.35 | 2.55 | 8.39 | 14.39 | 16.39 | 19.78 | 6.94 | 7.03 |

TABLE 2-continued

GEO datasets used for studying differentially expressed CEN/KT genes.

| | | | | | | | | | | | |
|---|---|---|---|---|---|---|---|---|---|---|---|
| CENP-O | 219472_at | 2.69 | 2.05 | 0.30 | 1.05 | 0.04 | 6.35 | 4.93 | 9.48 | 0.68 | 1.78 |
| | 226118_at | 4.92 | 1.88 | 0.05 | 1.44 | 4.61 | 16.95 | 10.16 | 18.59 | 1.14 | 2.83 |
| CENP-Q | 219294_at | 5.71 | 4.69 | 0.05 | 0.74 | 5.61 | 10.00 | 4.87 | 5.66 | 0.66 | 1.12 |
| CENP-R | 205176_s_at | 14.69 | 0.97 | 1.22 | 2.97 | 6.25 | 5.86 | 4.27 | 4.78 | 3.83 | 0.46 |
| KNL1 | 1552680_a_at | 7.99 | 1.84 | 1.41 | 1.82 | 2.77 | 14.73 | 14.03 | 24.03 | 5.33 | 1.66 |
| | 1552682_a_at | 0.92 | 1.94 | 0.09 | 1.37 | 2.35 | 8.81 | 6.42 | 9.34 | 2.26 | 0.69 |
| | 220247_at | 1.97 | 0.79 | 0.01 | 0.85 | 1.98 | 0.24 | 0.71 | 0.11 | 0.09 | 4.67 |
| | 228323_at | 14.71 | 6.61 | 0.08 | 2.50 | 2.96 | 16.43 | 17.40 | 29.41 | 7.99 | 5.42 |
| ZWINT | 204026_s_at | 9.55 | 4.53 | 0.02 | 3.48 | 9.28 | 14.75 | 17.70 | 21.83 | 8.72 | 6.53 |
| MIS12 | 221559_s_at | 8.02 | 3.20 | 1.37 | 0.10 | 0.56 | 0.13 | 0.68 | 0.10 | 0.84 | 0.76 |
| NSL1 | 209483_s_at | 0.40 | 0.04 | 0.14 | 0.40 | 0.45 | 4.67 | 1.29 | 1.62 | 6.30 | 0.49 |
| | 209484_s_at | 3.82 | 3.58 | 0.46 | 6.25 | 7.26 | 10.22 | 6.56 | 5.23 | 6.01 | 1.25 |
| | 230592_at | 2.81 | 2.93 | 0.30 | 0.54 | 1.44 | 3.16 | 0.59 | 3.73 | 0.05 | 0.64 |
| | 235799_at | 0.62 | 0.47 | 0.10 | 0.10 | 0.31 | 1.78 | 0.28 | 1.13 | 1.07 | 1.64 |
| PMF1 | 202337_at | 7.42 | 7.37 | 2.28 | 3.23 | 11.39 | 4.97 | 5.03 | 0.09 | 6.20 | 3.51 |
| KNL3 | 219512_at | 9.53 | 1.47 | 0.95 | 1.62 | 5.64 | 8.30 | 5.97 | 12.44 | 1.22 | 4.61 |
| NDC80 | 204162_at | 27.43 | 10.70 | 0.05 | 6.56 | 11.78 | 16.17 | 15.58 | 27.49 | 4.39 | 5.69 |
| SPC24 | 235572_at | 14.29 | 6.71 | 0.37 | 5.78 | 7.97 | 15.80 | 15.17 | 29.58 | 8.76 | 1.65 |
| SPC25 | 209891_at | 7.66 | 5.66 | 0.15 | 2.00 | 7.60 | 22.18 | 13.90 | 28.24 | 5.43 | 2.16 |
| NUF2 | 223381_at | 13.94 | 6.85 | 0.41 | 3.79 | 13.32 | 23.72 | 21.31 | 38.00 | 8.13 | 7.02 |

Numbers represent −log(p value). Bold font highlight indicates >2-fold change

We then investigated CEN/KT gene misregulation using TCGA RNA-seq data across different types of cancer. A recent study demonstrated a strong correlation between the FoxM1 transcription factor and kinetochore gene expression, and proposed that CEN/KT genes are simultaneously up-regulated by FoxM1 in cancers (Thiru et al., 2014). Consistent with this observation, we also detected strong correlations among many CEN/KT genes in diverse cancer types using co-expression correlation network analyses. However, the number of genes and correlation coefficients in this network vary greatly among different cancers, suggesting significantly different strength of co-expression within and between cancer types. For example, in several cancers such as bladder, cervical and uterine cancers, this sub-network contains many fewer nodes and edges than cancers such as AML, lung adenocarcinomas or lower grade brain cancers. This result suggests significant regulatory differences for CEN/KT gene expression among cancer types and/or among individuals within the same type.

B. A Subset of CEN/KT Genes have Significant Prognostic Value for Survival and Metastasis in Multiple Human Cancers To determine whether CEN/KT gene misregulation has prognostic value for cancer patients, we carried out meta-analyses using CEN/KT expression data from multiple cancer GEO datasets. First, we conducted a meta-analysis of the prognostic impact of the 31 CEN/KT gene expression levels in over 3,000 human breast cancer clinical samples using Breast Cancer Gene-Expression Miner v3.0 (BC-GenExMiner 3.0) (Jezequel et al., 2013). Overexpression of 22 individual CEN/KT genes and reduced expression of CENP-C are significantly associated with poor any event (AE)-free survival (p<0.05) and poor metastatic relapse (MR)-free survival (MRFS) (p<0.05) (Table 3).

TABLE 3

Any event-free survival and metastatic relapse-free survival of CEN/KT genes in breast cancers.

| | Breast Cancer AEFS | | Breast Cancer MRFS | | |
|---|---|---|---|---|---|
| Genes | HR (95% CI) | p-value | HR (95% CI) | p-value | |
| CENP-A | 1.47 (1.31-1.66) | <0.0001 | 1.56 (1.33-1.83) | <0.0001 | Overexpression |
| HJURP | 1.55 (1.37-1.76) | <0.0001 | 1.69 (1.43-1.98) | <0.0001 | Overexpression |
| M18BP1 | 0.96 (0.85-1.09) | 0.5668 | 0.93 (0.80-1.09) | 0.3998 | |
| MIS18A | 1.34 (1.18-1.51) | <0.0001 | 1.48 (1.26-1.74) | <0.0001 | Overexpression |
| MIS18B | 1.42 (1.26-1.61) | <0.0001 | 1.51 (1.28-1.77) | <0.0001 | Overexpression |
| CENP-C | 0.82 (0.75-0.91)* | 0.0001 | 0.78 (0.69-0.88)* | 0.0001 | Reduced expression |
| CENP-N | 1.61 (1.46-1.77) | <0.0001 | 1.82 (1.60-2.07) | <0.0001 | Overexpression |
| CENP-I | 1.44 (1.28-1.63) | <0.0001 | 1.46 (1.25-1.72) | <0.0001 | Overexpression |
| CENP-H | 1.27 (1.08-1.50) | 0.005 | 1.32 (1.01-1.72) | 0.0413 | Overexpression |
| CENP-T | 1.02 (0.90-1.17) | 0.7206 | 1.08 (0.91-1.28) | 0.3921 | |
| CENP-W | 1.95 (1.40-2.72) | 0.0001 | 2.13 (1.41-3.19) | 0.0003 | Overexpression |
| CENP-S | 1.14 (0.98-1.32) | 0.0899 | 1.10 (0.91-1.32) | 0.3313 | |
| CENP-X | 1.22 (1.12-1.34) | 0.0001 | 1.20 (1.06-1.36) | 0.0038 | Overexpression |
| CENP-M | 1.39 (1.23-1.57) | <0.0001 | 1.49 (1.27-1.75) | <0.0001 | Overexpression |
| CENP-U | 1.35 (1.19-1.52) | <0.0001 | 1.51 (1.29-1.77) | <0.0001 | Overexpression |
| CENP-L | 1.44 (1.22-1.70) | <0.0001 | 1.43 (1.15-1.79) | 0.0014 | Overexpression |
| CENP-K | 1.28 (1.10-1.48) | 0.0012 | 1.34 (1.10-1.65) | 0.0046 | Overexpression |
| CENP-O | 1.31 (1.16-1.48) | <0.0001 | 1.28 (1.09-1.50) | 0.0024 | Overexpression |
| CENP-P | 0.96 (0.79-1.16) | 0.6576 | 0.88 (0.69-1.13) | 0.3268 | |
| CENP-Q | 0.99 (0.88-1.12) | 0.8696 | 0.98 (0.84-1.15) | 0.8346 | |
| CENP-R | 0.96 (0.85-1.08) | 0.4688 | 0.90 (0.77-1.05) | 0.1652 | |
| KNL1 | 1.19 (1.08-1.32) | 0.0006 | 1.21 (1.07-1.38) | 0.0034 | Overexpression |
| ZWINT | 1.51 (1.37-1.67) | <0.0001 | 1.66 (1.46-1.89) | <0.0001 | Overexpression |

TABLE 3-continued

Any event-free survival and metastatic relapse-free survival of CEN/KT genes in breast cancers.

| Genes | Breast Cancer AEFS HR (95% CI) | p-value | Breast Cancer MRFS HR (95% CI) | p-value | |
|---|---|---|---|---|---|
| MIS12 | 1.14 (1.00-1.30) | 0.045 | 1.17 (0.98-1.39) | 0.0769 | |
| PMF1 | 0.96 (0.87-1.05) | 0.3813 | 0.99 (0.87-1.12) | 0.8274 | |
| NSL1 | 1.02 (0.90-1.14) | 0.7956 | 1.03 (0.88-1.21) | 0.6793 | |
| KNL3 | 1.26 (1.11-1.42) | 0.0003 | 1.44 (1.23-1.70) | <0.0001 | Overexpression |
| NDC80 | 1.32 (1.17-1.48) | <0.0001 | 1.38 (1.18-1.62) | <0.0001 | Overexpression |
| SPC24 | 1.54 (1.25-1.88) | <0.0001 | 1.66 (1.20-2.30) | 0.0024 | Overexpression |
| SPC25 | 1.32 (1.17-1.48) | <0.0001 | 1.36 (1.16-1.59) | 0.0001 | Overexpression |
| NUF2 | 1.32 (1.14-1.54) | 0.0003 | 1.41 (1.13-1.76) | 0.0025 | Overexpression |

Most of the identified 22 genes with the highest hazard ratio for AE-free and MR-free survival were also isolated in the co-expression correlation network analysis using TCGA breast adenocarcinoma data. Eleven identified genes (CENP-A, HJURP, MIS18A, MIS18B, CENP-C, CENP-N, CENP-H, CENP-I, CENP-M, CENP-K, CENP-L) are essential for centromere assembly. Analysis using K-M Plotter software based on a different algorithm identified most of the same genes plus several more genes (Table 4) (Gyorffy et al., 2010). We conclude that different CEN/KT genes can display distinct regulation and roles in cancer etiology, even when their functions are intimately related.

TABLE 4

Prognostic value of CEN/KT genes for breast cancer using K-M plotter.

| | BREAST CANCER OS (n = 1115) | | BREAST CANCER RFS (n = 3455) | | BREAST CANCER DMFS (n = 1609) | |
|---|---|---|---|---|---|---|
| | HR (95% CI) | p-value | HR (95% CI) | p-value | HR (95% CI) | p-value |
| CENP-A | 1.89 (1.49-2.42) | 1.60E-07 | 1.97 (1.75-2.22) | 0.00E+00 | 1.87 (1.52-2.3) | 1.90E-09 |
| HJURP | 1.73 (1.36-2.2) | 7.10E-06 | 1.72 (1.53-1.93) | 0.00E+00 | 1.87 (1.52-2.29) | 1.90E-09 |
| M18BP1 | 1.07 (0.85-1.36) | 5.50E-01 | 1.3 (1.16-1.46) | 6.20E-06 | 1.3 (1.06-1.59) | 1.10E-02 |
| MIS18A | 1.75 (1.38-2.23) | 4.10E-06 | 1.16 (1.03-1.3) | 1.30E-02 | 1.82 (1.48-2.24) | 7.50E-09 |
| MIS18B | 1.89 (1.49-2.41) | 1.50E-07 | 1.43 (1.27-1.61) | 1.30E-09 | 1.62 (1.33-1.99) | 2.50E-06 |
| CENP-C | 0.88 (0.69-1.12) | 3.00E-01 | 0.71 (0.63-0.8) | 8.10E-09 | 0.91 (0.74-1.11) | 3.40E-01 |
| CENP-N | 1.85 (1.45-2.36) | 4.90E-07 | 1.95 (1.73-2.19) | 0.00E+00 | 1.8 (1.46-2.21) | 1.70E-08 |
| CENP-I | 1.53 (1.2-1.94) | 5.10E-04 | 1.45 (1.29-1.62) | 3.30E-10 | 1.76 (1.44-2.17) | 4.30E-08 |
| CENP-H | NA | NA | NA | NA | NA | NA |
| CENP-T | 0.92 (0.72-1.17) | 4.90E-01 | 0.73 (0.65-0.83) | 1.70E-07 | 1.09 (0.89-1.33) | 4.20E-01 |
| CENP-W | NA | NA | NA | NA | NA | NA |
| CENP-S | HR = 1.09 (0.86-1.39) | 4.70E-01 | 1.1 (0.98-1.24) | 9.20E-02 | 0.92 (0.75-1.12) | 4.00E-01 |
| CENP-X | 1.07 (0.84-1.36) | 5.70E-01 | 1.39 (1.24-1.56) | 2.30E-08 | 1.28 (1.05-1.57) | 1.70E-02 |
| CENP-M | 1.55 (1.22-1.97) | 3.30E-04 | 1.49 (1.32-1.67) | 1.70E-11 | 1.4 (1.14-1.72) | 1.00E-03 |
| CENP-U | 1.75 (1.38-2.23) | 3.90E-06 | 1.98 (1.76-2.23) | 0.00E+00 | 1.79 (1.46-2.2) | 2.00E-08 |
| CENP-L | NA | NA | NA | NA | NA | NA |
| CENP-K | NA | NA | NA | NA | NA | NA |
| CENP-O | 0.92 (0.72-1.16) | 4.80E-01 | 0.8 (0.71-0.9) | 1.20E-04 | 0.93 (0.76-1.14) | 5.10E-01 |
| CENP-P | NA | NA | NA | NA | NA | NA |
| CENP-Q | 1.05 (0.83-1.33) | 7.00E-01 | 1.14 (1.02-1.28) | 2.40E-02 | 1.14 (0.93-1.39) | 2.20E-01 |
| CENP-R | 1.06 (0.84-1.35) | 6.20E-01 | 1.17 (1.05-1.32) | 6.50E-03 | 0.94 (0.77-1.15) | 5.80E-01 |
| KNL1 | 0.98 (0.77-1.24) | 8.60E-01 | 0.86 (0.76-0.96) | 9.70E-03 | 0.97 (0.79-1.18) | 7.40E-01 |
| ZWINT | 1.55 (1.22-1.97) | 2.80E-04 | 1.7 (1.51-1.91) | 0.00E+00 | 1.56 (1.27-1.91) | 1.70E-05 |
| MIS12 | 0.94 (0.74-1.2) | 6.40E-01 | 1.05 (0.93-1.17) | 4.40E-01 | 0.99 (0.81-1.21) | 9.10E-01 |
| NSL1 | 0.94 (0.74-1.19) | 5.80E-01 | 1.2 (1.07-1.35) | 2.20E-03 | 1.09 (0.89-1.34) | 3.90E-01 |
| PMF1 | 0.78 (0.61-0.99) | 4.00E-02 | 0.92 (0.82-1.03) | 1.50E-01 | 0.9 (0.73-1.1) | 3.00E-01 |
| KNL3 | 1.36 (1.07-1.72) | 1.20E-02 | 1.36 (1.21-1.52) | 2.30E-07 | 1.31 (1.07-1.61) | 8.00E-03 |
| NDC80 | 1.51 (1.19-1.91) | 6.80E-04 | 1.87 (1.66-2.11) | 0.00E+00 | 1.82 (1.48-2.24) | 6.40E-09 |
| SPC24 | NA | NA | NA | NA | NA | NA |
| SPC25 | 1.49 (1.18-1.9) | 9.40E-04 | 1.44 (1.28-1.61) | 8.30E-10 | 1.55 (1.26-1.9) | 2.10E-05 |
| NUF2 | NA | NA | NA | NA | NA | NA | required for stable assembly of nascent CENP-A at centromeres, implying an important role for centromere chromatin assembly in breast cancer progression. Notably, mis-expression of nine other CEN/KT genes (CENP-T, -S, -P, -Q, -R, M18BP1, PMF1, MIS12 and NSL1) demonstrated no significant prognostic value, even though they are also important or essential components of centromeres or kinetochores. For example, only the MIS18A and MIS18B subunits of the Mis18 complex show significant prognostic values, even though the third component M18BP1 is also OS=overall survival, RFS=relapse free survival, DMFS=distant metastasis free survival. For significant correlations, HR cell is italicized when HR>1, and HR cell is bold when HR<1 and p<0.05. NA=not applicable. NA indicates genes not included on U133A platform. For genes with more than one probe, the most sensitive probes and associated values are presented.

Moreover, we investigated prognostic values of CEN/KT gene expression for overall survival and disease progression in data from >1,600 lung cancer patients, >350 gastric cancer patients, and a smaller number (n<150) of stage I and stage II ovarian cancer patients, using K-M Plotter (Gyorffy et al., 2010). We identified 20 CEN/KT genes whose misexpression is indicative of lung cancer prognosis (p<0.05) (Table 5), 23 for gastric cancer prognosis (p<0.05) (Table 6), and 20 for early stage ovarian cancers (p<0.05) (Table 7). Most CEN/KT genes for prognosis of different types of cancers overlap (Table 8). These results suggest that many CENK/T gene expression levels are effective predictors of breast, lung, gastric, and early stage ovarian cancer prognosis.

TABLE 5

Prognostic value of CEN/KT genes for lung cancer using K-M plotter.

| Genes | LUNG CANCER OS (n = 1405) | | LUNG CANCER FP (n = 982) | |
|---|---|---|---|---|
| | HR (95% CI) | p-value | HR (95% CI) | p-value |
| CENP-A | 1.57 (1.35-1.83) | 5.60E-09 | 1.87 (1.51-2.31) | 6.00E-09 |
| HJURP | 1.73 (1.49-2.02) | 1.20E-12 | 1.96 (1.61-2.38) | 6.70E-12 |
| M18BP1 | 0.74 (0.63-0.86) | 8.40E-05 | 0.61 (0.49-0.75) | 3.80E-06 |
| MIS18A | 1.38 (1.18-1.61) | 3.20E-05 | 137 (1.11-1.7) | 0.0031 |
| MIS18B | 1.67 (1.43-1.94) | 3.80E-11 | 1.81 (1.46-2.24) | 3.20E-08 |
| CENP-C | 0.62 (0.53-0.72) | 5.50E-10 | 0.5 (0.4-0.62) | 1.40E-10 |
| CENP-N | 1.47 (1.27-1.72) | 5.60E-07 | 1.62 (1.31-2.01) | 6.90E-06 |
| CENP-I | 1.41 (1.21-1.64) | 8.30E-06 | 1.73 (1.4-2.14) | 3.50E-07 |
| CENP-H | NA | NA | NA | NA |
| CENP-T | 1.34 (1.15-1.56) | 1.50E-04 | 2.56 (1.26-1.93) | 3.90E-05 |
| CENP-W | NA | NA | NA | NA |
| CENP-S | 0.71 (0.61-0.83) | 1.10E-05 | 0.64 (0.52-0.79) | 3.60E-05 |
| CENP-X | 1.55 (1.33-1.8) | 1.80E-08 | 2.74 (1.4-2.15) | 3.00E-07 |
| CENP-M | 1.55 (1.33-1.8) | 1.30E-08 | 1.53 (1.24-1.89) | 7.50E-05 |
| CENP-U | 1.7 (1.46-1.98) | 8.60E-12 | 1.57 (1.27-1.94) | 2.60E-05 |
| CENP-L | NA | NA | NA | NA |
| CENP-K | NA | NA | NA | NA |
| CENP-O | 1.19 (1.02-1.38) | 2.50E-02 | 2.52 (1.23-1.88) | 8.60E-05 |
| CENP-P | NA | NA | NA | NA |
| CENP-Q | 0.82 (0.71-0.96) | 1.20E-02 | 0.86 (0.69-1.08) | 2.00E-01 |
| CENP-R | 1 (0.86-1.17) | 3.60E-01 | 1.1 (0.9-1.36) | 3.50E-01 |
| KNL1 | 0.93 (0.8-1.08) | 0.12 | 0.77 (0.6-1) | 0.05 |
| ZWINT | 1.5 (1.32-1.71) | 3.20E-10 | 1.52 (1.16-1.99) | 2.40E-03 |
| MIS12 | 0.73 (0.63-0.85) | 4.90E-05 | 0.62 (0.5-0.77) | 8.70E-06 |
| NSL1 | 0.68 (0.59-0.8) | 9.40E-07 | 0.64 (0.52-0.79) | 2.80E-05 |
| PMF1 | 0.86 (0.76-0.97) | 1.70E-02 | 1.01 (0.83-1.22) | 9.40E-01 |
| KNL3 | 1.08 (0.93-1.25) | 3.30E-01 | 1.09 (0.88-1.34) | 4.40E-01 |
| NDC80 | 1.29 (1.11-1.51) | 8.90E-04 | 1.21 (0.98-1.5) | 7.10E-02 |
| SPC24 | NA | NA | NA | NA |
| SPC25 | 1.69 (1.45-1.97) | 1.30E-11 | 1.99 (1.61-2.47) | 1.40E-10 |
| NUF2 | NA | NA | NA | NA |

OS=overall survival, RFS=relapse free survival, DMFS=distant metastasis free survival. For significant correlations, HR cell is italicized when HR>1 and p<0.05, and HR cell is bold when HR<1 and p<0.05. NA=not applicable. NA indicates genes not included on U133A platform. For genes with more than one probe, the most sensitive probes and associated values are presented.

TABLE 6

Prognostic value of CEN/KT genes for gastric cancer using K-M plotter.

| Genes | GASTRIC CANCER OS (n = 593) | | GASTRIC CANCER FP (n = 359) | |
|---|---|---|---|---|
| | HR (95% CI) | p-value | HR (95% CI) | p-value |
| CENP-A | 1.5 (1.23-1.82) | 5.90E-05 | 1.86 (1.45-2.37) | 5.00E-07 |
| HJURP | 1.7 (1.36-2.12) | 2.60E-06 | 2.23 (1.74-2.86) | 7.20E-11 |
| M18BP1 | 1.18 (0.95-1.47) | 1.40E-01 | 0.73 (0.56-0.96) | 2.50E-02 |
| MIS18A | 1.29 (1.04-1.6) | 1.90E-02 | 1.33 (1.04-1.7) | 0.024 |
| MIS18B | 1.28 (1.05-1.56) | 1.50E-02 | 1.55 (1.18-2.03) | 1.50E-03 |
| CENP-C | 0.78 (0.64-0.96) | 1.80E-02 | 0.8 (0.63-1.03) | 8.40E-02 |
| CENP-N | 1.54 (1.26-1.89) | 2.90E-05 | 2.06 (1.53-2.76) | 8.80E-07 |
| CENP-I | 1.52 (1.25-1.84) | 2.20E-05 | 1.75 (1.36-2.24) | 7.70E-06 |
| CENP-H | NA | NA | NA | NA |
| CENP-T | 1.15 (0.95-1.39) | 1.60E-01 | 1.61 (1.25-2.08) | 2.00E-04 |
| CENP-W | NA | NA | NA | NA |
| CENP-S | 1.44 (1.16-1.78) | 1.00E-03 | 1.37 (1.07-1.75) | 1.20E-02 |
| CENP-X | 0.67 (0.54-0.84) | 3.00E-04 | 0.56 (0.43-0.74) | 2.70E-05 |
| CENP-M | 1.38 (1.1-1.73) | 5.60E-03 | 1.51 (1.18-1.93) | 9.50E-04 |

TABLE 6-continued

Prognostic value of CEN/KT genes for gastric cancer using K-M plotter.

| | GASTRIC CANCER OS (n = 593) | | GASTRIC CANCER FP (n = 359) | |
|---|---|---|---|---|
| Genes | HR (95% CI) | p-value | HR (95% CI) | p-value |
| CENP-U | *1.48 (1.19-1.85)* | *4.40E-04* | *1.59 (1.22-2.06)* | *4.60E-04* |
| CENP-L | NA | NA | NA | NA |
| CENP-K | NA | NA | NA | NA |
| CENP-O | 1.16 (0.94-1.43) | 1.60E-01 | *1.53 (1.2-1.96)* | *5.90E-04* |
| CENP-P | NA | NA | NA | NA |
| CENP-Q | *1.59 (1.29-1.96)* | *1.30E-05* | *1.52 (1.14-2.02)* | *4.20E-03* |
| CENP-R | *1.43 (1.16-1.77)* | *7.50E-04* | *1.66 (1.29-2.13)* | *6.80E-05* |
| KNL1 | 0.82 (0.66-1.01) | 6.60E-02 | 0.8 (0.61-1.05) | 1.10E-01 |
| ZWINT | *1.39 (1.13-1.72)* | *1.80E-03* | *1.56 (1.22-2)* | *3.00E-04* |
| MIS12 | *1.28 (1.04-1.57)* | *1.80E-02* | *1.33 (1.02-1.74)* | *3.70E-02* |
| NSL1 | 0.88 (0.71-1.08) | 2.20E-01 | 0.74 (0.57-0.95) | 1.70E-02 |
| PMF1 | 0.82 (0.67-1) | 5.20E-02 | 0.71 (0.55-0.91) | 6.70E-03 |
| KNL3 | *1.24 (1.02-1.5)* | *3.00E-02* | *1.35 (1.05-1.75)* | *2.10E-02* |
| NDC80 | *1.54 (1.26-1.89)* | *2.10E-05* | *1.88 (1.44-2.45)* | *2.00E-06* |
| SPC24 | NA | NA | NA | NA |
| SPC25 | *1.45 (1.19-1.77)* | *2.10E-04* | *1.94 (1.45-2.58)* | *4.60E-06* |
| NUF2 | NA | NA | NA | NA |

OS=overall survival, FP=first progression. NA indicates that probes corresponding to the gene did not pass the qualifier filter. For significant correlations, HR cell is italicized when HR>1 and p<0.05 and HR cell is bold when HR<1 and p<0.05.

OS=overall survival, PFS=progression-free survival. NA indicates that probes corresponding to the gene did not pass the qualifier filter. For significant correlations, HR cell is italicized when HR>1 and p<0.05, and HR cell is bold when HR<1 and p<0.05.

TABLE 7

Prognostic value of CEN/KT genes for stages 1 and 2 combined ovarian cancer using K-M plotter.

| | OVARIAN CANCER OS (n = 133) | | OVARIAN CANCER PFS (n = 126) | |
|---|---|---|---|---|
| Genes | HR (95% CI) | p-value | HR (95% CI) | p-value |
| CENP-A | *9.2 (1.24-68.13)* | *8.20E-03* | *17.24 (2.37-125.29)* | *1.10E-04* |
| HJURP | *5.17 (1.54-17.35)* | *3.00E-03* | *3.12 (1.7-5.73)* | *1.10E-04* |
| M18BP1 | *3.65 (1.37-9.75)* | *5.60E-03* | *3.03 (1.28-7.16)* | *8.10E-03* |
| MIS18A | *7.59 (1.03-56.14)* | *1.90E-02* | *3.24 (1.71-6.13)* | *1.30E-04* |
| MIS18B | *4.78 (1.13-20.28)* | *1.90E-02* | *4.63 (1.65-12.95)* | *1.30E-03* |
| CENP-C | 0.43 (0.19-0.96) | 3.40E-02 | *3.34 (1.84-6.06)* | *2.70E-05* |
| CENP-N | *5.17 (1.54-17.29)* | *3.00E-03* | 2.36 (1-5.6) | 4.40E-02 |
| CENP-I | *3.85 (1.15-12.88)* | *1.80E-02* | *4.13 (1.63-10.51)* | *1.20E-03* |
| CENP-H | NA | NA | NA | NA |
| CENP-T | 1.49 (0.66-3.38) | 3.40E-01 | 1.35 (0.71-2.55) | 3.60E-01 |
| CENP-W | NA | NA | NA | NA |
| CENP-S | 1.49 (0.66-3.33) | 3.30E-01 | 1.81 (0.99-3.3) | 4.90E-02 |
| CENP-X | 1.84 (0.83-4.11) | 1.30E-01 | 0.49 (0.25-0.95) | 3.10E-02 |
| CENP-M | *4.36 (1.3-14.59)* | *9.20E-03* | *2.96 (1.37-6.38)* | *3.80E-03* |
| CENP-U | *4.94 (1.16-20.97)* | *1.60E-02* | *1.93 (1.06-3.5)* | *2.90E-02* |
| CENP-L | NA | NA | NA | NA |
| CENP-K | NA | NA | NA | NA |
| CENP-O | 1.97 (0.89-4.35) | 8.80E-02 | 0.73 (0.39-1.37) | 3.30E-01 |
| CENP-P | NA | NA | NA | NA |
| CENP-Q | 1.92 (0.86-4.28) | 1.10E-01 | *1.88 (1.02-3.46)* | *3.80E-02* |
| CENP-R | 0.38 (0.13-1.11) | 6.60E-02 | 1.33 (0.74-2.41) | 3.40E-01 |
| KNL1 | 1.66 (0.69-3.97) | 2.50E-01 | 0.47 (0.23-0.93) | 2.60E-02 |
| ZWINT | *2.6 (1.14-5.9)* | *1.80E-02* | *4.03 (2.02-8)* | *1.80E-05* |
| MIS12 | *3.79 (1.13-12.71)* | *2.00E-02* | 1.83 (0.98-3.42) | 5.40E-02 |
| NSL1 | *3.21 (1.27-8.07)* | *9.10E-03* | *3.83 (2.07-7.08)* | *4.60E-06* |
| PMF1 | *3.36 (1.44-7.84)* | *2.90E-03* | *2.86 (1.57-5.19)* | *3.20E-04* |
| KNL3 | *4.16 (1.53-11.29)* | *2.60E-03* | *3.92 (2-7.68)* | *2.00E-05* |
| NDC80 | *5.15 (2.03-13.09)* | *1.40E-04* | *3.94 (1.99-7.78)* | *2.40E-05* |
| SPC24 | NA | NA | NA | NA |
| SPC25 | *2.98 (1.24-7.16)* | *1.00E-02* | *4.17 (1.63-10.63)* | *1.20E-03* |
| NUF2 | NA | NA | NA | NA |

TABLE 8

Comparison of different gene lists from the tables above.

| Genes | breast cancer (GenExMiner) | breast cancer (K-M plotter) | lung Cancer (K-M Plotter) | gastric cancer (K-M Plotter) | differential | CES Genes |
|---|---|---|---|---|---|---|
| CENP-A | X | X | X | X | X | yes |
| HJURP | X | X | X | X | X | yes |
| M18BP1 | | X | # | # | | |
| MIS18A | X | X | X | X | | |
| MIS18B | X | X | X | X | X | yes |
| CENP-C | # | # | # | # | | |
| CENP-N | X | X | X | X | X | yes |
| CENP-I | X | X | X | X | | |
| CENP-H | X | NA | NA | NA | | |
| CENP-T | | X | X | X | | |
| CENP-W | X | NA | NA | NA | X | yes |
| CENP-S | | | # | X | | |
| CENP-X | X | X | X | # | | |
| CENP-M | X | X | X | X | X | yes |
| CENP-U | X | X | X | X | X | yes |
| CENP-L | X | NA | NA | NA | X | yes |
| CENP-K | X | NA | NA | NA | X | yes |
| CENP-O | X | # | X | X | | |
| CENP-P | NA | NA | NA | NA | | |
| CENP-Q | | X | # | X | | |
| CENP-R | | # | | X | | |
| KNL1 | X | X | | | X | |
| ZWINT | X | X | X | X | X | yes |
| MIS12 | | | # | X | | |
| NSL1 | | X | # | # | | |
| PMF1 | | # | # | # | | |
| KNL3 | X | X | | X | | |
| NDC80 | X | X | X | X | X | yes |
| SPC24 | X | NA | NA | NA | X | yes |
| SPC25 | X | X | X | X | X | yes |
| NUF2 | X | NA | NA | NA | X | yes |

NA = Not applicable.
"X" indicate overexpression.
"#" indicates reduced expression.

Figure 2:
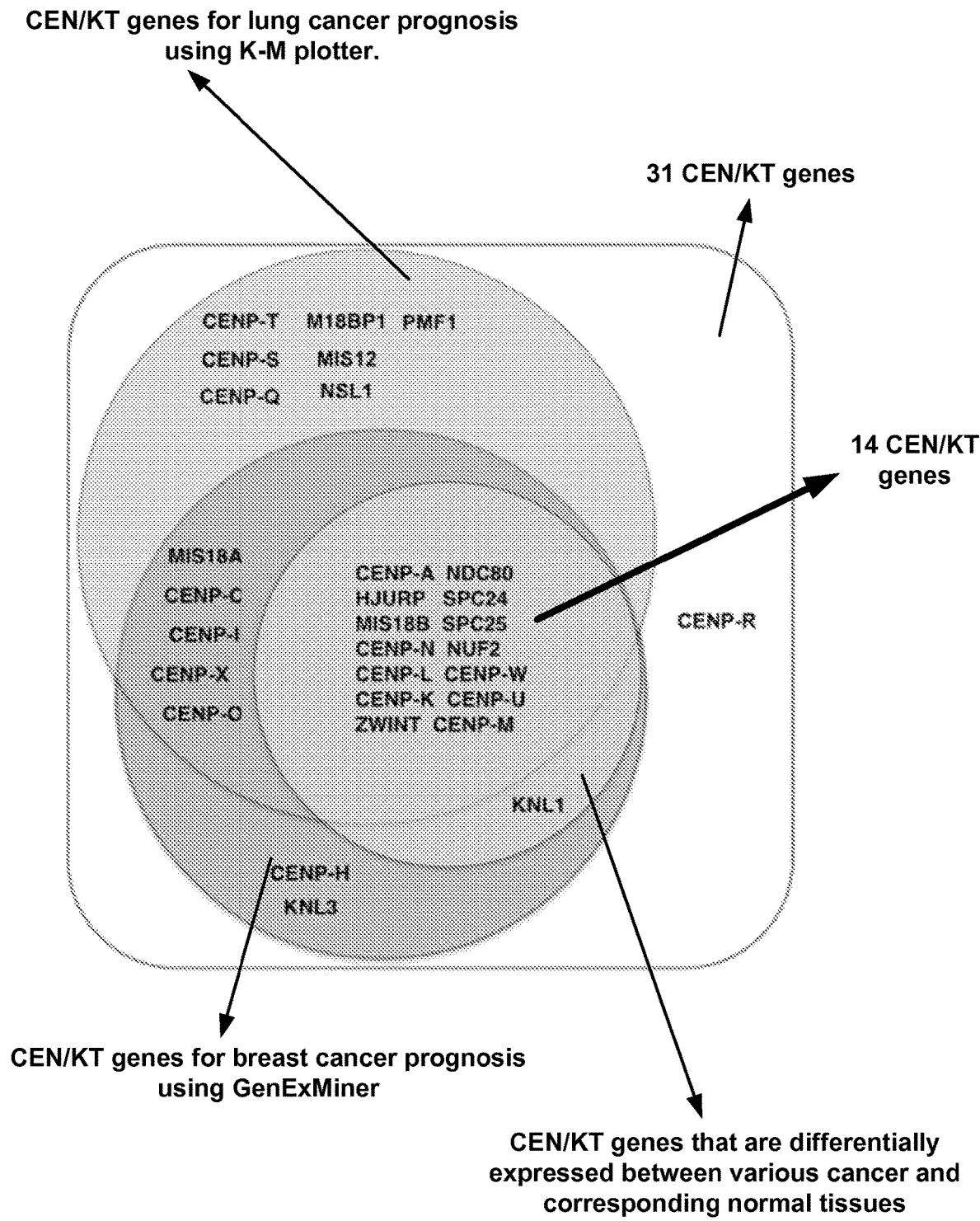
FIG. 2 shows a Venn diagram comparing three CEN/KT gene lists and identifies 14 CES genes as the core subset whose expression levels correlate with cancer progression. The lists include thirty-one CEN/KT genes; CEN/KT genes that are differentially expressed between various cancer and corresponding normal tissues as in FIG. 1C; CEN/KT genes for breast cancer prognosis using BC GenExMiner; and CEN/KT genes for lung cancer prognosis using K-M Plotter.

C. Centromere and Kinetochore Gene Expression Score (CES) is Indicative of the Level of Genomic Instability for Many Cancers We compared the gene lists obtained using different approaches and identified 14 CEN/KT genes in common (FIG. 2 and Table 8). The shared gene list contains 7 genes involved in CENP-A assembly and all 4 components of the NDC80 complex, but no MIS12 complex members. Based on the overlap, we consider misregulation of these 14 CEN/KT genes as the core subset that provides effective prognostic signatures for cancer progression and patient outcome for various cancer types (Table 9 and FIG. 2). Since individual genes in the list demonstrate overexpression in cancer samples, we propose that overall misregulation of the pathway and the extent can be represented by the sum of the individual gene expression levels rather than any single gene. We therefore defined the centromere and kinetochore gene expression score (CES) in a given sample as the sum of the $\log_2$(mRNA level) for the 14 CEN/KT genes.

TABLE 9

List of CES Genes

| CES Genes | |
|---|---|
| CENP-A | centromere |
| HJURP | |
| MIS18B | Mis18 |
| CENP-N | inner |
| CENP-M | kinetochore |
| CENP-W | |

TABLE 9-continued

List of CES Genes

| CES Genes | |
|---|---|
| CENP-U | |
| CENP-L | |
| CENP-K | |
| ZWINT | outer |
| NDC80 | kinetochore |
| NUF2 | |
| SPC24 | |
| SPC25 | |

Proper centromere and kinetochore function ensures faithful chromosome segregation and genome stability. We investigated whether CEN/KT gene misregulation is correlated with the extent of genome instability in cancer samples. TCGA datasets were used to compare CES values to the fraction of cancer genomes with CNA and mutation frequencies (Table 10). For many cancer types, including breast, low-grade brain gliomas and stomach adenocarcinomas, we detected a significant positive correlation between CES values and both CNA fractions and mutation frequencies (Spearman's rho, $p<0.05$, student-t test). For some cancers, such as lung adenocarcinomas, adrenocortical carcinomas, colorectal carcinomas, kidney renal clear cell (RCC) carcinomas, kidney renal papillary cell (RPC) carcinomas and ovarian serus cystadenocarcinomas, we only detected a significant correlation between CES values and either CNA fraction or mutation frequency. We observed no correlation for many cancers, such as cervical squamous cell carcinomas, glioblastomas and thyroid carcinomas. Overall, we conclude that there is significant correlation between CES values and the level of genome instability in multiple cancer types in TCGA datasets.

TABLE 10

Spearman's correlation cofficient between CES values and mutation frequencies and copy number alteration across TCGA datasets.

| Cancer Types | Mutation frequency | | | Copy Number Alteration | | |
|---|---|---|---|---|---|---|
| | Spearman's rho | p-value | N | Spearman's rho | p-value | N |
| Adrenocortical Cancinoma | 0.468 | 3.34E−06 | 72 | 0.046 | 0.703 | 72 |
| Bladder Urothelial Carcinoma | 0.240 | 6.23E−03 | 129 | 0.244 | 3.36E−08 | 353 |
| Lower Grade Glioma | 0.323 | 4.75E−08 | 273 | 0.483 | 1.51E−30 | 499 |
| Breast adenocarcinoma | 0.443 | 3.69E−48 | 975 | 0.539 | 3.40E−82 | 1076 |
| Cervical Squamous Cell Carcinoma and Endocervical Adenocarcinoma | 0.095 | 0.191 | 191 | 0.091 | 0.155 | 244 |
| Colectoral Carcinoma | 0.145 | 0.05 | 182 | −0.031 | 0.674 | 182 |
| Glioblastoma | 0.090 | 0.28 | 147 | 0.128 | 0.12 | 148 |
| Head&Neck SCC | 0.124 | 0.031 | 304 | 0.208 | 3.15E−06 | 494 |
| Kidney RCC | 0.036 | 0.466 | 410 | 0.179 | 4.70E−05 | 513 |
| Kidney RPC | 0.049 | 0.542 | 121 | 0.182 | 2.35E−03 | 276 |
| Lung ADC | 0.338 | 6.33E−06 | 171 | 0.290 | 7.51E−11 | 485 |
| Lung SCC | 0.236 | 1.53E−03 | 178 | 0.509 | 3.56E−34 | 498 |
| Ovarian Serous Cystadenocarcinoma | 0.071 | 0.368 | 161 | 0.133 | 0.031 | 262 |
| Prostate Adenocarcinoma | 0.349 | 1.60E−08 | 248 | 0.487 | 1.38E−29 | 474 |
| Skin cutaneous melanoma | 0.196 | 2.73E−04 | 339 | 0.066 | 0.152 | 468 |
| Stomach adenocarcinoma | 0.386 | 2.04E−08 | 198 | 0.377 | 2.76E−10 | 262 |
| Thyroid carcinoma | 0.056 | 0.273 | 391 | 0.036 | 0.427 | 489 |
| Uterine Carcinosarcoma | 0.432 | 8.97E−04 | 56 | 0.263 | 0.05 | 56 |

Significant (p <0.05) two tailed p-values for Spearman's coefficient correlation are highlighted by bold font.

Figure 3A:
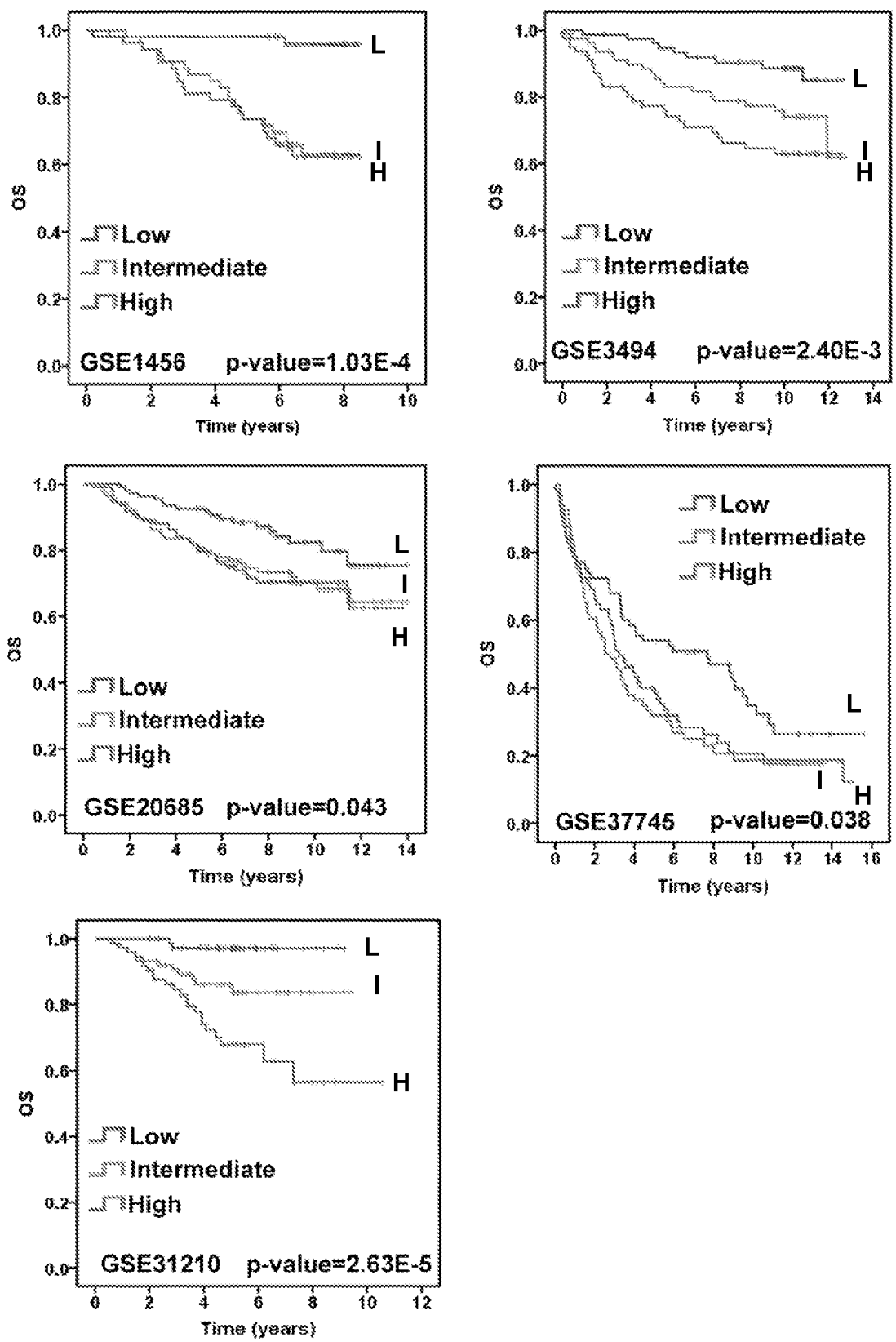
FIGS. 3A-3F illustrates that the centromere and kinetochore gene expression score (CES) is prognostic for overall survival, disease-free survival and distant metastasis-free survival using breast and lung cancer datasets. Patients were divided into CES high, medium or low groups for each specified GEO dataset. GEO datasets and log-rank p-values are indicated. Kaplan-Meier survival curves show that the CES is prognostic for overall survival (OS) for breast and lung cancer patients (FIG. 3A). Kaplan-Meier survival curves show that the CES is prognostic for disease-free survival (DFS) for breast and lung cancer patients (FIG. 3B). Kaplan-Meier survival curve shows that the CES is prognostic for distant metastasis-free survival (DMFS) for ER$^+$ breast cancer patients (FIG. 3C).
Figure 3B:
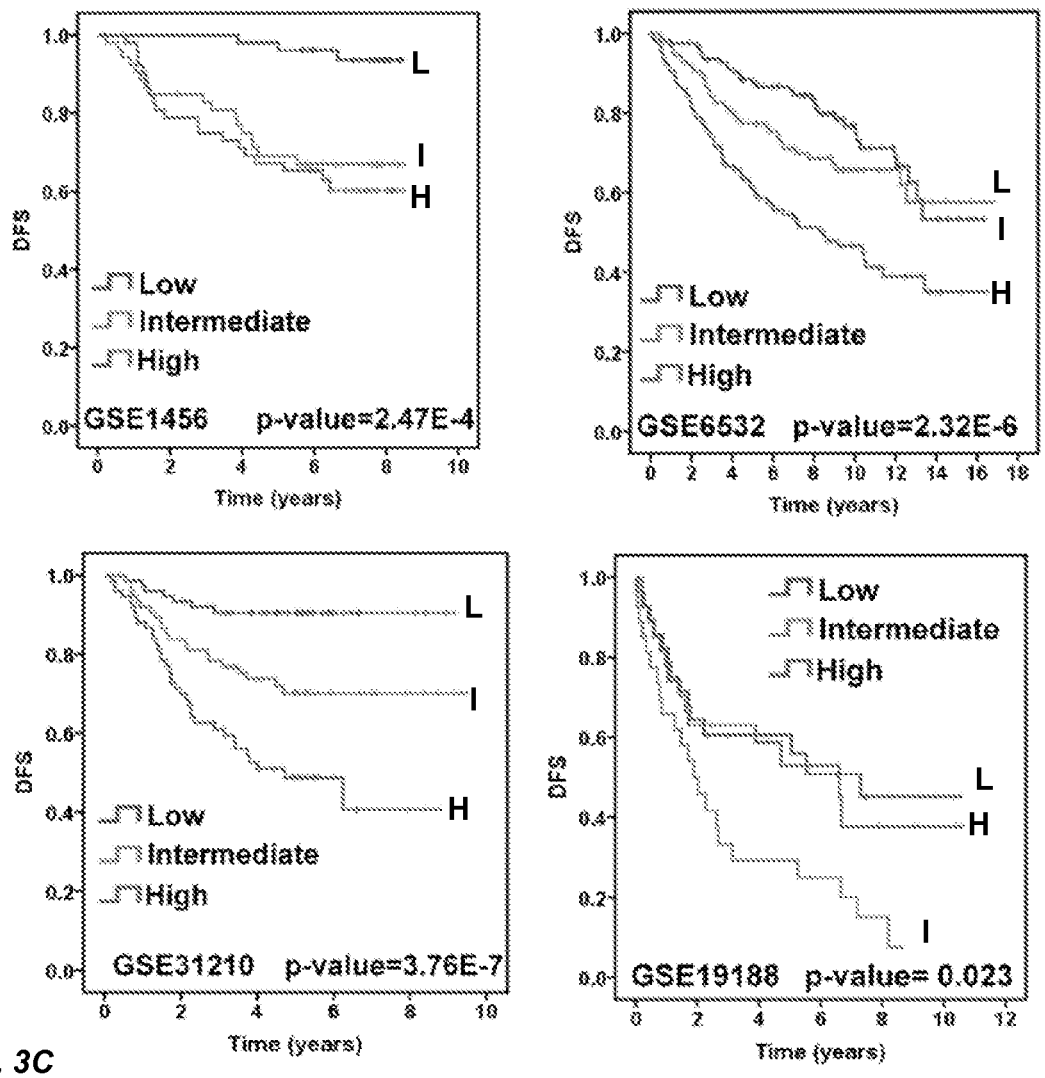
Figure 3C:
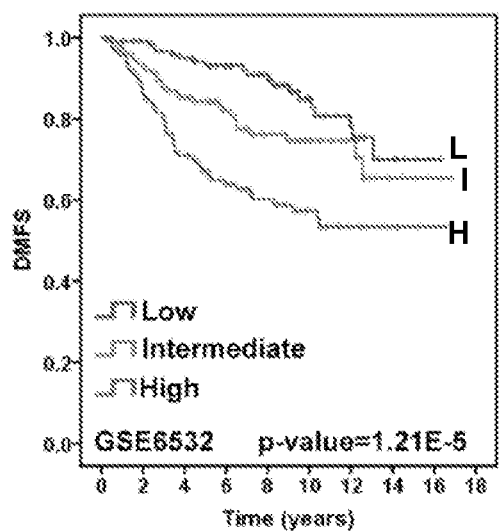

D. CES is Prognostic for Cancer Patient Overall Survival, Relapse and Distant Metastasis We evaluated the CES system for prognosis of cancer patient survival using breast and lung cancer microarray datasets. We split patients for each test GEO dataset into high, medium and low CES groups by dividing the full CES range of a dataset into tertiles. Kaplan-Meier survival curves demonstrated that the CES system effectively predicts overall survival (OS) and disease-free survival (DFS) for breast and lung cancer datasets. In general, patients with lower CES values have significantly better prognosis for both OS (FIG. 3A) and DFS (FIG. 3B). Notably, for lung cancer dataset GSE19188, patients in both the high and low CES groups show significantly better DFS than those with medium CES, which is possibly due to better response of high CES patients to adjuvant treatments (Botling et al., 2013) (see below). We also determined prognostic value of the CES for breast cancer distant metastasis-free survival (DMFS) using dataset GSE6532 (Loi, 2007). Kaplan-Meier curves showed that high CES patients have significantly worse DMFS (p=1.21E-05, FIG. 3C) than those with low CES.

To better understand the impact of CEN/KT gene misregulation on cancer progression, we analyzed breast cancer data with clinicopathological information. ER− tumors tend to be more aggressive, and positive lymph nodes indicate cancer invasion. We find that high CES values significantly correlate with advanced tumor grade and negative ER status (p<0.05), but have no significant correlation with patient age, tumor size, lymph node status or tumor stage (data not shown). Moreover, we found significant correlations between misregulation of many CEN/KT genes and poor AE-free and MR-free survival for ER+breast cancer patients regardless of lymph node status (Table 11, p<0.05). These analyses suggest that CEN/KT gene misexpression can predict patient survival and disease progression for pathologically classified breast cancers.

TABLE 11

Prognostic value of individual CEN/KT genes for breast cancers with clinicopathological information.

| | p-value AE-free survival | | | | p-value MR-free survival | | | |
|---|---|---|---|---|---|---|---|---|
| Gene name | N+, ER+ | N−, ER+ | N+, ER− | N−, ER− | N+, ER+ | N−, ER+ | N+, ER− | N−, ER− |
| CENP-A | 0.0407 | <0.0001 | 0.247 | 0.245 | 0.1092 | <0.0001 | 0.0423 | 0.196 |
| HJURP | 0.0001 | <0.0001 | 0.7176 | 0.534 | 0.0022 | <0.0001 | 0.3109 | 0.676 |
| M18BP1 | 0.8638 | 0.8429 | 0.0822 | 0.523 | 0.9256 | 0.5233 | 0.1423 | 0.695 |
| MIS18A | 0.0246 | 0.2008 | 0.0823 | 0.103 | 0.0899 | 0.0343 | 0.2567 | 0.441 |
| MIS18B | 0.0173 | 0.0001 | 0.07 | 0.334 | 0.0486 | 0.0003 | 0.0151 | 0.534 |
| CENP-C | 0.6629 | 0.0966 | 0.2412 | 0.346 | 0.4351 | 0.0036 | 0.4788 | 0.042 |
| CENP-N | 0.0601 | <0.0001 | 0.5045 | 0.441 | 0.4172 | <0.0001 | 0.2694 | 0.813 |
| CENP-I | 0.0029 | 0.0002 | 0.4031 | 0.881 | 0.0465 | 0.0034 | 0.6094 | 0.937 |

TABLE 11-continued

Prognostic value of individual CEN/KT genes for breast cancers with clinicopathological information.

| | p-value AE-free survival | | | | p-value MR-free survival | | | |
|---|---|---|---|---|---|---|---|---|
| Gene name | N+, ER+ | N−, ER+ | N+, ER− | N−, ER− | N+, ER+ | N−, ER+ | N+, ER− | N−, ER− |
| CENP-H | 0.0417 | 0.7757 | 0.87 | 0.751 | 0.1094 | 0.1989 | 0.6952 | 0.765 |
| CENP-T | 0.5857 | 0.1209 | 0.0525 | 0.748 | 0.2311 | 0.2491 | 0.2937 | 0.98 |
| CENP-W | 0.2808 | 0.0054 | 0.1119 | 0.929 | 0.0779 | 0.0045 | 0.0668 | 0.756 |
| CENP-S | 0.7168 | 0.1122 | 0.6003 | 0.499 | 0.4346 | 0.3601 | 0.6644 | 0.865 |
| CENP-X | 0.0502 | 0.0036 | 0.9954 | 0.527 | 0.0155 | 0.0421 | 0.2276 | 0.58 |
| CENP-M | 0.0077 | 0.0003 | 0.6798 | 0.551 | 0.0071 | 0.0005 | 0.322 | 0.721 |
| CENP-U | 0.1553 | 0.0007 | 0.9789 | 0.941 | 0.0134 | 0.0001 | 0.7316 | 0.227 |
| CENP-L | 0.0179 | 0.403 | 0.8631 | 0.11 | 0.1092 | 0.5438 | 0.7616 | 0.996 |
| CENP-K | 0.6084 | 0.1594 | 0.5005 | 0.645 | 0.6674 | 0.5904 | 0.3571 | 0.736 |
| CENP-O | 0.0059 | 0.1174 | 0.5991 | 0.452 | 0.0426 | 0.5381 | 0.2694 | 0.908 |
| CENP-P | 0.8499 | 0.4767 | 0.2822 | 0.246 | 0.8073 | 0.1364 | 0.6465 | 0.246 |
| CENP-Q | 0.4007 | 0.8576 | 0.1232 | 0.782 | 0.4123 | 0.2321 | 0.3785 | 0.459 |
| CENP-R | 0.6737 | 0.6343 | 0.5745 | 0.99 | 0.2943 | 0.4 | 0.1213 | 0.999 |
| KNL1 | 0.0332 | 0.2529 | 0.5922 | 0.336 | 0.0035 | 0.3585 | 0.4865 | 0.165 |
| MIS12 | 0.2789 | 0.0833 | 0.386 | 0.475 | 0.0949 | 0.3634 | 0.9375 | 0.099 |
| NSL1 | 0.3705 | 0.2677 | 0.445 | 0.046 | 0.7039 | 0.4334 | 0.581 | 0.03 |
| KNL3 | 0.0457 | 0.0044 | 0.1049 | 0.973 | 0.0031 | 0.0036 | 0.9868 | 0.51 |
| NDC80 | 0.0967 | 0.0005 | 0.4815 | 0.817 | 0.0873 | 0.0072 | 0.8999 | 0.615 |
| SPC24 | 0.1865 | 0.0016 | 0.2107 | 0.726 | 0.0753 | 0.8263 | 0.9996 | 0.939 |
| SPC25 | 0.0193 | <0.0001 | 0.2205 | 0.76 | 0.0551 | 0.0003 | 0.3055 | 0.953 |
| NUF2 | 0.0409 | 0.1901 | 0.3714 | 0.957 | 0.0767 | 0.5886 | 0.5009 | 0.687 |

Breast cancers also can be divided into subtypes based on gene expression signatures (Parker et al., 2009). Basal-like, HER2+(both usually ER−) and luminal B (ER+) subtypes tumors are more aggressive than luminal A (ER+) and normal-like. We observe that more aggressive molecular subtypes associate with higher average CES values (p<0.05). Using BC GenExMiner software, we found that 17 CEN/KT genes display higher expression in basal-like, HER2+ and luminal B breast cancers, compared to normal-like and luminal A tumors, with several showing significant (p<0.05) correlation with poor AE-free survival within normal breast-like, luminal A and luminal B subtype tumors (Table 12). These results indicate that CEN/KT misregulation varies among different breast cancer subtypes.

TABLE 12

Prognostic value of individual CEN/KT genes for breast cancers with subtype information.

| | BC Subtype | | | | | | | | | |
|---|---|---|---|---|---|---|---|---|---|---|
| Gene name | Basal-like AE-free survival HR (95% CI) | p-value | HER2+ AE-free survival HR (95% CI) | p-value | Luminal A AE-free survival HR (95% CI) | p-value | Luminal B AE-free survival HR (95% CI) | p-value | Normal breast-like AE-free survival HR (95% CI) | p-value |
| CENP-A | 0.98 (0.73-1.32) | 0.9081 | .89 (0.66-1.19) | 0.4214 | 1.24 (0.93-1.65) | 0.1461 | 1.40 (1.09-1.80) | 0.0075 | 1.59 (1.06-2.39) | 0.026 |
| HJURP | 1.01 (0.76-1.33) | 0.9705 | 0.84 (0.61-1.14) | 0.2553 | 1.37 (1.03-1.83) | 0.0323 | 1.41 (1.10-1.81) | 0.0073 | 1.96 (1.32-2.90) | 0.0008 |
| M18BP1 | 0.93 (0.71-1.23) | 0.6235 | 0.86 (0.63-1.17) | 0.3444 | 1.27 (0.96-1.67) | 0.0978 | 0.66 (0.51-0.85) | 0.0015 | 0.96 (0.66-1.39) | 0.8147 |
| MIS18A | 1.14 (0.86-1.52) | 0.3598 | 1.09 (0.80-1.50) | 0.5719 | 1.12 (0.84-1.48) | 0.4436 | 1.19 (0.93-1.53) | 0.161 | 1.15 (0.79-1.69) | 0.4585 |
| MIS18B | 1.11 (0.84-1.48) | 0.4577 | 0.94 (0.70-1.28) | 0.7108 | 1.38 (1.03-1.85) | 0.0289 | 1.35 (1.06-1.73) | 0.0159 | 1.13 (0.76-1.68) | 0.5476 |
| CENP-T | 1.25 (0.92-1.70) | 0.1539 | 0.98 (0.70-1.37) | 0.9037 | 0.79 (0.59-1.06) | 0.1166 | 0.86 (0.65-1.13) | 0.2667 | 0.91 (0.60-1.36) | 0.635 |
| CENP-W | 0.68 (0.33-1.42) | 0.3088 | 1.40 (0.67-2.90) | 0.3678 | 0.98 (0.40-2.38) | 0.9667 | 1.15 (0.63-2.09) | 0.6425 | 1.09 (0.40-2.97) | 0.8626 |
| CENP-S | 0.80 (0.57-1.13) | 0.2034 | 1.16 (0.80-1.66) | 0.4354 | 1.13 (0.82-1.55) | 0.4668 | 0.95 (0.71-1.27) | 0.7359 | 0.76 (0.46-1.26) | 0.2829 |
| CENP-X | 1.03 (0.77-1.36) | 0.8553 | 0.91 (0.68-1.23) | 0.5469 | 1.10 (0.83-1.46) | 0.512 | 1.25 (0.98-1.60) | 0.0762 | 1.12 (0.77-1.64) | 0.5596 |
| CENP-C | 1.24 (0.95-1.64) | 0.1179 | 0.88 (0.65-1.18) | 0.3905 | 0.89 (0.67-1.18) | 0.4287 | 0.79 (0.62-1.01) | 0.0636 | 1.11 (0.77-1.59) | 0.5851 |
| CENP-N | 0.90 (0.67-1.20) | 0.4716 | 1.04 (0.76-1.43) | 0.8006 | 1.26 (0.94-1.69) | 0.1267 | 1.48 (1.15-1.92) | 0.0027 | 1.00 (0.67-1.47) | 0.9804 |
| CENP-M | 1.00 (0.75-1.33) | 0.991 | 1.18 (0.86-1.61) | 0.3101 | 1.11 (0.83-1.49) | 0.4707 | 1.37 (1.06-1.76) | 0.015 | 1.26 (0.85-1.88) | 0.2473 |
| CENP-U | 1.03 (0.77-1.36) | 0.8564 | 0.99 (0.72-1.36) | 0.941 | 1.15 (0.87-1.53) | 0.3226 | 1.22 (0.95-1.58) | 0.1213 | 1.28 (0.87-1.90) | 0.2132 |

TABLE 12-continued

Prognostic value of individual CEN/KT genes for breast cancers with subtype information.

| | BC Subtype | | | | | | | | | |
|---|---|---|---|---|---|---|---|---|---|---|
| Gene name | Basal-like AE-free survival HR (95% CI) | p-value | HER2+ AE-free survival HR (95% CI) | p-value | Luminal A AE-free survival HR (95% CI) | p-value | Luminal B AE-free survival HR (95% CI) | p-value | Normal breast-like AE-free survival HR (95% CI) | p-value |
| CENP-H | 1.13 (0.73-1.76) | 0.5861 | 0.98 (0.65-1.47) | 0.9058 | 1.38 (0.93-2.04) | 0.1082 | 1.03 (0.73-1.46) | 0.8652 | 1.27 (0.79-2.03) | 0.3308 |
| CENP-I | 1.07 (0.81-1.41) | 0.6476 | 1.24 (0.92-1.65) | 0.1538 | 1.54 (1.16-2.03) | 0.0028 | 1.16 (0.91-1.48) | 0.2249 | 1.30 (0.89-1.89) | 0.171 |
| CENP-L | 1.05 (0.71-1.56) | 0.7951 | 1.01 (0.68-1.50) | 0.9466 | 1.52 (1.04-2.22) | 0.0299 | 1.23 (0.89-1.71) | 0.2055 | 1.39 (0.83-2.32) | 0.2123 |
| CENP-K | 1.30 (0.86-1.95) | 0.2097 | 0.96 (0.65-1.41) | 0.8263 | 1.53 (1.05-2.24) | 0.0276 | 0.94 (0.69-1.28) | 0.6992 | 1.21 (0.77-1.88) | 0.4082 |
| CENP-O | 0.94 (0.71-1.25) | 0.6862 | 1.08 (0.78-1.48) | 0.655 | 1.01 (0.76-1.34) | 0.9583 | 1.35 (1.05-1.74) | 0.0175 | 1.41 (0.96-2.06) | 0.0777 |
| CENP-P | 0.83 (0.51-1.36) | 0.4675 | 0.93 (0.60-1.45) | 0.7648 | 1.09 (0.68-1.73) | 0.7246 | 0.93 (0.65-1.33) | 0.6902 | 1.58 (0.86-2.88) | 0.1387 |
| CENP-Q | 0.80 (0.60-1.07) | 0.1273 | 0.81 (0.59-1.10) | 0.1803 | 1.01 (0.76-1.34) | 0.9339 | 0.95 (0.74-1.22) | 0.6922 | 0.83 (0.56-1.21) | 0.3252 |
| CENP-R | 0.95 (0.73-1.24) | 0.6977 | 0.87 (0.65-1.16) | 0.3527 | 1.11 (0.85-1.46) | 0.4483 | 0.88 (0.69-1.12) | 0.2892 | 0.74 (0.50-1.07) | 0.1097 |
| KNL1 | 0.77 (0.58-1.04) | 0.0896 | 0.72 (0.52-1.00) | 0.0508 | 1.25 (0.93-1.68) | 0.1357 | 0.95 (0.74-1.23) | 0.7076 | 1.13 (0.76-1.68) | 0.5546 |
| MIS12 | 0.96 (0.72-1.29) | 0.8007 | 1.25 (0.89-1.76) | 0.1938 | 1.22 (0.91-1.64) | 0.1814 | 1.02 (0.78-1.33) | 0.904 | 1.21 (0.81-1.80) | 0.3432 |
| NSL1 | 1.12 (0.86-1.47) | 0.4023 | 0.94 (0.70-1.26) | 0.6779 | 1.02 (0.78-1.34) | 0.8801 | 0.98 (0.77-1.24) | 0.8407 | 0.91 (0.63-1.31) | 0.6015 |
| KNL3 | 0.96 (0.73-1.27) | 0.7981 | 0.82 (0.60-1.12) | 0.2116 | 1.21 (0.91-1.61) | 0.1895 | 1.16 (0.90-1.49) | 0.2504 | 0.94 (0.63-1.39) | 0.7496 |
| NDC80 | 0.93 (0.70-1.22) | 0.591 | 1.15 (0.85-1.56) | 0.355 | 1.04 (0.79-1.37) | 0.7725 | 0.98 (0.77-1.25) | 0.8681 | 1.13 (0.77-1.65) | 0.5474 |
| SPC24 | 0.81 (0.45-1.48) | 0.4995 | 1.20 (0.74-1.93) | 0.4646 | 1.63 (1.00-2.63) | 0.0478 | 1.25 (0.85-1.84) | 0.2578 | 1.86 (1.01-3.42) | 0.0466 |
| SPC25 | 1.07 (0.81-1.40) | 0.6358 | 0.92 (0.68-1.24) | 0.5797 | 0.97 (0.73-1.29) | 0.8357 | 1.22 (0.96-1.56) | 0.1115 | 1.49 (1.00-2.22) | 0.051 |
| NUF2 | 0.84 (0.57-1.23) | 0.3732 | 0.95 (0.66-1.39) | 0.8041 | 1.45 (1.00-2.11) | 0.0507 | 1.24 (0.91-1.69) | 0.1728 | 1.18 (0.73-1.91) | 0.4893 |

Table indicates hazard ratio (HR) and associated p values for each CEN/KT gene for AE-free survival for different breast cancer subtypes. HR and p-values with significant prognostic value (p < 0.05) for breast cancer subtypes are in bold.

Figure 3D:
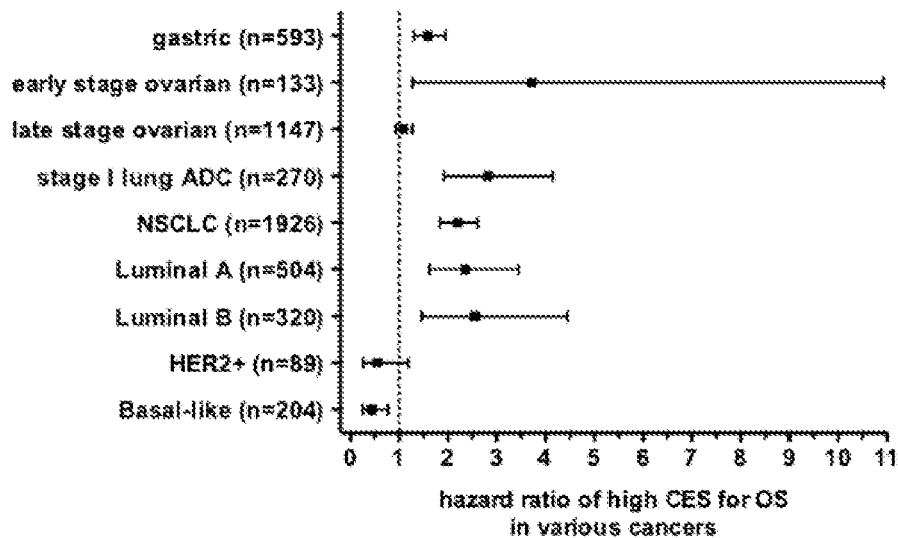
Figure 3E:
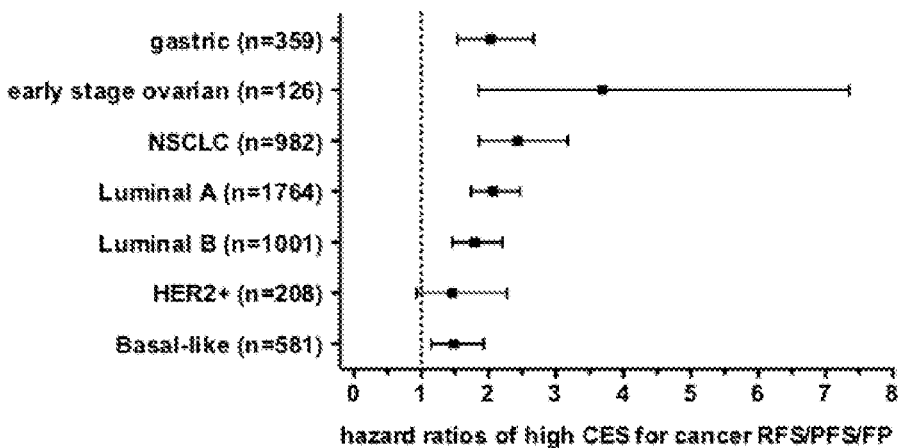
Figure 3F:
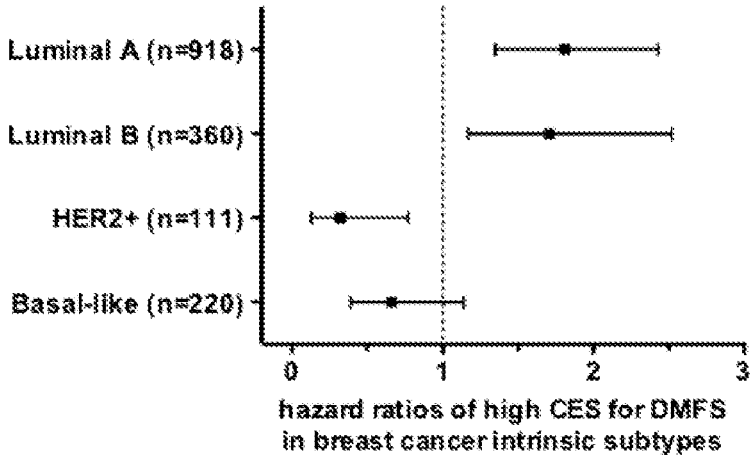

Finally, to confirm and extend the observed prognostic value for the CES system, we performed meta-analysis on breast, lung, gastric, and ovarian cancer patients using K-M Plotter (FIGS. 3D-3F). For breast cancers, we focused on ER+ intrinsic subtypes. High CES values effectively predict poor patient survival for both luminal A and B tumors. Within basal-like and HER2+ subtypes, we observed opposite correlation between CES values and OS and DMFS, which may be due to sensitivity of high CES tumors to therapies and/or the detrimental effects of very high levels of CIN on cancer cell fitness (see below). In addition, meta-analysis shows that the CES system effectively predicts patient survival for lung, gastric and early stage ovarian cancer patients (FIGS. 3D and 3E). Notably, our results suggest that the CES system predicts patient survival for stage I lung adenocarcinomas. Taken together, the analysis suggests that the CES can be useful for predicting patient survival, relapse and metastasis for multiple cancer types.

Figure 4A:
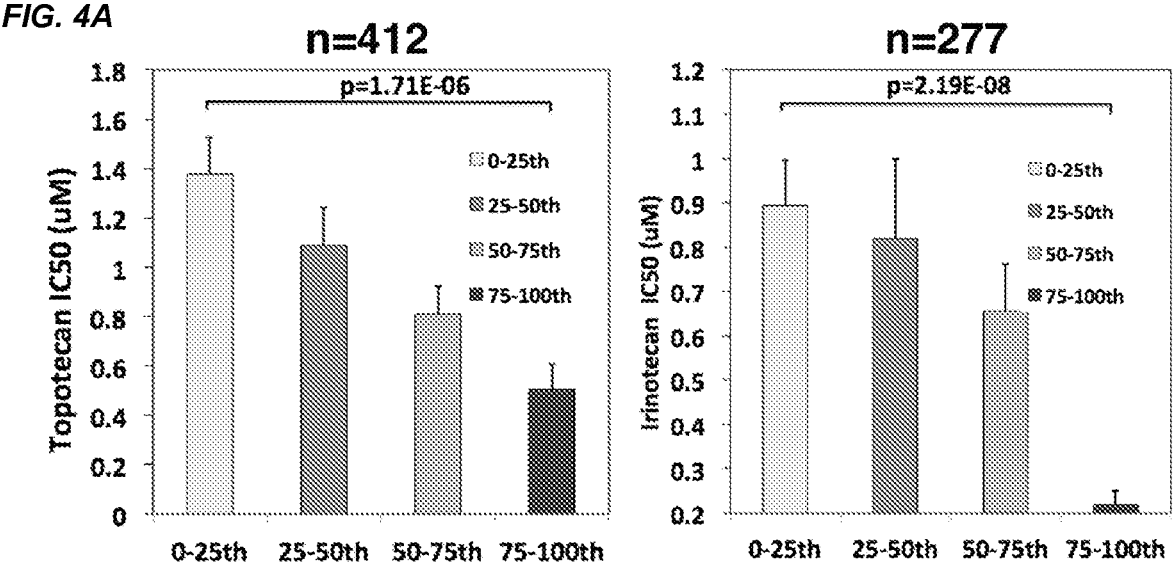
FIGS. 4A-4D demonstrates that CES values predict sensitivity to Topo I inhibitors in CCLE cell lines, and are predictive for lung cancer patient outcome after adjuvant chemotherapy and for breast cancer patient response to radiotherapy.
Figure 5A:
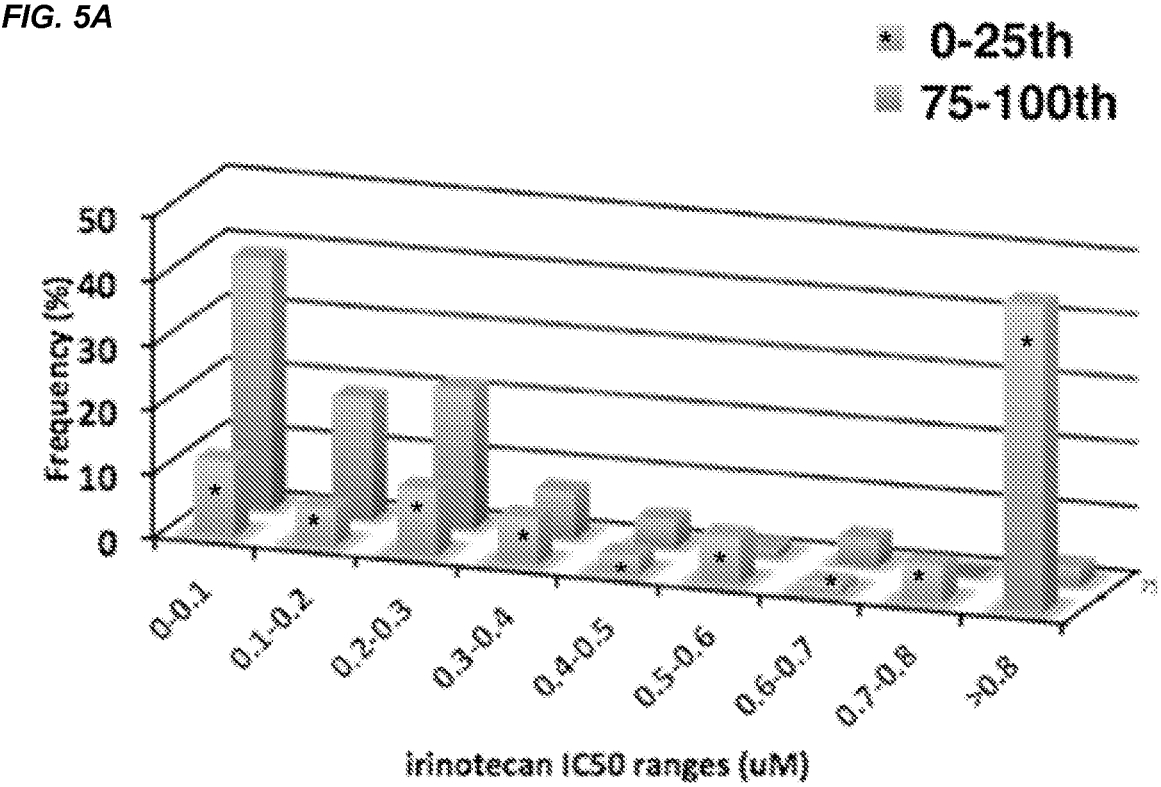
FIGS. 5A and 5B provide percentage frequency bar graphs of irinotecan (FIG. 5A) and topotecan (FIG. 5B) $IC_{50}$ for CCLE cell lines in the top (75-100%) and bottom (0-25%) CES quartiles demonstrate inverse correlations between CES and drug $IC_{50}$.
Figure 5B:
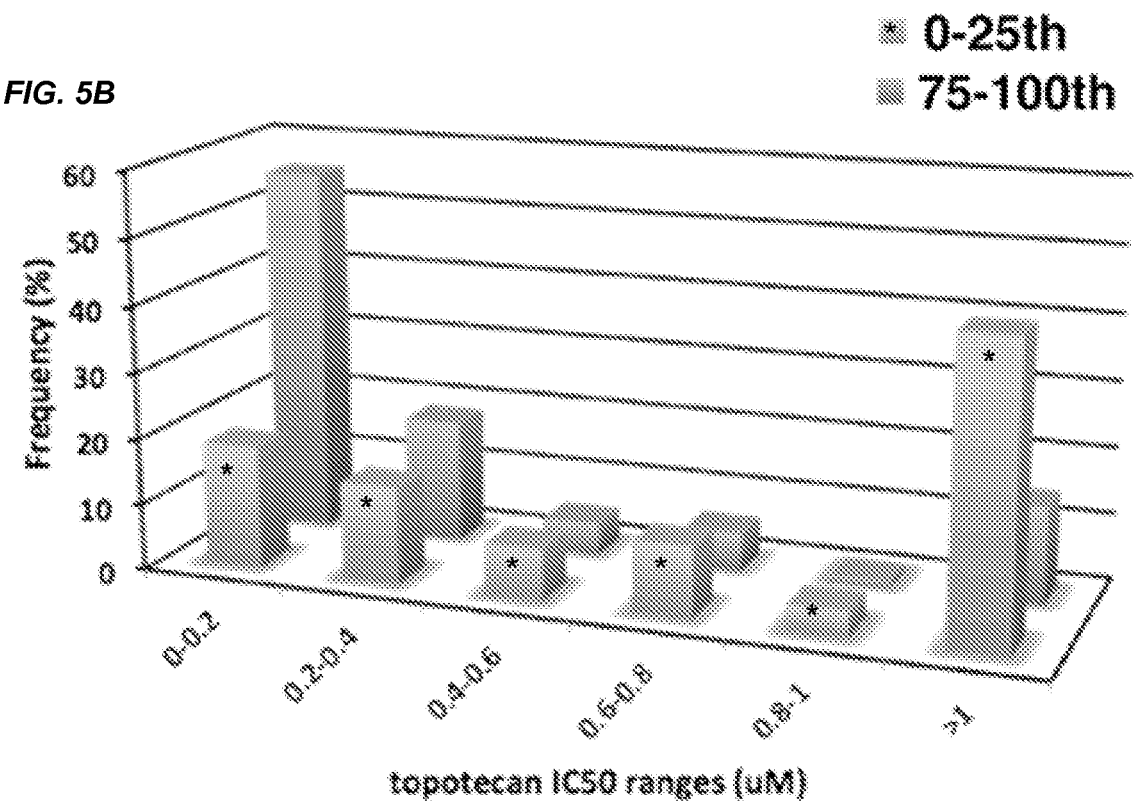

E. CES Predicts Sensitivity to DNA Damaging Agents and Patient Response to Adjuvant Chemotherapy Therapy The strong association between high CES values and genomic instability predicts that high CES cancer cells are under genotoxic stress and thus will be more sensitive to additional DNA damage. We mined the Cancer Cell Line Encyclopedia (CCLE) data, which contains information on both drug treatment and gene expression (Barretina et al., 2012). CCLE cell lines were binned into quartiles according to their CES values, we compared the top and bottom CES quartiles for the IC50 of the Topo I inhibitors and DNA damaging agents irinotecan and topotecan. Notably, cancer cell lines in the top CES quartile display significantly lower IC50s than those in the bottom quartile (p=2.19E0-8 for irinotecan and p=1.71E-06 for topotecan, respectively, student-t test) (FIGS. 4A, 5A and 5B). Consistently, cell line CES values and IC50 of Topo I inhibitors are inversely correlated with strong significance (Spearman's rho, r=−0.3836, p<0.000001 for irinotecan and r=−0.3394, p<0.000001 for topotecan, respectively) (Table 12). Moreover, we detected significant correlation between cell line CES and IC50s for irinotecan and topotecan for several cancer types after breaking down the cell lines according to their tissue of origin. We conclude that high CES cancer cell lines are more sensitive to Topo I inhibitors compared to low CES lines.

TABLE 13

Correlation between irinotecan and topotecan IC50 and CES value in CCLE cell lines.

| CCLE cell lines | Irinotecan | | | topotecan | | |
|---|---|---|---|---|---|---|
| | Spearman's rho | student-t (p-value) | n | Spearman's rho | student-t (p-value) | n |
| breast | −0.6441 | 0.007 | 16 | −0.2468 | 0.281 | 21 |
| lung | −0.4186 | 0.005 | 44 | −0.4252 | 0.0001 | 77 |
| ovary | −0.6226 | 0.003 | 20 | −0.4685 | 0.018 | 25 |
| haematopoietic and lymphoid | −0.3439 | 0.017 | 48 | −0.092 | 0.468 | 65 |
| skin | 0.2 | 0.327 | 26 | −0.1634 | 0.364 | 33 |
| CNS | −0.2034 | 0.436 | 17 | −0.1255 | 0.568 | 23 |
| pancreas | −0.4387 | 0.078 | 17 | −0.1429 | 0.536 | 21 |
| Overall pool | −0.3836 | <.000001 | 277 | −0.3394 | <.000001 | 412 |

Figure 4B:
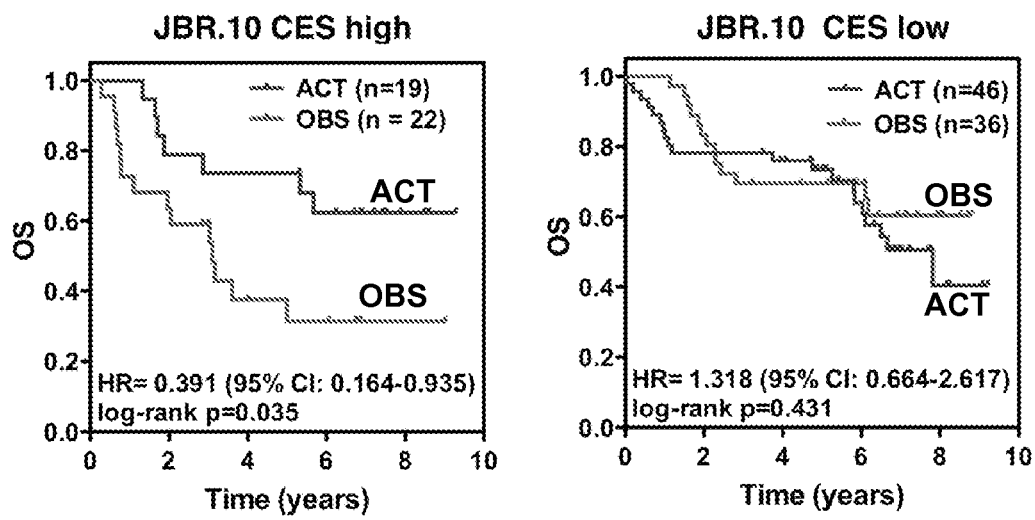
Figure 4C:
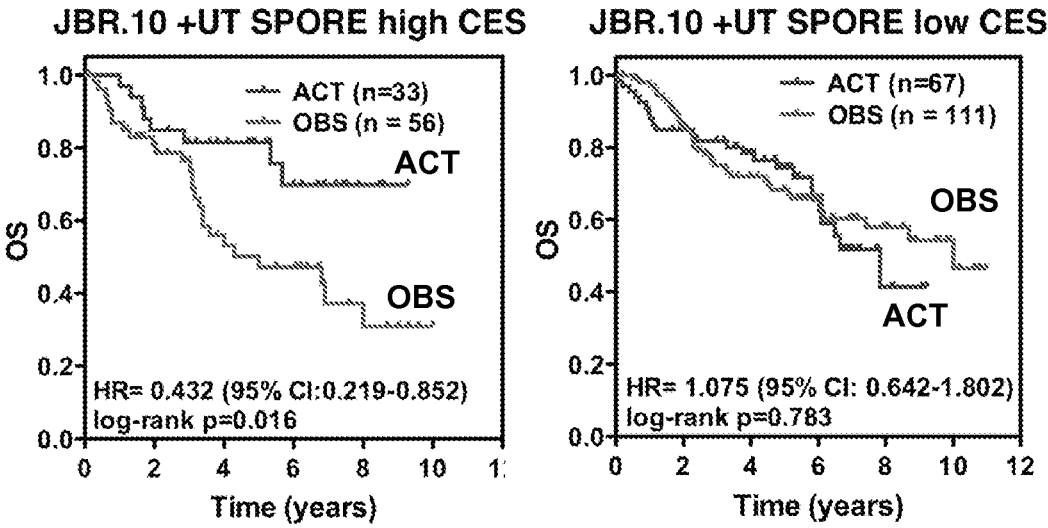
Figure 4D:
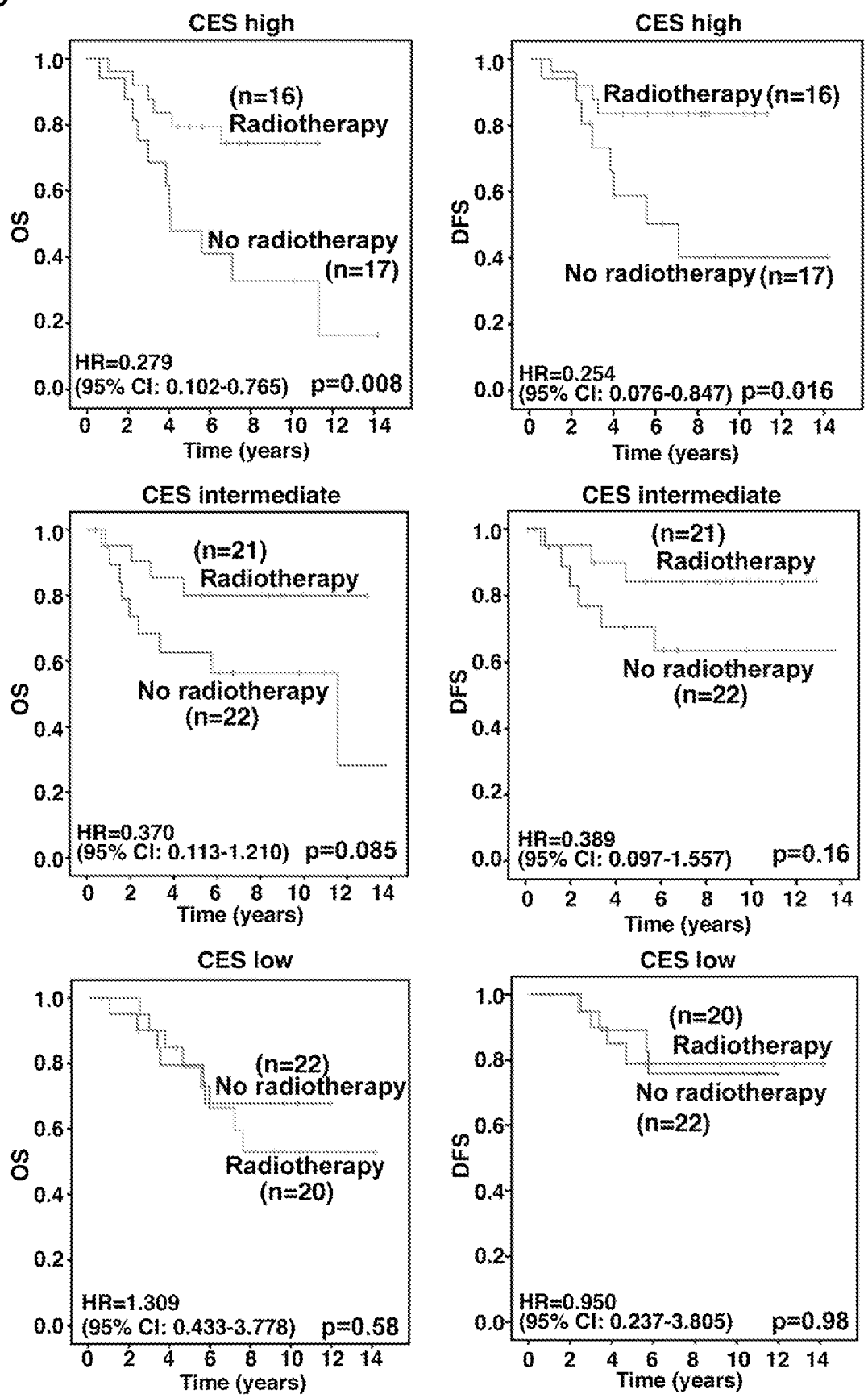
Figure 6A:
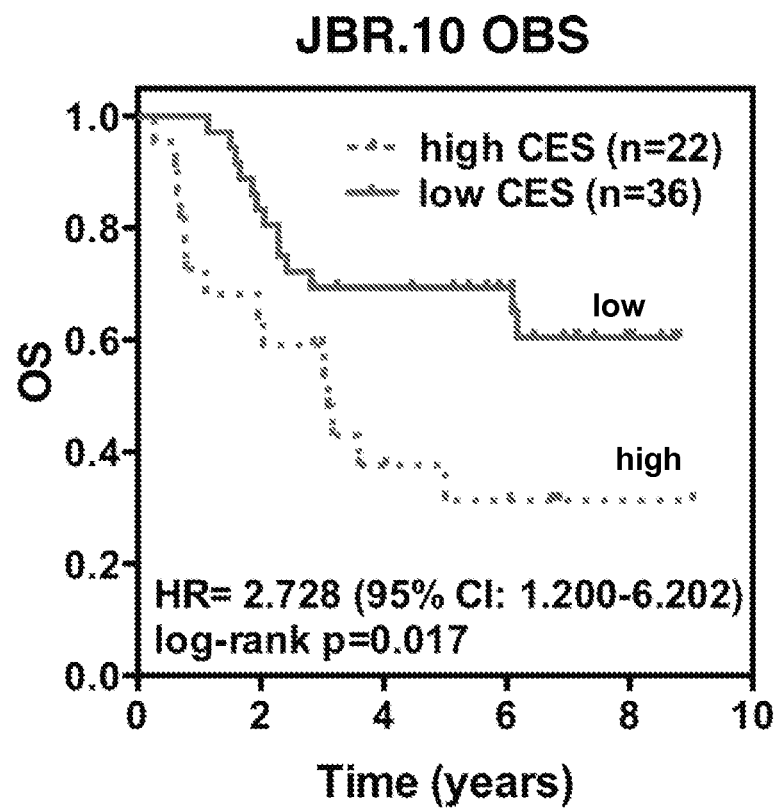
FIGS. 6A and 6B provide survival analyses showing that ACT specifically improves OS for high CES NSCLC patients of JBR.10 trial. High CES is associated with poor OS for patients without adjuvant therapy (OBS) (FIG. 6A). High CES is not associated with poor OS for patients with chemotherapy (ACT) (FIG. 6B).
Figure 6B:
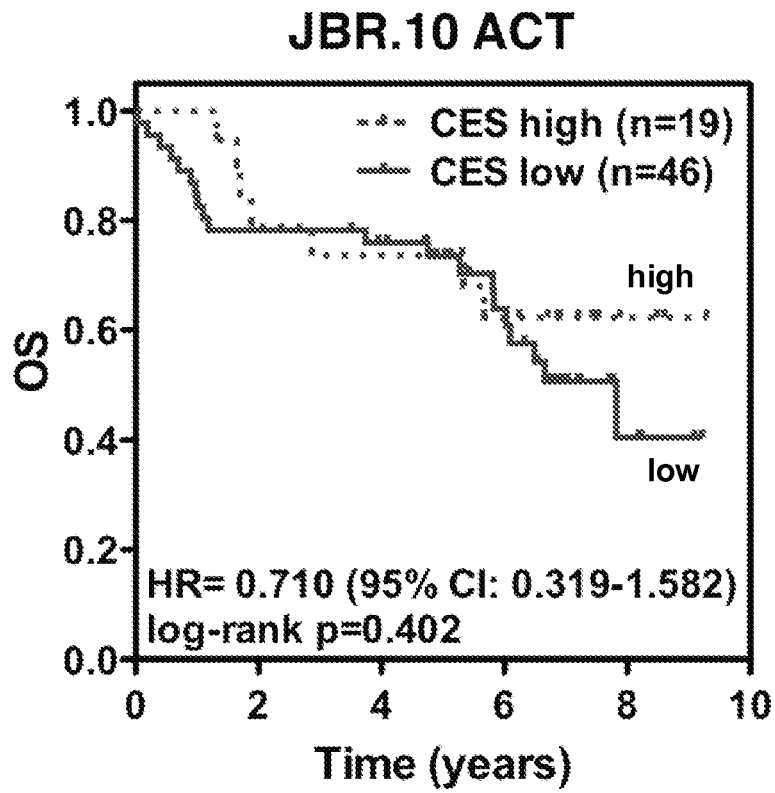

We then used the JBR.10 clinical trial dataset (GSE14814) to determine if early stage non-small cell lung cancers (NSCLC) with high CES values are more sensitive to adjuvant chemotherapy (FIG. 4B). In this prospective clinical trial, post-surgery early stage NSCLC patients were randomly assigned for adjuvant chemotherapy (ACT) including cisplatin, which causes DNA damage and promotes apoptosis, and vinorelbine, which inhibits mitosis through interactions with tubulin, or with no treatment (OBS) (Zhu et al., 2010). We divided patients into CES high (top tertile) and low (lower two tertiles) groups. For the OBS group, high CES predicts poor OS compared to low CES (HR=2.728, p=0.017), validating the prognosis power of the CES system (FIG. 6A). ACT effectively negated the adverse effect associated with high CES (HR=0.710, p=0.402), suggesting prediction power of the CES system for chemosensitivity (FIG. 6B). Indeed, ACT significantly improved overall survival for high CES patients compared to OBS (HR=0.391, log-rank p=0.035) (FIG. 4B, left). This effect is specific for the high CES group because there is no significant benefit associated with ACT for the low CES group (HR=1.318, log-rank p=0.431) (FIG. 4B, right). We also examined the UT lung SPORE NSCLC dataset (GSE41274) (Tang et al., 2013) (FIG. 4C). Post-surgery patients in this dataset were either treated with ACT including cisplatin and mainly taxanes, or received no treatment (OBS). We observed a similar trend for ACT on high CES patients without statistical significance (HR.233, log-rank p=0.110) possibly due to small sample size and relatively short follow-up time for ACT patients (FIG. 6B). Therefore, we performed meta-analysis combining the two datasets (FIG. 4C), and our results showed that ACT significantly improved poor OS associated with high CES in early stage NSCLC (HR.432, p=0.016) using the meta-dataset (FIG. 4C, left). Again this power is specific for the high CES group because ACT showed no such impact for low CES group (HR=1.075, p=0.783) (FIG. 4C, right). Importantly, meta-analysis showed that ACT specifically improved 5-year survival for the high CES group (81.5% for ACT versus 47.3% for OBS, p=0.002) but not for the low CES group (74.4% for ACT versus 68.4% for OBS, p=0.347). Taken together, our results suggest that the CES system is useful in predicting patient sensitivity to adjuvant chemotherapy, including cisplatin for NSCLC.

Figure 7A:
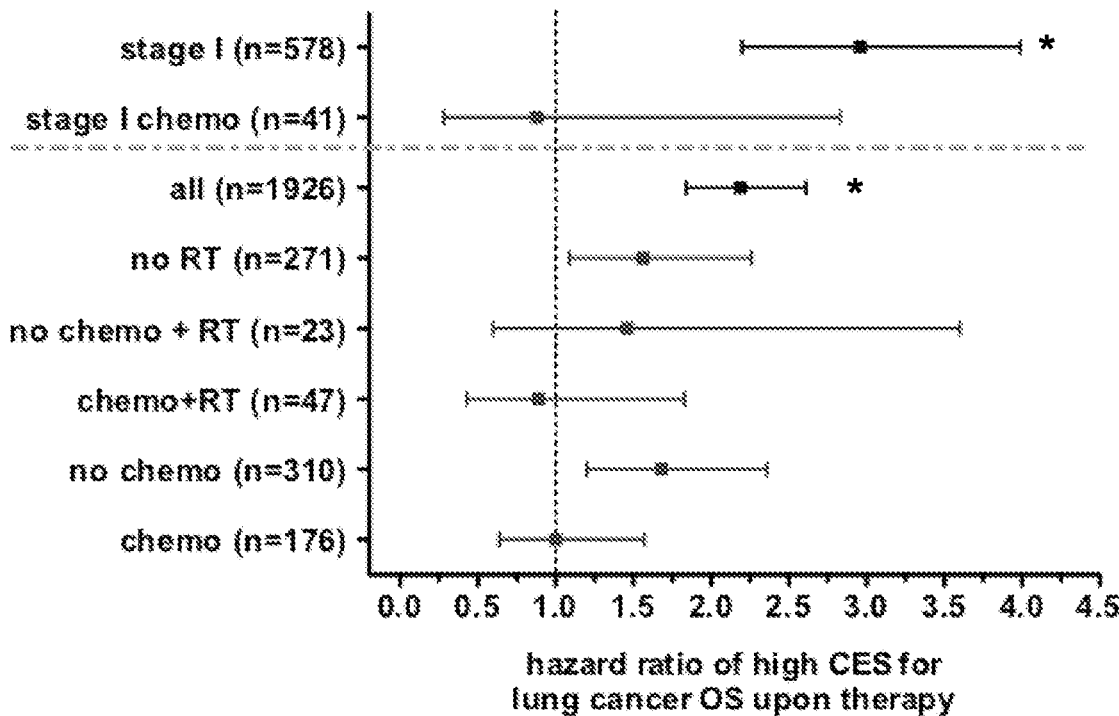
FIGS. 7A-7E provide forest plots showing that high CES is associated with sensitivity to adjuvant therapies for several cancer types. Squares denote HR, and left and right limits of the bars indicate 95% CI.
Figure 7B:
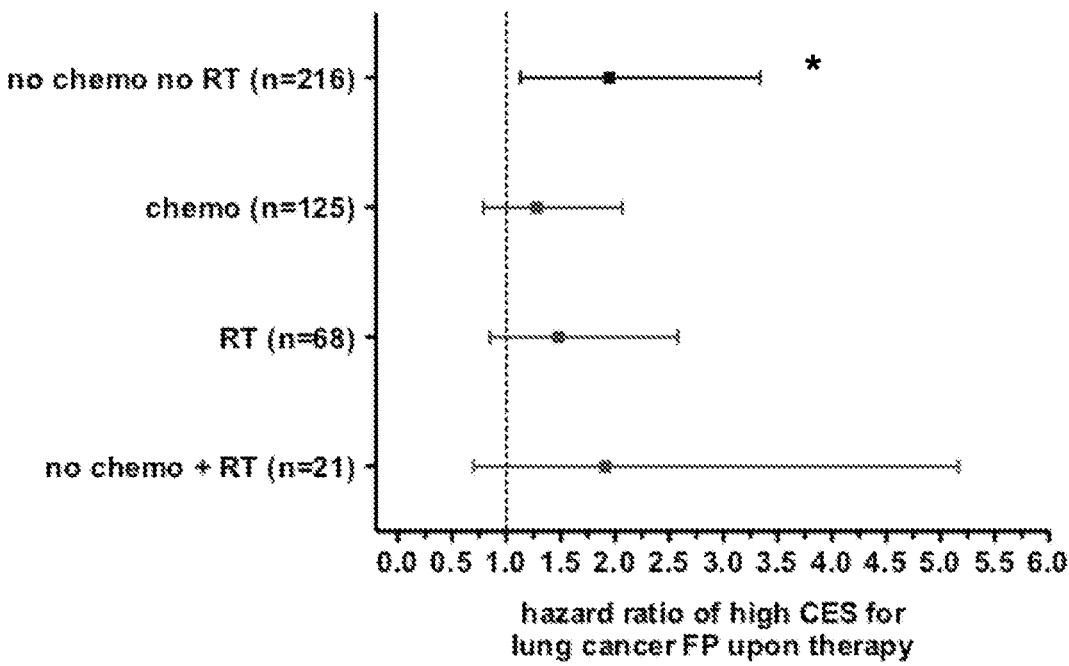
Figure 7C:
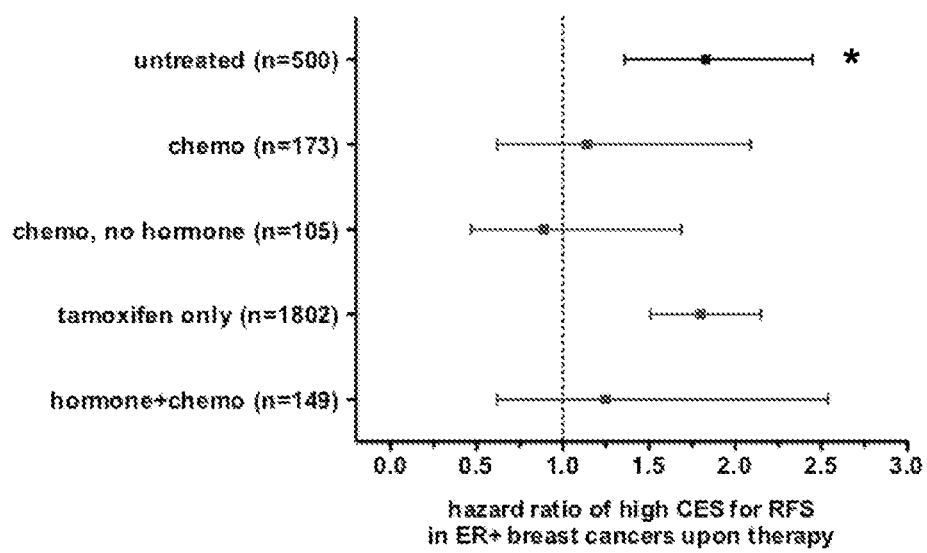
Figure 7D:
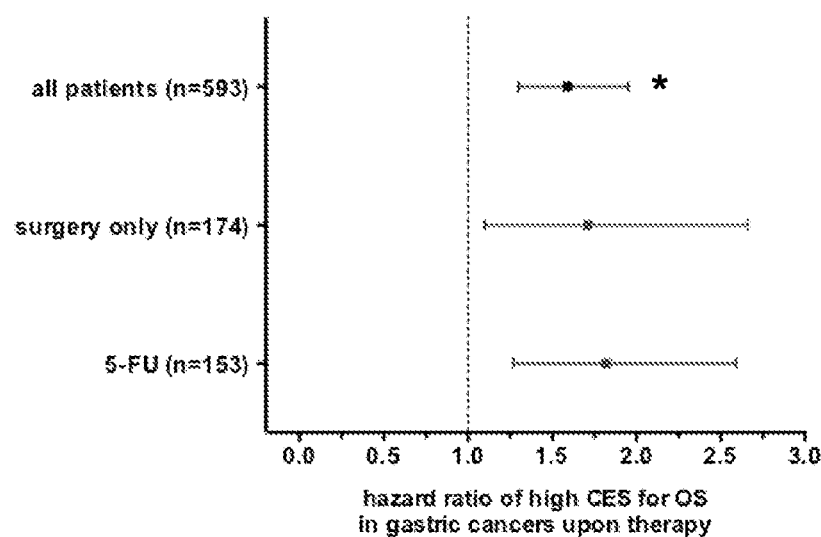
Figure 7E:
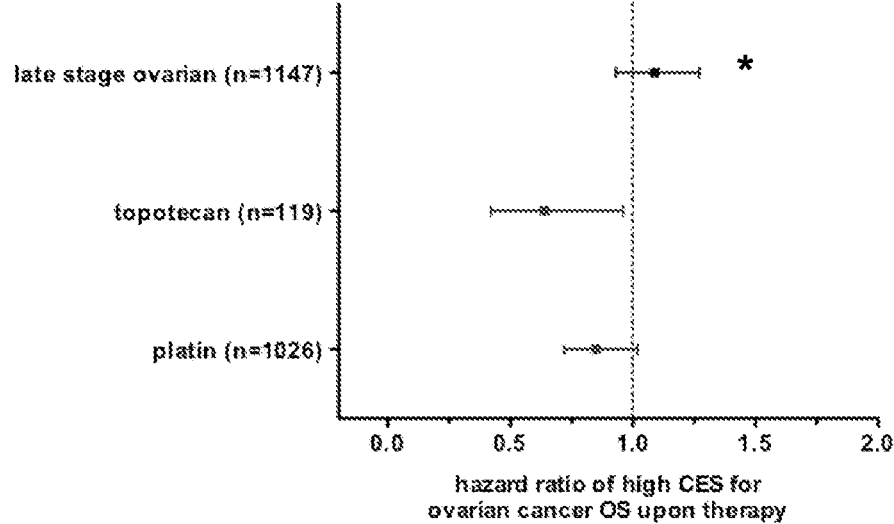
Figure 8A:
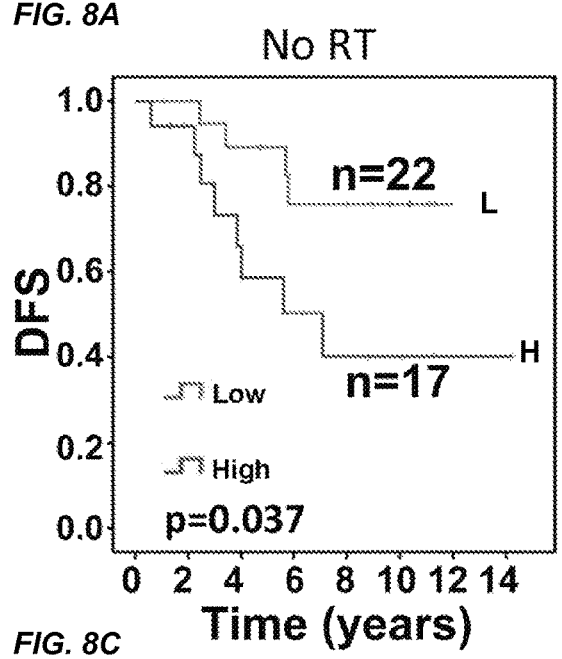
FIGS. 8A-8D provides Kaplan-Meier survival curves of breast cancer patient survival with high and low CES values, with or without RT. DFS=Disease-free survival and OS=overall survival. High CES values associate with poor DFS and OS, respectively, without RT (p<0.05) (FIGS. 8A and 8C). After RT, patients with high CES values show hazard ratios that are not statistically distinguishable from those with low CES values for DFS and OS, respectively (p>0.05) (FIGS. 8B and 8D).
Figure 8B:
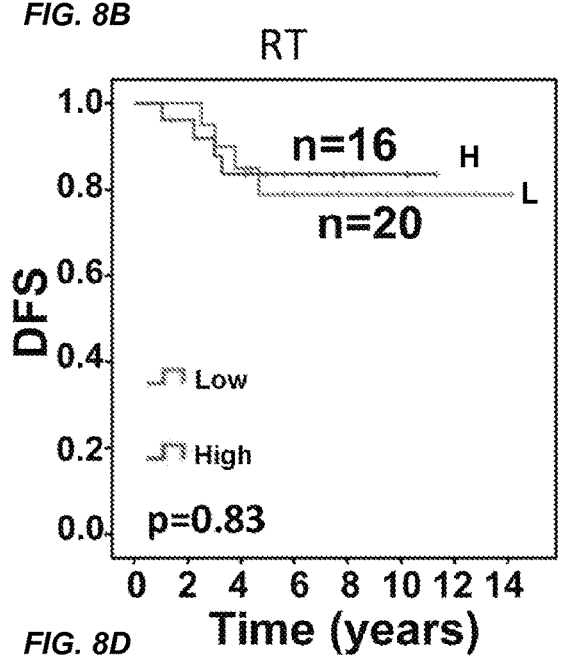
Figure 8C:
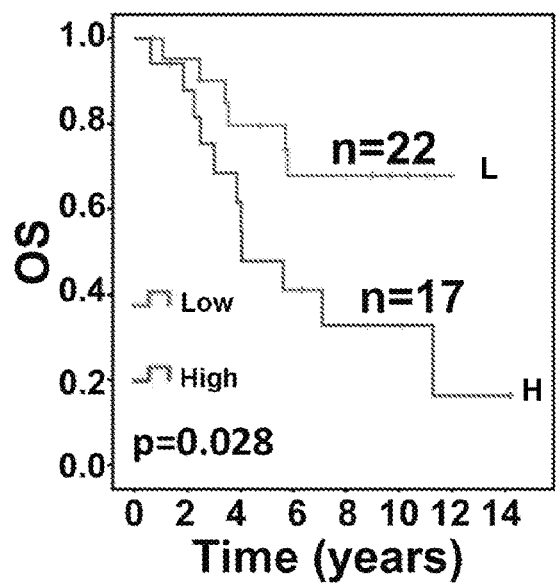
Figure 8D:
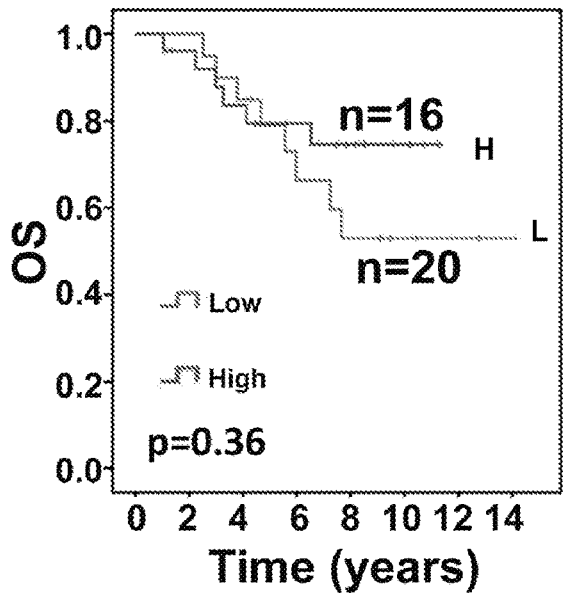

To address small sample sizes in individual datasets when predicting drug sensitivity, we performed meta-analysis on chemo-sensitivity for several cancer types using K-M Plotter. For NSCLC, the CES showed prediction value in chemo-sensitivity for both OS and risk of first progression (FP) (FIGS. 7A and 7B). For breast cancers, we focused on ER+ tumors because many patients suffer from relapse sometime after endocrine therapy with unclear causes. For systematically untreated patients with ER+ tumors, high CES values are associated with significantly poor relapse-free survival (RFS) as expected (HR=1.83, p=4.3E-05) (FIG. 7C). Chemotherapy with or without hormone therapy (HR=1.14, p=0.67), but not tamoxifen alone (HR=1.80, p=4E-11), effectively reduced hazard ratio associated with high CES, implying contribution of CIN to relapse in ER+ breast cancer patients after hormone therapy. For gastric cancers, no significant prediction power was detected for sensitivity to 5-FU (FIG. 7D). For ovarian cancers, most patients had late stage tumors, for which CES does not significantly predict patient OS (HR=1.09, p=0.29). Nevertheless, both platin and topotecan reduced hazards associated with high CES (FIG. 7E), and topotecan (HR.63, p=0.029) showed some superiority to platin (HR=0.85, p=0.075). We noted that in CCLE ovarian cancer cell lines, high CES value also correlates with increased topotecan sensitivity (Spearman's rho, r=−0.469, p=0.018) (Table 13). These results suggest that the CES system may be useful to predict patient sensitivity to adjuvant chemotherapy for multiple cancer types.

F. CES Predicts Patient Response to Radiation Therapy in Breast and Lung Cancers In light of the results on drug sensitivity, we reasoned that if centromere misregulation is a shared important property among different cancer types, the CES system may be also predictive for radiation therapy (RT) that damages DNA and causes apoptosis. We determined whether the CES correlates with cancer patient outcome following RT. Using a breast cancer dataset, we found that upon RT, patients with high CES values displayed both improved overall survival (HR.279, p=0.008) and disease-free survival (HR=0.254, p=0.016) compared to without RT. In contrast, there was no survival benefit associated with RT for patients in the low CES group (HR=1.309, p=0.58 for OS and HR=0.950, p=0.98 for DFS) (FIG. 4E). For the patient group with intermediate CES values, we observed intermediate HR although the correlation was not significant (HR=0.370, p=0.085 for OS, and HR=0.389, p=0.16 for DFS, respectively). Further analyses suggest that the association between RT and better prognosis was specific for the patient group with high CES (FIGS. 8A-8D). We then performed meta-analysis on lung cancer data using K-M Plotter and the results are consistent with the results in breast cancers (FIGS. 7A and 7B). Our analyses suggest that the CES system effectively predicts cancer patient sensitivity to RT as well as chemotherapy.

Discussion

In this study, using a hypothesis-driven approach focused on a specific cellular structure regulating chromosome segregation, we identified a subset of 14 CEN/KT genes whose overexpression is a shared property of and is prognostic for a wide spectrum of human cancers (Table 9). We defined the CES as the sum of the mRNA expression levels for the fourteen genes. We show that the CES value is prognostic for overall survival, cancer relapse and disease progression in several cancer types. It is also prognostic for breast cancer luminal subtypes and early stage NSCLCs. Moreover, the CES forecasts sensitivity to DNA damaging compounds in cancer cell lines and patient datasets, and patient sensitivity to radiotherapy. Importantly, the CES value is significantly correlated with the levels of CNA and mutation frequencies for many cancer types. This result is consistent with numerous basic research studies in cell lines and model organisms showing that misregulation of centromere and kinetochore structure causes chromosome missegregation and rearrangements and contributes to CIN (Allshire and Karpen, 2008; Black et al., 2010). For example, misregulation of CES genes including CENP-A and HJURP causes defective chromosome segregation. Such severe defects may cause chromosome bridging and micronuclei (Mishra et al., 2011), which in turn lead to structural aberrations and DNA damage (Janssen et al., 2011). This idea is further supported by the fact that 50% of the CES genes are involved in assembly of CENP-A nucleosomes, which is the structural foundation for centromere function and propagation, and kinetochore formation in mitosis. These proteins together comprise an epigenetic pathway for replenishing centromeric CENP-A nucleosomes through each cell cycle. Surprisingly, none of the essential MIS12 complex members passed our significance threshold for inclusion in the CES gene list. The results suggest that misregulation of centromere and kinetochore, especially the process of centromere replenishment, is a key mechanism of CIN and genomic instability in many cancers. The genomic defects contribute to cancer progression on one hand, but also appear to be a burden when passing certain threshold on the other as evidenced by sensitivity to further DNA damage.

We have demonstrated that the CES system represents a novel biomarker that effectively predicts the level of genomic instability, patient survival, and the impact of DNA damaging therapies for many cancers. Our results indicate that variation among individual tumors within the same cancer type not only predicts cancer patient survival and disease progression, but also forecasts sensitivity to several DNA damaging agents in cancer cell lines, patient outcome after adjuvant radiotherapy, or adjuvant chemotherapy including specific DNA damaging compounds such as cisplatin. Specific association of improved patient survival after RT or chemotherapy with high CES values suggests that the CES system is useful in identifying patients at high risk for relapse and disease progression, and which patients are likely to respond favorably to specific treatments.

The universal requirement for centromeres and kinetochores in genome maintenance implies that the application may go beyond just one type of cancer, as supported by the prognostic power of the CES in breast, lung, gastric and early stage ovarian cancers. In addition, significant chromosome abnormalities and CIN were observed in pre-cancerous lesions in breast and other tissues (Man et al., 2003). Importantly, CEN/KT genes are misexpressed in a fraction of breast DCIS, early stage liver cancers display higher CES while non-cancerous dysplasia do not, and CEN/KT genes are overexpressed only in metastatic prostate cancers compared to benign tumors and non-metastatic cancers. These observations show that the CES system is useful for early diagnosis and to help avoid problems associated with over-diagnosis.

In addition to potential applications for cancer management, our results have important implications related to cancer progression and genomic instability. A major hypothesis that underlies this study and the CES system is that misexpression of CEN/KT genes impairs centromere and kinetochore functions, leading to increased chromosomal abnormalities and genotoxic stress. Consistent with this hypothesis, high CES values are correlated with high levels of genomic instability in a large number of clinical samples from multiple cancers (Table 2). This hypothesis is further supported by mechanistic studies. Perturbation of centromere and kinetochore components causes aberrant functions that increase genome instability, such as defective mitotic checkpoints, spindle attachments, chromosome congression and sister chromatid separation. Overexpression of *Drosophila* CENP-A or tethering human HJURP to non-centromeric regions leads to neo-centromeres and structural rearrangements (Barnhart et al., 2011; Heun et al., 2006; Mendiburo et al., 2011). On the other hand, depletion and perhaps the presence of excess centromere proteins, can cause endogenous centromere dysfunction, whole chromosome aneuploidy, or mitotic arrest by checkpoint activation (Blower and Karpen, 2001; Cheeseman et al., 2008; Foltz et al., 2006; Okada et al., 2006).

Extreme CIN appears to be detrimental to cancer cell fitness (Hiley and Swanton, 2014; Siegel and Amon, 2012). A possible application for the CES system is its effectiveness at predicting sensitivity to radiation and chemotherapeutic drugs for cancer patients. A simple explanation for the observed sensitivity of high CES tumors is that radiation, cisplatin and Topo I inhibitors increase DNA damage to a level that cannot be effectively repaired. This implies that modulating doses or changing patient sensitivity thresholds may benefit patients with medium CES tumors.

In addition to the 'CIN threshold' model, sensitivity of high CES cancers may be explained by direct involvement of some of the CES genes in DNA repair. For example, HJURP was shown to be important in DNA repair in cancer cell lines (Kato et al., 2007), and we have previously demonstrated radio-sensitivity of cancers and cell lines with higher HJURP levels (Hu et al., 2010). The role of CENP-A in DNA damage and repair is unclear and may rely on genetic and cellular contexts (Lacoste et al., 2014; Mathew et al., 2014; Zeitlin et al., 2009). In addition, CENP-S/CENP-X is also known as the MHF complex, which stimulates replication fork remodeling by FANCM in DNA repair (Yan et al., 2010). It is conceivable that overexpression of the CES gene CENP-W may favor formation of CENP-S/-X/-T/-W complexes at centromeres and deplete the pool of available CENP-S/-X for repair. If centromere misregulation enhances CIN and genome instability on one hand, and suppresses effective DNA repair on the other, the CES system may identify a group of patients that are extremely sensitive to further DNA damage.

Although CEN/KT genes are essential for proliferation, it is unlikely that their misexpression simply reflects faster proliferation rates in cancers. We emphasize that the primary consequences of centromere and kinetochore defects are chromosome missegregation and genomic abnormalities (Allshire and Karpen, 2008), which induce cell cycle arrest and cell death as secondary effects (Allshire and Karpen, 2008; Heun et al., 2006). Indeed, multiple experiments support this conclusion. First, mitotically active tissues do not necessarily overexpress CEN/KT genes compared with corresponding differentiated normal tissues. For example, we did not observe CEN/KT misexpression in advanced liver dysplastic tissues or many breast DCIS compared to corresponding normal tissues. Similarly, small intestine inflammatory lesions characteristic of non-cancerous, cryptic hyperplasia in coeliac disease do not misexpress CEN/KT genes (Bracken et al., 2008). Second, mRNA levels for many CEN/KT genes do not fluctuate in the cell cycle (Thiru et al., 2014). Third, we tested several CEN/KT genes including CENP-A and HJURP in isogenic breast cancer progression cell lines, and found that they are dramatically upregulated during cancer progression, even though these cell lines have similar doubling times (Zhang, W., unpublished data; Stampfer, M., personal comm.). Fourth, a pure role in proliferation would imply that mRNA levels for CEN/KT genes should always change in the same direction and show similar prognostic value for cancers. However, several essential CEN/KT genes have no prognostic value even when their binding partners in the same complex do (FIG. 2). Furthermore, for some genes such as CENP-C, reduced expression correlates with more aggressive tumors in several types of cancers. Finally, high CES values correlate with high levels of CIN, which is known to lead to reduced proliferation (Lee et al., 2011). For example, overexpression of CENP-A causes cell cycle arrest due to chromosome missegregation. Together, existing evidence argues that the functions of CEN/KT genes are to ensure genome stability rather than simply promoting proliferation.

Specifically killing cells that contain chromosome aberrations has been proposed for cancer therapy (Roschke and Kirsch, 2005). Here we identified a group of genes whose misregulation relate to drug sensitivity. It may be possible in the future to develop novel small molecules that modulate centromere assembly and centromere/kinetochore structure, which could help overcome drug resistance due to CIN or increase cancer cell response to specific therapies.

Materials and Methods

A. Datasets Used in this Study

The misregulation of CEN/KT genes and their impact on prognosis were assessed using several published microarray data sets profiled with Affymetrix GeneChip arrays (HG-U133A and B or HG-U133 Plus 2.0). Microarray datasets were downloaded from the GEO website. Normalized UT SPORE NSCLC dataset was directly obtained from Drs. Yang Xie and Hao Tang at UT Southwestern. CEN/KT mRNA expression levels, fraction of copy number alteration, and frequency of gene mutations for the set of samples in each TCGA study were obtained from cBioPortal (Gao et al., 2013).

B. Meta-Analysis of Individual CEN/KT Genes and the CES for Cancer Prognosis Using Kaplan-Meier Survival Curves We performed meta-analysis for breast cancer AE-survival, MR-free survival, breast cancer subtype, and breast cancers with clinicopathological information on 17 breast cancer datasets using bc-GenExMiner v3.1, and for breast, lung, gastric and ovarian cancers using K-M Plotter following respective tutorials (Gyorffy et al., 2013; Jezequel et al., 2012). For meta-analysis using K-M Plotter for prognosis, we chose to use the top CES terile as high CES group, and the rest as low CES group. For meta-analysis on sensitivity to adjuvant therapies using K-M Plotter, we chose to use automatically computed best performing CES threshold for patient stratification in all dataset to increase detection sensitivity, even though tertile or median method gave similar results with statistical significance for many datasets. The K-M Plotter software only incorporates genes with probes present on both U133A+B to ensure comparability between datasets for meta-analysis, thus it excluded 7 CEN/KT genes including CENP-H, -W, -L, -K, -P, SPC24 and NUF2, of which 5 are also CES genes. Therefore, we used the 9 remaining CES genes, e.g., CENP-A, HJURP, MIS18B, CENP-N, CENP-M, CENP-U, ZWINT, NDC80, and SPC25, as a simplified version of the CES when using K-M Plotter.

C. Gene Co-Expression Network Construction

The CEN/KT gene co-expression correlation networks were constructed for each cancer type using TCGA datasets downloaded from the cBioPortal (Gao et al., 2013). A network of CEN/KT genes was constructed using Cytoscape 2.8.0 software (www.cytoscape.org) with the Expression-Correlation plugin (the website at baderlab.org/Software/ExpressionCorrelation). Correlation coeffecients exceeding a threshold ($R \geq 0.4$) were displayed as edges between genes represented by nodes. Nodes with fewer edges were arranged to the left of the network and those with more edges to the right.

D. Statistical Analysis

The Statistical Analysis of Microarrays (SAM) Excel add-on package (the website at www-stat.stanford.edu/~tibs/SAM/) was used to identify differences between normal and tumor tissues in expression levels of CEN/KT genes ($FDR \leq 0.05$ and fold changes $\geq 2$). Sample clustering was performed on the CEN/KT gene expression profiles using hierarchical clustering in Cluster 3.0 and Java Treeview 1.1.6r4 to group samples by centroid. For CCLE drug sensitivity, analysis was performed in Excel (Microsoft) and GraphPad. Kaplan-Meier survival curves for the CES system were generated for patients to evaluate differences in disease-free survival (DFS), stratified into groups of high (upper tertile), intermediate (middle tertile) and low (lower tertile) CES to evaluate differences in disease-free survival (DFS). For NSCLC JBR.10 trial and UT lung SPORE datasets for chemotherapy prediction, CES high patient group contains patients of the top CES tertile, and the rest two tertiles are defined as CES low. Statistical analyses were performed using the Statistical Package for the Social Sciences version 11.5 (SPSS, Inc., Chicago, Ill.) and Prism 6.0 GraphPad. Forest plots for meta-analysis on CES prognosis and treatment sensitivity were generated in Prism 6.0. For NSCLC JBR.10 and UT SPORE meta-analysis on sensitivity to adjuvant chemotherapy, we pooled the top CES tertiles and lower two CES tertiles from the two datasets for meta-groups, respectively, and Kaplan-Meier survival curves were made in Prims 6.0. Five-year survival was analyzed by chi-square test for significance.

REFERENCES

Allshire, R. C. (1997). Centromeres, checkpoints and chromatid cohesion. Curr Opin Genet Dev 7, 264-273.

Allshire, R. C., and Karpen, G. H. (2008). Epigenetic regulation of centromeric chromatin: old dogs, new tricks? Nature Reviews Genetics 9, 923-937.

Artandi, S. E., and DePinho, R. A. (2010). Telomeres and telomerase in cancer. Carcinogenesis 31, 9-18.

Barnhart, M. C., Kuich, P. H., Stellfox, M. E., Ward, J. A., Bassett, E. A., Black, B. E., and Foltz, D. R. (2011).

HJURP is a CENP-A chromatin assembly factor sufficient to form a functional de novo kinetochore. J Cell Biol 194, 229-243.

Barretina, J., Caponigro, G., Stransky, N., Venkatesan, K., Margolin, A. A., Kim, S., Wilson, C. J., Lehar, J., Kryukov, G. V., Sonkin, D., et al. (2012). The Cancer Cell Line Encyclopedia enables predictive modelling of anticancer drug sensitivity. Nature 483, 603-607.

Beroukhim, R., Mermel, C. H., Porter, D., Wei, G., Raychaudhuri, S., Donovan, J., Barretina, J., Boehm, J. S., Dobson, J., Urashima, M., et al. (2010). The landscape of somatic copy-number alteration across human cancers. Nature, pp. 899-905.

Black, B. E., and Cleveland, D. W. (2011). Epigenetic centromere propagation and the nature of CENP-a nucleosomes. Cell 144, 471-479.

Black, B. E., Jansen, L. E., Foltz, D. R., and Cleveland, D. W. (2010). Centromere identity, function, and epigenetic propagation across cell divisions. Cold Spring Harb Symp Quant Biol 75, 403-418.

Blower, M. D., and Karpen, G. H. (2001). The role of Drosophila CID in kinetochore formation, cell-cycle progression and heterochromatin interactions. Nat Cell Biol 3, 730-739.

Blower, M. D., Sullivan, B. A., and Karpen, G. H. (2002). Conserved organization of centromeric chromatin in flies and humans. Dev Cell 2, 319-330.

Botling, J., Edlund, K., Lohr, M., Hellwig, B., Holmberg, L., Lambe, M., Berglund, A., Ekman, S., Bergqvist, M., Ponten, F., et al. (2013). Biomarker discovery in non-small cell lung cancer: integrating gene expression profiling, meta-analysis, and tissue microarray validation. Chin Cancer Res 19, 194-204.

Boveri, T. (1902). Ueber mehrpolige Mitosen als Mittel zur Analyse des Zellkerns. vehr d phys med Ges zu Wurzburg NF 35, 67-90.

Boveri, T. (1914). Zur Frage der Enstehung maligner Tumoren (The Origin od Malignant Tumors) (Jena: Gustav Fischer).

Bracken, S., Byrne, G., Kelly, J., Jackson, J., and Feighery, C. (2008). Altered gene expression in highly purified enterocytes from patients with active coeliac disease. BMC genomics 9, 377.

Carter, S. L., Eklund, A. C., Kohane, I. S., Harris, L. N., and Szallasi, Z. (2006). A signature of chromosomal instability inferred from gene expression profiles predicts clinical outcome in multiple human cancers. In Nat Genet, pp. 1043-1048.

Cheeseman, I. M., and Desai, A. (2008). Molecular architecture of the kinetochore-microtubule interface. Nature reviews Molecular cell biology 9, 33-46.

Cheeseman, I. M., Hori, T., Fukagawa, T., and Desai, A. (2008). KNL1 and the CENP-H/I/K Complex Coordinately Direct Kinetochore Assembly in Vertebrates. Molecular biology of the cell 19, 587-594.

Cleveland, D. W., Mao, Y., and Sullivan, K. F. (2003). Centromeres and kinetochores: from epigenetics to mitotic checkpoint signaling. Cell 112, 407-421.

de Bruin, E. C., McGranahan, N., Mitter, R., Salm, M., Wedge, D. C., Yates, L., Jamal-Hanjani, M., Shaft, S., Murugaesu, N., Rowan, A. J., et al. (2014). Spatial and temporal diversity in genomic instability processes defines lung cancer evolution. Science 346, 251-256.

Dunleavy, E. M., Roche, D., Tagami, H., Lacoste, N., Ray-Gallet, D., Nakamura, Y., Daigo, Y., Nakatani, Y., and Almouzni-Pettinotti, G. (2009). HJURP is a cell-cycle-dependent maintenance and deposition factor of CENP-A at centromeres. Cell 137, 485-497.

Earnshaw, W. C., Bernat, R. L., Cooke, C. A., and Rothfield, N. F. (1991). Role of the centromere/kinetochore in cell cycle control. Cold Spring Harb Symp Quant Biol 56, 675-685.

Foltz, D. R., Jansen, L. E., Bailey, A. O., Yates, J. R., 3rd, Bassett, E. A., Wood, S., Black, B. E., and Cleveland, D. W. (2009). Centromere-specific assembly of CENP-a nucleosomes is mediated by HJURP. Cell 137, 472-484.

Foltz, D. R., Jansen, L. E., Black, B. E., Bailey, A. O., Yates, J. R., 3rd, and Cleveland, D. W. (2006). The human CENP-A centromeric nucleosome-associated complex. Nat Cell Biol 8, 458-469.

Fujita, Y., Hayashi, T., Kiyomitsu, T., Toyoda, Y., Kokubu, A., Obuse, C., and Yanagida, M. (2007). Priming of centromere for CENP-A recruitment by human hMis18alpha, hMis18beta, and M18BP1. Dev Cell 12, 17-30.

Gao, J., Aksoy, B. A., Dogrusoz, U., Dresdner, G., Gross, B., Sumer, S. O., Sun, Y., Jacobsen, A., Sinha, R., Larsson, E., et al. (2013). Integrative analysis of complex cancer genomics and clinical profiles using the cBioPortaL Science signaling 6, pll.

Geigl, J. B., Obenauf, A. C., Schwarzbraun, T., and Speicher, M. R. (2008). Defining 'chromosomal instability'. Trends in genetics: TIG 24, 64-69.

Gyorffy, B., Lanczky, A., Eklund, A. C., Denkert, C., Budczies, J., Li, Q., and Szallasi, Z. (2010). An online survival analysis tool to rapidly assess the effect of 22,277 genes on breast cancer prognosis using microarray data of 1,809 patients. Breast Cancer Res Treat 123, 725-731.

Gyorffy, B., Surowiak, P., Budczies, J., and Lanczky, A. (2013). Online survival analysis software to assess the prognostic value of biomarkers using transcriptomic data in non-small-cell lung cancer. PLoS One 8, e82241.

Hanahan, D., and Weinberg, R. A. (2011). Hallmarks of cancer: the next generation. In Cell, pp. 646-674.

Heun, P., Erhardt, S., Blower, M. D., Weiss, S., Skora, A. D., and Karpen, G. H. (2006). Mislocalization of the Drosophila centromere-specific histone CID promotes formation of functional ectopic kinetochores. Dev Cell 10, 303-315.

Hiley, C. T., and Swanton, C. (2014). Spatial and temporal cancer evolution: causes and consequences of tumour diversity. Clinical medicine 14 Suppl 6, s33-37.

Hori, T., Amano, M., Suzuki, A., Backer, C. B., Welburn, J. P., Dong, Y., McEwen, B. F., Shang, W.-H., Suzuki, E., Okawa, K., et al. (2008). CCAN makes multiple contacts with centromeric DNA to provide distinct pathways to the outer kinetochore. Cell 135, 1039-1052.

Hu, Z., Huang, G., Sadanandam, A., Gu, S., Lenburg, M. E., Pai, M., Bayani, N., Blakely, E. A., Gray, J. W., and Mao, J.-H. (2010). The expression level of HJURP has an independent prognostic impact and predicts the sensitivity to radiotherapy in breast cancer. In Breast Cancer Res, pp. R18.

Janssen, A., van der Burg, M., Szuhai, K., Kops, G. J., and Medema, R. H. (2011). Chromosome segregation errors as a cause of DNA damage and structural chromosome aberrations. Science 333, 1895-1898.

Jezequel, P., Campone, M., Gouraud, W., Guerin-Charbonnel, C., Leux, C., Ricolleau, G., and Campion, L. (2012). bc-GenExMiner: an easy-to-use online platform for gene prognostic analyses in breast cancer. Breast cancer research and treatment 131, 765-775.

Jezequel, P., Frenel, J. S., Campion, L., Guerin-Charbonnel, C., Gouraud, W., Ricolleau, G., and Campone, M. (2013). bc-GenExMiner 3.0: new mining module computes breast cancer gene expression correlation analyses. Database (Oxford) 2013, bas060.

Kato, T., Sato, N., Hayama, S., Yamabuki, T., Ito, T., Miyamoto, M., Kondo, S., Nakamura, Y., and Daigo, Y. (2007). Activation of Holliday junction recognizing protein involved in the chromosomal stability and immortality of cancer cells. Cancer Res 67, 8544-8553.

Kops, G. J. P. L., Weaver, B. A. A., and Cleveland, D. W. (2005). On the road to cancer: aneuploidy and the mitotic checkpoint. In Nature reviews Cancer, pp. 773-785.

Lacoste, N., Woolfe, A., Tachiwana, H., Garea, A. V., Barth, T., Cantaloube, S., Kurumizaka, H., Imhof, A., and Almouzni, G. (2014). Mislocalization of the centromeric histone variant CenH3/CENP-A in human cells depends on the chaperone DAXX. Molecular cell 53, 631-644.

Lee, A. J. X., Endesfelder, D., Rowan, A. J., Walther, A., Birkbak, N.J., Futreal, P. A., Downward, J., Szallasi, Z., Tomlinson, I. P. M., Howell, M., et al. (2011). Chromosomal instability confers intrinsic multidrug resistance. In Cancer Research, pp. 1858-1870.

Loi (2007). Definition of clinically distinct molecular subtypes in estrogen receptor-positive breast carcinomas through genomic grade (vol 25, pg 1239, 2007). Journal of Clinical Oncology 25, 3790-3790.

Mathew, V., Pauleau, A. L., Steffen, N., Bergner, A., Becker, P. B., and Erhardt, S. (2014). The histone-fold protein CHRAC14 influences chromatin composition in response to DNA damage. Cell reports 7, 321-330.

Mathijssen, R. H., Loos, W. J., Verweij, J., and Sparreboom, A. (2002). Pharmacology of topoisomerase I inhibitors irinotecan (CPT-11) and topotecan. Current cancer drug targets 2, 103-123.

Mcgovern, S. L., Qi, Y., Pusztai, L., Symmans, W. F., and Buchholz, T. A. (2012). Centromere protein-A, an essential centromere protein, is a prognostic marker for relapse in estrogen receptor-positive breast cancer. Breast Cancer Res, pp. R72.

Mellone, B. G., Zhang, W., and Karpen, G. H. (2009). Frodos found: Behold the CENP-a "Ring" bearers. Cell, pp. 409-412.

Mendiburo, M. J., Padeken, J., Fillop, S., Schepers, A., and Heun, P. (2011). Drosophila CENH3 Is Sufficient for Centromere Formation. Science 334, 686-690.

Mishra, P. K., Au, W. C., Choy, J. S., Kuich, P. H., Baker, R. E., Foltz, D. R., and Basrai, M. A. (2011). Misregulation of Scm3p/HJURP causes chromosome instability in Saccharomyces cerevisiae and human cells. PLoS Genet 7, e1002303.

Moree, B., Meyer, C. B., Fuller, C. J., and Straight, A. F. (2011). CENP-C recruits M18BP1 to centromeres to promote CENP-A chromatin assembly. The Journal of Cell Biology 194, 855-871.

Nathanson, D. A., Gini, B., Mottahedeh, J., Visnyei, K., Koga, T., Gomez, G., Eskin, A., Hwang, K., Wang, J., Masui, K., et al. (2014). Targeted therapy resistance mediated by dynamic regulation of extrachromosomal mutant EGFR DNA. Science 343, 72-76.

Negrini, S., Gorgoulis, V. G., and Halazonetis, T. D. (2010). Genomic instability—an evolving hallmark of cancer. Nat Rev Mol Cell Biol, pp. 220-228.

Nfic-Zainal, S., Van Loo, P., Wedge, D. C., Alexandrov, L. B., Greenman, C. D., Lau, K. W., Raine, K., Jones, D., Marshall, J., Ramakrishna, M., et al. (2012). The life history of 21 breast cancers. Cell 149, 994-1007.

Nishino, T., Takeuchi, K., Gascoigne, K. E., Suzuki, A., Hori, T., Oyama, T., Morikawa, K., Cheeseman, I. M., and Fukagawa, T. (2012). CENP-T-W-S-X forms a unique centromeric chromatin structure with a histone-like fold. Cell 148, 487-501.

Okada, M., Cheeseman, I. M., Hori, T., Okawa, K., McLeod, I. X., Yates, J. R., 3rd, Desai, A., and Fukagawa, T. (2006). The CENP-H-I complex is required for the efficient incorporation of newly synthesized CENP-A into centromeres. Nat Cell Biol 8, 446-457.

Parker, J. S., Mullins, M., Cheang, M. C., Leung, S., Voduc, D., Vickery, T., Davies, S., Fauron, C., He, X., Hu, Z., et al. (2009). Supervised risk predictor of breast cancer based on intrinsic subtypes. J Clin Oncol 27, 1160-1167.

Perpelescu, M., and Fukagawa, T. (2011). The ABCs of CENPs. Chromosoma 120, 425-446.

Pierotti, M. A., Sozzi, Gabriella, Croce, Carlo M. (2003). Holland-Frei Cancer Medicine, 6th Edition, 6th Edition edn (Hamilton (ON): BC Decker).

Pihan, G. A., Wallace, J., Zhou, Y., and Doxsey, S. J. (2003). Centrosome abnormalities and chromosome instability occur together in pre-invasive carcinomas. Cancer Research, pp. 1398-1404.

Roschke, A. V., and Kirsch, I. R. (2005). Targeting cancer cells by exploiting karyotypic complexity and chromosomal instability. In Cell Cycle, pp. 679-682.

Schvartzman, J. M., Sotillo, R., and Benezra, R. (2010). Mitotic chromosomal instability and cancer: mouse modelling of the human disease. Nature reviews Cancer 10, 102-115.

Siegel, J. J., and Amon, A. (2012). New insights into the troubles of aneuploidy. Annu Rev Cell Dev Biol 28, 189-214.

Sullivan, B. A., and Karpen, G. H. (2004). Centromeric chromatin exhibits a histone modification pattern that is distinct from both euchromatin and heterochromatin. Nature structural & molecular biology 11, 1076-1083.

Swanton, C., Marani, M., Pardo, O., Warne, P. H., Kelly, G., Sahai, E., Elustondo, F., Chang, J., Temple, J., Ahmed, A. A., et al. (2007). Regulators of mitotic arrest and ceramide metabolism are determinants of sensitivity to paclitaxel and other chemotherapeutic drugs. Cancer cell 11, 498-512.

Tang, H., Xiao, G., Behrens, C., Schiller, J., Allen, J., Chow, C.-W., Suraokar, M., Corvalan, A., Mao, J., White, M. A., et al. (2013). A 12-gene set predicts survival benefits from adjuvant chemotherapy in non-small cell lung cancer patients. Clin Cancer Res, pp. 1577-1586.

Thiru, P., Kern, D. M., McKinley, K. L., Monda, J. K., Rago, F., Su, K. C., Tsinman, T., Yarar, D., Bell, G. W., and Cheeseman, I. M. (2014). Kinetochore genes are coordinately up-regulated in human tumors as part of a FoxM1-related cell division program. Mol Biol Cell 25, 1983-1994.

Tomonaga, T., Matsushita, K., Ishibashi, M., Nezu, M., Shimada, H., Ochiai, T., Yoda, K., and Nomura, F. (2005). Centromere protein H is up-regulated in primary human colorectal cancer and its overexpression induces aneuploidy. Cancer Res 65, 4683-4689.

Tomonaga, T., Matsushita, K., Yamaguchi, S., Oohashi, T., Shimada, H., Ochiai, T., Yoda, K., and Nomura, F. (2003). Overexpression and mistargeting of centromere protein-A in human primary colorectal cancer. Cancer Res 63, 3511-3516.

Weaver, B. A. A., and Cleveland, D. W. (2006). Does aneuploidy cause cancer? In Curr Opin Cell Biol, pp. 658-667.

Weaver, B. A. A., Silk, A. D., Montagna, C., Verdier-Pinard, P., and Cleveland, D. W. (2007). Aneuploidy acts both oncogenically and as a tumor suppressor. In Cancer Cell, pp. 25-36.

Yachida, S., Jones, S., Bozic, I., Antal, T., Leary, R., Fu, B., Kamiyama, M., Hruban, R. H., Eshleman, J. R., Nowak, M. A., et al. (2010). Distant metastasis occurs late during the genetic evolution of pancreatic cancer. Nature 467, 1114-1117.

Yan, Z., Delannoy, M., Ling, C., Daee, D., Osman, F., Muniandy, P. A., Shen, X., Oostra, A. B., Du, H., Steltenpool, J., et al. (2010). A histone-fold complex and FANCM form a conserved DNA-remodeling complex to maintain genome stability. Molecular cell 37, 865-878.

Zeitlin, S. G., Baker, N. M., Chapados, B. R., Soutoglou, E., Wang, J. Y., Berns, M. W., and Cleveland, D. W. (2009). Double-strand DNA breaks recruit the centromeric histone CENP-A. Proc Natl Acad Sci USA 106, 15762-15767.

Zhang, J., Fujimoto, J., Zhang, J., Wedge, D. C., Song, X., Zhang, J., Seth, S., Chow, C. W., Cao, Y., Gumbs, C., et al. (2014). Intratumor heterogeneity in localized lung adenocarcinomas delineated by multiregion sequencing. Science 346, 256-259.

Zhu, C. Q., Ding, K., Strumpf, D., Weir, B. A., Meyerson, M., Pennell, N., Thomas, R. K., Naoki, K., Ladd-Acosta, C., Liu, N., et al. (2010). Prognostic and predictive gene signature for adjuvant chemotherapy in resected non-small-cell lung cancer. J Clin Oncol 28, 4417-4424.

```
>gi|12803733|gb|AAH02703.1| CENPA protein sapiens+
MGPRRRSRKPEAPRRRSPSPTPTPGPSRRGPSLGASSHQHSRRRQGWLKEIRKLQKSTHLLIRKLPFSRL
AREICVKFTRGVDFNWQAQALLALQEAAEAFLVHLFEDAYLLTLHAGRVTLFPKDVQLARRIRGLEEGLG
(SEQ ID NO: 1)

>gi|83816964|ref|NP_060880.3| Holliday junction recognition protein
isoform a [Homo sapiens]
MLGTLRAMEGEDVEDDQLLQKLRASRRRFQRRMQRLIEKYNQPFEDTPVVQMATLTYETPQGLRIWGGRL
IKERNEGEIQDSSMKPADRTDGSVQAAAWGPELPSHRTVLGADSKSGEVDATSDQEESVAWALAPAVPQS
PLKNELRRKYLTQVDILLQGAEYFECAGNRAGRDVRVTPLPSLASPAVPAPGYCSRISRKSPGDPAKPAS
SPREWDPLHPSSTDMALVPRNDSLSLQETSSSSFLSSQPFEDDDICNVTISDLYAGMLHSMSRLLSTKPS
SIISTKTFIMQNWNSRRRHRYKSRMNKTYCKGARRSQRSSKENFIPCSEPVKGTGALRDCKNVLDVSCRK
TGLKLEKAFLEVNRPQIHKLDPSWKERKVTPSKYSSLIYFDSSATYNLDEENRFRTLKWLISPVKIVSRP
TIRQGHGENRQREIEIRFDQLHREYCLSPRNQPRRMCLPDSWAMNMYRGGPASPGGLQGLETRRLSLPSS
KAKAKSLSEAFENLGKRSLEAGRCLPKSDSSSSLPKTNPTHSATRPQQTSDLHVQGNSSGIFRKSVSPSK
TLSVPDKEVPGHGRNRYDEIKEEFDKLHQKYCLKSPGQMTVPLCIGVSTDKASMEVRYQTEGFLGKLNPD
PHFQGFQKLPSSPLGCRKSLLGSTAIEAPSSTCVARAITRDGTRDHQFPAKRPRLSEPQGSGRQGNSLGA
SDGVDNTVRPGDQGSSSQPNSEERGENTSYRMEEKSDFMLEKLETKSV (SEQ ID NO: 2)

>gi|545477999|ref|NP_001269891.1| Holliday junction recognition protein
isoform b [Homo sapiens]
MLGTLRAMEGEDVEDDQLLQKLRASRRRFQRRMQRLIEKYNQPFEDTPVVQMATLTYETPQGLRIWGGRL
IKERNEGEIQPAVPQSPLKNELRRKYLTQVDILLQGAEYFECAGNRAGRDVRVTPLPSLASPAVPAPGYC
SRISRKSPGDPAKPASSPREWDPLHPSSTDMALVPRNDSLSLQETSSSSFLSSQPFEDDDICNVTISDLY
AGMLHSMSRLLSTKPSSIISTKTFIMQNWNSRRRHRYKSRMNKTYCKGARRSQRSSKENFIPCSEPVKGT
GALRDCKNVLDVSCRKTGLKLEKAFLEVNRPQIHKLDPSWKERKVTPSKYSSLIYFDSSATYNLDEENRF
RTLKWLISPVKIVSRPTIRQGHGENRQREIEIRFDQLHREYCLSPRNQPRRMCLPDSWAMNMYRGGPASP
GGLQGLETRRLSLPSSKAKAKSLSEAFENLGKRSLEAGRCLPKSDSSSSLPKTNPTHSATRPQQTSDLHV
QGNSSGIFRKSVSPSKTLSVPDKEVPGHGRNRYDEIKEEFDKLHQKYCLKSPGQMTVPLCIGVSTDKASM
EVRYQTEGFLGKLNPDPHFQGFQKLPSSPLGCRKSLLGSTAIEAPSSTCVARAITRDGTRDHQFPAKRPR
LSEPQGSGRQGNSLGASDGVDNTVRPGDQGSSSQPNSEERGENTSYRMEEKSDFMLEKLETKSV (SEQ
ID NO: 3)

>gi|545478902|ref|NP_001269892.1| Holliday junction recognition protein
isoform c [Homo sapiens]
MLGTLRAMEGEDVEDDQLLQKLRASRRRFQRRMQRLIEKYNQPFEDTPVVQMATLTYETPQGLRIWGGRL
IKERNEGEIQCAGNRAGRDVRVTPLPSLASPAVPAPGYCSRISRKSPGDPAKPASSPREWDPLHPSSTDM
ALVPRNDSLSLQETSSSSFLSSQPFEDDDICNVTISDLYAGMLHSMSRLLSTKPSSIISTKTFIMQNWNS
RRRHRYKSRMNKTYCKGARRSQRSSKENFIPCSEPVKGTGALRDCKNVLDVSCRKTGLKLEKAFLEVNRP
QIHKLDPSWKERKVTPSKYSSLIYFDSSATYNLDEENRFRTLKWLISPVKIVSRPTIRQGHGENRQREIE
IRFDQLHREYCLSPRNQPRRMCLPDSWAMNMYRGGPASPGGLQGLETRRLSLPSSKAKAKSLSEAFENLG
KRSLEAGRCLPKSDSSSSLPKTNPTHSATRPQQTSDLHVQGNSSGIFRKSVSPSKTLSVPDKEVPGHGRN
RYDEIKEEFDKLHQKYCLKSPGQMTVPLCIGVSTDKASMEVRYQTEGFLGKLNPDPHFQGFQKLPSSPLG
CRKSLLGSTAIEAPSSTCVARAITRDGTRDHQFPAKRPRLSEPQGSGRQGNSLGASDGVDNTVRPGDQGS
SSQPNSEERGENTSYRMEEKSDFMLEKLETKSV (SEQ ID NO: 4)

>gi|9506437|ref|NP_061817.1| protein Mis18-alpha[Homo sapiens]
MAGVRSLRCSRGCAGGCECGDKGKCSDSSLLGKRLSEDSSRHQLLQKWASMWSSMSEDASVADMERAQLE
EEAAAAEERPLVFLCSGCRRPLGDSLSWVASQEDTNCILLRCVSCNVSVDKEQKLSKREKENGCVLETLC
CAGCSLNLGYVYRCTPKNLDYKRDLFCLSVEAIESYVLGSSEKQIVSEDKELFNLESRVEIEKSLTQMED
VLKALQMKLWEAESKLSFATCKS (SEQ ID NO: 5)

>gi|24307929|ref|NP_009211.1| protein Mis18-beta sapiens+
MAAQPLRHRSRCATPPRGDFCGGTERAIDQASFTTSMEWDTQVVKGSSPLGPAGLGAEEPAAGPQLPSWL
QPERCAVFQCAQCHAVLADSVHLAWDLSRSLGAVVFSRVTNNVVLEAPFLVGIEGSLKGSTYNLLFCGSC
GIPVGFHLYSTHAALAALRGHFCLSSDKMVCYLLKTKAIVNASEMDIQNVPLSEKIAELKEKIVLTHNRL
KSLMKILSEVTPDQSKPEN (SEQ ID NO: 6)

>gi|119625950|gb|EAX05545.1| centromere protein C 1, isoform CRA_a
[Homo sapiens]
MAASGLDHLKNGYRRRFCRPSRARDINTEQGQNVLEILQDCFEEKSLANDFSTNSTKSVPNSTRKIKDTC
IQSPSKECQKSHPKSVPVSSKKKEASLQFVVEPSEATNRSVQAHEVHQKILATDVSSKNTPDSKKISSRN
```

-continued

INDHHSEADEEFYLSVGSPSVLLDAKTSVSQNVIPSSAQKRETYTFENSVNMLPSSTEVSVKTKKRLNFD
DKVMLKKIEIDNKVSDEEDKTSEGQERKPSGSSQNRIRDSEYEIQRQAKKSFSTLFLETVKRKSESSPIV
RHAATAPPHSCPPDDTKLIEDEFIIDESDQSFASRSWITIPRKAGSLKQRTISPAESTALFQGRKSREKH
HNILPKTLANDKHSHKPHPVETSQPSDKTVLDTSYALIGETVNNYRSTKYEMYSKNAEKPSRSKRTIKQK
QRRKFMAKPAEEQLDVGQSKDENIHTSHITQDEFQRNSDRNMEEHEEMGNDCVSKKQMPPVGSKKSSTRK
DKEESKKKRFSSESKNKLVPEEVTSTVTKSRRISRRPSDWWVVKSEESPVYSNSSVRNELPMHHNSSRKS
TKKTNQSSKNIRKKTIPLKRQKTATKGNQRVQKFLNAEGSGGIVGHDEISRCSLSEPLESDEADLAKKKN
LDCSRSTRSSKNEDNIMTAQNVPLKPQTSGYTCNIPTESNLDSGEHKTSVLEESGPSRLNNNYLMSGKND
VDDEEVHGSSDDSKQSKVIPKNRIHHKLVLPSNTPNVRRTKRTRLKPLEYWRGERIDYQGRPSGGFVISG
VLSPDTISSKRKAKENIGKVNKKSNKKRICLDNDERKTNLMVNLGIPLGDPLQPTRVKDPETREIILMDL
VRPQDTYQFFVKHGELKVYKTLDTPFFSTGKLILGPQEEKGKQHVGQDILVFYVNFGDLLCTLHETPYIL
STGDSFYVPSGNYYNIKNLRNEESVLLFTQIKR (SEQ ID NO: 7)

>gi|119625951|gb|EAX05546.1| centromere protein C 1, isoform CRA_b
[Homo sapiens]
MAASGLDHLKNGYRRRFCRPSRARDINTEQGQNVLEILQDCFEEKSLANDFSTNSTKSVPNSTRKIKDTC
IQSPSKECQKSHPKSVPVSSKKKEASLQFVVEPSEATNRSVQAHEVHQKILATDVSSKNTPDSKKISSRN
INDHHSEADEEFYLSVGSPSVLLDAKTSVSQNVIPSSAQKRETYTFENSVNMLPSSTEVSVKTKKRLNFD
DKVMLKKIEIDNKVSDEEDKTSEGQERKPSGSSQNRIRDSEYEIQRQAKKSFSTLFLETVKRKSESSPIV
RHAATAPPHSCPPDDTKLIEDEFIIDESDQSFASRSWITIPRKAGSLKQRTISPAESTALFQGRKSREKH
HNILPKTLANDKHSHKPHPVETSQPSDKTVLDTSYALIGETVNNYRSTKYEMYSKNAEKPSRSKRTIKQK
QRRKFMAKPAEEQLDVGQSKDENIHTSHITQDEFQRNSDRNMEEHEEMGNDCVSKKQMPPVGSKKSSTRK
DKEESKKKRFSSESKNKLVPEEVTSTVTKSRRISRRPSDWWVVKSEESCLKC (SEQ ID NO: 8)

>gi|395132501|ref|NP_060925.2| centromere protein N isoform 3
[Homo sapiens]
MDETVAEFIKRTILKIPMNELTTILKAWDFLSENQLQTVNFRQRKESVVQHLIHLCEEKRASISDAALLD
IIYMQFHQHQKVWEVFQMSKGPGEDVDLFDMKQFKNSFKKILQRALKNVTVSFRETEENAVWIRIAWGTQ
YTKPNQYKPTYVVYYSQTPYAFTSSSMLRRNTPLLGQELEATGKIYLRQEEIILDITEMKKACN
(SEQ ID NO: 9)

>gi|395132497|ref|NP_001257403.1| centromere protein N isoform 5
[Homo sapiens]
MDETVAEFIKRTILKIPMNELTTILKAWDFLSENQLQTVNFRQRKESVVQHLIHLCEEKRASISDAALLD
IIYMQFHQHQKVWEVFQMSKGPGEDVDLFDMKQFKNSFKKILQRALKNVTVSFRETEENAVWIRIAWGTQ
YTKPNQYKPTYVVYYSQTPYAFTSSSMLRRNTPLLGQTFETHNSTTPLQERSLGLDINMDSRIIHENIVE
KERVQRITQETFGDYPQPQLEFAQYKLETKFKSGLNGSILAEREEPLRCLIKFSSPHLLEALKSLAPAGI
ADAPLSPLLTCIPNKRMNYFKIRDK (SEQ ID NO: 10)

>gi|395132495|ref|NP_001257402.1| centromere protein N isoform 4
[Homo sapiens]
MDETVAEFIKRTILKIPMNELTTILKAWDFLSENQLQTVNFRQRKESVVQHLIHLCEEKRASISDAALLD
IICEDVDLFDMKQFKNSFKKILQRALKNVTVSFRETEENAVWIRIAWGTQYTKPNQYKPTYVVYYSQTPY
AFTSSSMLRRNTPLLGQALTIASKHHQIVKMDLRSRYLDSLKAIVFKQYNQTFETHNSTTPLQERSLGLD
INMDSRIIHENIVEKERVQRITQETFGDYPQPQLEFAQYKLETKFKSGLNGSILAEREEPLRCLIKFSSP
HLLEALKSLAPAGIADAPLSPLLTCIPNKRMNYFKIRDK (SEQ ID NO: 11)

>gi|395132493|ref|NP_001094094.2| centromere protein N isoform 2
[Homo sapiens]
MDETVAEFIKRTILKIPMNELTTILKAWDFLSENQLQTVNFRQRKESVVQHLIHLCEEKRASISDAALLD
IIYMQFHQHQKVWEVFQMSKGPGEDVDLFDMKQFKNSFKKILQRALKNVTVSFRETEENAVWIRIAWGTQ
YTKPNQYKPTYVVYYSQTPYAFTSSSMLRRNTPLLGQALTIASKHHQIVKMDLRSRYLDSLKAIVFKQYN
QTFETHNSTTPLQERSLGLDINMDSRIIHENIVEKERVQRITQETFGDYPQPQLEFAQYKLETKFKSGLN
GSILAEREEPLRCLIKFSSPHLLEALKSLAPAGIADAPLSPLLTCIPNKRMNYFKIRDK
(SEQ ID NO: 12)

>gi|395132491|ref|NP_001094095.2| centromere protein N isoform 1
[Homo sapiens]
MDETVAEFIKRTILKIPMNELTTILKAWDFLSENQLQTVNFRQRKESVVQHLIHLCEEKRASISDAALLD
IIYMQFHQHQKVWEVFQMSKGPGEDVDLFDMKQFKNSFKKILQRALKNVTVSFRETEENAVWIRIAWGTQ
YTKPNQYKPTYVVYYSQTPYAFTSSSMLRRNTPLLGQALTIASKHHQIVKMDLRSRYLDSLKAIVFKQYN
QTFETHNSTTPLQERSLGLDINMDSRIIHENIVEKERVQRITQETFGDYPQPQLEFAQYKLETKFKSGLN
GSILAEREEPLRCLIKFSSPHLLEALKSLAPAALVCRIQKLLCYSGSHSQGTQDPSSWQKDLYLLFVPLY
PRC (SEQ ID NO: 13)

>gi|77416860|sp|Q92674.2| CENPI_HUMAN RecName: Full = Centromere protein I;
Short = CENP-I; AltName: Full = FSH primary response protein 1; AltName:
Full = Follicle-stimulating hormone primary response protein; AltName:
Full = Interphase centromere complex protein 19; AltName: Full = Leucine-rich
primary response protein 1
MSPQKRVKNVQAQNRTSQGSSSFQTTLSAWKVKQDPSNSKNISKHGQNNPVGDYEHADDQAEEDALQMAV
GYFEKGPIKASQNKDKTLEKHLKTVENVAWKNGLASEEIDILLNIALSGKFGNAVNTRILKCMIPATVIS
EDSVVKAVSWLCVGKCSGSTKVLFYRWLVAMFDFIDRKEQINLLYGFFFASLQDDALCPYVCHLLYLLTK
KENVKPFRVRKLLDLQAKMGMQPHLQALLSLYKFFAPALISVSLPVRKKIYFKNSENLWKTALLAVKQRN
RGPSPEPLKLMLGPANVRPLKRKWNSLSVIPVLNSSSYTKECGKKEMSLSDCLNRSGSFPLEQLQSFPQL
LQNIHCLELPSQMGSVLNNSLLLHYINCVRDEPVLLRFYYWLSQTLQEECIWYKVNNYEHGKEFTNPLDT
IIRAECFLQEGFYSCEAFLYKSLPLWDGLCCRSQFLQLVSWIPFSSFSEVKPLLFDHLAQLFFTSTIYFK
CSVLQSLKELLQNWLLWLSMDIHMKPVTNSPLETTLGGSMNSVSKLIHYVGWLSTTAMRLESNNTFLLHF
ILDFYEKVCDIYINYNLPLVVLFPPGIFYSALLSDTSILNQLCFIMHRYRKNLTAAKKNELVQKTKSEF
NFSSKTYQEFNHYLTSMVGCLWTSKPFGKGIYIDPEILEKTGVAEYKNSLNVVHHPSFLSYAVSFLLQES
PEERTVNVSSIRGKKWSWYLDYLFSQGLQGLKLFIRSSVHHSSIPRAEGINCNNQY (SEQ ID NO: 14)

```
>gi|74733576|sp|Q9H3R5.1| CENPH_HUMAN RecName: Full = Centromere protein H;
Short = CENP-H; AltName: Full = Interphase centromere complex protein 35
MEEQPQMQDADEPADSGGEGRAGGPPQVAGAQAACSEDRMTLLLRLRAQTKQQLLEYKSMVDASEEKTPE
QIMQEKQIEAKIEDLENEIEEVKVAFEIKKLALDRMRLSTALKKNLEKISRQSSVLMDNMKHLLELNKLI
MKSQQESWDLEEKLLDIRKKRLQLKQASESKLLEIQTEKNKQKIDLDSMENSERIKIIRQNLQMEIKITT
VIQHVFQNLILGSKVNWAEDPALKEIVLQEKNVDMM (SEQ ID NO: 15)

>gi|557357675|ref|NP_001273454.1| centromere protein W isoform c
[Homo sapiens]
MALSTIVSQRKQIKRKAPRGFLKRVFKRKKPQLRLEKSGDLLKSPGQTLVRVNVESLTRSMYWPQQR
(SEQ ID NO: 16)

>gi|557355812|ref|NP_001273453.1| centromere protein W isoform a
[Homo sapiens]
MALSTIVSQRKQIKRKAPRGFLKRVFKRKKPQLRLEKSGDLLVRFHPFSGWEWGTGEVHLNCLLFVHRLA
EESRTNACASKCRVINKEHVLAAAKVILKKSRG (SEQ ID NO: 17)

>gi|60302883|ref|NP_001012525.1| centromere protein W isoform b
[Homo sapiens]
MALSTIVSQRKQIKRKAPRGFLKRVFKRKKPQLRLEKSGDLLVHLNCLLFVHRLAEESRTNACASKCRVI
NKEHVLAAAKVILKKSRG (SEQ ID NO: 18)

>gi|401871068|ref|NP_001257936.1| centromere protein X isoform 3
[Homo sapiens]
MEGAGAGSGFRKELVSRLLHLHFKDDKTKEAAVRGVRQAQAEDALRVDVDQLEKLLDF (SEQ ID NO: 19)

>gi|401871066|ref|NP_001257935.1| centromere protein X isoform 1
[Homo sapiens]
MEGAGAGSGFRKELVSRLLHLHFKDDKTKVSGDALQLMVELLKVFVVEAAVRGVRQAQAEDALRVDVDQL
EKVLPQLLLDF (SEQ ID NO: 20)

>gi|71559139|ref|NP_659435.2| centromere protein X isoform 2 [Homo sapiens]
MEGAGAGSGFRKELVSRLLHLHFKDDKTKEAAVRGVRQAQAEDALRVDVDQLEKVLPQLLLDF
(SEQ ID NO: 21)

>gi|50845414|ref|NP_001002876.1| centromere protein M isoform b
[Homo sapiens]
MSVLRPLDKLPGLNTATILLVGTEDALLQQLADSMLKEDCASELKVHLAKSLPLPSSVNRPRIDLIVFVV
NLHSKYSLQNTEESLRHVDASFFLGKVCFLATGGGRL (SEQ ID NO: 22)

>gi|13129022|ref|NP_076958.1| centromere protein M isoform a [Homo sapiens]
MSVLRPLDKLPGLNTATILLVGTEDALLQQLADSMLKEDCASELKVHLAKSLPLPSSVNRPRIDLIVFVV
NLHSKYSLQNTEESLRHVDASFFLGKVCFLATGAGRESHCSIHRHTVVKLAHTYQSPLLYCDLEVEGFRA
TMAQRLVRVLQICAGHVPGVSALNLLSLLRSSEGPSLEDL (SEQ ID NO: 23)

>gi|158966691|ref|NP_001103685.1| centromere protein M isoform c
[Homo sapiens]
MGRVWDLPGVLKVEGFRATMAQRLVRVLQICAGHVPGVSALNLLSLLRSSEGPSLEDL
(SEQ ID NO: 24)

>gi|74712714|sp|Q71F23.1| CENPU_HUMAN RecName: Full = Centromere protein U;
Short = CENP-U; AltName: Full = Centromere protein of 50 kDa; Short = CENP-50;
AltName: Full = Interphase centromere complex protein 24; AltName: Full = KSHV
latent nuclear antigen-interacting protein 1; AltName: Full = MLF1-
interacting protein; AltName: Full = Polo-box-interacting protein 1
MAPRGRRRPRPHRSEGARRSKNTLERTHSMKDKAGQKCKPIDVFDFPDNSDVSSIGRLGENEKDEETYET
FDPPLHSTAIYADEEEFSKHCGLSLSSTPPGKEAKRSSDTSGNEASEIESVKISAKKPGRKLRPISDDSE
SIEESDTRRKVKSAEKISTQRHEVIRTTASSELSEKPAESVTSKKTGPLSAQPSVEKENLAIESQSKTQK
KGKISHDKRKKSRSKAIGSDTSDIVHIWCPEGMKTSDIKELNIVLPEFEKTHLEHQQRIESKVCKAAIAT
FYVNVKEQFIKMLKESQMLTNLKRKNAKMISDIEKKRQRMIEVQDELLRLEPQLKQLQTKYDELKERKSS
LRNAAYFLSNLKQLYQDYSDVQAQEPNVKETYDSSSLPALLFKARTLLGAESHLRNINHQLEKLLDQG
(SEQ ID NO: 25)

>gi|113958992|gb|ABI49143.1| MLF1 interacting protein isoform 2
[Homo sapiens]
MAPRGRRRPRPHRSEGARRSKNTLERTHSMKDKAGQKCKPIDVFDFPDNSDVSSIGRLGENEKDEETYET
FDPPLHSTAIYADEEEFSKHCGLSLSSTPPGKEAKRSSDTSGNEASEIESVKISAKKPGRKLRPISDDSE
SIEESDTRRKVKSAEKISTQRHEVIRTTASSELSEKPAESVTSKKTGPLSAQPSVEKENLAIESQSKTQK
KGKISHDKRKKSRSKAIGSDTSDIVHIWCPEGMKTSDIKELNIVLPEFEKTHLEHQQRIESKVCKAAIAT
FYVNVKEQFIKMLKESQMLTNLKRKNAKVRATAETTTNKI (SEQ ID NO: 26)

>gi|113958976|gb|ABI49142.1| MLF1 interacting protein isoform 1
[Homo sapiens]
MAPRGRRRPRPHRSEGARRSKNTLERTHSMKDKAGQKCKPIDVFDFPDNSDVSSIGRLGENEKDEETYET
FDPPLHSTAIYADEEEFSKHCGLSLSSTPPGKEAKRSSDTSGNEASEIESVKISAKKPGRKLRPISDDSE
SIEESDTRRKVKSAEKISTQRHEVIRTTASSELSEKPAESVTSKKTGPLSAQPSVEKENLAIESQSKTQK
KGKISHDKRKKSRSKAIGSDTSDIVHIWCPEGMKTSDIKELNIVLPEFEKTHLEHQQRIESKVCKAAIAT
FYVNVKEQFIKMLKESQMLTNLKRKNAKMISDIEKKRQRMIEVQDELLRLWTGAGLW (SEQ ID NO: 27)
```

>gi|306482665|ref|NP_001182361.1| myeloid leukemia factor 1 isoform 3
[Homo sapiens]
MLKEVLQREGKSYKSETLMYIKKARASENKLSESILAHRENMRQMIRSFSEPFGRDLLSISDGRGRAHNR
RGHNDGEDSLTATSCSLVPFGDFGGMHTDVSSFQTMDQMVSNMRNYMQKLERNFGQLSVDPNGHSFCSSS
VMTYSKIGDEPPKVFQASTQTRRAPGGIKETRKAMRDSDSGLEKMAIGHHIHDRAHVIKKSKNKKTGDEE
VNQEFINMNESDAHAFDEEWQSEVLKYKPGRHNLGNTRMRSVGHENPGSRELKRREKPQQSPAIEHGRRS
NVLGDKLHIKGSSVKSNKK (SEQ ID NO: 28)

>gi|283945459|ref|NP_001164653.1| centromere protein L isoform 2
[Homo sapiens]
MDSYSAPESTPSASSRPEDYFIGATPLQKRLESVRKQSSFILTPPRRKIPQCSQLQEDVDPQKVAFLLHK
QWTLYSLTPLYKFSYSNLKEYSRLLNAFIVAEKQKGLAVEVGEDFNIKVIFSTLLGMKGTQRDPEAFLVQ
IVSKSQLPSENREGKVLWTGWFCCVFGDSLLETVSEDFTCLPLFLANGAESNTAIIGTWFQKTFDCYFSP
LAINAFNLSWMAAMWTACKMDHYVATTEFLWSVPCSPQSLDISFAIHPEDAKALWDSVHKTPGEVTQEEV
DLFMDCLYSHFRHFKIHLSATRLVRVSTSVASAHTDGKIKILCHKYLIGVLAYLTELAIFQIE
(SEQ ID NO: 29)

>gi|1876085081ref|NP_001120653.1| centromere protein L isoform 1
[Homo sapiens]
MDSYSAPESTPSASSRPEDYFIGATPLQKRLESVRKQSSFILTPPRRKIPQCSQLQEDVDPQKVAFLLHK
QWTLYSLTPLYKFSYSNLKEYSRLLNAFIVAEKQKGLAVEVGEDFNIKVIFSTLLGMKGTQRDPEAFLVQ
GLILSPRLEYSGTILVDCNLCLLGSSDPSTLAFQVAGTAGACHHTRIVSKSQLPSENREGKVLWTGWFCC
VFGDSLLETVSEDFTCLPLFLANGAESNTAIIGTWFQKTFDCYFSPLAINAFNLSWMAAMWTACKMDHYV
ATTEFLWSVPCSPQSLDISFAIHPEDAKALWDSVHKTPGEVTQEEVDLFMDCLYSHFRHFKIHLSATRL
VRVSTSVASAHTDGKIKILCHKYLIGVLAYLTELAIFQIE (SEQ ID NO: 30)

>gi|74732954|sp|Q9BS16.1| CENPK_HUMAN RecName: Full = Centromere protein K;
Short = CENP-K; AltName: Full = Interphase centromere complex protein 37;
AltName: Full = Protein AF-5alpha; AltName: Full = p33
MNQEDLDPDSTTDVGDVTNTEEELIRECEEMWKDMEECQNKLSLIGTETLTDSNAQLSLLIMQVKCLTAE
LSQWQKKTPETIPLTEDVLITLGKEEFQKLRQDLEMVLSTKESKNEKLKEDLEREQRWLDEQQQIMESLN
VLHSELKNKVETFSESRIFNELKTKMLNIKEYKEKLLSTLGEFLEDHFPLPDRSVKKKKKNIQESSVNLI
TLHEMLEILINRLFDVPHDPYVKISDSFWPPYVELLLRNGIALRHPEDPTRIRLEAFHQ
(SEQ ID NO: 31)

>gi|315221159|ref|NP_001186732.1| centromere protein O isoform 2
[Homo sapiens]
MAGI LASGLGVLAHLERLETQVSRSRKQSEELQSVQAQEGALGTKIHKLRRLRDELRAVVRHRRASVKAC
IANVEPNQTVEINEQEALEEKLENVKAILQAYHFTGLSGKLTSRGVCVCISTAFEGNLLDSYFVDLVIQK
PLRIHHHSVPVFIPLEEIAAKYLQTNIQHFLFSLCEYLNAYSGRKYQADRLQSDFAALLTGPLQRNPLCN
LLSFTYKLDPGGQSFPPFCARLLYKDLTATLPTDVTVTCQGVEVLSTSWEEQRASHETLFCTKPLHQVFAS
FTRKGEKLDMSLVS (SEQ ID NO: 32)

>gi|13236565|ref|NP_077298.1| centromere protein O isoform 1 sapiens+
MEQANPLRPDGESKGGVLAHLERLETQVSRSRKQSEELQSVQAQEGALGTKIHKLRRLRDELRAVVRHRR
ASVKACIANVEPNQTVEINEQEALEEKLENVKAILQAYHFTGLSGKLTSRGVCVCISTAFEGNLLDSYFV
DLVIQKPLRIHHHSVPVFIPLEEIAAKYLQTNIQHFLFSLCEYLNAYSGRKYQADRLQSDFAALLTGPLQ
RNPLCNLLSFTYKLDPGGQSFPPFCARLLYKDLTATLPTDVTVTCQGVEVLSTSWEEQRASHETLFCTKPL
HQVFASFTRKGEKLDMSLVS (SEQ ID NO: 33)

>gi|444299651|ref|NP_653091.3| protein CASC5 isoform 2 sapiens+
MDGVSSEANEENDNIERPVRRRHSSILKPPRSPLQDLRGGNERVQESNALRNKKNSRRVSFADTIKVFQT
ESHMKIVRKSEMEETETGENLLLIQNKKLEDNYCEITGMNTLLSAPIHTQMQQKEFSIIEHTRERKHAND
QTVIFSDENQMDLTSSHTVMITKGLLDNPISEKSTKIDTTSFLANLKLHTEDSRMKKEVNFSVDQNTSSE
NKIDFNDFIKRLKTGKCSAFPDVPDKENFEIPIYSKEPNSASSTHQMHVSLKEDENNSNITRLFREKDDG
MNFTQCHTANIQTLLIPTSSETNSRESKGNDITIYGNDFMDLTFNHTLQILPATGNFSEIENQTQNAMDVT
TGYGTKASGNKTVFKSKQNTAFQDLSINSADKIHITRSHIMGAETHIVSQTCNQDARILAMTPESIYSNP
SIQGCKTVFYSSCNDAMEMTKCLSNMREEKNLLKHDSNYAKMYCNPDAMSSLTEKTIYSGEENMDITKSH
TVAIDNQIFKQDQSNVQIAAAPTPEKEMMLQNLMTTSEDGKMNVNCNSVPHVSKERIQQSLSNPLSISLT
DRKTELLSGENMDLTESHTSNLGSQVPLAAYNLAPESTSESHSQSKSSSDECEEITKSRNEPFQRSDIIA
KNSLTDTWNKDKDWVLKILPYLDKSPQSADCNQEIATSHNIVYCGGVLDKQITNRNTVSWEQSLFSTTK
PLFSSGQFSMKNHDTAISSHTVKSVLGQNSKLAEPLRKSLSNPTPDYCHDKMIICSEEEQNMDLTKSHTV
VIGFGPSELQELGKTNLEHTTGQLTTMNRQIAVKVEKCGKSPIEKSGVLKSNCIMDVLEDESVQKPKFPK
EKQNVKIWGRKSVGGPKIDKTIVFSEDDKNDMDITKSYTIEINHRPLLEKRDCHLVPLAGTSETILYTCR
QDDMEITRSHTTALECKTVSPDEITTRPMDKTVVFVDNHVELEMTESHTVFIDYQEKERTDRPNFELSQR
KSLGTPTVICTPTEESVFFPGNGESDRLVANDSQLTPLEEWSNNRGPVEVADNMELSKSATCKNIKDVQS
PGFLNEPLSSKSQRRKSLKLKNDKTIVFSENHKNDMDITQSCMVTDLDGTLFPEAFDLPNLFSDSGFEGL
CGQDDMEITRSHTTALECKTLLPNEIAIRPMDKTVLFTDNYSDLEVTDSHTVFIDCQATEKILEENPKFG
IGKGKNLGVSFPKDNSCVQEIAEKQALAVGNKIVLHTEQKQQLFAATNRTTNEIIKPFHSAAMDEKVIGKV
VDQACTLEKAQVESCQLNNRDRRNVDFTSSHATAVCGSSDNYSCLPNVISCTDNLEGSAMLLCDKDEEKA
NYCPVQNDLAYANDFASEYYLESEGQPLSAPCPLLEKEEVIQTSTKGQLDCVITLHKDQDLIKDPRNLLA
NQTLVYSQDLGEMTKLNSKRVSFKLPKDQMKVYDDIYVIPQPHFSTDQPPLPKKGQSSINKEEVILSKA
GNKSLNIIENSSAPICENKPKILNSEEWFAAACKKELKENIQTTNYNTALDFHSNSDVTKQVIQTHVNAG
EAPDPVITSNVPCFHSIKPNLNNLNGKTGEFLAFQTVHLPPLPEQLLELGNKAHNDMHIVQATEIHNINI
ISSNAKDSRDEENKKSHNGAETTSLPPKTVFKDKVRRCSLGIFLPRLPNKSNCIMDVLEDLEQIPADTTD
INHLETQPVSSKDSGIGSVAGKLNLSPSQYINEENLPVYPDEINSSDSINIETEEKALIETYQKEISPYE
NKMGKTCNSQKRTWVQEEEDIHKEKKIRKNEIKFSDTTQDREIFDHHTEEDIDKSANSVLIKNLSRTPSS
CSSSLDSIKADGTSLDFSTYRSSQMESQFLRDTICEESLREKLQDGRITIREFFILLQVHILIQKPRQSN
LPGNFTVNTPPTPEDLMLSQYVYRPKIQIYREDCEARRQKIEELKLSASNQDKLLVDINKNLWEKMRHCS
DKELKAFGIYLNKISCFTKMTKVFTHQGKVALYGKLVQSAQNEREKLQIKIDEMDKILKKIDNCLTEME -continued
TETKNLEDEEKNNPVEEWDSEMRAAEKELEQLKTEEEELQRNLLELEVQKEQTLAQIDFMQKQRNRTEEL
LDQLSLSEWDVVEWSDDQAVFTFVYDTIQLTITFEESVVGFPFLDKRYRKIVDVNFQSLLDEDQAPPSSL
LVHKLIFQYVEEKESWKKTCTTQHQLPKMLEEFSLVVHHCRLLGEEIEYLKRWGPNYNLMNIDINNNELR
LLFSSSAAFAKFEITLFLSAYYPSVPLPSTIQNHVGNTSQDDIATILSKVPLENNYLKNVVKQIYQDLFQ
DCHFYH (SEQ ID NO: 34)

>gi|444299649|ref|NP_733468.3| protein CASC5 isoform 1 sapiens+
MDGVSSEANEENDNIERPVRRRHSSILKPPRSPLQDLRGGNERVQESNALRNKKNSRRVSFADTIKVFQT
ESHMKIVRKSEMEGCSAMVPSQLQLLPPGFKRFSCLSLPETETGENLLLIQNKKLEDNYCEITGMNTLLS
APIHTQMQQKEFSIIEHTRERKHANDQTVIFSDENQMDLTSSHTVMITKGLLDNPISEKSTKIDTTSFLA
NLKLHTEDSRMKKEVNFSVDQNTSSENKIDFNDFIKRLKTGKCSAFPDVPDKENFEIPIYSKEPNSASST
HQMHVSLKEDENNSNITRLFREKDDGMNFTQCHTANIQTLIPTSSETNSRESKGNDITIYGNDFMDLTFN
HTLQILPATGNFSEIENQTQNAMDVTTGYGTKASGNKTVFKSKQNTAFQDLSINSADKIHITRSHIMGAE
THIVSQTCNQDARILAMTPESIYSNPSIQGCKTVFYSSCNDAMEMTKCLSNMREEKNLLKHDSNYAKMYC
NPDAMSSLTEKTIYSGEENMDITKSHTVAIDNQIFKQDQSNVQIAAAPTPEKEMMLQNLMTTSEDGKMNV
NCNSVPHVSKERIQQSLSNPLSISLTDRKTELLSGENMDLTESHTSNLGSQVPLAAYNLAPESTSESHSQ
SKSSSDECEEITKSRNEPFQRSDIIAKNSLTDTWNKDKDWVLKILPYLDKDSPQSADCNQEIATSHNIVY
CGGVLDKQITNRNTVSWEQSLFSTTKPLFSSGQFSMKNHDTAISSHTVKSVLGQNSKLAEPLRKSLSNPT
PDYCHDKMIICSEEEQNMDLTKSHTVVIGFGPSELQELGKTNLEHTTGQLTTMNRQIAVKVEKCGKSPIE
KSGVLKSNCIMDVLEDESVQKPKFPKEKQNVKIWGRKSVGGPKIDKTIVFSEDDKNDMDITKSYTIEINH
RPLLEKRDCHLVPLAGTSETILYTCRQDDMEITRSHTTALECKTVSPDEITTRPMDKTVVFVDNHVELEM
TESHTVFIDYQEKERTDRPNFELSQRKSLGTPTVICTPTEESVFFPGNGESDRLVANDSQLTPLEEWSNN
RGPVEVADNMELSKSATCKNIKDVQSPGFLNEPLSSKSQRRKSLKLKNDKTIVFSENHKNDMDITQSCMV
EIDNESALEDKEDFHLAGASKTILYSCGQDDMEITRSHTTALECKTLLPNEIAIRPMDKTVLFTDNYSDL
EVTDSHTVFIDCQATEKILEENPKFGIGKGKNLGVSFPKDNSCVQEIAEKQALAVGNKIVLHTEQKQQLF
AATNRTTNEIIKFHSAAMDEKVIGKVVDQACTLEKAQVESCQLNNRDRRNVDFTSSHATAVCGSSDNYSC
LPNVISCTDNLEGSAMLLCDKDEEKANYCPVQNDLAYANDFASEYYLESEGQPLSAPCPLLEKEEVIQTS
TKGQLDCVITLHKDQDLIKDPRNLLANQTLVYSQDLGEMTKLNSKRVSFKLPKDQMKVYVDDIYVIPQPH
FSTDQPPLPKKGQSSINKEEVILSKAGNKSLNIIENSSAPICENKPKILNSEEWFAAACKKELKENIQTT
NYNTALDFHSNSDVTKQVIQTHVNAGEAPDPVITSNVPCFHSIKPNLNNLNGKTGEFLAFQTVHLPPLPE
QLLELGNKAHNDMHIVQATEIHNINIISSNAKDSRDEENKKSHNGAETTSLPPKTVFKDKVRRCSLGIFL
PRLPNKRNCSVTGIDDLEQIPADTTDINHLETQPVSSKDSGIGSVAGKLNLSPSQYINEENLPVYPDEIN
SSDSINIETEEKALIETYQKEISPYENKMGKTCNSQKRTWVQEEEDIHKEKKIRKNEIKFSDTTQDREIF
DHHTEEDIDKSANSVLIKNLSRTPSSCSSSLDSIKADGTSLDFSTYRSQMESQFLRDTICEESLREKLQ
DGRITIREFFILLQVHILIQKPRQSNLPGNFTVNTPPTPEDLMLSQYVYRPKIQIYREDCEARRQKIEEL
KLSASNQDKLLVDINKNLWEKMRHCSDKELKAFGIYLNKIKSCFTKMTKVFTHQGKVALYGKLVQSAQNE
REKLQIKIDEMDKILKKIDNCLTEMETETKNLEDEEKNNPVEEWDSEMRAAEKELEQLKTEEEELQRNLL
ELEVQKEQTLAQIDFMQKQRNRTEELLDQLSLSEWDVVEWSDDQAVFTFVYDTIQLTITFEESVVGFPFL
DKRYRKIVDVNFQSLLDEDQAPPSSLLVHKLIFQYVEEKESWKKTCTTQHQLPKMLEEFSLVVHHCRLLG
EEIEYLKRWGPNYNLMNIDINNNELRLLFSSSAAFAKFEITLFLSAYYPSVPLPSTIQNHVGNTSQDDIA
TILSKVPLENNYLKNVVKQIYQDLFQDCHFYH (SEQ ID NO: 35)

>gi|119612836|gb|EAW92430.1| cancer susceptibility candidate 5, isoform
CRA_b [Homo sapiens]
MDGVSSEANEENDNIERPVRRRHSSILKPPRSPLQDLRGGNERVQESNALRNKKNSRRVSFADTIKVFQT
ESHMKIVRKSEMEETETGENLLLIQNKKLEDNYCEITGMNTLLSAPIHTQMQQKEFSIIEHTRERKHAND
QTVIFSDENQMDLTSSHTVMITKGLLDNPISEKSTKIDTTSFLANLKLHTEDSRMKKEVNFSVDQNTSSE
NKIDENDFIKRLKTGKCSAFPDVPDKENFEIPIYSKEPNSASSTHQMHVSLKEDENNSNITRLFREKDDG
MNFTQCHTANIQTLIPTSSETNSRESKGNDITIYGNDFMDLTFNHTLQILPATGNFSEIENQTQNAMDVT
TGYGTKASGNKTVFKSKQNTAFQDLSINSADKIHITRSHIMGAETHIVSQTCNQDARILAMTPESIYSNP
SIQGCKTVFYSSCNDAMEMTKCLSNMREEKNLLKHDSNYSKMYCNPDAMSSLTEKTIYSGEENMDITKSH
TVAIDNQIFKQDQSNVQIAAAPTPEKEMMLQNLMTTSEDGKMNVNCNSVPHVSKERIQQSLSNPLSISLT
DRKTELLSGENMDLTESHTSNLGSQVPLAAYNLAPESTSESHSQSKSSSDECEEITKSRNEPFQRSDIIA
KNSLTDTWNKDKDWVLKILPYLDKDSPQSADCNQEIATSHNIVYCGGVLDKQITNRNTVSWEQSLFSTTK
PLFSSGQFSMKNHDTAISSHTVKSVLGQNSKLAEPLRKSLSNPTPDYCHDKMIICSEEEQNMDLTKSHTV
VIGFGPSELQELGKTNLEHTTGQLTTMNRQIAVKVEKCGKSPIEKSGVLKSNCIMDVLEDESVQKPKFPK
EKQNVKIWGRKSVGGPKIDKTIVFSEDDKNDMDITKSYTIEINHRPLLEKRDCHLVPLAGTSETILYTCG
QDDMEITRSHTTALECKTVSPDEITTRPMDKTVVFVDNHVELEMTESHTVFIDYQEKERTDRPNFELSQR
KSLGTPTVICTPTEESVFFPGNGESDRLVANDSQLTPLEEWSNNRGPVEVADNMELSKSATCKNIKDVQS
PGFLNEPLSSKSQRRKSLKLKNDKTIVFSENHKNDMDITQSCMVEIDNESALEDKEDFHLAGASKTILYS
CGQDDMEITRSHTTALECKTLLPNEIAIRPMDKTVLFTDNYSDLEVTDSHTVFIDCQATEKILEENPKFG
IGKGKNLGVSFPKDNSCVQEIAEKQALAVGNKIVLHTEQKQQLFAATNRTTNEIIKFHSAAMDEKVIGKV
VDQACTLEKAQVESCQLNNRDRRNVDFTSSHATAVCGSSDNYSCLPNVISCTDNLEGSAMLLCDKDEEKA
NYCPVQNDLAYANDFASEYYLESEGQPLSAPCPLLEKEEVIQTSTKGQLDCVITLHKDQDLIKDPRNLLA
NQTLVYSQDLGEMTKLNSKRVSFKLPKDQMKVYVDDIYVIPQPHFSTDQPPLPKKGQSSINKEEVILSKA
GNKSLNIIENSSAPICENKPKILNSEEWFAAACKKELKENIQTTNYNTALDFHSNSDVTKQVIQTHVNAG
EAPDPVITSNVPCFHSIKPNLNNLNGKTGEFLAFQTVHLPPLPEQLLELGNKAHNDMHIVQATEIHNINI
ISSNAKDSRDEENKKSHNGAETTSLPPKTVFKDKVRRCSVTGIDDLEQIPADTTD
INHLETQPVSSKDSGIGSVAGKLNLSPSQYINEENLPVYPDEINSSDSINIETEEKALIETYQKEISPYE
NKMGKTCNSQKRTWVQEEEDIHKEKKIRKNEIKFSDTTQDREVSSVLNQRMFLNFGFCFVFLNCGYSQIL
ILVSGRQKIIIST (SEQ ID NO: 36)

>gi|119612835|gb|EAW92429.1| cancer susceptibility candidate 5, isoform
CRA_a, partial [Homo sapiens]
MDGVSSEANEENDNIERPVRRRHSSILKPPRSPLQDLRGGNERVQESNALRNKKNSRRVSFADTIKVFQT
ESHMKIVRKSEMEETETGENLLLIQNKKLEDNYCEITGMNTLLSAPIHTQMQQKEFSIIEHTRERKHAND
QTVIFSDENQMDLTSSHTVMITKGLLDNPISEKSTKIDTTSFLANLKLHTEDSRMKKEVNFSVDQNTSSE
NKIDENDFIKRLKTGKCSAFPDVPDKENFEIPIYSKEPNSASSTHQMHVSLKEDENNSNITRLFREKDDG
MNFTQCHTANIQTLIPTSSETNSRESKGNDITIYGNDFMDLTFNHTLQILPATGNFSEIENQTQNAMDVT
TGYGTKASGNKTVFKSKQNTAFQDLSINSADKIHITRSHIMGAETHIVSQTCNQDARILAMTPESIYSNP
SIQGCKTVFYSSCNDAMEMTKCLSNMREEKNLLKHDSNYSKMYCNPDAMSSLTEKTIYSGEENMDITKSH -continued TVAIDNQIFKQDQSNVQIAAAPTPEKEMMLQNLMTTSEDGKMNVNCNSVPHVSKERIQQSLSNPLSISLT
DRKTELLSGENMDLTESHTSNLGSQVPLAAYNLAPESTSESHSQSKSSSDECEEITKSRNEPFQRSDIIA
KNSLTDTWNKDKDWVLKILPYLDKDSPQSADCNQEIATSHNIVYCGGVLDKQITNRNTVSWEQSLFSTTK
PLFSSGQFSMKNHDTAISSHTVKSVLGQNSKLAEPLRKSLSNPTPDYCHDKMIICSEEEQNMDLTKSHTV
VIGFGPSELQELGKTNLEHTTGQLTTMNRQIAVKVEKCGKSPIEKSGVLKSNCIMDVLEDESVQKPKFPK
EKQNVKIWGRKSVGGPKIDKTIVFSEDDKNDMDITKSYTIEINHRPLLEKRDCHLVPLAGTSETILYTCG
QDDMEITRSHTTALECKTVSPDEITTRPMDKTVVFVDNHVELEMESHTVFIDYQEKERTDRPNFELSQR
KSLGTPTVICTPTEESVFFPGNGESDRLVANDSQLTPLEEWSNNRGPVEVADNMELSKSATCKNIKDVQS
PGFLNEPLSSKSQRRKSLKLKNDKTIVFSENHKNDMDITQSCMVEIDNESALEDKEDFHLAGASKTILYS
CGQDDMEITRSHTTALECKTLLPNEIAIRPMDKTVLFTDNYSDLEVTDSHTVFIDCQATEKILEENPKFG
IGKGKNLGVSFPKDNSCVQEIAEKQALAVGNKIVLHTEQKQQLFAATNRTTNEIIKFHSAAMDEKVIGKV
VDQCATLEKAQVESCQLNNRDRRNVDFTSSHATAVCGSSDNYSCLPNVISCTDNLEGSAMLLCDKDEEKA
NYCPVQNDLAYANDFASEYYLESEGQPLSAPCPLLEKEEVIQTSTKGQLDCVITLHKDQDLIKDPRNLLA
NQTLVYSQDLGEMTKLNSKRVSFKLPKDQMKVYVDDIYVIPQPHFSTDQPPLPKKGQSSINKEEVILSKA
GNKSLNIIENSSAPICENKPKILNSEEWFAAACKKELKENIQTTNYNTALDFHSNSDVTKQVIQTHVNAG
EAPDPVITSNVPCFHSIKPNLNNLNGKTGEFLAFQTVHLPPLPEQLLELGNKAHNDMHIVQATEIHNINI
ISSNAKDSRDEENKKSHNGAETTSLPPKTVFKDKVRRCSLGIFLPRLPNKRNCSVTGIDDLEQIPADTTD
INHLETQPVSSKDSGIGSVAGKLNLSPSQYINEENLPVYPDEINSSDSINIETEEKALIETYQKEISPYE
NKMGKTCNSQKRTWVQEEEDIHKEKKIRKNEIKFSDTTQDREIFDHHTEEDIDKSANSVLIKNLSRTPSS
CSSSLDSIKADGTSLDFSTYRSSQMESQFLRDTICEESLREKLQDGRITIREFFILLQVHILIQKPRQSN
LPGNFTVNTPPTPEDLMLSQYVYRPKIQIYREDCEARRQKIEELKLSASNQDKLLVDINKNLWEKMRHCS
DKELKAFGIYLNKIKSCFTKMTKVFTHQGKVALYGKLVQSAQNEREKLQIKIDEMDKILKKIDNCLTEME
TETKNLEDEEKNNPVEEWDSEMRAAEKELEQLKTEEEELQRNLLELEVQKEQTLAQIDFMQKQRNRTEEL
LDQLSLSEWDVVEWSDDQAVFTFVYDTIQLTITFEESVVGFPFLDKRYRKIVDVNFQSLLDEDQAPPSSL
LVHKLIFQYVEEKESWKKTCTTQHQL (SEQ ID NO: 37)

>gi|110349759|ref|NP_056286.3| kinetochore-associated protein NSL1 homolog
isoform 1 [Homo sapiens]
MAGSPELVVLDPPWDKELAAGTESQALVSATPREDFRVRCTSKRAVTEMLQLCGRFVQKLGDALPEEIRE
PALRDAQWTFESAVQENISINGQAWQEASDNCFMDSDIKVLEDQFDEIIVDIATKRKQYPRKILECVIKT
IKAKQEILKQYHPVVHPLDLKYDPDPAPHMENLKCRGETVAKEISEAMKSLPALIEQGEGFSQVLRMQPV
IHLQRIHQEVFSSCHRKPDAKPENFITQIETTPTETASRKTSDMVLKRKQTKDCPQRKWYPLRPKKINLD
T (SEQ ID NO: 38)

>gi|110349761|ref|NP_001036014.1| kinetochore-associated protein NSL1
homolog isoform 2 [Homo sapiens]
MAGSPELVVLDPPWDKELAAGTESQALVSATPREDFRVRCTSKRAVTEMLQLCGRFVQKLGDALPEEIRE
PALRDAQWTFESAVQENISINGQAWQEASDNCFMDSDIKVLEDQFDEIIVDIATKRKQYPRKILECVIKT
IKAKQEILKQYHPVVHPLDLKYDPDPVLNGNAFNFSPFNMMLAVDLSYMVFITSSPSYGKFEMQRGNSSK
GDQ (SEQ ID NO: 39)

>gi|223972618|ref|NP_079194.3| kinetochore-associated protein DSN1 homolog
isoform 1 [Homo sapiens]
MTSVTRSEIIDEKGPVMSKTHDHQLESSLSPVEVFAKTSASLEMNQGVSEERIHLGSSPKKGGNCDLSHQ
ERLQSKSLHLSPQEQSASYQDRRQSWRRASMKETNRRKSLHPIHQGITELSRSISVDLAESKRLGCLLLS
SFQFSIQKLEPFLRDTKGFSLESFRAKASSLSEELKHFADGLETDGTLQKCFEDSNGKASDFSLEASVAE
MKEYITKFSLERQTWDQLLLHYQQEAKEILSRGSTEAKITEVKVEPMTYLGSSQNEVLNTKPDYQKILQN
QSKVFDCMELVMDELQGSVKQLQAFMDESTQCFQKVSVQLGKRSMQQLDPSPARKLLKLQLQNPPAIHGS
GSGSCQ (SEQ ID NO: 40)

>gi|223890153|ref|NP_001138790.1| kinetochore-associated protein DSN1
homolog isoform 3 [Homo sapiens]
MSKTHDHQLESSLSPVEVFAKTSASLEMNQGVSEERIHLGSSPKKGGNCDLSHQERLQSKSLHLSPQEQS
ASYQDRRQSWRRASMKETNRRKSLHPIHQGITELSRSISVDLAESKRLGCLLLSSFQFSIQKLEPFLRDT
KGFSLESFRAKASSLSEELKHFADGLETDGTLQKCFEDSNGKASDFSLEASVAEMKEYITKFSLERQTWD
QLLLHYQQEAKEILSRGSTEAKITEVKVEPMTYLGSSQNEVLNTKPDYQKILQNQSKVFDCMELVMDELQ
GSVKQLQAFMDESTQCFQKVSVQLGKRSMQQLDPSPARKLLKLQLQNPPAIHGSGSGSCQ
(SEQ ID NO: 41)

>gi|223890151|ref|NP_001138789.1| kinetochore-associated protein DSN1
homolog isoform 2 [Homo sapiens]
MTSVTRSEIIDELSRSISVDLAESKRLGCLLLSSFQFSIQKLEPFLRDTKGFSLESFRAKASSLSEELKH
FADGLETDGTLQKCFEDSNGKASDFSLEASVAEMKEYITKFSLERQTWDQLLLHYQQEAKEILSRGSTEA
KITEVKVEPMTYLGSSQNEVLNTKPDYQKILQNQSKVFDCMELVMDELQGSVKQLQAFMDESTQCFQKVS
VQLGKRSMQQLDPSPARKLLKLQLQNPPAIHGSGSGSCQ (SEQ ID NO: 42)

>gi|74735330|sp|O14777.1| NDC80_HUMAN RecName: Full = Kinetochore protein
NDC80 homolog; AltName: Full = Highly expressed in cancer protein; AltName:
Full = inetochore protein Hec1; Short = HsHec1; AltName: Full = Kinetochore-
associated protein 2; AltName: Full = Retinoblastoma-associated protein HEC
MKRSSVSSGGAGRLSMQELRSQDVNKQGLYTPQTKEKPTFGKLSINKPTSERKVSLFGKRTSGHGSRNSQ
LGIFSSSEKIKDPRPLNDKAFIQQCIRQLCEFLTENGYAHNVSMKSLQAPSVKDFLKIFTFLYGFLCPSY
ELPDTKFEEEVPRIFKDLGYPFALSKSSMYTVGAPHTWPHIVAALVWLIDCIKIHTAMKESSPLFDDGQP
WGEETEDGIMHNKLFLDYTIKCYESFMSGADSFDEMNAELQSKLKDLFNVDAFKLESLEAKNRALNEQIA
RLEQEREKEPNRLESLRKLKASLQGDVQKYQAYMSNLESHSAILDQKLNGLNEEIARVELECETIKQENT
RLQNIIDNQKYSVADIERINHERNELQQTINKLTKDLEAEQQKLWNEELKYARGKEAIETQLKEENHKLAR
KLKLIPKGAENSKGYDFEIKFNPEAGANCLVKYRAQVYPLKELLNETEEEINKALNKKMGLEDTLEQLN
AMITESKRSVRTLKEEVQKLDDLYQQKIKEAEEEDEKCASELESLEKHKHLLESTVNQGLSEAMNELDAV
QREYQLVVQTTTEERRKVGNNLQRLLEMVATHVGSVEKHLEEQIAKVDREYEECMSEDLSENIKEIRDKY
EKKATLIKSSEE (SEQ ID NO: 43)

>gi|32698866|ref|NP_872319.1| kinetochore protein Spc24 [Homo sapiens]
MAAFRDIEEVSQGLLSLLGANRAEAQQRRLLGRHEQVVERLLETQDGAEKQLREILTMEKEVAQSLLNAK
EQVHQGGVELQQLEAGLQEAGEEDTRLKASLLQLTRELEELKEIEADLERQEKEVDEDTTVTIPSAVYVA
QLYHQVSKIEWDYECEPGMVKGIHHGPSVAQPIHLDSTQLSRKFISDYLWSLVDTEW (SEQ ID NO: 44)

>gi|48146511|emb|CAG33478.1| Spc25 [Homo sapiens]
MVEDELALFDKSINEFWNKFKSTDTSCQMAGLRDTYKDSIKAFAEKLSVKLKEEERMVEMFLEYQNQISR
QNKLIQEKKDNLLKLIAEVKGKKQELEVLTANIQDLKEEYSRKKETISTANKANAERLKRLQKSADLYKD
RLGLEIRKIYGEKLQFIFTNIDPKNPESPFMFSLHLNEARDYEVSDSAPHLEGLAEFQENVRKTNNFSAF
LANVRKAFTATVYN (SEQ ID NO: 45)

>gi|115311829|sp|Q9BZD4.2| NUF2_HUMAN RecName: Full = Kinetochore protein
Nuf2; Short = hNuf2; Short = hNuf2R; Short = hsNuf2; AltName: Full = Cell division
cycle-associated protein 1
METLSFPRYNVAEIVIHIRNKILTGADGKNLTKNDLYPNPKPEVLHMIYMRALQIVYGIRLEHFYMMPVN
SEVMYPHLMEGFLPFSNLVTHLDSFLPICRVNDFETADILCPKAKRTSRFLSGIINFIHFREACRETYME
FLWQYKSSADKMQQLNAAHQEALMKLERLDSVPVEEQEEFKQLSDGIQELQQSLNQDFHQKTIVLQEGNS
QKKSNISEKTKRLNELKLSVVSLKEIQESLKTKIVDSPEKLKNYKEKMKDTVQKLKNARQEVVEKYEIYG
DSVDCLPSCQLEVQLYQKKIQDLSDNREKLASILKESLNLEDQIESDESELKKLKTEENSFKRLMIVKKE
KLATAQFKINKKHEDVKQYKRTVIEDCNKVQEKRGAVYERVTTINQEIQKIKLGIQQLKDAAEREKLKSQ
EIFLNLKTALEKYHDGIEKAAEDSYAKIDEKTAELKRKMFKMST (SEQ ID NO: 46)

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A microarray for detecting expression of a gene panel for predicting likelihood of cancer progression in a patient, wherein the microarray consists of: CENP-A, HJURP, M1S18B, CENP-N, CENP-M, CENP-W, CENP-U, CENP-L, CENP-K, ZWINT, NDC80, NUF2, SPC24, and SPC25; and wherein the probes are immobilized by covalent bonds to a solid support, and each probe is 15 to 80 nucleotides in length.

2. A hybridization assay composition comprising the microarray of claim 1 and an RNA sample obtained sample from a tumor from a patient that has cancer; or a cDNA obtained from RNA from the tumor.

3. The hybridization assay of claim 2, wherein the the tumor is from early stage breast cancer, an early stage non-small cell lung cancer, or an early stage ovarian cancer.

4. The hybridization assay of claim 3, wherein the breast cancer is luminal A.

5. The hybridization assay of claim 3, wherein the breast cancer is luminal B.

6. The hybridization assay of claim 3, wherein the breast cancer is breast cancer is ER positive breast cancer.

7. A kit comprising amplification primers and probes, wherein the amplification primers and probes consist of amplification primers and probes that are specific for amplifying and detecting expression of a gene panel consisting of: CENP-A, HJURP, M1S18B, CENP-N, CENP-M, CENP-W, CENP-U, CENP-L, CENP-K, ZWINT, NDC80, NUF2, SPC24, and SPC25; and wherein the amplification primers or probes, or both the amplification primers and probes, are attached to a detectable label that is a radioisotope, a fluorophore, a chemiluminescent agent, or an enzyme.

* * * * *

SEQUENCE LISTING

```
<160> NUMBER OF SEQ ID NOS: 46

<210> SEQ ID NO 1
<211> LENGTH: 140
<212> TYPE: PRT
<213> ORGANISM: Homo sapiens

<400> SEQUENCE: 1

Met Gly Pro Arg Arg Ser Arg Lys Pro Glu Ala Pro Arg Arg
1               5                   10                  15

Ser Pro Ser Pro Thr Pro Thr Pro Gly Pro Ser Arg Arg Gly Pro Ser
            20                  25                  30

Leu Gly Ala Ser Ser His Gln His Ser Arg Arg Arg Gln Gly Trp Leu
        35                  40                  45

Lys Glu Ile Arg Lys Leu Gln Lys Ser Thr His Leu Leu Ile Arg Lys
    50                  55                  60

Leu Pro Phe Ser Arg Leu Ala Arg Glu Ile Cys Val Lys Phe Thr Arg
65                  70                  75                  80

Gly Val Asp Phe Asn Trp Gln Ala Gln Ala Leu Leu Ala Leu Gln Glu
                85                  90                  95

Ala Ala Glu Ala Phe Leu Val His Leu Phe Glu Asp Ala Tyr Leu Leu
            100                 105                 110

Thr Leu His Ala Gly Arg Val Thr Leu Phe Pro Lys Asp Val Gln Leu
        115                 120                 125

Ala Arg Arg Ile Arg Gly Leu Glu Glu Gly Leu Gly
    130                 135                 140

<210> SEQ ID NO 2
<211> LENGTH: 748
<212> TYPE: PRT
<213> ORGANISM: Homo sapiens

<400> SEQUENCE: 2

Met Leu Gly Thr Leu Arg Ala Met Glu Gly Glu Asp Val Glu Asp Asp
1               5                   10                  15

Gln Leu Leu Gln Lys Leu Arg Ala Ser Arg Arg Arg Phe Gln Arg Arg
```

-continued

```
             20                  25                  30
Met Gln Arg Leu Ile Glu Lys Tyr Asn Gln Pro Phe Glu Asp Thr Pro
             35                  40                  45

Val Val Gln Met Ala Thr Leu Thr Tyr Glu Thr Pro Gln Gly Leu Arg
             50                  55                  60

Ile Trp Gly Gly Arg Leu Ile Lys Glu Arg Asn Glu Gly Glu Ile Gln
 65                  70                  75                  80

Asp Ser Ser Met Lys Pro Ala Asp Arg Thr Asp Gly Ser Val Gln Ala
                     85                  90                  95

Ala Ala Trp Gly Pro Glu Leu Pro Ser His Arg Thr Val Leu Gly Ala
                    100                 105                 110

Asp Ser Lys Ser Gly Glu Val Asp Ala Thr Ser Asp Gln Glu Glu Ser
                115                 120                 125

Val Ala Trp Ala Leu Ala Pro Ala Val Pro Gln Ser Pro Leu Lys Asn
            130                 135                 140

Glu Leu Arg Arg Lys Tyr Leu Thr Gln Val Asp Ile Leu Leu Gln Gly
145                 150                 155                 160

Ala Glu Tyr Phe Glu Cys Ala Gly Asn Arg Ala Gly Arg Asp Val Arg
                165                 170                 175

Val Thr Pro Leu Pro Ser Leu Ala Ser Pro Ala Val Pro Ala Pro Gly
                180                 185                 190

Tyr Cys Ser Arg Ile Ser Arg Lys Ser Pro Gly Asp Pro Ala Lys Pro
                195                 200                 205

Ala Ser Ser Pro Arg Glu Trp Asp Pro Leu His Pro Ser Ser Thr Asp
            210                 215                 220

Met Ala Leu Val Pro Arg Asn Asp Ser Leu Ser Leu Gln Glu Thr Ser
225                 230                 235                 240

Ser Ser Ser Phe Leu Ser Ser Gln Pro Phe Glu Asp Asp Asp Ile Cys
                245                 250                 255

Asn Val Thr Ile Ser Asp Leu Tyr Ala Gly Met Leu His Ser Met Ser
                260                 265                 270

Arg Leu Leu Ser Thr Lys Pro Ser Ser Ile Ile Ser Thr Lys Thr Phe
            275                 280                 285

Ile Met Gln Asn Trp Asn Ser Arg Arg Arg His Arg Tyr Lys Ser Arg
            290                 295                 300

Met Asn Lys Thr Tyr Cys Lys Gly Ala Arg Arg Ser Gln Arg Ser Ser
305                 310                 315                 320

Lys Glu Asn Phe Ile Pro Cys Ser Glu Pro Val Lys Gly Thr Gly Ala
                325                 330                 335

Leu Arg Asp Cys Lys Asn Val Leu Asp Val Ser Cys Arg Lys Thr Gly
                340                 345                 350

Leu Lys Leu Glu Lys Ala Phe Leu Glu Val Asn Arg Pro Gln Ile His
            355                 360                 365

Lys Leu Asp Pro Ser Trp Lys Glu Arg Lys Val Thr Pro Ser Lys Tyr
            370                 375                 380

Ser Ser Leu Ile Tyr Phe Asp Ser Ser Ala Thr Tyr Asn Leu Asp Glu
385                 390                 395                 400

Glu Asn Arg Phe Arg Thr Leu Lys Trp Leu Ile Ser Pro Val Lys Ile
                405                 410                 415

Val Ser Arg Pro Thr Ile Arg Gln Gly His Gly Glu Asn Arg Gln Arg
                420                 425                 430

Glu Ile Glu Ile Arg Phe Asp Gln Leu His Arg Glu Tyr Cys Leu Ser
            435                 440                 445
```

```
Pro Arg Asn Gln Pro Arg Arg Met Cys Leu Pro Asp Ser Trp Ala Met
    450                 455                 460

Asn Met Tyr Arg Gly Gly Pro Ala Ser Pro Gly Gly Leu Gln Gly Leu
465                 470                 475                 480

Glu Thr Arg Arg Leu Ser Leu Pro Ser Ser Lys Ala Lys Ala Lys Ser
                485                 490                 495

Leu Ser Glu Ala Phe Glu Asn Leu Gly Lys Arg Ser Leu Glu Ala Gly
            500                 505                 510

Arg Cys Leu Pro Lys Ser Asp Ser Ser Ser Leu Pro Lys Thr Asn
        515                 520                 525

Pro Thr His Ser Ala Thr Arg Pro Gln Gln Thr Ser Asp Leu His Val
    530                 535                 540

Gln Gly Asn Ser Ser Gly Ile Phe Arg Lys Ser Val Ser Pro Ser Lys
545                 550                 555                 560

Thr Leu Ser Val Pro Asp Lys Glu Val Pro Gly His Gly Arg Asn Arg
                565                 570                 575

Tyr Asp Glu Ile Lys Glu Glu Phe Asp Lys Leu His Gln Lys Tyr Cys
            580                 585                 590

Leu Lys Ser Pro Gly Gln Met Thr Val Pro Leu Cys Ile Gly Val Ser
        595                 600                 605

Thr Asp Lys Ala Ser Met Glu Val Arg Tyr Gln Thr Glu Gly Phe Leu
610                 615                 620

Gly Lys Leu Asn Pro Asp Pro His Phe Gln Gly Phe Gln Lys Leu Pro
625                 630                 635                 640

Ser Ser Pro Leu Gly Cys Arg Lys Ser Leu Leu Gly Ser Thr Ala Ile
                645                 650                 655

Glu Ala Pro Ser Ser Thr Cys Val Ala Arg Ala Ile Thr Arg Asp Gly
            660                 665                 670

Thr Arg Asp His Gln Phe Pro Ala Lys Arg Pro Arg Leu Ser Glu Pro
        675                 680                 685

Gln Gly Ser Gly Arg Gln Gly Asn Ser Leu Gly Ala Ser Asp Gly Val
    690                 695                 700

Asp Asn Thr Val Arg Pro Gly Asp Gln Gly Ser Ser Ser Gln Pro Asn
705                 710                 715                 720

Ser Glu Glu Arg Gly Glu Asn Thr Ser Tyr Arg Met Glu Glu Lys Ser
                725                 730                 735

Asp Phe Met Leu Glu Lys Leu Glu Thr Lys Ser Val
            740                 745

<210> SEQ ID NO 3
<211> LENGTH: 694
<212> TYPE: PRT
<213> ORGANISM: Homo sapiens

<400> SEQUENCE: 3

Met Leu Gly Thr Leu Arg Ala Met Glu Gly Glu Asp Val Glu Asp Asp
1               5                   10                  15

Gln Leu Leu Gln Lys Leu Arg Ala Ser Arg Arg Phe Gln Arg Arg
            20                  25                  30

Met Gln Arg Leu Ile Glu Lys Tyr Asn Gln Pro Phe Glu Asp Thr Pro
        35                  40                  45

Val Val Gln Met Ala Thr Leu Thr Tyr Glu Thr Pro Gln Gly Leu Arg
    50                  55                  60

Ile Trp Gly Gly Arg Leu Ile Lys Glu Arg Asn Glu Gly Glu Ile Gln
```

-continued

```
            65                  70                  75                  80
Pro Ala Val Pro Gln Ser Pro Leu Lys Asn Glu Leu Arg Arg Lys Tyr
                    85                  90                  95

Leu Thr Gln Val Asp Ile Leu Leu Gln Gly Ala Glu Tyr Phe Glu Cys
                100                 105                 110

Ala Gly Asn Arg Ala Gly Arg Asp Val Arg Val Thr Pro Leu Pro Ser
            115                 120                 125

Leu Ala Ser Pro Ala Val Pro Ala Pro Gly Tyr Cys Ser Arg Ile Ser
        130                 135                 140

Arg Lys Ser Pro Gly Asp Pro Ala Lys Pro Ala Ser Ser Pro Arg Glu
145                 150                 155                 160

Trp Asp Pro Leu His Pro Ser Ser Thr Asp Met Ala Leu Val Pro Arg
                165                 170                 175

Asn Asp Ser Leu Ser Leu Gln Glu Thr Ser Ser Ser Ser Phe Leu Ser
                180                 185                 190

Ser Gln Pro Phe Glu Asp Asp Ile Cys Asn Val Thr Ile Ser Asp
        195                 200                 205

Leu Tyr Ala Gly Met Leu His Ser Met Ser Arg Leu Leu Ser Thr Lys
        210                 215                 220

Pro Ser Ser Ile Ile Ser Thr Lys Thr Phe Ile Met Gln Asn Trp Asn
225                 230                 235                 240

Ser Arg Arg Arg His Arg Tyr Lys Ser Arg Met Asn Lys Thr Tyr Cys
                245                 250                 255

Lys Gly Ala Arg Arg Ser Gln Arg Ser Ser Lys Glu Asn Phe Ile Pro
            260                 265                 270

Cys Ser Glu Pro Val Lys Gly Thr Gly Ala Leu Arg Asp Cys Lys Asn
        275                 280                 285

Val Leu Asp Val Ser Cys Arg Lys Thr Gly Leu Lys Leu Glu Lys Ala
        290                 295                 300

Phe Leu Glu Val Asn Arg Pro Gln Ile His Lys Leu Asp Pro Ser Trp
305                 310                 315                 320

Lys Glu Arg Lys Val Thr Pro Ser Lys Tyr Ser Ser Leu Ile Tyr Phe
                325                 330                 335

Asp Ser Ser Ala Thr Tyr Asn Leu Asp Glu Glu Asn Arg Phe Arg Thr
            340                 345                 350

Leu Lys Trp Leu Ile Ser Pro Val Lys Ile Val Ser Arg Pro Thr Ile
        355                 360                 365

Arg Gln Gly His Gly Glu Asn Arg Gln Arg Glu Ile Glu Ile Arg Phe
370                 375                 380

Asp Gln Leu His Arg Glu Tyr Cys Leu Ser Pro Arg Asn Gln Pro Arg
385                 390                 395                 400

Arg Met Cys Leu Pro Asp Ser Trp Ala Met Asn Met Tyr Arg Gly Gly
                405                 410                 415

Pro Ala Ser Pro Gly Gly Leu Gln Gly Leu Glu Thr Arg Arg Leu Ser
            420                 425                 430

Leu Pro Ser Ser Lys Ala Lys Ala Lys Ser Leu Ser Glu Ala Phe Glu
        435                 440                 445

Asn Leu Gly Lys Arg Ser Leu Glu Ala Gly Arg Cys Leu Pro Lys Ser
        450                 455                 460

Asp Ser Ser Ser Leu Pro Lys Thr Asn Pro Thr His Ser Ala Thr
465                 470                 475                 480

Arg Pro Gln Gln Thr Ser Asp Leu His Val Gln Gly Asn Ser Ser Gly
                485                 490                 495
```

```
Ile Phe Arg Lys Ser Val Ser Pro Ser Lys Thr Leu Ser Val Pro Asp
            500                 505                 510

Lys Glu Val Pro Gly His Gly Arg Asn Arg Tyr Asp Glu Ile Lys Glu
        515                 520                 525

Glu Phe Asp Lys Leu His Gln Lys Tyr Cys Leu Lys Ser Pro Gly Gln
    530                 535                 540

Met Thr Val Pro Leu Cys Ile Gly Val Ser Thr Asp Lys Ala Ser Met
545                 550                 555                 560

Glu Val Arg Tyr Gln Thr Glu Gly Phe Leu Gly Lys Leu Asn Pro Asp
                565                 570                 575

Pro His Phe Gln Gly Phe Gln Lys Leu Pro Ser Ser Pro Leu Gly Cys
            580                 585                 590

Arg Lys Ser Leu Leu Gly Ser Thr Ala Ile Glu Ala Pro Ser Ser Thr
        595                 600                 605

Cys Val Ala Arg Ala Ile Thr Arg Asp Gly Thr Arg Asp His Gln Phe
    610                 615                 620

Pro Ala Lys Arg Pro Arg Leu Ser Glu Pro Gln Gly Ser Gly Arg Gln
625                 630                 635                 640

Gly Asn Ser Leu Gly Ala Ser Asp Gly Val Asp Asn Thr Val Arg Pro
                645                 650                 655

Gly Asp Gln Gly Ser Ser Ser Gln Pro Asn Ser Glu Glu Arg Gly Glu
            660                 665                 670

Asn Thr Ser Tyr Arg Met Glu Glu Lys Ser Asp Phe Met Leu Glu Lys
        675                 680                 685

Leu Glu Thr Lys Ser Val
        690

<210> SEQ ID NO 4
<211> LENGTH: 663
<212> TYPE: PRT
<213> ORGANISM: Homo sapiens

<400> SEQUENCE: 4

Met Leu Gly Thr Leu Arg Ala Met Glu Gly Glu Asp Val Glu Asp Asp
1               5                   10                  15

Gln Leu Gln Lys Leu Arg Ala Ser Arg Arg Phe Gln Arg Arg
            20                  25                  30

Met Gln Arg Leu Ile Glu Lys Tyr Asn Gln Pro Phe Glu Asp Thr Pro
        35                  40                  45

Val Val Gln Met Ala Thr Leu Thr Tyr Glu Thr Pro Gln Gly Leu Arg
    50                  55                  60

Ile Trp Gly Gly Arg Leu Ile Lys Glu Arg Asn Glu Gly Glu Ile Gln
65                  70                  75                  80

Cys Ala Gly Asn Arg Ala Gly Arg Asp Val Arg Val Thr Pro Leu Pro
                85                  90                  95

Ser Leu Ala Ser Pro Ala Val Pro Ala Pro Gly Tyr Cys Ser Arg Ile
            100                 105                 110

Ser Arg Lys Ser Pro Gly Asp Pro Ala Lys Pro Ala Ser Ser Pro Arg
        115                 120                 125

Glu Trp Asp Pro Leu His Pro Ser Ser Thr Asp Met Ala Leu Val Pro
    130                 135                 140

Arg Asn Asp Ser Leu Ser Leu Gln Glu Thr Ser Ser Ser Ser Phe Leu
145                 150                 155                 160

Ser Ser Gln Pro Phe Glu Asp Asp Asp Ile Cys Asn Val Thr Ile Ser
```

```
                165                 170                 175
Asp Leu Tyr Ala Gly Met Leu His Ser Met Ser Arg Leu Leu Ser Thr
            180                 185                 190

Lys Pro Ser Ser Ile Ile Ser Thr Lys Thr Phe Ile Met Gln Asn Trp
            195                 200                 205

Asn Ser Arg Arg His Arg Tyr Lys Ser Arg Met Asn Lys Thr Tyr
            210                 215                 220

Cys Lys Gly Ala Arg Arg Ser Gln Arg Ser Ser Lys Glu Asn Phe Ile
225                 230                 235                 240

Pro Cys Ser Glu Pro Val Lys Gly Thr Gly Ala Leu Arg Asp Cys Lys
                245                 250                 255

Asn Val Leu Asp Val Ser Cys Arg Lys Thr Gly Leu Lys Leu Glu Lys
                260                 265                 270

Ala Phe Leu Glu Val Asn Arg Pro Gln Ile His Lys Leu Asp Pro Ser
                275                 280                 285

Trp Lys Glu Arg Lys Val Thr Pro Ser Lys Tyr Ser Ser Leu Ile Tyr
            290                 295                 300

Phe Asp Ser Ser Ala Thr Tyr Asn Leu Asp Glu Glu Asn Arg Phe Arg
305                 310                 315                 320

Thr Leu Lys Trp Leu Ile Ser Pro Val Lys Ile Val Ser Arg Pro Thr
                325                 330                 335

Ile Arg Gln Gly His Gly Glu Asn Arg Gln Arg Glu Ile Glu Ile Arg
                340                 345                 350

Phe Asp Gln Leu His Arg Glu Tyr Cys Leu Ser Pro Arg Asn Gln Pro
            355                 360                 365

Arg Arg Met Cys Leu Pro Asp Ser Trp Ala Met Asn Met Tyr Arg Gly
            370                 375                 380

Gly Pro Ala Ser Pro Gly Gly Leu Gln Gly Leu Glu Thr Arg Arg Leu
385                 390                 395                 400

Ser Leu Pro Ser Ser Lys Ala Lys Ala Lys Ser Leu Ser Glu Ala Phe
                405                 410                 415

Glu Asn Leu Gly Lys Arg Ser Leu Glu Ala Gly Arg Cys Leu Pro Lys
            420                 425                 430

Ser Asp Ser Ser Ser Ser Leu Pro Lys Thr Asn Pro Thr His Ser Ala
            435                 440                 445

Thr Arg Pro Gln Gln Thr Ser Asp Leu His Val Gln Gly Asn Ser Ser
            450                 455                 460

Gly Ile Phe Arg Lys Ser Val Ser Pro Ser Lys Thr Leu Ser Val Pro
465                 470                 475                 480

Asp Lys Glu Val Pro Gly His Gly Arg Asn Arg Tyr Asp Glu Ile Lys
                485                 490                 495

Glu Glu Phe Asp Lys Leu His Gln Lys Tyr Cys Leu Lys Ser Pro Gly
                500                 505                 510

Gln Met Thr Val Pro Leu Cys Ile Gly Val Ser Thr Asp Lys Ala Ser
                515                 520                 525

Met Glu Val Arg Tyr Gln Thr Glu Gly Phe Leu Gly Lys Leu Asn Pro
            530                 535                 540

Asp Pro His Phe Gln Gly Phe Lys Leu Pro Ser Pro Leu Gly
545                 550                 555                 560

Cys Arg Lys Ser Leu Leu Gly Ser Thr Ala Ile Glu Ala Pro Ser Ser
                565                 570                 575

Thr Cys Val Ala Arg Ala Ile Thr Arg Asp Gly Thr Arg Asp His Gln
                580                 585                 590
```

```
Phe Pro Ala Lys Arg Pro Arg Leu Ser Glu Pro Gln Gly Ser Gly Arg
            595                 600                 605

Gln Gly Asn Ser Leu Gly Ala Ser Asp Gly Val Asp Asn Thr Val Arg
610                 615                 620

Pro Gly Asp Gln Gly Ser Ser Ser Gln Pro Asn Ser Glu Glu Arg Gly
625                 630                 635                 640

Glu Asn Thr Ser Tyr Arg Met Glu Glu Lys Ser Asp Phe Met Leu Glu
                645                 650                 655

Lys Leu Glu Thr Lys Ser Val
            660

<210> SEQ ID NO 5
<211> LENGTH: 233
<212> TYPE: PRT
<213> ORGANISM: Homo sapiens

<400> SEQUENCE: 5

Met Ala Gly Val Arg Ser Leu Arg Cys Ser Arg Gly Cys Ala Gly Gly
1               5                   10                  15

Cys Glu Cys Gly Asp Lys Gly Lys Cys Ser Asp Ser Ser Leu Leu Gly
            20                  25                  30

Lys Arg Leu Ser Glu Asp Ser Ser Arg His Gln Leu Leu Gln Lys Trp
        35                  40                  45

Ala Ser Met Trp Ser Ser Met Ser Glu Asp Ala Ser Val Ala Asp Met
    50                  55                  60

Glu Arg Ala Gln Leu Glu Glu Ala Ala Ala Glu Glu Arg Pro
65                  70                  75                  80

Leu Val Phe Leu Cys Ser Gly Cys Arg Arg Pro Leu Gly Asp Ser Leu
                85                  90                  95

Ser Trp Val Ala Ser Gln Glu Asp Thr Asn Cys Ile Leu Leu Arg Cys
            100                 105                 110

Val Ser Cys Asn Val Ser Val Asp Lys Glu Gln Lys Leu Ser Lys Arg
        115                 120                 125

Glu Lys Glu Asn Gly Cys Val Leu Glu Thr Leu Cys Cys Ala Gly Cys
    130                 135                 140

Ser Leu Asn Leu Gly Tyr Val Tyr Arg Cys Thr Pro Lys Asn Leu Asp
145                 150                 155                 160

Tyr Lys Arg Asp Leu Phe Cys Leu Ser Val Glu Ala Ile Glu Ser Tyr
                165                 170                 175

Val Leu Gly Ser Ser Glu Lys Gln Ile Val Ser Glu Asp Lys Glu Leu
            180                 185                 190

Phe Asn Leu Glu Ser Arg Val Glu Ile Glu Lys Ser Leu Thr Gln Met
        195                 200                 205

Glu Asp Val Leu Lys Ala Leu Gln Met Lys Leu Trp Glu Ala Glu Ser
    210                 215                 220

Lys Leu Ser Phe Ala Thr Cys Lys Ser
225                 230

<210> SEQ ID NO 6
<211> LENGTH: 229
<212> TYPE: PRT
<213> ORGANISM: Homo sapiens

<400> SEQUENCE: 6

Met Ala Ala Gln Pro Leu Arg His Arg Ser Arg Cys Ala Thr Pro Pro
1               5                   10                  15
```

Arg Gly Asp Phe Cys Gly Gly Thr Glu Arg Ala Ile Asp Gln Ala Ser
            20                  25                  30

Phe Thr Thr Ser Met Glu Trp Asp Thr Gln Val Val Lys Gly Ser Ser
            35                  40                  45

Pro Leu Gly Pro Ala Gly Leu Gly Ala Glu Pro Ala Ala Gly Pro
 50                  55                  60

Gln Leu Pro Ser Trp Leu Gln Pro Glu Arg Cys Ala Val Phe Gln Cys
 65                  70                  75                  80

Ala Gln Cys His Ala Val Leu Ala Asp Ser Val His Leu Ala Trp Asp
                 85                  90                  95

Leu Ser Arg Ser Leu Gly Ala Val Val Phe Ser Arg Val Thr Asn Asn
            100                 105                 110

Val Val Leu Glu Ala Pro Phe Leu Val Gly Ile Glu Gly Ser Leu Lys
            115                 120                 125

Gly Ser Thr Tyr Asn Leu Leu Phe Cys Gly Ser Cys Gly Ile Pro Val
130                 135                 140

Gly Phe His Leu Tyr Ser Thr His Ala Ala Leu Ala Ala Leu Arg Gly
145                 150                 155                 160

His Phe Cys Leu Ser Ser Asp Lys Met Val Cys Tyr Leu Leu Lys Thr
                165                 170                 175

Lys Ala Ile Val Asn Ala Ser Glu Met Asp Ile Gln Asn Val Pro Leu
            180                 185                 190

Ser Glu Lys Ile Ala Glu Leu Lys Glu Lys Ile Val Leu Thr His Asn
            195                 200                 205

Arg Leu Lys Ser Leu Met Lys Ile Leu Ser Glu Val Thr Pro Asp Gln
    210                 215                 220

Ser Lys Pro Glu Asn
225

<210> SEQ ID NO 7
<211> LENGTH: 943
<212> TYPE: PRT
<213> ORGANISM: Homo sapiens

<400> SEQUENCE: 7

Met Ala Ala Ser Gly Leu Asp His Leu Lys Asn Gly Tyr Arg Arg Arg
1               5                   10                  15

Phe Cys Arg Pro Ser Arg Ala Arg Asp Ile Asn Thr Glu Gln Gly Gln
            20                  25                  30

Asn Val Leu Glu Ile Leu Gln Asp Cys Phe Glu Glu Lys Ser Leu Ala
            35                  40                  45

Asn Asp Phe Ser Thr Asn Ser Thr Lys Ser Val Pro Asn Ser Thr Arg
 50                  55                  60

Lys Ile Lys Asp Thr Cys Ile Gln Ser Pro Ser Lys Glu Cys Gln Lys
 65                  70                  75                  80

Ser His Pro Lys Ser Val Pro Ser Ser Lys Lys Glu Ala Ser
                 85                  90                  95

Leu Gln Phe Val Val Glu Pro Ser Glu Ala Thr Asn Arg Ser Val Gln
            100                 105                 110

Ala His Glu Val His Gln Lys Ile Leu Ala Thr Asp Val Ser Ser Lys
            115                 120                 125

Asn Thr Pro Asp Ser Lys Lys Ile Ser Ser Arg Asn Ile Asn Asp His
130                 135                 140

His Ser Glu Ala Asp Glu Glu Phe Tyr Leu Ser Val Gly Ser Pro Ser

```
            145                 150                 155                 160
Val Leu Leu Asp Ala Lys Thr Ser Val Ser Gln Asn Val Ile Pro Ser
                165                 170                 175

Ser Ala Gln Lys Arg Glu Thr Tyr Thr Phe Glu Asn Ser Val Asn Met
                180                 185                 190

Leu Pro Ser Ser Thr Glu Val Ser Val Lys Thr Lys Lys Arg Leu Asn
                195                 200                 205

Phe Asp Asp Lys Val Met Leu Lys Lys Ile Glu Ile Asp Asn Lys Val
    210                 215                 220

Ser Asp Glu Glu Asp Lys Thr Ser Glu Gly Gln Glu Arg Lys Pro Ser
225                 230                 235                 240

Gly Ser Ser Gln Asn Arg Ile Arg Asp Ser Glu Tyr Glu Ile Gln Arg
                245                 250                 255

Gln Ala Lys Lys Ser Phe Ser Thr Leu Phe Leu Glu Thr Val Lys Arg
                260                 265                 270

Lys Ser Glu Ser Ser Pro Ile Val Arg His Ala Ala Thr Ala Pro Pro
                275                 280                 285

His Ser Cys Pro Pro Asp Asp Thr Lys Leu Ile Glu Asp Glu Phe Ile
    290                 295                 300

Ile Asp Glu Ser Asp Gln Ser Phe Ala Ser Arg Ser Trp Ile Thr Ile
305                 310                 315                 320

Pro Arg Lys Ala Gly Ser Leu Lys Gln Arg Thr Ile Ser Pro Ala Glu
                325                 330                 335

Ser Thr Ala Leu Phe Gln Gly Arg Lys Ser Arg Glu Lys His His Asn
                340                 345                 350

Ile Leu Pro Lys Thr Leu Ala Asn Asp Lys His Ser His Lys Pro His
                355                 360                 365

Pro Val Glu Thr Ser Gln Pro Ser Asp Lys Thr Val Leu Asp Thr Ser
    370                 375                 380

Tyr Ala Leu Ile Gly Glu Thr Val Asn Asn Tyr Arg Ser Thr Lys Tyr
385                 390                 395                 400

Glu Met Tyr Ser Lys Asn Ala Glu Lys Pro Ser Arg Ser Lys Arg Thr
                405                 410                 415

Ile Lys Gln Lys Gln Arg Arg Lys Phe Met Ala Lys Pro Ala Glu Glu
                420                 425                 430

Gln Leu Asp Val Gly Gln Ser Lys Asp Glu Asn Ile His Thr Ser His
                435                 440                 445

Ile Thr Gln Asp Glu Phe Gln Arg Asn Ser Asp Arg Asn Met Glu Glu
    450                 455                 460

His Glu Glu Met Gly Asn Asp Cys Val Ser Lys Lys Gln Met Pro Pro
465                 470                 475                 480

Val Gly Ser Lys Lys Ser Ser Thr Arg Lys Asp Lys Glu Glu Ser Lys
                485                 490                 495

Lys Lys Arg Phe Ser Ser Glu Ser Lys Asn Lys Leu Val Pro Glu Glu
                500                 505                 510

Val Thr Ser Thr Val Thr Lys Ser Arg Arg Ile Ser Arg Arg Pro Ser
                515                 520                 525

Asp Trp Trp Val Val Lys Ser Glu Glu Ser Pro Val Tyr Ser Asn Ser
    530                 535                 540

Ser Val Arg Asn Glu Leu Pro Met His His Asn Ser Ser Arg Lys Ser
545                 550                 555                 560

Thr Lys Lys Thr Asn Gln Ser Ser Lys Asn Ile Arg Lys Lys Thr Ile
                565                 570                 575
```

Pro Leu Lys Arg Gln Lys Thr Ala Thr Lys Gly Asn Gln Arg Val Gln
            580                 585                 590

Lys Phe Leu Asn Ala Glu Gly Ser Gly Ile Val Gly His Asp Glu
        595                 600                 605

Ile Ser Arg Cys Ser Leu Ser Glu Pro Leu Glu Ser Asp Glu Ala Asp
    610                 615                 620

Leu Ala Lys Lys Lys Asn Leu Asp Cys Ser Arg Ser Thr Arg Ser Ser
625                 630                 635                 640

Lys Asn Glu Asp Asn Ile Met Thr Ala Gln Asn Val Pro Leu Lys Pro
                645                 650                 655

Gln Thr Ser Gly Tyr Thr Cys Asn Ile Pro Thr Glu Ser Asn Leu Asp
            660                 665                 670

Ser Gly Glu His Lys Thr Ser Val Leu Glu Glu Ser Gly Pro Ser Arg
        675                 680                 685

Leu Asn Asn Asn Tyr Leu Met Ser Gly Lys Asn Asp Val Asp Asp Glu
    690                 695                 700

Glu Val His Gly Ser Ser Asp Asp Ser Lys Gln Ser Lys Val Ile Pro
705                 710                 715                 720

Lys Asn Arg Ile His His Lys Leu Val Leu Pro Ser Asn Thr Pro Asn
                725                 730                 735

Val Arg Arg Thr Lys Arg Thr Arg Leu Lys Pro Leu Glu Tyr Trp Arg
            740                 745                 750

Gly Glu Arg Ile Asp Tyr Gln Gly Arg Pro Ser Gly Gly Phe Val Ile
        755                 760                 765

Ser Gly Val Leu Ser Pro Asp Thr Ile Ser Ser Lys Arg Lys Ala Lys
    770                 775                 780

Glu Asn Ile Gly Lys Val Asn Lys Lys Ser Asn Lys Lys Arg Ile Cys
785                 790                 795                 800

Leu Asp Asn Asp Glu Arg Lys Thr Asn Leu Met Val Asn Leu Gly Ile
                805                 810                 815

Pro Leu Gly Asp Pro Leu Gln Pro Thr Arg Val Lys Asp Pro Glu Thr
            820                 825                 830

Arg Glu Ile Ile Leu Met Asp Leu Val Arg Pro Gln Asp Thr Tyr Gln
        835                 840                 845

Phe Phe Val Lys His Gly Glu Leu Lys Val Tyr Lys Thr Leu Asp Thr
    850                 855                 860

Pro Phe Phe Ser Thr Gly Lys Leu Ile Leu Gly Pro Gln Glu Glu Lys
865                 870                 875                 880

Gly Lys Gln His Val Gly Gln Asp Ile Leu Val Phe Tyr Val Asn Phe
                885                 890                 895

Gly Asp Leu Leu Cys Thr Leu His Glu Thr Pro Tyr Ile Leu Ser Thr
            900                 905                 910

Gly Asp Ser Phe Tyr Val Pro Ser Gly Asn Tyr Tyr Asn Ile Lys Asn
        915                 920                 925

Leu Arg Asn Glu Glu Ser Val Leu Leu Phe Thr Gln Ile Lys Arg
    930                 935                 940

<210> SEQ ID NO 8
<211> LENGTH: 542
<212> TYPE: PRT
<213> ORGANISM: Homo sapiens

<400> SEQUENCE: 8

Met Ala Ala Ser Gly Leu Asp His Leu Lys Asn Gly Tyr Arg Arg Arg

-continued

```
1               5                   10                  15
Phe Cys Arg Pro Ser Arg Ala Arg Asp Ile Asn Thr Glu Gln Gly Gln
                20                  25                  30

Asn Val Leu Glu Ile Leu Gln Asp Cys Phe Glu Glu Lys Ser Leu Ala
                35                  40                  45

Asn Asp Phe Ser Thr Asn Ser Thr Lys Ser Val Pro Asn Ser Thr Arg
            50                  55                  60

Lys Ile Lys Asp Thr Cys Ile Gln Ser Pro Ser Lys Glu Cys Gln Lys
65                  70                  75                  80

Ser His Pro Lys Ser Val Pro Val Ser Ser Lys Lys Glu Ala Ser
                    85                  90                  95

Leu Gln Phe Val Val Glu Pro Ser Glu Ala Thr Asn Arg Ser Val Gln
                100                 105                 110

Ala His Glu Val His Gln Lys Ile Leu Ala Thr Asp Val Ser Ser Lys
                115                 120                 125

Asn Thr Pro Asp Ser Lys Lys Ile Ser Ser Arg Asn Ile Asn Asp His
            130                 135                 140

His Ser Glu Ala Asp Glu Glu Phe Tyr Leu Ser Val Gly Ser Pro Ser
145                 150                 155                 160

Val Leu Leu Asp Ala Lys Thr Ser Val Ser Gln Asn Val Ile Pro Ser
                    165                 170                 175

Ser Ala Gln Lys Arg Glu Thr Tyr Thr Phe Glu Asn Ser Val Asn Met
                180                 185                 190

Leu Pro Ser Ser Thr Glu Val Ser Val Lys Thr Lys Lys Arg Leu Asn
                195                 200                 205

Phe Asp Asp Lys Val Met Leu Lys Lys Ile Glu Ile Asp Asn Lys Val
        210                 215                 220

Ser Asp Glu Glu Asp Lys Thr Ser Glu Gly Gln Glu Arg Lys Pro Ser
225                 230                 235                 240

Gly Ser Ser Gln Asn Arg Ile Arg Asp Ser Glu Tyr Glu Ile Gln Arg
                    245                 250                 255

Gln Ala Lys Lys Ser Phe Ser Thr Leu Phe Leu Glu Thr Val Lys Arg
                260                 265                 270

Lys Ser Glu Ser Ser Pro Ile Val Arg His Ala Ala Thr Ala Pro Pro
        275                 280                 285

His Ser Cys Pro Pro Asp Asp Thr Lys Leu Ile Glu Asp Glu Phe Ile
        290                 295                 300

Ile Asp Glu Ser Asp Gln Ser Phe Ala Ser Arg Ser Trp Ile Thr Ile
305                 310                 315                 320

Pro Arg Lys Ala Gly Ser Leu Lys Gln Arg Thr Ile Ser Pro Ala Glu
                    325                 330                 335

Ser Thr Ala Leu Phe Gln Gly Arg Lys Ser Arg Glu Lys His His Asn
                340                 345                 350

Ile Leu Pro Lys Thr Leu Ala Asn Asp Lys His Ser Lys Pro His
        355                 360                 365

Pro Val Glu Thr Ser Gln Pro Ser Asp Lys Thr Val Leu Asp Thr Ser
        370                 375                 380

Tyr Ala Leu Ile Gly Glu Thr Val Asn Asn Tyr Arg Ser Thr Lys Tyr
385                 390                 395                 400

Glu Met Tyr Ser Lys Asn Ala Glu Lys Pro Ser Arg Ser Lys Arg Thr
                    405                 410                 415

Ile Lys Gln Lys Gln Arg Arg Lys Phe Met Ala Lys Pro Ala Glu Glu
                420                 425                 430
```

Gln Leu Asp Val Gly Gln Ser Lys Asp Glu Asn Ile His Thr Ser His
        435                 440                 445

Ile Thr Gln Asp Glu Phe Gln Arg Asn Ser Asp Arg Asn Met Glu Glu
    450                 455                 460

His Glu Glu Met Gly Asn Asp Cys Val Ser Lys Lys Gln Met Pro Pro
465                 470                 475                 480

Val Gly Ser Lys Lys Ser Ser Thr Arg Lys Asp Lys Glu Gly Ser Lys
                485                 490                 495

Lys Lys Arg Phe Ser Ser Glu Ser Lys Asn Lys Leu Val Pro Glu Glu
            500                 505                 510

Val Thr Ser Thr Val Thr Lys Ser Arg Arg Ile Ser Arg Arg Pro Ser
        515                 520                 525

Asp Trp Trp Val Val Lys Ser Glu Gly Ser Cys Leu Lys Cys
        530                 535                 540

<210> SEQ ID NO 9
<211> LENGTH: 204
<212> TYPE: PRT
<213> ORGANISM: Homo sapiens

<400> SEQUENCE: 9

Met Asp Glu Thr Val Ala Glu Phe Ile Lys Arg Thr Ile Leu Lys Ile
1               5                   10                  15

Pro Met Asn Glu Leu Thr Thr Ile Leu Lys Ala Trp Asp Phe Leu Ser
            20                  25                  30

Glu Asn Gln Leu Gln Thr Val Asn Phe Arg Gln Arg Lys Glu Ser Val
        35                  40                  45

Val Gln His Leu Ile His Leu Cys Glu Glu Lys Arg Ala Ser Ile Ser
    50                  55                  60

Asp Ala Ala Leu Leu Asp Ile Ile Tyr Met Gln Phe His Gln His Gln
65                  70                  75                  80

Lys Val Trp Glu Val Phe Gln Met Ser Lys Gly Pro Gly Glu Asp Val
                85                  90                  95

Asp Leu Phe Asp Met Lys Gln Phe Lys Asn Ser Phe Lys Lys Ile Leu
            100                 105                 110

Gln Arg Ala Leu Lys Asn Val Thr Val Ser Phe Arg Glu Thr Glu Glu
        115                 120                 125

Asn Ala Val Trp Ile Arg Ile Ala Trp Gly Thr Gln Tyr Thr Lys Pro
    130                 135                 140

Asn Gln Tyr Lys Pro Thr Tyr Val Val Tyr Ser Gln Thr Pro Tyr Tyr
145                 150                 155                 160

Ala Phe Thr Ser Ser Ser Met Leu Arg Arg Asn Thr Pro Leu Leu Gly
                165                 170                 175

Gln Glu Leu Glu Ala Thr Gly Lys Ile Tyr Leu Arg Gln Glu Glu Ile
            180                 185                 190

Ile Leu Asp Ile Thr Glu Met Lys Lys Ala Cys Asn
        195                 200

<210> SEQ ID NO 10
<211> LENGTH: 305
<212> TYPE: PRT
<213> ORGANISM: Homo sapiens

<400> SEQUENCE: 10

Met Asp Glu Thr Val Ala Glu Phe Ile Lys Arg Thr Ile Leu Lys Ile
1               5                   10                  15

```
Pro Met Asn Glu Leu Thr Thr Ile Leu Lys Ala Trp Asp Phe Leu Ser
        20                  25                  30

Glu Asn Gln Leu Gln Thr Val Asn Phe Arg Gln Arg Lys Glu Ser Val
            35                  40                  45

Val Gln His Leu Ile His Leu Cys Glu Glu Lys Arg Ala Ser Ile Ser
 50                  55                  60

Asp Ala Ala Leu Leu Asp Ile Ile Tyr Met Gln Phe His Gln His Gln
 65                  70                  75                  80

Lys Val Trp Glu Val Phe Gln Met Ser Lys Gly Pro Gly Glu Asp Val
                85                  90                  95

Asp Leu Phe Asp Met Lys Gln Phe Lys Asn Ser Phe Lys Lys Ile Leu
               100                 105                 110

Gln Arg Ala Leu Lys Asn Val Thr Val Ser Phe Arg Glu Thr Glu Glu
           115                 120                 125

Asn Ala Val Trp Ile Arg Ile Ala Trp Gly Thr Gln Tyr Thr Lys Pro
130                 135                 140

Asn Gln Tyr Lys Pro Thr Tyr Val Val Tyr Ser Gln Thr Pro Tyr
145                 150                 155                 160

Ala Phe Thr Ser Ser Met Leu Arg Arg Asn Thr Pro Leu Leu Gly
                165                 170                 175

Gln Thr Phe Glu Thr His Asn Ser Thr Thr Pro Leu Gln Glu Arg Ser
            180                 185                 190

Leu Gly Leu Asp Ile Asn Met Asp Ser Arg Ile Ile His Glu Asn Ile
        195                 200                 205

Val Glu Lys Glu Arg Val Gln Arg Ile Thr Gln Thr Phe Gly Asp
210                 215                 220

Tyr Pro Gln Pro Gln Leu Glu Phe Ala Gln Tyr Lys Leu Glu Thr Lys
225                 230                 235                 240

Phe Lys Ser Gly Leu Asn Gly Ser Ile Leu Ala Glu Arg Glu Pro
                245                 250                 255

Leu Arg Cys Leu Ile Lys Phe Ser Ser Pro His Leu Leu Glu Ala Leu
            260                 265                 270

Lys Ser Leu Ala Pro Ala Gly Ile Ala Asp Ala Pro Leu Ser Pro Leu
        275                 280                 285

Leu Thr Cys Ile Pro Asn Lys Arg Met Asn Tyr Phe Lys Ile Arg Asp
    290                 295                 300

Lys
305

<210> SEQ ID NO 11
<211> LENGTH: 319
<212> TYPE: PRT
<213> ORGANISM: Homo sapiens

<400> SEQUENCE: 11

Met Asp Glu Thr Val Ala Glu Phe Ile Lys Arg Thr Ile Leu Lys Ile
 1               5                  10                  15

Pro Met Asn Glu Leu Thr Thr Ile Leu Lys Ala Trp Asp Phe Leu Ser
            20                  25                  30

Glu Asn Gln Leu Gln Thr Val Asn Phe Arg Gln Arg Lys Glu Ser Val
        35                  40                  45

Val Gln His Leu Ile His Leu Cys Glu Glu Lys Arg Ala Ser Ile Ser
 50                  55                  60

Asp Ala Ala Leu Leu Asp Ile Ile Cys Glu Asp Val Asp Leu Phe Asp
```

```
                65                  70                  75                  80
Met Lys Gln Phe Lys Asn Ser Phe Lys Lys Ile Leu Gln Arg Ala Leu
                    85                  90                  95

Lys Asn Val Thr Val Ser Phe Arg Glu Thr Glu Glu Asn Ala Val Trp
                100                 105                 110

Ile Arg Ile Ala Trp Gly Thr Gln Tyr Thr Lys Pro Asn Gln Tyr Lys
            115                 120                 125

Pro Thr Tyr Val Val Tyr Tyr Ser Gln Thr Pro Tyr Ala Phe Thr Ser
        130                 135                 140

Ser Ser Met Leu Arg Arg Asn Thr Pro Leu Leu Gly Gln Ala Leu Thr
145                 150                 155                 160

Ile Ala Ser Lys His His Gln Ile Val Lys Met Asp Leu Arg Ser Arg
                165                 170                 175

Tyr Leu Asp Ser Leu Lys Ala Ile Val Phe Lys Gln Tyr Asn Gln Thr
                180                 185                 190

Phe Glu Thr His Asn Ser Thr Thr Pro Leu Gln Glu Arg Ser Leu Gly
            195                 200                 205

Leu Asp Ile Asn Met Asp Ser Arg Ile Ile His Glu Asn Ile Val Glu
        210                 215                 220

Lys Glu Arg Val Gln Arg Ile Thr Gln Glu Thr Phe Gly Asp Tyr Pro
225                 230                 235                 240

Gln Pro Gln Leu Glu Phe Ala Gln Tyr Lys Leu Glu Thr Lys Phe Lys
                245                 250                 255

Ser Gly Leu Asn Gly Ser Ile Leu Ala Glu Arg Glu Pro Leu Arg
                260                 265                 270

Cys Leu Ile Lys Phe Ser Ser Pro His Leu Leu Glu Ala Leu Lys Ser
            275                 280                 285

Leu Ala Pro Ala Gly Ile Ala Asp Ala Pro Leu Ser Pro Leu Leu Thr
        290                 295                 300

Cys Ile Pro Asn Lys Arg Met Asn Tyr Phe Lys Ile Arg Asp Lys
305                 310                 315

<210> SEQ ID NO 12
<211> LENGTH: 339
<212> TYPE: PRT
<213> ORGANISM: Homo sapiens

<400> SEQUENCE: 12

Met Asp Glu Thr Val Ala Glu Phe Ile Lys Arg Thr Ile Leu Lys Ile
1               5                   10                  15

Pro Met Asn Glu Leu Thr Thr Ile Leu Lys Ala Trp Asp Phe Leu Ser
                20                  25                  30

Glu Asn Gln Leu Gln Thr Val Asn Phe Arg Gln Arg Lys Glu Ser Val
            35                  40                  45

Val Gln His Leu Ile His Leu Cys Glu Glu Lys Arg Ala Ser Ile Ser
        50                  55                  60

Asp Ala Ala Leu Leu Asp Ile Ile Tyr Met Gln Phe His Gln His Gln
65                  70                  75                  80

Lys Val Trp Glu Val Phe Gln Met Ser Lys Gly Pro Gly Glu Asp Val
                85                  90                  95

Asp Leu Phe Asp Met Lys Gln Phe Lys Asn Ser Phe Lys Lys Ile Leu
            100                 105                 110

Gln Arg Ala Leu Lys Asn Val Thr Val Ser Phe Arg Glu Thr Glu Glu
        115                 120                 125
```

-continued

```
Asn Ala Val Trp Ile Arg Ile Ala Trp Gly Thr Gln Tyr Thr Lys Pro
    130                 135                 140

Asn Gln Tyr Lys Pro Thr Tyr Val Val Tyr Tyr Ser Gln Thr Pro Tyr
145                 150                 155                 160

Ala Phe Thr Ser Ser Met Leu Arg Arg Asn Thr Pro Leu Leu Gly
                    165                 170                 175

Gln Ala Leu Thr Ile Ala Ser Lys His His Gln Ile Val Lys Met Asp
                180                 185                 190

Leu Arg Ser Arg Tyr Leu Asp Ser Leu Lys Ala Ile Val Phe Lys Gln
                195                 200                 205

Tyr Asn Gln Thr Phe Glu Thr His Asn Ser Thr Thr Pro Leu Gln Glu
210                 215                 220

Arg Ser Leu Gly Leu Asp Ile Asn Met Asp Ser Arg Ile Ile His Glu
225                 230                 235                 240

Asn Ile Val Glu Lys Glu Arg Val Gln Arg Ile Thr Gln Glu Thr Phe
                    245                 250                 255

Gly Asp Tyr Pro Gln Pro Gln Leu Glu Phe Ala Gln Tyr Lys Leu Glu
                260                 265                 270

Thr Lys Phe Lys Ser Gly Leu Asn Gly Ser Ile Leu Ala Glu Arg Glu
                275                 280                 285

Glu Pro Leu Arg Cys Leu Ile Lys Phe Ser Ser Pro His Leu Leu Glu
290                 295                 300

Ala Leu Lys Ser Leu Ala Pro Ala Gly Ile Ala Asp Ala Pro Leu Ser
305                 310                 315                 320

Pro Leu Leu Thr Cys Ile Pro Asn Lys Arg Met Asn Tyr Phe Lys Ile
                    325                 330                 335

Arg Asp Lys

<210> SEQ ID NO 13
<211> LENGTH: 353
<212> TYPE: PRT
<213> ORGANISM: Homo sapiens

<400> SEQUENCE: 13

Met Asp Glu Thr Val Ala Glu Phe Ile Lys Arg Thr Ile Leu Lys Ile
1               5                   10                  15

Pro Met Asn Glu Leu Thr Thr Ile Leu Lys Ala Trp Asp Phe Leu Ser
                20                  25                  30

Glu Asn Gln Leu Gln Thr Val Asn Phe Arg Gln Arg Lys Glu Ser Val
            35                  40                  45

Val Gln His Leu Ile His Leu Cys Glu Glu Lys Arg Ala Ser Ile Ser
        50                  55                  60

Asp Ala Ala Leu Leu Asp Ile Ile Tyr Met Gln Phe His Gln His Gln
65                  70                  75                  80

Lys Val Trp Glu Val Phe Gln Met Ser Lys Gly Pro Gly Glu Asp Val
                85                  90                  95

Asp Leu Phe Asp Met Lys Gln Phe Lys Asn Ser Phe Lys Lys Ile Leu
            100                 105                 110

Gln Arg Ala Leu Lys Asn Val Thr Val Ser Phe Arg Glu Thr Glu Glu
        115                 120                 125

Asn Ala Val Trp Ile Arg Ile Ala Trp Gly Thr Gln Tyr Thr Lys Pro
    130                 135                 140

Asn Gln Tyr Lys Pro Thr Tyr Val Val Tyr Tyr Ser Gln Thr Pro Tyr
145                 150                 155                 160
```

```
Ala Phe Thr Ser Ser Ser Met Leu Arg Arg Asn Thr Pro Leu Leu Gly
                165                 170                 175

Gln Ala Leu Thr Ile Ala Ser Lys His His Gln Ile Val Lys Met Asp
            180                 185                 190

Leu Arg Ser Arg Tyr Leu Asp Ser Leu Lys Ala Ile Val Phe Lys Gln
        195                 200                 205

Tyr Asn Gln Thr Phe Glu Thr His Asn Ser Thr Thr Pro Leu Gln Glu
    210                 215                 220

Arg Ser Leu Gly Leu Asp Ile Asn Met Asp Ser Arg Ile Ile His Glu
225                 230                 235                 240

Asn Ile Val Glu Lys Glu Arg Val Gln Arg Ile Thr Gln Glu Thr Phe
                245                 250                 255

Gly Asp Tyr Pro Gln Pro Gln Leu Glu Phe Ala Gln Tyr Lys Leu Glu
            260                 265                 270

Thr Lys Phe Lys Ser Gly Leu Asn Gly Ser Ile Leu Ala Glu Arg Glu
        275                 280                 285

Glu Pro Leu Arg Cys Leu Ile Lys Phe Ser Ser Pro His Leu Leu Glu
    290                 295                 300

Ala Leu Lys Ser Leu Ala Pro Ala Ala Leu Val Cys Arg Ile Gln Lys
305                 310                 315                 320

Leu Leu Cys Tyr Ser Gly Ser His Ser Gln Gly Thr Gln Asp Pro Ser
                325                 330                 335

Ser Trp Gln Lys Asp Leu Tyr Leu Leu Phe Val Pro Leu Tyr Pro Arg
            340                 345                 350

Cys

<210> SEQ ID NO 14
<211> LENGTH: 756
<212> TYPE: PRT
<213> ORGANISM: Homo sapiens

<400> SEQUENCE: 14

Met Ser Pro Gln Lys Arg Val Lys Asn Val Gln Ala Gln Asn Arg Thr
1               5                   10                  15

Ser Gln Gly Ser Ser Phe Gln Thr Thr Leu Ser Ala Trp Lys Val
            20                  25                  30

Lys Gln Asp Pro Ser Asn Ser Lys Asn Ile Ser Lys His Gly Gln Asn
        35                  40                  45

Asn Pro Val Gly Asp Tyr Glu His Ala Asp Gln Ala Glu Glu Asp
    50                  55                  60

Ala Leu Gln Met Ala Val Gly Tyr Phe Glu Lys Gly Pro Ile Lys Ala
65                  70                  75                  80

Ser Gln Asn Lys Asp Lys Thr Leu Glu Lys His Leu Lys Thr Val Glu
                85                  90                  95

Asn Val Ala Trp Lys Asn Gly Leu Ala Ser Glu Glu Ile Asp Ile Leu
            100                 105                 110

Leu Asn Ile Ala Leu Ser Gly Lys Phe Gly Asn Ala Val Asn Thr Arg
        115                 120                 125

Ile Leu Lys Cys Met Ile Pro Ala Thr Val Ile Ser Glu Asp Ser Val
    130                 135                 140

Val Lys Ala Val Ser Trp Leu Cys Val Gly Lys Cys Ser Gly Ser Thr
145                 150                 155                 160

Lys Val Leu Phe Tyr Arg Trp Leu Val Ala Met Phe Asp Phe Ile Asp
                165                 170                 175
```

```
Arg Lys Glu Gln Ile Asn Leu Leu Tyr Gly Phe Phe Phe Ala Ser Leu
            180                 185                 190

Gln Asp Asp Ala Leu Cys Pro Tyr Val Cys His Leu Leu Tyr Leu Leu
        195                 200                 205

Thr Lys Lys Glu Asn Val Lys Pro Phe Arg Val Arg Lys Leu Leu Asp
    210                 215                 220

Leu Gln Ala Lys Met Gly Met Gln Pro His Leu Gln Ala Leu Leu Ser
225                 230                 235                 240

Leu Tyr Lys Phe Phe Ala Pro Ala Leu Ile Ser Val Ser Leu Pro Val
            245                 250                 255

Arg Lys Lys Ile Tyr Phe Lys Asn Ser Glu Asn Leu Trp Lys Thr Ala
            260                 265                 270

Leu Leu Ala Val Lys Gln Arg Asn Arg Gly Pro Ser Pro Glu Pro Leu
        275                 280                 285

Lys Leu Met Leu Gly Pro Ala Asn Val Arg Pro Leu Lys Arg Lys Trp
    290                 295                 300

Asn Ser Leu Ser Val Ile Pro Val Leu Asn Ser Ser Tyr Thr Lys
305                 310                 315                 320

Glu Cys Gly Lys Lys Glu Met Ser Leu Ser Asp Cys Leu Asn Arg Ser
            325                 330                 335

Gly Ser Phe Pro Leu Glu Gln Leu Gln Ser Phe Pro Gln Leu Leu Gln
        340                 345                 350

Asn Ile His Cys Leu Glu Leu Pro Ser Gln Met Gly Ser Val Leu Asn
    355                 360                 365

Asn Ser Leu Leu His Tyr Ile Asn Cys Val Arg Asp Glu Pro Val
370                 375                 380

Leu Leu Arg Phe Tyr Tyr Trp Leu Ser Gln Thr Leu Gln Glu Glu Cys
385                 390                 395                 400

Ile Trp Tyr Lys Val Asn Asn Tyr Glu His Gly Lys Glu Phe Thr Asn
            405                 410                 415

Phe Leu Asp Thr Ile Ile Arg Ala Glu Cys Phe Leu Gln Glu Gly Phe
        420                 425                 430

Tyr Ser Cys Glu Ala Phe Leu Tyr Lys Ser Leu Pro Leu Trp Asp Gly
    435                 440                 445

Leu Cys Cys Arg Ser Gln Phe Leu Gln Leu Val Ser Trp Ile Pro Phe
450                 455                 460

Ser Ser Phe Ser Glu Val Lys Pro Leu Leu Phe Asp His Leu Ala Gln
465                 470                 475                 480

Leu Phe Phe Thr Ser Thr Ile Tyr Phe Lys Cys Ser Val Leu Gln Ser
            485                 490                 495

Leu Lys Glu Leu Leu Gln Asn Trp Leu Leu Trp Leu Ser Met Asp Ile
        500                 505                 510

His Met Lys Pro Val Thr Asn Ser Pro Leu Glu Thr Leu Gly Gly
    515                 520                 525

Ser Met Asn Ser Val Ser Lys Leu Ile His Tyr Val Gly Trp Leu Ser
530                 535                 540

Thr Thr Ala Met Arg Leu Glu Ser Asn Asn Thr Phe Leu Leu His Phe
545                 550                 555                 560

Ile Leu Asp Phe Tyr Glu Lys Val Cys Asp Ile Tyr Ile Asn Tyr Asn
            565                 570                 575

Leu Pro Leu Val Val Leu Phe Pro Pro Gly Ile Phe Tyr Ser Ala Leu
        580                 585                 590

Leu Ser Leu Asp Thr Ser Ile Leu Asn Gln Leu Cys Phe Ile Met His
```

```
                    595                 600                 605
Arg Tyr Arg Lys Asn Leu Thr Ala Ala Lys Lys Asn Glu Leu Val Gln
        610                 615                 620
Lys Thr Lys Ser Glu Phe Asn Phe Ser Ser Lys Thr Tyr Gln Glu Phe
625                 630                 635                 640
Asn His Tyr Leu Thr Ser Met Val Gly Cys Leu Trp Thr Ser Lys Pro
                    645                 650                 655
Phe Gly Lys Gly Ile Tyr Ile Asp Pro Glu Ile Leu Glu Lys Thr Gly
                660                 665                 670
Val Ala Glu Tyr Lys Asn Ser Leu Asn Val Val His His Pro Ser Phe
            675                 680                 685
Leu Ser Tyr Ala Val Ser Phe Leu Leu Gln Glu Ser Pro Glu Glu Arg
        690                 695                 700
Thr Val Asn Val Ser Ser Ile Arg Gly Lys Lys Trp Ser Trp Tyr Leu
705                 710                 715                 720
Asp Tyr Leu Phe Ser Gln Gly Leu Gln Gly Leu Lys Leu Phe Ile Arg
                    725                 730                 735
Ser Ser Val His His Ser Ser Ile Pro Arg Ala Glu Gly Ile Asn Cys
                740                 745                 750
Asn Asn Gln Tyr
            755

<210> SEQ ID NO 15
<211> LENGTH: 247
<212> TYPE: PRT
<213> ORGANISM: Homo sapiens

<400> SEQUENCE: 15

Met Glu Glu Gln Pro Gln Met Gln Asp Ala Asp Glu Pro Ala Asp Ser
1               5                   10                  15
Gly Gly Glu Gly Arg Ala Gly Gly Pro Pro Gln Val Ala Gly Ala Gln
                20                  25                  30
Ala Ala Cys Ser Glu Asp Arg Met Thr Leu Leu Leu Arg Leu Arg Ala
            35                  40                  45
Gln Thr Lys Gln Gln Leu Leu Glu Tyr Lys Ser Met Val Asp Ala Ser
        50                  55                  60
Glu Glu Lys Thr Pro Glu Gln Ile Met Gln Glu Lys Gln Ile Glu Ala
65                  70                  75                  80
Lys Ile Glu Asp Leu Glu Asn Glu Ile Glu Glu Val Lys Val Ala Phe
                85                  90                  95
Glu Ile Lys Lys Leu Ala Leu Asp Arg Met Arg Leu Ser Thr Ala Leu
                100                 105                 110
Lys Lys Asn Leu Glu Lys Ile Ser Arg Gln Ser Ser Val Leu Met Asp
            115                 120                 125
Asn Met Lys His Leu Leu Glu Leu Asn Lys Leu Ile Met Lys Ser Gln
        130                 135                 140
Gln Glu Ser Trp Asp Leu Glu Glu Lys Leu Leu Asp Ile Arg Lys Lys
145                 150                 155                 160
Arg Leu Gln Leu Lys Gln Ala Ser Glu Ser Lys Leu Leu Glu Ile Gln
                165                 170                 175
Thr Glu Lys Asn Lys Gln Lys Ile Asp Leu Asp Ser Met Glu Asn Ser
                180                 185                 190
Glu Arg Ile Lys Ile Ile Arg Gln Asn Leu Gln Met Glu Ile Lys Ile
            195                 200                 205
```

```
Thr Thr Val Ile Gln His Val Phe Gln Asn Leu Ile Leu Gly Ser Lys
            210                 215                 220

Val Asn Trp Ala Glu Asp Pro Ala Leu Lys Glu Ile Val Leu Gln Leu
225                 230                 235                 240

Glu Lys Asn Val Asp Met Met
                245

<210> SEQ ID NO 16
<211> LENGTH: 67
<212> TYPE: PRT
<213> ORGANISM: Homo sapiens

<400> SEQUENCE: 16

Met Ala Leu Ser Thr Ile Val Ser Gln Arg Lys Gln Ile Lys Arg Lys
1               5                   10                  15

Ala Pro Arg Gly Phe Leu Lys Arg Val Phe Lys Arg Lys Lys Pro Gln
            20                  25                  30

Leu Arg Leu Glu Lys Ser Gly Asp Leu Leu Lys Ser Pro Gly Gln Thr
        35                  40                  45

Leu Val Arg Val Asn Val Glu Ser Leu Thr Arg Ser Met Tyr Trp Pro
    50                  55                  60

Gln Gln Arg
65

<210> SEQ ID NO 17
<211> LENGTH: 103
<212> TYPE: PRT
<213> ORGANISM: Homo sapiens

<400> SEQUENCE: 17

Met Ala Leu Ser Thr Ile Val Ser Gln Arg Lys Gln Ile Lys Arg Lys
1               5                   10                  15

Ala Pro Arg Gly Phe Leu Lys Arg Val Phe Lys Arg Lys Lys Pro Gln
            20                  25                  30

Leu Arg Leu Glu Lys Ser Gly Asp Leu Leu Val Arg Phe His Pro Phe
        35                  40                  45

Ser Gly Trp Glu Trp Gly Thr Gly Glu Val His Leu Asn Cys Leu Leu
    50                  55                  60

Phe Val His Arg Leu Ala Glu Glu Ser Arg Thr Asn Ala Cys Ala Ser
65                  70                  75                  80

Lys Cys Arg Val Ile Asn Lys Glu His Val Leu Ala Ala Ala Lys Val
            85                  90                  95

Ile Leu Lys Lys Ser Arg Gly
            100

<210> SEQ ID NO 18
<211> LENGTH: 88
<212> TYPE: PRT
<213> ORGANISM: Homo sapiens

<400> SEQUENCE: 18

Met Ala Leu Ser Thr Ile Val Ser Gln Arg Lys Gln Ile Lys Arg Lys
1               5                   10                  15

Ala Pro Arg Gly Phe Leu Lys Arg Val Phe Lys Arg Lys Lys Pro Gln
            20                  25                  30

Leu Arg Leu Glu Lys Ser Gly Asp Leu Leu Val His Leu Asn Cys Leu
        35                  40                  45

Leu Phe Val His Arg Leu Ala Glu Glu Ser Arg Thr Asn Ala Cys Ala
```

```
                50                  55                  60
Ser Lys Cys Arg Val Ile Asn Lys Glu His Val Leu Ala Ala Ala Lys
 65                  70                  75                  80

Val Ile Leu Lys Lys Ser Arg Gly
                 85

<210> SEQ ID NO 19
<211> LENGTH: 58
<212> TYPE: PRT
<213> ORGANISM: Homo sapiens

<400> SEQUENCE: 19

Met Glu Gly Ala Gly Ala Gly Ser Gly Phe Arg Lys Glu Leu Val Ser
  1               5                  10                  15

Arg Leu Leu His Leu His Phe Lys Asp Asp Lys Thr Lys Glu Ala Ala
                 20                  25                  30

Val Arg Gly Val Arg Gln Ala Gln Ala Glu Asp Ala Leu Arg Val Asp
             35                  40                  45

Val Asp Gln Leu Glu Lys Leu Leu Asp Phe
         50                  55

<210> SEQ ID NO 20
<211> LENGTH: 81
<212> TYPE: PRT
<213> ORGANISM: Homo sapiens

<400> SEQUENCE: 20

Met Glu Gly Ala Gly Ala Gly Ser Gly Phe Arg Lys Glu Leu Val Ser
  1               5                  10                  15

Arg Leu Leu His Leu His Phe Lys Asp Asp Lys Thr Lys Val Ser Gly
                 20                  25                  30

Asp Ala Leu Gln Leu Met Val Glu Leu Leu Lys Val Phe Val Val Glu
             35                  40                  45

Ala Ala Val Arg Gly Val Arg Gln Ala Gln Ala Glu Asp Ala Leu Arg
         50                  55                  60

Val Asp Val Asp Gln Leu Glu Lys Val Leu Pro Gln Leu Leu Leu Asp
 65                  70                  75                  80

Phe

<210> SEQ ID NO 21
<211> LENGTH: 63
<212> TYPE: PRT
<213> ORGANISM: Homo sapiens

<400> SEQUENCE: 21

Met Glu Gly Ala Gly Ala Gly Ser Gly Phe Arg Lys Glu Leu Val Ser
  1               5                  10                  15

Arg Leu Leu His Leu His Phe Lys Asp Asp Lys Thr Lys Glu Ala Ala
                 20                  25                  30

Val Arg Gly Val Arg Gln Ala Gln Ala Glu Asp Ala Leu Arg Val Asp
             35                  40                  45

Val Asp Gln Leu Glu Lys Val Leu Pro Gln Leu Leu Leu Asp Phe
         50                  55                  60

<210> SEQ ID NO 22
<211> LENGTH: 107
<212> TYPE: PRT
<213> ORGANISM: Homo sapiens
```

```
<400> SEQUENCE: 22

Met Ser Val Leu Arg Pro Leu Asp Lys Leu Pro Gly Leu Asn Thr Ala
1               5                   10                  15

Thr Ile Leu Leu Val Gly Thr Glu Asp Ala Leu Leu Gln Gln Leu Ala
                20                  25                  30

Asp Ser Met Leu Lys Glu Asp Cys Ala Ser Glu Leu Lys Val His Leu
            35                  40                  45

Ala Lys Ser Leu Pro Leu Pro Ser Ser Val Asn Arg Pro Arg Ile Asp
        50                  55                  60

Leu Ile Val Phe Val Val Asn Leu His Ser Lys Tyr Ser Leu Gln Asn
65                  70                  75                  80

Thr Glu Glu Ser Leu Arg His Val Asp Ala Ser Phe Phe Leu Gly Lys
                85                  90                  95

Val Cys Phe Leu Ala Thr Gly Gly Gly Arg Leu
                100                 105

<210> SEQ ID NO 23
<211> LENGTH: 180
<212> TYPE: PRT
<213> ORGANISM: Homo sapiens

<400> SEQUENCE: 23

Met Ser Val Leu Arg Pro Leu Asp Lys Leu Pro Gly Leu Asn Thr Ala
1               5                   10                  15

Thr Ile Leu Leu Val Gly Thr Glu Asp Ala Leu Leu Gln Gln Leu Ala
                20                  25                  30

Asp Ser Met Leu Lys Glu Asp Cys Ala Ser Glu Leu Lys Val His Leu
            35                  40                  45

Ala Lys Ser Leu Pro Leu Pro Ser Ser Val Asn Arg Pro Arg Ile Asp
        50                  55                  60

Leu Ile Val Phe Val Val Asn Leu His Ser Lys Tyr Ser Leu Gln Asn
65                  70                  75                  80

Thr Glu Glu Ser Leu Arg His Val Asp Ala Ser Phe Phe Leu Gly Lys
                85                  90                  95

Val Cys Phe Leu Ala Thr Gly Ala Gly Arg Glu Ser His Cys Ser Ile
                100                 105                 110

His Arg His Thr Val Val Lys Leu Ala His Thr Tyr Gln Ser Pro Leu
            115                 120                 125

Leu Tyr Cys Asp Leu Glu Val Glu Gly Phe Arg Ala Thr Met Ala Gln
        130                 135                 140

Arg Leu Val Arg Val Leu Gln Ile Cys Ala Gly His Val Pro Gly Val
145                 150                 155                 160

Ser Ala Leu Asn Leu Leu Ser Leu Leu Arg Ser Ser Glu Gly Pro Ser
                165                 170                 175

Leu Glu Asp Leu
            180

<210> SEQ ID NO 24
<211> LENGTH: 58
<212> TYPE: PRT
<213> ORGANISM: Homo sapiens

<400> SEQUENCE: 24

Met Gly Arg Val Trp Asp Leu Pro Gly Val Leu Lys Val Glu Gly Phe
1               5                   10                  15

Arg Ala Thr Met Ala Gln Arg Leu Val Arg Val Leu Gln Ile Cys Ala
```

-continued

```
                20                  25                  30
Gly His Val Pro Gly Val Ser Ala Leu Asn Leu Leu Ser Leu Leu Arg
                35                  40                  45

Ser Ser Glu Gly Pro Ser Leu Glu Asp Leu
    50                  55

<210> SEQ ID NO 25
<211> LENGTH: 418
<212> TYPE: PRT
<213> ORGANISM: Homo sapiens

<400> SEQUENCE: 25

Met Ala Pro Arg Gly Arg Arg Pro Arg Pro His Arg Ser Glu Gly
1               5                   10                  15

Ala Arg Arg Ser Lys Asn Thr Leu Glu Arg Thr His Ser Met Lys Asp
                20                  25                  30

Lys Ala Gly Gln Lys Cys Lys Pro Ile Asp Val Phe Asp Phe Pro Asp
                35                  40                  45

Asn Ser Asp Val Ser Ser Ile Gly Arg Leu Gly Glu Asn Glu Lys Asp
        50                  55                  60

Glu Glu Thr Tyr Glu Thr Phe Asp Pro Leu His Ser Thr Ala Ile
65                  70                  75                  80

Tyr Ala Asp Glu Glu Glu Phe Ser Lys His Cys Gly Leu Ser Leu Ser
                    85                  90                  95

Ser Thr Pro Pro Gly Lys Glu Ala Lys Arg Ser Ser Asp Thr Ser Gly
                100                 105                 110

Asn Glu Ala Ser Glu Ile Glu Ser Val Lys Ile Ser Ala Lys Lys Pro
            115                 120                 125

Gly Arg Lys Leu Arg Pro Ile Ser Asp Asp Ser Glu Ser Ile Glu Glu
        130                 135                 140

Ser Asp Thr Arg Arg Lys Val Lys Ser Ala Glu Lys Ile Ser Thr Gln
145                 150                 155                 160

Arg His Glu Val Ile Arg Thr Thr Ala Ser Ser Glu Leu Ser Glu Lys
                165                 170                 175

Pro Ala Glu Ser Val Thr Ser Lys Lys Thr Gly Pro Leu Ser Ala Gln
                180                 185                 190

Pro Ser Val Glu Lys Glu Asn Leu Ala Ile Glu Ser Gln Ser Lys Thr
            195                 200                 205

Gln Lys Lys Gly Lys Ile Ser His Asp Lys Arg Lys Ser Arg Ser
        210                 215                 220

Lys Ala Ile Gly Ser Asp Thr Ser Asp Ile Val His Ile Trp Cys Pro
225                 230                 235                 240

Glu Gly Met Lys Thr Ser Asp Ile Lys Glu Leu Asn Ile Val Leu Pro
                245                 250                 255

Glu Phe Glu Lys Thr His Leu Glu His Gln Gln Arg Ile Glu Ser Lys
                260                 265                 270

Val Cys Lys Ala Ala Ile Ala Thr Phe Tyr Val Asn Val Lys Glu Gln
            275                 280                 285

Phe Ile Lys Met Leu Lys Glu Ser Gln Met Leu Thr Asn Leu Lys Arg
        290                 295                 300

Lys Asn Ala Lys Met Ile Ser Asp Ile Glu Lys Arg Gln Arg Met
305                 310                 315                 320

Ile Glu Val Gln Asp Glu Leu Leu Arg Leu Glu Pro Gln Leu Lys Gln
                325                 330                 335
```

-continued

```
Leu Gln Thr Lys Tyr Asp Glu Leu Lys Glu Arg Lys Ser Ser Leu Arg
            340                 345                 350

Asn Ala Ala Tyr Phe Leu Ser Asn Leu Lys Gln Leu Tyr Gln Asp Tyr
        355                 360                 365

Ser Asp Val Gln Ala Gln Glu Pro Asn Val Lys Glu Thr Tyr Asp Ser
    370                 375                 380

Ser Ser Leu Pro Ala Leu Leu Phe Lys Ala Arg Thr Leu Leu Gly Ala
385                 390                 395                 400

Glu Ser His Leu Arg Asn Ile Asn His Gln Leu Glu Lys Leu Leu Asp
                405                 410                 415

Gln Gly
```

<210> SEQ ID NO 26
<211> LENGTH: 320
<212> TYPE: PRT
<213> ORGANISM: Homo sapiens

<400> SEQUENCE: 26

```
Met Ala Pro Arg Gly Arg Arg Pro Arg Pro His Arg Ser Glu Gly
1               5                   10                  15

Ala Arg Arg Ser Lys Asn Thr Leu Glu Arg Thr His Ser Met Lys Asp
            20                  25                  30

Lys Ala Gly Gln Lys Cys Lys Pro Ile Asp Val Phe Asp Phe Pro Asp
        35                  40                  45

Asn Ser Asp Val Ser Ser Ile Gly Arg Leu Gly Glu Asn Glu Lys Asp
    50                  55                  60

Glu Glu Thr Tyr Glu Thr Phe Asp Pro Pro Leu His Ser Thr Ala Ile
65                  70                  75                  80

Tyr Ala Asp Glu Glu Glu Phe Ser Lys His Cys Gly Leu Ser Leu Ser
                85                  90                  95

Ser Thr Pro Pro Gly Lys Glu Ala Lys Arg Ser Ser Asp Thr Ser Gly
            100                 105                 110

Asn Glu Ala Ser Glu Ile Glu Ser Val Lys Ile Ser Ala Lys Lys Pro
        115                 120                 125

Gly Arg Lys Leu Arg Pro Ile Ser Asp Asp Ser Glu Ser Ile Glu Glu
    130                 135                 140

Ser Asp Thr Arg Arg Lys Val Lys Ser Ala Glu Lys Ile Ser Thr Gln
145                 150                 155                 160

Arg His Glu Val Ile Arg Thr Thr Ala Ser Ser Glu Leu Ser Glu Lys
                165                 170                 175

Pro Ala Glu Ser Val Thr Ser Lys Lys Thr Gly Pro Leu Ser Ala Gln
            180                 185                 190

Pro Ser Val Glu Lys Glu Asn Leu Ala Ile Glu Ser Gln Ser Lys Thr
        195                 200                 205

Gln Lys Lys Gly Lys Ile Ser His Asp Lys Arg Lys Lys Ser Arg Ser
    210                 215                 220

Lys Ala Ile Gly Ser Asp Thr Ser Asp Ile Val His Ile Trp Cys Pro
225                 230                 235                 240

Glu Gly Met Lys Thr Ser Asp Ile Lys Glu Leu Asn Ile Val Leu Pro
                245                 250                 255

Glu Phe Glu Lys Thr His Leu Glu His Gln Gln Arg Ile Glu Ser Lys
            260                 265                 270

Val Cys Lys Ala Ala Ile Ala Thr Phe Tyr Val Asn Val Lys Glu Gln
        275                 280                 285
```

```
Phe Ile Lys Met Leu Lys Glu Ser Gln Met Leu Thr Asn Leu Lys Arg
    290                 295                 300

Lys Asn Ala Lys Val Arg Ala Thr Ala Glu Thr Thr Thr Asn Lys Ile
305                 310                 315                 320

<210> SEQ ID NO 27
<211> LENGTH: 337
<212> TYPE: PRT
<213> ORGANISM: Homo sapiens

<400> SEQUENCE: 27

Met Ala Pro Arg Gly Arg Arg Pro Arg Pro His Arg Ser Glu Gly
1               5                   10                  15

Ala Arg Arg Ser Lys Asn Thr Leu Glu Arg Thr His Ser Met Lys Asp
                20                  25                  30

Lys Ala Gly Gln Lys Cys Lys Pro Ile Asp Val Phe Asp Phe Pro Asp
            35                  40                  45

Asn Ser Asp Val Ser Ser Ile Gly Arg Leu Gly Glu Asn Glu Lys Asp
50                  55                  60

Glu Glu Thr Tyr Glu Thr Phe Asp Pro Pro Leu His Ser Thr Ala Ile
65                  70                  75                  80

Tyr Ala Asp Glu Glu Glu Phe Ser Lys His Cys Gly Leu Ser Leu Ser
                85                  90                  95

Ser Thr Pro Pro Gly Lys Glu Ala Lys Arg Ser Ser Asp Thr Ser Gly
            100                 105                 110

Asn Glu Ala Ser Glu Ile Glu Ser Val Lys Ile Ser Ala Lys Lys Pro
        115                 120                 125

Gly Arg Lys Leu Arg Pro Ile Ser Asp Asp Ser Glu Ser Ile Glu Glu
130                 135                 140

Ser Asp Thr Arg Arg Lys Val Lys Ser Ala Glu Lys Ile Ser Thr Gln
145                 150                 155                 160

Arg His Glu Val Ile Arg Thr Thr Ala Ser Ser Glu Leu Ser Glu Lys
                165                 170                 175

Pro Ala Glu Ser Val Thr Ser Lys Lys Thr Gly Pro Leu Ser Ala Gln
            180                 185                 190

Pro Ser Val Glu Lys Glu Asn Leu Ala Ile Glu Ser Gln Ser Lys Thr
        195                 200                 205

Gln Lys Lys Gly Lys Ile Ser His Asp Lys Arg Lys Ser Arg Ser
210                 215                 220

Lys Ala Ile Gly Ser Asp Thr Ser Asp Ile Val His Ile Trp Cys Pro
225                 230                 235                 240

Glu Gly Met Lys Thr Ser Asp Ile Lys Glu Leu Asn Ile Val Leu Pro
                245                 250                 255

Glu Phe Glu Lys Thr His Leu Glu His Gln Gln Arg Ile Glu Ser Lys
            260                 265                 270

Val Cys Lys Ala Ala Ile Ala Thr Phe Tyr Val Asn Val Lys Glu Gln
        275                 280                 285

Phe Ile Lys Met Leu Lys Glu Ser Gln Met Leu Thr Asn Leu Lys Arg
290                 295                 300

Lys Asn Ala Lys Met Ile Ser Asp Ile Glu Lys Lys Arg Gln Arg Met
305                 310                 315                 320

Ile Glu Val Gln Asp Glu Leu Leu Arg Leu Trp Thr Gly Ala Gly Leu
                325                 330                 335

Trp
```

```
<210> SEQ ID NO 28
<211> LENGTH: 299
<212> TYPE: PRT
<213> ORGANISM: Homo sapiens

<400> SEQUENCE: 28

Met Leu Lys Glu Val Leu Gln Arg Glu Gly Lys Ser Tyr Lys Ser Glu
1               5                   10                  15

Thr Leu Met Tyr Ile Lys Lys Ala Arg Ala Ser Glu Asn Lys Leu Ser
            20                  25                  30

Glu Ser Ile Leu Ala His Arg Glu Asn Met Arg Gln Met Ile Arg Ser
        35                  40                  45

Phe Ser Glu Pro Phe Gly Arg Asp Leu Leu Ser Ile Ser Asp Gly Arg
    50                  55                  60

Gly Arg Ala His Asn Arg Arg Gly His Asn Asp Gly Glu Asp Ser Leu
65                  70                  75                  80

Thr Ala Thr Ser Cys Ser Leu Val Pro Phe Gly Asp Phe Gly Gly Met
                85                  90                  95

His Thr Asp Val Ser Ser Phe Gln Thr Met Asp Gln Met Val Ser Asn
            100                 105                 110

Met Arg Asn Tyr Met Gln Lys Leu Glu Arg Asn Phe Gly Gln Leu Ser
        115                 120                 125

Val Asp Pro Asn Gly His Ser Phe Cys Ser Ser Val Met Thr Tyr
    130                 135                 140

Ser Lys Ile Gly Asp Glu Pro Pro Lys Val Phe Gln Ala Ser Thr Gln
145                 150                 155                 160

Thr Arg Arg Ala Pro Gly Gly Ile Lys Glu Thr Arg Lys Ala Met Arg
                165                 170                 175

Asp Ser Asp Ser Gly Leu Glu Lys Met Ala Ile Gly His His Ile His
            180                 185                 190

Asp Arg Ala His Val Ile Lys Lys Ser Lys Asn Lys Lys Thr Gly Asp
        195                 200                 205

Glu Glu Val Asn Gln Glu Phe Ile Asn Met Asn Glu Ser Asp Ala His
    210                 215                 220

Ala Phe Asp Glu Glu Trp Gln Ser Glu Val Leu Lys Tyr Lys Pro Gly
225                 230                 235                 240

Arg His Asn Leu Gly Asn Thr Arg Met Arg Ser Val Gly His Glu Asn
                245                 250                 255

Pro Gly Ser Arg Glu Leu Lys Arg Arg Glu Lys Pro Gln Gln Ser Pro
            260                 265                 270

Ala Ile Glu His Gly Arg Arg Ser Asn Val Leu Gly Asp Lys Leu His
        275                 280                 285

Ile Lys Gly Ser Ser Val Lys Ser Asn Lys Lys
    290                 295

<210> SEQ ID NO 29
<211> LENGTH: 344
<212> TYPE: PRT
<213> ORGANISM: Homo sapiens

<400> SEQUENCE: 29

Met Asp Ser Tyr Ser Ala Pro Glu Ser Thr Pro Ser Ala Ser Ser Arg
1               5                   10                  15

Pro Glu Asp Tyr Phe Ile Gly Ala Thr Pro Leu Gln Lys Arg Leu Glu
            20                  25                  30
```

-continued

Ser Val Arg Lys Gln Ser Ser Phe Ile Leu Thr Pro Arg Arg Lys
          35                  40                  45

Ile Pro Gln Cys Ser Gln Leu Gln Glu Asp Val Asp Pro Gln Lys Val
 50                  55                  60

Ala Phe Leu Leu His Lys Gln Trp Thr Leu Tyr Ser Leu Thr Pro Leu
 65                  70                  75                  80

Tyr Lys Phe Ser Tyr Ser Asn Leu Lys Glu Tyr Ser Arg Leu Leu Asn
                 85                  90                  95

Ala Phe Ile Val Ala Glu Lys Gln Lys Gly Leu Ala Val Glu Val Gly
                100                 105                 110

Glu Asp Phe Asn Ile Lys Val Ile Phe Ser Thr Leu Leu Gly Met Lys
            115                 120                 125

Gly Thr Gln Arg Asp Pro Glu Ala Phe Leu Val Gln Ile Val Ser Lys
130                 135                 140

Ser Gln Leu Pro Ser Glu Asn Arg Glu Gly Lys Val Leu Trp Thr Gly
145                 150                 155                 160

Trp Phe Cys Cys Val Phe Gly Asp Ser Leu Leu Glu Thr Val Ser Glu
                165                 170                 175

Asp Phe Thr Cys Leu Pro Leu Phe Leu Ala Asn Gly Ala Glu Ser Asn
                180                 185                 190

Thr Ala Ile Ile Gly Thr Trp Phe Gln Lys Thr Phe Asp Cys Tyr Phe
            195                 200                 205

Ser Pro Leu Ala Ile Asn Ala Phe Asn Leu Ser Trp Met Ala Ala Met
210                 215                 220

Trp Thr Ala Cys Lys Met Asp His Tyr Val Ala Thr Thr Glu Phe Leu
225                 230                 235                 240

Trp Ser Val Pro Cys Ser Pro Gln Ser Leu Asp Ile Ser Phe Ala Ile
                245                 250                 255

His Pro Glu Asp Ala Lys Ala Leu Trp Asp Ser Val His Lys Thr Pro
                260                 265                 270

Gly Glu Val Thr Gln Glu Val Asp Leu Phe Met Asp Cys Leu Tyr
            275                 280                 285

Ser His Phe His Arg His Phe Lys Ile His Leu Ser Ala Thr Arg Leu
290                 295                 300

Val Arg Val Ser Thr Ser Val Ala Ser Ala His Thr Asp Gly Lys Ile
305                 310                 315                 320

Lys Ile Leu Cys His Lys Tyr Leu Ile Gly Val Leu Ala Tyr Leu Thr
                325                 330                 335

Glu Leu Ala Ile Phe Gln Ile Glu
            340

<210> SEQ ID NO 30
<211> LENGTH: 390
<212> TYPE: PRT
<213> ORGANISM: Homo sapiens

<400> SEQUENCE: 30

Met Asp Ser Tyr Ser Ala Pro Glu Ser Thr Pro Ser Ala Ser Ser Arg
 1               5                  10                  15

Pro Glu Asp Tyr Phe Ile Gly Ala Thr Pro Leu Gln Lys Arg Leu Glu
                20                  25                  30

Ser Val Arg Lys Gln Ser Ser Phe Ile Leu Thr Pro Arg Arg Lys
          35                  40                  45

Ile Pro Gln Cys Ser Gln Leu Gln Glu Asp Val Asp Pro Gln Lys Val
 50                  55                  60

```
Ala Phe Leu Leu His Lys Gln Trp Thr Leu Tyr Ser Leu Thr Pro Leu
 65                  70                  75                  80

Tyr Lys Phe Ser Tyr Ser Asn Leu Lys Glu Tyr Ser Arg Leu Leu Asn
                 85                  90                  95

Ala Phe Ile Val Ala Glu Lys Gln Lys Gly Leu Ala Val Glu Val Gly
            100                 105                 110

Glu Asp Phe Asn Ile Lys Val Ile Phe Ser Thr Leu Leu Gly Met Lys
            115                 120                 125

Gly Thr Gln Arg Asp Pro Glu Ala Phe Leu Val Gln Gly Leu Ile Leu
130                 135                 140

Ser Pro Arg Leu Glu Tyr Ser Gly Thr Ile Leu Val Asp Cys Asn Leu
145                 150                 155                 160

Cys Leu Leu Gly Ser Ser Asp Pro Ser Thr Leu Ala Phe Gln Val Ala
                165                 170                 175

Gly Thr Ala Gly Ala Cys His His Thr Arg Ile Val Ser Lys Ser Gln
            180                 185                 190

Leu Pro Ser Glu Asn Arg Glu Gly Lys Val Leu Trp Thr Gly Trp Phe
            195                 200                 205

Cys Cys Val Phe Gly Asp Ser Leu Leu Glu Thr Val Ser Glu Asp Phe
210                 215                 220

Thr Cys Leu Pro Leu Phe Leu Ala Asn Gly Ala Glu Ser Asn Thr Ala
225                 230                 235                 240

Ile Ile Gly Thr Trp Phe Gln Lys Thr Phe Asp Cys Tyr Phe Ser Pro
                245                 250                 255

Leu Ala Ile Asn Ala Phe Asn Leu Ser Trp Met Ala Ala Met Trp Thr
                260                 265                 270

Ala Cys Lys Met Asp His Tyr Val Ala Thr Thr Glu Phe Leu Trp Ser
            275                 280                 285

Val Pro Cys Ser Pro Gln Ser Leu Asp Ile Ser Phe Ala Ile His Pro
290                 295                 300

Glu Asp Ala Lys Ala Leu Trp Asp Ser Val His Lys Thr Pro Gly Glu
305                 310                 315                 320

Val Thr Gln Glu Glu Val Asp Leu Phe Met Asp Cys Leu Tyr Ser His
                325                 330                 335

Phe His Arg His Phe Lys Ile His Leu Ser Ala Thr Arg Leu Val Arg
                340                 345                 350

Val Ser Thr Ser Val Ala Ser Ala His Thr Asp Gly Lys Ile Lys Ile
            355                 360                 365

Leu Cys His Lys Tyr Leu Ile Gly Val Leu Ala Tyr Leu Thr Glu Leu
            370                 375                 380

Ala Ile Phe Gln Ile Glu
385                 390

<210> SEQ ID NO 31
<211> LENGTH: 269
<212> TYPE: PRT
<213> ORGANISM: Homo sapiens

<400> SEQUENCE: 31

Met Asn Gln Glu Asp Leu Asp Pro Asp Ser Thr Thr Asp Val Gly Asp
  1               5                  10                  15

Val Thr Asn Thr Glu Glu Glu Leu Ile Arg Glu Cys Glu Glu Met Trp
             20                  25                  30

Lys Asp Met Glu Glu Cys Gln Asn Lys Leu Ser Leu Ile Gly Thr Glu
```

```
                   35                  40                  45
Thr Leu Thr Asp Ser Asn Ala Gln Leu Ser Leu Leu Ile Met Gln Val
 50                  55                  60

Lys Cys Leu Thr Ala Glu Leu Ser Gln Trp Gln Lys Lys Thr Pro Glu
 65                  70                  75                  80

Thr Ile Pro Leu Thr Glu Asp Val Leu Ile Thr Leu Gly Lys Glu Glu
                 85                  90                  95

Phe Gln Lys Leu Arg Gln Asp Leu Glu Met Val Leu Ser Thr Lys Glu
                100                 105                 110

Ser Lys Asn Glu Lys Leu Lys Glu Asp Leu Glu Arg Glu Gln Arg Trp
            115                 120                 125

Leu Asp Glu Gln Gln Gln Ile Met Glu Ser Leu Asn Val Leu His Ser
130                 135                 140

Glu Leu Lys Asn Lys Val Glu Thr Phe Ser Glu Ser Arg Ile Phe Asn
145                 150                 155                 160

Glu Leu Lys Thr Lys Met Leu Asn Ile Lys Glu Tyr Lys Glu Lys Leu
                165                 170                 175

Leu Ser Thr Leu Gly Glu Phe Leu Glu Asp His Phe Pro Leu Pro Asp
            180                 185                 190

Arg Ser Val Lys Lys Lys Lys Asn Ile Gln Glu Ser Ser Val Asn
        195                 200                 205

Leu Ile Thr Leu His Glu Met Leu Glu Ile Leu Ile Asn Arg Leu Phe
210                 215                 220

Asp Val Pro His Asp Pro Tyr Val Lys Ile Ser Asp Ser Phe Trp Pro
225                 230                 235                 240

Pro Tyr Val Glu Leu Leu Arg Asn Gly Ile Ala Leu Arg His Pro
                245                 250                 255

Glu Asp Pro Thr Arg Ile Arg Leu Glu Ala Phe His Gln
            260                 265

<210> SEQ ID NO 32
<211> LENGTH: 294
<212> TYPE: PRT
<213> ORGANISM: Homo sapiens

<400> SEQUENCE: 32

Met Ala Gly Ile Leu Ala Ser Gly Leu Gly Val Leu Ala His Leu Glu
 1               5                  10                  15

Arg Leu Glu Thr Gln Val Ser Arg Ser Arg Lys Gln Ser Glu Glu Leu
                20                  25                  30

Gln Ser Val Gln Ala Gln Gly Ala Leu Gly Thr Lys Ile His Lys
            35                  40                  45

Leu Arg Arg Leu Arg Asp Glu Leu Arg Ala Val Arg His Arg Arg
 50                  55                  60

Ala Ser Val Lys Ala Cys Ile Ala Asn Val Glu Pro Asn Gln Thr Val
 65                  70                  75                  80

Glu Ile Asn Glu Gln Glu Ala Leu Glu Lys Leu Glu Asn Val Lys
                85                  90                  95

Ala Ile Leu Gln Ala Tyr His Phe Thr Gly Leu Ser Gly Lys Leu Thr
                100                 105                 110

Ser Arg Gly Val Cys Val Cys Ile Ser Thr Ala Phe Glu Gly Asn Leu
            115                 120                 125

Leu Asp Ser Tyr Phe Val Asp Leu Val Ile Gln Lys Pro Leu Arg Ile
130                 135                 140
```

```
His His His Ser Val Pro Val Phe Ile Pro Leu Glu Glu Ile Ala Ala
145                 150                 155                 160

Lys Tyr Leu Gln Thr Asn Ile Gln His Phe Leu Phe Ser Leu Cys Glu
                165                 170                 175

Tyr Leu Asn Ala Tyr Ser Gly Arg Lys Tyr Gln Ala Asp Arg Leu Gln
            180                 185                 190

Ser Asp Phe Ala Ala Leu Leu Thr Gly Pro Leu Gln Arg Asn Pro Leu
        195                 200                 205

Cys Asn Leu Leu Ser Phe Thr Tyr Lys Leu Asp Pro Gly Gly Gln Ser
    210                 215                 220

Phe Pro Phe Cys Ala Arg Leu Leu Tyr Lys Asp Leu Thr Ala Thr Leu
225                 230                 235                 240

Pro Thr Asp Val Thr Val Thr Cys Gln Gly Val Glu Val Leu Ser Thr
                245                 250                 255

Ser Trp Glu Glu Gln Arg Ala Ser His Glu Thr Leu Phe Cys Thr Lys
            260                 265                 270

Pro Leu His Gln Val Phe Ala Ser Phe Thr Arg Lys Gly Glu Lys Leu
        275                 280                 285

Asp Met Ser Leu Val Ser
    290

<210> SEQ ID NO 33
<211> LENGTH: 300
<212> TYPE: PRT
<213> ORGANISM: Homo sapiens

<400> SEQUENCE: 33

Met Glu Gln Ala Asn Pro Leu Arg Pro Asp Gly Glu Ser Lys Gly Gly
1               5                   10                  15

Val Leu Ala His Leu Glu Arg Leu Glu Thr Gln Val Ser Arg Ser Arg
            20                  25                  30

Lys Gln Ser Glu Glu Leu Gln Ser Val Gln Ala Gln Glu Gly Ala Leu
        35                  40                  45

Gly Thr Lys Ile His Lys Leu Arg Arg Leu Arg Asp Glu Leu Arg Ala
    50                  55                  60

Val Val Arg His Arg Arg Ala Ser Val Lys Ala Cys Ile Ala Asn Val
65                  70                  75                  80

Glu Pro Asn Gln Thr Val Glu Ile Asn Glu Gln Glu Ala Leu Glu Glu
                85                  90                  95

Lys Leu Glu Asn Val Lys Ala Ile Leu Gln Ala Tyr His Phe Thr Gly
            100                 105                 110

Leu Ser Gly Lys Leu Thr Ser Arg Gly Val Cys Val Cys Ile Ser Thr
        115                 120                 125

Ala Phe Glu Gly Asn Leu Leu Asp Ser Tyr Phe Val Asp Leu Val Ile
    130                 135                 140

Gln Lys Pro Leu Arg Ile His His Ser Val Pro Val Phe Ile Pro
145                 150                 155                 160

Leu Glu Glu Ile Ala Ala Lys Tyr Leu Gln Thr Asn Ile Gln His Phe
                165                 170                 175

Leu Phe Ser Leu Cys Glu Tyr Leu Asn Ala Tyr Ser Gly Arg Lys Tyr
            180                 185                 190

Gln Ala Asp Arg Leu Gln Ser Asp Phe Ala Ala Leu Leu Thr Gly Pro
        195                 200                 205

Leu Gln Arg Asn Pro Leu Cys Asn Leu Leu Ser Phe Thr Tyr Lys Leu
    210                 215                 220
```

```
Asp Pro Gly Gly Gln Ser Phe Pro Phe Cys Ala Arg Leu Leu Tyr Lys
225                 230                 235                 240

Asp Leu Thr Ala Thr Leu Pro Thr Asp Val Thr Val Thr Cys Gln Gly
            245                 250                 255

Val Glu Val Leu Ser Thr Ser Trp Glu Glu Gln Arg Ala Ser His Glu
        260                 265                 270

Thr Leu Phe Cys Thr Lys Pro Leu His Gln Val Phe Ala Ser Phe Thr
    275                 280                 285

Arg Lys Gly Glu Lys Leu Asp Met Ser Leu Val Ser
290                 295                 300

<210> SEQ ID NO 34
<211> LENGTH: 2316
<212> TYPE: PRT
<213> ORGANISM: Homo sapiens

<400> SEQUENCE: 34

Met Asp Gly Val Ser Ser Glu Ala Asn Glu Glu Asn Asp Asn Ile Glu
1               5                   10                  15

Arg Pro Val Arg Arg His Ser Ser Ile Leu Lys Pro Pro Arg Ser
            20                  25                  30

Pro Leu Gln Asp Leu Arg Gly Gly Asn Glu Arg Val Gln Glu Ser Asn
        35                  40                  45

Ala Leu Arg Asn Lys Lys Asn Ser Arg Arg Val Ser Phe Ala Asp Thr
    50                  55                  60

Ile Lys Val Phe Gln Thr Glu Ser His Met Lys Ile Val Arg Lys Ser
65                  70                  75                  80

Glu Met Glu Glu Thr Glu Thr Gly Glu Asn Leu Leu Leu Ile Gln Asn
                85                  90                  95

Lys Lys Leu Glu Asp Asn Tyr Cys Glu Ile Thr Gly Met Asn Thr Leu
            100                 105                 110

Leu Ser Ala Pro Ile His Thr Gln Met Gln Gln Lys Glu Phe Ser Ile
        115                 120                 125

Ile Glu His Thr Arg Glu Arg Lys His Ala Asn Asp Gln Thr Val Ile
    130                 135                 140

Phe Ser Asp Glu Asn Gln Met Asp Leu Thr Ser Ser His Thr Val Met
145                 150                 155                 160

Ile Thr Lys Gly Leu Leu Asp Asn Pro Ile Ser Glu Lys Ser Thr Lys
                165                 170                 175

Ile Asp Thr Thr Ser Phe Leu Ala Asn Leu Lys Leu His Thr Glu Asp
            180                 185                 190

Ser Arg Met Lys Lys Glu Val Asn Phe Ser Val Asp Gln Asn Thr Ser
        195                 200                 205

Ser Glu Asn Lys Ile Asp Phe Asn Asp Phe Ile Lys Arg Leu Lys Thr
    210                 215                 220

Gly Lys Cys Ser Ala Phe Pro Asp Val Pro Asp Lys Glu Asn Phe Glu
225                 230                 235                 240

Ile Pro Ile Tyr Ser Lys Glu Pro Asn Ser Ala Ser Ser Thr His Gln
                245                 250                 255

Met His Val Ser Leu Lys Glu Asp Glu Asn Asn Ser Asn Ile Thr Arg
            260                 265                 270

Leu Phe Arg Glu Lys Asp Asp Gly Met Asn Phe Thr Gln Cys His Thr
        275                 280                 285

Ala Asn Ile Gln Thr Leu Ile Pro Thr Ser Ser Glu Thr Asn Ser Arg
```

```
            290                 295                 300
Glu Ser Lys Gly Asn Asp Ile Thr Ile Tyr Gly Asn Asp Phe Met Asp
305                 310                 315                 320
Leu Thr Phe Asn His Thr Leu Gln Ile Leu Pro Ala Thr Gly Asn Phe
                325                 330                 335
Ser Glu Ile Glu Asn Gln Thr Gln Asn Ala Met Asp Val Thr Thr Gly
            340                 345                 350
Tyr Gly Thr Lys Ala Ser Gly Asn Lys Thr Val Phe Lys Ser Lys Gln
            355                 360                 365
Asn Thr Ala Phe Gln Asp Leu Ser Ile Asn Ser Ala Asp Lys Ile His
            370                 375                 380
Ile Thr Arg Ser His Ile Met Gly Ala Glu Thr His Ile Val Ser Gln
385                 390                 395                 400
Thr Cys Asn Gln Asp Ala Arg Ile Leu Ala Met Thr Pro Glu Ser Ile
                405                 410                 415
Tyr Ser Asn Pro Ser Ile Gln Gly Cys Lys Thr Val Phe Tyr Ser Ser
                420                 425                 430
Cys Asn Asp Ala Met Glu Met Thr Lys Cys Leu Ser Asn Met Arg Glu
                435                 440                 445
Glu Lys Asn Leu Leu Lys His Asp Ser Asn Tyr Ala Lys Met Tyr Cys
450                 455                 460
Asn Pro Asp Ala Met Ser Ser Leu Thr Glu Lys Thr Ile Tyr Ser Gly
465                 470                 475                 480
Glu Glu Asn Met Asp Ile Thr Lys Ser His Thr Val Ala Ile Asp Asn
                485                 490                 495
Gln Ile Phe Lys Gln Asp Gln Ser Asn Val Gln Ile Ala Ala Ala Pro
                500                 505                 510
Thr Pro Glu Lys Glu Met Met Leu Gln Asn Leu Met Thr Thr Ser Glu
                515                 520                 525
Asp Gly Lys Met Asn Val Asn Cys Asn Ser Val Pro His Val Ser Lys
                530                 535                 540
Glu Arg Ile Gln Gln Ser Leu Ser Asn Pro Leu Ser Ile Ser Leu Thr
545                 550                 555                 560
Asp Arg Lys Thr Glu Leu Leu Ser Gly Glu Asn Met Asp Leu Thr Glu
                565                 570                 575
Ser His Thr Ser Asn Leu Gly Ser Gln Val Pro Leu Ala Ala Tyr Asn
                580                 585                 590
Leu Ala Pro Glu Ser Thr Ser Glu Ser His Ser Gln Ser Lys Ser Ser
                595                 600                 605
Ser Asp Glu Cys Glu Glu Ile Thr Lys Ser Arg Asn Glu Pro Phe Gln
                610                 615                 620
Arg Ser Asp Ile Ile Ala Lys Asn Ser Leu Thr Asp Thr Trp Asn Lys
625                 630                 635                 640
Asp Lys Asp Trp Val Leu Lys Ile Leu Pro Tyr Leu Asp Lys Asp Ser
                645                 650                 655
Pro Gln Ser Ala Asp Cys Asn Gln Glu Ile Ala Thr Ser His Asn Ile
                660                 665                 670
Val Tyr Cys Gly Gly Val Leu Asp Lys Gln Ile Thr Asn Arg Asn Thr
                675                 680                 685
Val Ser Trp Glu Gln Ser Leu Phe Ser Thr Thr Lys Pro Leu Phe Ser
                690                 695                 700
Ser Gly Gln Phe Ser Met Lys Asn His Asp Thr Ala Ile Ser Ser His
705                 710                 715                 720
```

```
Thr Val Lys Ser Val Leu Gly Gln Asn Ser Lys Leu Ala Glu Pro Leu
            725                 730                 735

Arg Lys Ser Leu Ser Asn Pro Thr Pro Asp Tyr Cys His Asp Lys Met
            740                 745                 750

Ile Ile Cys Ser Glu Glu Gln Asn Met Asp Leu Thr Lys Ser His
            755                 760                 765

Thr Val Val Ile Gly Phe Gly Pro Ser Glu Leu Gln Glu Leu Gly Lys
770                 775                 780

Thr Asn Leu Glu His Thr Thr Gly Gln Leu Thr Thr Met Asn Arg Gln
785                 790                 795                 800

Ile Ala Val Lys Val Glu Lys Cys Gly Lys Ser Pro Ile Glu Lys Ser
            805                 810                 815

Gly Val Leu Lys Ser Asn Cys Ile Met Asp Val Leu Gly Asp Glu Ser
            820                 825                 830

Val Gln Lys Pro Lys Phe Pro Lys Glu Lys Gln Asn Val Lys Ile Trp
            835                 840                 845

Gly Arg Lys Ser Val Gly Gly Pro Lys Ile Asp Lys Thr Ile Val Phe
            850                 855                 860

Ser Glu Asp Asp Lys Asn Asp Met Asp Ile Thr Lys Ser Tyr Thr Ile
865                 870                 875                 880

Glu Ile Asn His Arg Pro Leu Leu Glu Lys Arg Asp Cys His Leu Val
                885                 890                 895

Pro Leu Ala Gly Thr Ser Glu Thr Ile Leu Tyr Thr Cys Arg Gln Asp
            900                 905                 910

Asp Met Glu Ile Thr Arg Ser His Thr Thr Ala Leu Glu Cys Lys Thr
            915                 920                 925

Val Ser Pro Asp Glu Ile Thr Thr Arg Pro Met Asp Lys Thr Val Val
            930                 935                 940

Phe Val Asp Asn His Val Glu Leu Glu Met Thr Glu Ser His Thr Val
945                 950                 955                 960

Phe Ile Asp Tyr Gln Glu Lys Glu Arg Thr Asp Arg Pro Asn Phe Glu
            965                 970                 975

Leu Ser Gln Arg Lys Ser Leu Gly Thr Pro Thr Val Ile Cys Thr Pro
            980                 985                 990

Thr Glu Glu Ser Val Phe Phe Pro  Gly Asn Gly Glu Ser Asp Arg Leu
            995                 1000                1005

Val Ala  Asn Asp Ser Gln Leu  Thr Pro Leu Glu Glu  Trp Ser Asn
    1010                1015                 1020

Asn Arg  Gly Pro Val Glu Val  Ala Asp Asn Met Glu  Leu Ser Lys
    1025                1030                 1035

Ser Ala  Thr Cys Lys Asn Ile  Lys Asp Val Gln Ser  Pro Gly Phe
    1040                1045                 1050

Leu Asn  Glu Pro Leu Ser Ser  Lys Ser Gln Arg Arg  Lys Ser Leu
    1055                1060                 1065

Lys Leu  Lys Asn Asp Lys Thr  Ile Val Phe Ser Glu  Asn His Lys
    1070                1075                 1080

Asn Asp  Met Asp Ile Thr Gln  Ser Cys Met Val Glu  Ile Asp Asn
    1085                1090                 1095

Glu Ser  Ala Leu Glu Asp Lys  Glu Asp Phe His Leu  Ala Gly Ala
    1100                1105                 1110

Ser Lys  Thr Ile Leu Tyr Ser  Cys Gly Gln Asp Asp  Met Glu Ile
    1115                1120                 1125
```

```
Thr Arg Ser His Thr Thr Ala Leu Glu Cys Lys Thr Leu Leu Pro
1130                1135                1140

Asn Glu Ile Ala Ile Arg Pro Met Asp Lys Thr Val Leu Phe Thr
1145                1150                1155

Asp Asn Tyr Ser Asp Leu Glu Val Thr Asp Ser His Thr Val Phe
1160                1165                1170

Ile Asp Cys Gln Ala Thr Glu Lys Ile Leu Glu Glu Asn Pro Lys
1175                1180                1185

Phe Gly Ile Gly Lys Gly Lys Asn Leu Gly Val Ser Phe Pro Lys
1190                1195                1200

Asp Asn Ser Cys Val Gln Glu Ile Ala Glu Lys Gln Ala Leu Ala
1205                1210                1215

Val Gly Asn Lys Ile Val Leu His Thr Glu Gln Lys Gln Gln Leu
1220                1225                1230

Phe Ala Ala Thr Asn Arg Thr Thr Asn Glu Ile Ile Lys Phe His
1235                1240                1245

Ser Ala Ala Met Asp Glu Lys Val Ile Gly Lys Val Val Asp Gln
1250                1255                1260

Ala Cys Thr Leu Glu Lys Ala Gln Val Glu Ser Cys Gln Leu Asn
1265                1270                1275

Asn Arg Asp Arg Arg Asn Val Asp Phe Thr Ser Ser His Ala Thr
1280                1285                1290

Ala Val Cys Gly Ser Ser Asp Asn Tyr Ser Cys Leu Pro Asn Val
1295                1300                1305

Ile Ser Cys Thr Asp Asn Leu Glu Gly Ser Ala Met Leu Leu Cys
1310                1315                1320

Asp Lys Asp Glu Glu Lys Ala Asn Tyr Cys Pro Val Gln Asn Asp
1325                1330                1335

Leu Ala Tyr Ala Asn Asp Phe Ala Ser Glu Tyr Tyr Leu Glu Ser
1340                1345                1350

Glu Gly Gln Pro Leu Ser Ala Pro Cys Pro Leu Leu Glu Lys Glu
1355                1360                1365

Glu Val Ile Gln Thr Ser Thr Lys Gly Gln Leu Asp Cys Val Ile
1370                1375                1380

Thr Leu His Lys Asp Gln Asp Leu Ile Lys Asp Pro Arg Asn Leu
1385                1390                1395

Leu Ala Asn Gln Thr Leu Val Tyr Ser Gln Asp Leu Gly Glu Met
1400                1405                1410

Thr Lys Leu Asn Ser Lys Arg Val Ser Phe Lys Leu Pro Lys Asp
1415                1420                1425

Gln Met Lys Val Tyr Val Asp Asp Ile Tyr Val Ile Pro Gln Pro
1430                1435                1440

His Phe Ser Thr Asp Gln Pro Pro Leu Pro Lys Lys Gly Gln Ser
1445                1450                1455

Ser Ile Asn Lys Glu Glu Val Ile Leu Ser Lys Ala Gly Asn Lys
1460                1465                1470

Ser Leu Asn Ile Ile Glu Asn Ser Ser Ala Pro Ile Cys Glu Asn
1475                1480                1485

Lys Pro Lys Ile Leu Asn Ser Glu Glu Trp Phe Ala Ala Ala Cys
1490                1495                1500

Lys Lys Glu Leu Lys Glu Asn Ile Gln Thr Thr Asn Tyr Asn Thr
1505                1510                1515

Ala Leu Asp Phe His Ser Asn Ser Asp Val Thr Lys Gln Val Ile
```

```
               1520                1525                1530

Gln Thr His Val Asn Ala Gly Glu Ala Pro Asp Pro Val Ile Thr
    1535                1540                1545

Ser Asn Val Pro Cys Phe His Ser Ile Lys Pro Asn Leu Asn Asn
    1550                1555                1560

Leu Asn Gly Lys Thr Gly Glu Phe Leu Ala Phe Gln Thr Val His
    1565                1570                1575

Leu Pro Pro Leu Pro Glu Gln Leu Leu Glu Leu Gly Asn Lys Ala
    1580                1585                1590

His Asn Asp Met His Ile Val Gln Ala Thr Glu Ile His Asn Ile
    1595                1600                1605

Asn Ile Ile Ser Ser Asn Ala Lys Asp Ser Arg Asp Glu Glu Asn
    1610                1615                1620

Lys Lys Ser His Asn Gly Ala Glu Thr Thr Ser Leu Pro Pro Lys
    1625                1630                1635

Thr Val Phe Lys Asp Lys Val Arg Arg Cys Ser Leu Gly Ile Phe
    1640                1645                1650

Leu Pro Arg Leu Pro Asn Lys Arg Asn Cys Ser Val Thr Gly Ile
    1655                1660                1665

Asp Asp Leu Glu Gln Ile Pro Ala Asp Thr Thr Asp Ile Asn His
    1670                1675                1680

Leu Glu Thr Gln Pro Val Ser Ser Lys Asp Ser Gly Ile Gly Ser
    1685                1690                1695

Val Ala Gly Lys Leu Asn Leu Ser Pro Ser Gln Tyr Ile Asn Glu
    1700                1705                1710

Glu Asn Leu Pro Val Tyr Pro Asp Glu Ile Asn Ser Ser Asp Ser
    1715                1720                1725

Ile Asn Ile Glu Thr Glu Glu Lys Ala Leu Ile Glu Thr Tyr Gln
    1730                1735                1740

Lys Glu Ile Ser Pro Tyr Glu Asn Lys Met Gly Lys Thr Cys Asn
    1745                1750                1755

Ser Gln Lys Arg Thr Trp Val Gln Glu Glu Asp Ile His Lys
    1760                1765                1770

Glu Lys Lys Ile Arg Lys Asn Glu Ile Lys Phe Ser Asp Thr Thr
    1775                1780                1785

Gln Asp Arg Glu Ile Phe Asp His His Thr Glu Glu Asp Ile Asp
    1790                1795                1800

Lys Ser Ala Asn Ser Val Leu Ile Lys Asn Leu Ser Arg Thr Pro
    1805                1810                1815

Ser Ser Cys Ser Ser Ser Leu Asp Ser Ile Lys Ala Asp Gly Thr
    1820                1825                1830

Ser Leu Asp Phe Ser Thr Tyr Arg Ser Ser Gln Met Glu Ser Gln
    1835                1840                1845

Phe Leu Arg Asp Thr Ile Cys Glu Glu Ser Leu Arg Glu Lys Leu
    1850                1855                1860

Gln Asp Gly Arg Ile Thr Ile Arg Glu Phe Phe Ile Leu Leu Gln
    1865                1870                1875

Val His Ile Leu Ile Gln Lys Pro Arg Gln Ser Asn Leu Pro Gly
    1880                1885                1890

Asn Phe Thr Val Asn Thr Pro Pro Thr Pro Glu Asp Leu Met Leu
    1895                1900                1905

Ser Gln Tyr Val Tyr Arg Pro Lys Ile Gln Ile Tyr Arg Glu Asp
    1910                1915                1920
```

```
Cys Glu Ala Arg Arg Gln Lys Ile Glu Leu Lys Leu Ser Ala
    1925            1930            1935

Ser Asn Gln Asp Lys Leu Leu Val Asp Ile Asn Lys Asn Leu Trp
    1940            1945            1950

Glu Lys Met Arg His Cys Ser Asp Lys Glu Leu Lys Ala Phe Gly
    1955            1960            1965

Ile Tyr Leu Asn Lys Ile Lys Ser Cys Phe Thr Lys Met Thr Lys
    1970            1975            1980

Val Phe Thr His Gln Gly Lys Val Ala Leu Tyr Gly Lys Leu Val
    1985            1990            1995

Gln Ser Ala Gln Asn Glu Arg Glu Lys Leu Gln Ile Lys Ile Asp
    2000            2005            2010

Glu Met Asp Lys Ile Leu Lys Lys Ile Asp Asn Cys Leu Thr Glu
    2015            2020            2025

Met Glu Thr Glu Thr Lys Asn Leu Glu Asp Glu Lys Asn Asn
    2030            2035            2040

Pro Val Glu Glu Trp Asp Ser Glu Met Arg Ala Ala Glu Lys Glu
    2045            2050            2055

Leu Glu Gln Leu Lys Thr Glu Glu Glu Leu Gln Arg Asn Leu
    2060            2065            2070

Leu Glu Leu Glu Val Gln Lys Glu Gln Thr Leu Ala Gln Ile Asp
    2075            2080            2085

Phe Met Gln Lys Gln Arg Asn Arg Thr Glu Glu Leu Leu Asp Gln
    2090            2095            2100

Leu Ser Leu Ser Glu Trp Asp Val Val Glu Trp Ser Asp Asp Gln
    2105            2110            2115

Ala Val Phe Thr Phe Val Tyr Asp Thr Ile Gln Leu Thr Ile Thr
    2120            2125            2130

Phe Glu Glu Ser Val Val Gly Phe Pro Phe Leu Asp Lys Arg Tyr
    2135            2140            2145

Arg Lys Ile Val Asp Val Asn Phe Gln Ser Leu Leu Asp Glu Asp
    2150            2155            2160

Gln Ala Pro Pro Ser Ser Leu Leu Val His Lys Leu Ile Phe Gln
    2165            2170            2175

Tyr Val Glu Glu Lys Glu Ser Trp Lys Lys Thr Cys Thr Thr Gln
    2180            2185            2190

His Gln Leu Pro Lys Met Leu Glu Glu Phe Ser Leu Val Val His
    2195            2200            2205

His Cys Arg Leu Leu Gly Glu Glu Ile Glu Tyr Leu Lys Arg Trp
    2210            2215            2220

Gly Pro Asn Tyr Asn Leu Met Asn Ile Asp Ile Asn Asn Asn Glu
    2225            2230            2235

Leu Arg Leu Leu Phe Ser Ser Ala Ala Phe Ala Lys Phe Glu
    2240            2245            2250

Ile Thr Leu Phe Leu Ser Ala Tyr Tyr Pro Ser Val Pro Leu Pro
    2255            2260            2265

Ser Thr Ile Gln Asn His Val Gly Asn Thr Ser Gln Asp Asp Ile
    2270            2275            2280

Ala Thr Ile Leu Ser Lys Val Pro Leu Glu Asn Asn Tyr Leu Lys
    2285            2290            2295

Asn Val Val Lys Gln Ile Tyr Gln Asp Leu Phe Gln Asp Cys His
    2300            2305            2310
```

Phe Tyr His
    2315

<210> SEQ ID NO 35
<211> LENGTH: 2342
<212> TYPE: PRT
<213> ORGANISM: Homo sapiens

<400> SEQUENCE: 35

Met Asp Gly Val Ser Ser Glu Ala Asn Glu Asn Asp Asn Ile Glu
1               5                   10                  15

Arg Pro Val Arg Arg His Ser Ser Ile Leu Lys Pro Pro Arg Ser
                20                  25                  30

Pro Leu Gln Asp Leu Arg Gly Gly Asn Glu Arg Val Gln Glu Ser Asn
                35                  40                  45

Ala Leu Arg Asn Lys Lys Asn Ser Arg Arg Val Ser Phe Ala Asp Thr
50                      55                      60

Ile Lys Val Phe Gln Thr Glu Ser His Met Lys Ile Val Arg Lys Ser
65                      70                      75                  80

Glu Met Glu Gly Cys Ser Ala Met Val Pro Ser Gln Leu Gln Leu Leu
                85                  90                  95

Pro Pro Gly Phe Lys Arg Phe Ser Cys Leu Ser Leu Pro Glu Thr Glu
                100                 105                 110

Thr Gly Glu Asn Leu Leu Leu Ile Gln Asn Lys Lys Leu Glu Asp Asn
                115                 120                 125

Tyr Cys Glu Ile Thr Gly Met Asn Thr Leu Leu Ser Ala Pro Ile His
                130                 135                 140

Thr Gln Met Gln Gln Lys Glu Phe Ser Ile Ile Glu His Thr Arg Glu
145                     150                     155                 160

Arg Lys His Ala Asn Asp Gln Thr Val Ile Phe Ser Asp Glu Asn Gln
                165                 170                 175

Met Asp Leu Thr Ser Ser His Thr Val Met Ile Thr Lys Gly Leu Leu
                180                 185                 190

Asp Asn Pro Ile Ser Glu Lys Ser Thr Lys Ile Asp Thr Thr Ser Phe
                195                 200                 205

Leu Ala Asn Leu Lys Leu His Thr Glu Asp Ser Arg Met Lys Lys Glu
210                     215                     220

Val Asn Phe Ser Val Asp Gln Asn Thr Ser Ser Glu Asn Lys Ile Asp
225                     230                     235                 240

Phe Asn Asp Phe Ile Lys Arg Leu Lys Thr Gly Lys Cys Ser Ala Phe
                245                 250                 255

Pro Asp Val Pro Asp Lys Glu Asn Phe Glu Ile Pro Ile Tyr Ser Lys
                260                 265                 270

Glu Pro Asn Ser Ala Ser Ser Thr His Gln Met His Val Ser Leu Lys
                275                 280                 285

Glu Asp Glu Asn Asn Ser Asn Ile Thr Arg Leu Phe Arg Glu Lys Asp
                290                 295                 300

Asp Gly Met Asn Phe Thr Gln Cys His Thr Ala Asn Ile Gln Thr Leu
305                     310                     315                 320

Ile Pro Thr Ser Ser Glu Thr Asn Ser Arg Glu Ser Lys Gly Asn Asp
                325                 330                 335

Ile Thr Ile Tyr Gly Asn Asp Phe Met Asp Leu Thr Phe Asn His Thr
                340                 345                 350

Leu Gln Ile Leu Pro Ala Thr Gly Asn Phe Ser Glu Ile Glu Asn Gln
                355                 360                 365

-continued

Thr Gln Asn Ala Met Asp Val Thr Thr Gly Tyr Gly Thr Lys Ala Ser
    370                 375                 380

Gly Asn Lys Thr Val Phe Lys Ser Lys Gln Asn Thr Ala Phe Gln Asp
385                 390                 395                 400

Leu Ser Ile Asn Ser Ala Asp Lys Ile His Ile Thr Arg Ser His Ile
            405                 410                 415

Met Gly Ala Glu Thr His Ile Val Ser Gln Thr Cys Asn Gln Asp Ala
            420                 425                 430

Arg Ile Leu Ala Met Thr Pro Glu Ser Ile Tyr Ser Asn Pro Ser Ile
            435                 440                 445

Gln Gly Cys Lys Thr Val Phe Tyr Ser Ser Cys Asn Asp Ala Met Glu
    450                 455                 460

Met Thr Lys Cys Leu Ser Asn Met Arg Glu Glu Lys Asn Leu Leu Lys
465                 470                 475                 480

His Asp Ser Asn Tyr Ala Lys Met Tyr Cys Asn Pro Asp Ala Met Ser
                485                 490                 495

Ser Leu Thr Glu Lys Thr Ile Tyr Ser Gly Glu Glu Asn Met Asp Ile
                500                 505                 510

Thr Lys Ser His Thr Val Ala Ile Asp Asn Gln Ile Phe Lys Gln Asp
    515                 520                 525

Gln Ser Asn Val Gln Ile Ala Ala Ala Pro Thr Pro Glu Lys Glu Met
    530                 535                 540

Met Leu Gln Asn Leu Met Thr Thr Ser Glu Asp Gly Lys Met Asn Val
545                 550                 555                 560

Asn Cys Asn Ser Val Pro His Val Ser Lys Glu Arg Ile Gln Gln Ser
                565                 570                 575

Leu Ser Asn Pro Leu Ser Ile Ser Leu Thr Asp Arg Lys Thr Glu Leu
                580                 585                 590

Leu Ser Gly Glu Asn Met Asp Leu Thr Glu Ser His Thr Ser Asn Leu
            595                 600                 605

Gly Ser Gln Val Pro Leu Ala Ala Tyr Asn Leu Ala Pro Glu Ser Thr
        610                 615                 620

Ser Glu Ser His Ser Gln Ser Lys Ser Ser Ser Asp Glu Cys Glu Glu
625                 630                 635                 640

Ile Thr Lys Ser Arg Asn Glu Pro Phe Gln Arg Ser Asp Ile Ile Ala
                645                 650                 655

Lys Asn Ser Leu Thr Asp Thr Trp Asn Lys Asp Lys Asp Trp Val Leu
                660                 665                 670

Lys Ile Leu Pro Tyr Leu Asp Lys Asp Ser Pro Gln Ser Ala Asp Cys
            675                 680                 685

Asn Gln Glu Ile Ala Thr Ser His Asn Ile Val Tyr Cys Gly Gly Val
        690                 695                 700

Leu Asp Lys Gln Ile Thr Asn Arg Asn Thr Val Ser Trp Glu Gln Ser
705                 710                 715                 720

Leu Phe Ser Thr Thr Lys Pro Leu Phe Ser Ser Gly Gln Phe Ser Met
                725                 730                 735

Lys Asn His Asp Thr Ala Ile Ser Ser His Thr Val Lys Ser Val Leu
            740                 745                 750

Gly Gln Asn Ser Lys Leu Ala Glu Pro Leu Arg Lys Ser Leu Ser Asn
        755                 760                 765

Pro Thr Pro Asp Tyr Cys His Asp Lys Met Ile Ile Cys Ser Glu Glu
    770                 775                 780

```
Glu Gln Asn Met Asp Leu Thr Lys Ser His Thr Val Val Ile Gly Phe
785                 790                 795                 800

Gly Pro Ser Glu Leu Gln Glu Leu Gly Lys Thr Asn Leu Glu His Thr
            805                 810                 815

Thr Gly Gln Leu Thr Thr Met Asn Arg Gln Ile Ala Val Lys Val Glu
        820                 825                 830

Lys Cys Gly Lys Ser Pro Ile Glu Lys Ser Gly Val Leu Lys Ser Asn
                835                 840                 845

Cys Ile Met Asp Val Leu Glu Asp Ser Val Gln Lys Pro Lys Phe
    850                 855                 860

Pro Lys Glu Lys Gln Asn Val Lys Ile Trp Gly Arg Lys Ser Val Gly
865                 870                 875                 880

Gly Pro Lys Ile Asp Lys Thr Ile Val Phe Ser Glu Asp Lys Asn
            885                 890                 895

Asp Met Asp Ile Thr Lys Ser Tyr Thr Ile Glu Ile Asn His Arg Pro
                900                 905                 910

Leu Leu Glu Lys Arg Asp Cys His Leu Val Pro Leu Ala Gly Thr Ser
            915                 920                 925

Glu Thr Ile Leu Tyr Thr Cys Arg Gln Asp Asp Met Glu Ile Thr Arg
        930                 935                 940

Ser His Thr Thr Ala Leu Glu Cys Lys Thr Val Ser Pro Asp Glu Ile
945                 950                 955                 960

Thr Thr Arg Pro Met Asp Lys Thr Val Val Phe Val Asp Asn His Val
                965                 970                 975

Glu Leu Glu Met Thr Glu Ser His Thr Val Phe Ile Asp Tyr Gln Glu
            980                 985                 990

Lys Glu Arg Thr Asp Arg Pro Asn Phe Glu Leu Ser Gln Arg Lys Ser
        995                 1000                1005

Leu Gly Thr Pro Thr Val Ile Cys Thr Pro Thr Glu Glu Ser Val
    1010                1015                1020

Phe Phe Pro Gly Asn Gly Glu Ser Asp Arg Leu Val Ala Asn Asp
    1025                1030                1035

Ser Gln Leu Thr Pro Leu Glu Glu Trp Ser Asn Asn Arg Gly Pro
    1040                1045                1050

Val Glu Val Ala Asp Asn Met Glu Leu Ser Lys Ser Ala Thr Cys
    1055                1060                1065

Lys Asn Ile Lys Asp Val Gln Ser Pro Gly Phe Leu Asn Glu Pro
    1070                1075                1080

Leu Ser Ser Lys Ser Gln Arg Arg Lys Ser Leu Lys Leu Lys Asn
    1085                1090                1095

Asp Lys Thr Ile Val Phe Ser Glu Asn His Lys Asn Asp Met Asp
    1100                1105                1110

Ile Thr Gln Ser Cys Met Val Glu Ile Asp Asn Glu Ser Ala Leu
    1115                1120                1125

Glu Asp Lys Glu Asp Phe His Leu Ala Gly Ala Ser Lys Thr Ile
    1130                1135                1140

Leu Tyr Ser Cys Gly Gln Asp Met Glu Ile Thr Arg Ser His
    1145                1150                1155

Thr Thr Ala Leu Glu Cys Lys Thr Leu Leu Pro Asn Glu Ile Ala
    1160                1165                1170

Ile Arg Pro Met Asp Lys Thr Val Leu Phe Thr Asp Asn Tyr Ser
    1175                1180                1185

Asp Leu Glu Val Thr Asp Ser His Thr Val Phe Ile Asp Cys Gln
```

-continued

```
            1190                1195                1200
Ala Thr Glu Lys Ile Leu Glu Glu Asn Pro Lys Phe Gly Ile Gly
            1205                1210                1215
Lys Gly Lys Asn Leu Gly Val Ser Phe Pro Lys Asp Asn Ser Cys
            1220                1225                1230
Val Gln Glu Ile Ala Glu Lys Gln Ala Leu Ala Val Gly Asn Lys
            1235                1240                1245
Ile Val Leu His Thr Glu Gln Lys Gln Gln Leu Phe Ala Ala Thr
            1250                1255                1260
Asn Arg Thr Thr Asn Glu Ile Ile Lys Phe His Ser Ala Ala Met
            1265                1270                1275
Asp Glu Lys Val Ile Gly Lys Val Val Asp Gln Ala Cys Thr Leu
            1280                1285                1290
Glu Lys Ala Gln Val Glu Ser Cys Gln Leu Asn Asn Arg Asp Arg
            1295                1300                1305
Arg Asn Val Asp Phe Thr Ser Ser His Ala Thr Ala Val Cys Gly
            1310                1315                1320
Ser Ser Asp Asn Tyr Ser Cys Leu Pro Asn Val Ile Ser Cys Thr
            1325                1330                1335
Asp Asn Leu Glu Gly Ser Ala Met Leu Leu Cys Asp Lys Asp Glu
            1340                1345                1350
Glu Lys Ala Asn Tyr Cys Pro Val Gln Asn Asp Leu Ala Tyr Ala
            1355                1360                1365
Asn Asp Phe Ala Ser Glu Tyr Tyr Leu Glu Ser Glu Gly Gln Pro
            1370                1375                1380
Leu Ser Ala Pro Cys Pro Leu Leu Glu Lys Glu Glu Val Ile Gln
            1385                1390                1395
Thr Ser Thr Lys Gly Gln Leu Asp Cys Val Ile Thr Leu His Lys
            1400                1405                1410
Asp Gln Asp Leu Ile Lys Asp Pro Arg Asn Leu Leu Ala Asn Gln
            1415                1420                1425
Thr Leu Val Tyr Ser Gln Asp Leu Gly Glu Met Thr Lys Leu Asn
            1430                1435                1440
Ser Lys Arg Val Ser Phe Lys Leu Pro Lys Asp Gln Met Lys Val
            1445                1450                1455
Tyr Val Asp Asp Ile Tyr Val Ile Pro Gln Pro His Phe Ser Thr
            1460                1465                1470
Asp Gln Pro Pro Leu Pro Lys Lys Gly Gln Ser Ser Ile Asn Lys
            1475                1480                1485
Glu Glu Val Ile Leu Ser Lys Ala Gly Asn Lys Ser Leu Asn Ile
            1490                1495                1500
Ile Glu Asn Ser Ser Ala Pro Ile Cys Glu Asn Lys Pro Lys Ile
            1505                1510                1515
Leu Asn Ser Glu Glu Trp Phe Ala Ala Ala Cys Lys Lys Glu Leu
            1520                1525                1530
Lys Glu Asn Ile Gln Thr Thr Asn Tyr Asn Thr Ala Leu Asp Phe
            1535                1540                1545
His Ser Asn Ser Asp Val Thr Lys Gln Val Ile Gln Thr His Val
            1550                1555                1560
Asn Ala Gly Glu Ala Pro Asp Pro Val Ile Thr Ser Asn Val Pro
            1565                1570                1575
Cys Phe His Ser Ile Lys Pro Asn Leu Asn Asn Leu Asn Gly Lys
            1580                1585                1590
```

-continued

Thr Gly Glu Phe Leu Ala Phe Gln Thr Val His Leu Pro Pro Leu
1595                1600                1605

Pro Glu Gln Leu Leu Glu Leu Gly Asn Lys Ala His Asn Asp Met
1610                1615                1620

His Ile Val Gln Ala Thr Glu Ile His Asn Ile Asn Ile Ile Ser
1625                1630                1635

Ser Asn Ala Lys Asp Ser Arg Asp Glu Glu Asn Lys Lys Ser His
1640                1645                1650

Asn Gly Ala Glu Thr Thr Ser Leu Pro Pro Lys Thr Val Phe Lys
1655                1660                1665

Asp Lys Val Arg Arg Cys Ser Leu Gly Ile Phe Leu Pro Arg Leu
1670                1675                1680

Pro Asn Lys Arg Asn Cys Ser Val Thr Gly Ile Asp Asp Leu Glu
1685                1690                1695

Gln Ile Pro Ala Asp Thr Thr Asp Ile Asn His Leu Glu Thr Gln
1700                1705                1710

Pro Val Ser Ser Lys Asp Ser Gly Ile Gly Ser Val Ala Gly Lys
1715                1720                1725

Leu Asn Leu Ser Pro Ser Gln Tyr Ile Asn Glu Glu Asn Leu Pro
1730                1735                1740

Val Tyr Pro Asp Glu Ile Asn Ser Ser Asp Ser Ile Asn Ile Glu
1745                1750                1755

Thr Glu Glu Lys Ala Leu Ile Glu Thr Tyr Gln Lys Glu Ile Ser
1760                1765                1770

Pro Tyr Glu Asn Lys Met Gly Lys Thr Cys Asn Ser Gln Lys Arg
1775                1780                1785

Thr Trp Val Gln Glu Glu Asp Ile His Lys Glu Lys Lys Ile
1790                1795                1800

Arg Lys Asn Glu Ile Lys Phe Ser Asp Thr Thr Gln Asp Arg Glu
1805                1810                1815

Ile Phe Asp His His Thr Glu Glu Asp Ile Asp Lys Ser Ala Asn
1820                1825                1830

Ser Val Leu Ile Lys Asn Leu Ser Arg Thr Pro Ser Ser Cys Ser
1835                1840                1845

Ser Ser Leu Asp Ser Ile Lys Ala Asp Gly Thr Ser Leu Asp Phe
1850                1855                1860

Ser Thr Tyr Arg Ser Ser Gln Met Glu Ser Gln Phe Leu Arg Asp
1865                1870                1875

Thr Ile Cys Glu Glu Ser Leu Arg Glu Lys Leu Gln Asp Gly Arg
1880                1885                1890

Ile Thr Ile Arg Glu Phe Phe Ile Leu Leu Gln Val His Ile Leu
1895                1900                1905

Ile Gln Lys Pro Arg Gln Ser Asn Leu Pro Gly Asn Phe Thr Val
1910                1915                1920

Asn Thr Pro Pro Thr Pro Glu Asp Leu Met Leu Ser Gln Tyr Val
1925                1930                1935

Tyr Arg Pro Lys Ile Gln Ile Tyr Arg Glu Asp Cys Glu Ala Arg
1940                1945                1950

Arg Gln Lys Ile Glu Glu Leu Lys Leu Ser Ala Ser Asn Gln Asp
1955                1960                1965

Lys Leu Leu Val Asp Ile Asn Lys Asn Leu Trp Glu Lys Met Arg
1970                1975                1980

```
His Cys Ser Asp Lys Glu Leu Lys Ala Phe Gly Ile Tyr Leu Asn
1985                1990                1995

Lys Ile Lys Ser Cys Phe Thr Lys Met Thr Lys Val Phe Thr His
2000                2005                2010

Gln Gly Lys Val Ala Leu Tyr Gly Lys Leu Val Gln Ser Ala Gln
2015                2020                2025

Asn Glu Arg Glu Lys Leu Gln Ile Lys Ile Asp Glu Met Asp Lys
2030                2035                2040

Ile Leu Lys Lys Ile Asp Asn Cys Leu Thr Glu Met Glu Thr Glu
2045                2050                2055

Thr Lys Asn Leu Glu Asp Glu Glu Lys Asn Asn Pro Val Glu Glu
2060                2065                2070

Trp Asp Ser Glu Met Arg Ala Ala Glu Lys Glu Leu Glu Gln Leu
2075                2080                2085

Lys Thr Glu Glu Glu Glu Leu Gln Arg Asn Leu Leu Glu Leu Glu
2090                2095                2100

Val Gln Lys Glu Gln Thr Leu Ala Gln Ile Asp Phe Met Gln Lys
2105                2110                2115

Gln Arg Asn Arg Thr Glu Glu Leu Leu Asp Gln Leu Ser Leu Ser
2120                2125                2130

Glu Trp Asp Val Val Glu Trp Ser Asp Gln Ala Val Phe Thr
2135                2140                2145

Phe Val Tyr Asp Thr Ile Gln Leu Thr Ile Thr Phe Glu Glu Ser
2150                2155                2160

Val Val Gly Phe Pro Phe Leu Asp Lys Arg Tyr Arg Lys Ile Val
2165                2170                2175

Asp Val Asn Phe Gln Ser Leu Leu Asp Glu Asp Gln Ala Pro Pro
2180                2185                2190

Ser Ser Leu Leu Val His Lys Leu Ile Phe Gln Tyr Val Glu Glu
2195                2200                2205

Lys Glu Ser Trp Lys Lys Thr Cys Thr Thr Gln His Gln Leu Pro
2210                2215                2220

Lys Met Leu Glu Glu Phe Ser Leu Val Val His His Cys Arg Leu
2225                2230                2235

Leu Gly Glu Glu Ile Glu Tyr Leu Lys Arg Trp Gly Pro Asn Tyr
2240                2245                2250

Asn Leu Met Asn Ile Asp Ile Asn Asn Asn Glu Leu Arg Leu Leu
2255                2260                2265

Phe Ser Ser Ala Ala Phe Ala Lys Phe Glu Ile Thr Leu Phe
2270                2275                2280

Leu Ser Ala Tyr Tyr Pro Ser Val Pro Leu Pro Ser Thr Ile Gln
2285                2290                2295

Asn His Val Gly Asn Thr Ser Gln Asp Asp Ile Ala Thr Ile Leu
2300                2305                2310

Ser Lys Val Pro Leu Glu Asn Asn Tyr Leu Lys Asn Val Val Lys
2315                2320                2325

Gln Ile Tyr Gln Asp Leu Phe Gln Asp Cys His Phe Tyr His
2330                2335                2340

<210> SEQ ID NO 36
<211> LENGTH: 1833
<212> TYPE: PRT
<213> ORGANISM: Homo sapiens

<400> SEQUENCE: 36
```

-continued

```
Met Asp Gly Val Ser Ser Glu Ala Asn Glu Asn Asp Asn Ile Glu
1               5                   10                  15

Arg Pro Val Arg Arg His Ser Ser Ile Leu Lys Pro Arg Ser
            20                  25                  30

Pro Leu Gln Asp Leu Arg Gly Gly Asn Glu Arg Val Gln Glu Ser Asn
                35                  40                  45

Ala Leu Arg Asn Lys Lys Asn Ser Arg Arg Val Ser Phe Ala Asp Thr
50                  55                  60

Ile Lys Val Phe Gln Thr Glu Ser His Met Lys Ile Val Arg Lys Ser
65                  70                  75                  80

Glu Met Glu Glu Thr Glu Thr Gly Glu Asn Leu Leu Leu Ile Gln Asn
                85                  90                  95

Lys Lys Leu Glu Asp Asn Tyr Cys Glu Ile Thr Gly Met Asn Thr Leu
                100                 105                 110

Leu Ser Ala Pro Ile His Thr Gln Met Gln Gln Lys Glu Phe Ser Ile
                115                 120                 125

Ile Glu His Thr Arg Glu Arg Lys His Ala Asn Asp Gln Thr Val Ile
                130                 135                 140

Phe Ser Asp Glu Asn Gln Met Asp Leu Thr Ser Ser His Thr Val Met
145                 150                 155                 160

Ile Thr Lys Gly Leu Leu Asp Asn Pro Ile Ser Glu Lys Ser Thr Lys
                165                 170                 175

Ile Asp Thr Thr Ser Phe Leu Ala Asn Leu Lys Leu His Thr Glu Asp
                180                 185                 190

Ser Arg Met Lys Lys Glu Val Asn Phe Ser Val Asp Gln Asn Thr Ser
                195                 200                 205

Ser Glu Asn Lys Ile Asp Phe Asn Asp Phe Ile Lys Arg Leu Lys Thr
                210                 215                 220

Gly Lys Cys Ser Ala Phe Pro Asp Val Pro Asp Lys Glu Asn Phe Glu
225                 230                 235                 240

Ile Pro Ile Tyr Ser Lys Glu Pro Asn Ser Ala Ser Ser Thr His Gln
                245                 250                 255

Met His Val Ser Leu Lys Glu Asp Glu Asn Asn Ser Asn Ile Thr Arg
                260                 265                 270

Leu Phe Arg Glu Lys Asp Asp Gly Met Asn Phe Thr Gln Cys His Thr
                275                 280                 285

Ala Asn Ile Gln Thr Leu Ile Pro Thr Ser Ser Glu Thr Asn Ser Arg
290                 295                 300

Glu Ser Lys Gly Asn Asp Ile Thr Ile Tyr Gly Asn Asp Phe Met Asp
305                 310                 315                 320

Leu Thr Phe Asn His Thr Leu Gln Ile Leu Pro Ala Thr Gly Asn Phe
                325                 330                 335

Ser Glu Ile Glu Asn Gln Thr Gln Asn Ala Met Asp Val Thr Thr Gly
                340                 345                 350

Tyr Gly Thr Lys Ala Ser Gly Asn Lys Thr Val Phe Lys Ser Lys Gln
                355                 360                 365

Asn Thr Ala Phe Gln Asp Leu Ser Ile Asn Ser Ala Asp Lys Ile His
    370                 375                 380

Ile Thr Arg Ser His Ile Met Gly Ala Glu Thr His Ile Val Ser Gln
385                 390                 395                 400

Thr Cys Asn Gln Asp Ala Arg Ile Leu Ala Met Thr Pro Glu Ser Ile
                405                 410                 415
```

```
Tyr Ser Asn Pro Ser Ile Gln Gly Cys Lys Thr Val Phe Tyr Ser Ser
            420                 425                 430

Cys Asn Asp Ala Met Glu Met Thr Lys Cys Leu Ser Asn Met Arg Glu
            435                 440                 445

Glu Lys Asn Leu Leu Lys His Asp Ser Asn Tyr Ser Lys Met Tyr Cys
        450                 455                 460

Asn Pro Asp Ala Met Ser Ser Leu Thr Glu Lys Thr Ile Tyr Ser Gly
465                 470                 475                 480

Glu Glu Asn Met Asp Ile Thr Lys Ser His Thr Val Ala Ile Asp Asn
                485                 490                 495

Gln Ile Phe Lys Gln Asp Gln Ser Asn Val Gln Ile Ala Ala Ala Pro
            500                 505                 510

Thr Pro Glu Lys Glu Met Met Leu Gln Asn Leu Met Thr Thr Ser Glu
            515                 520                 525

Asp Gly Lys Met Asn Val Asn Cys Asn Ser Val Pro His Val Ser Lys
        530                 535                 540

Glu Arg Ile Gln Gln Ser Leu Ser Asn Pro Leu Ser Ile Ser Leu Thr
545                 550                 555                 560

Asp Arg Lys Thr Glu Leu Leu Ser Gly Glu Asn Met Asp Leu Thr Glu
                565                 570                 575

Ser His Thr Ser Asn Leu Gly Ser Gln Val Pro Leu Ala Ala Tyr Asn
            580                 585                 590

Leu Ala Pro Glu Ser Thr Ser Glu Ser His Ser Gln Ser Lys Ser Ser
            595                 600                 605

Ser Asp Glu Cys Glu Ile Thr Lys Ser Arg Asn Glu Pro Phe Gln
610                 615                 620

Arg Ser Asp Ile Ile Ala Lys Asn Ser Leu Thr Asp Thr Trp Asn Lys
625                 630                 635                 640

Asp Lys Asp Trp Val Leu Lys Ile Leu Pro Tyr Leu Asp Lys Asp Ser
                645                 650                 655

Pro Gln Ser Ala Asp Cys Asn Gln Glu Ile Ala Thr Ser His Asn Ile
            660                 665                 670

Val Tyr Cys Gly Gly Val Leu Asp Lys Gln Ile Thr Asn Arg Asn Thr
            675                 680                 685

Val Ser Trp Glu Gln Ser Leu Phe Ser Thr Thr Lys Pro Leu Phe Ser
        690                 695                 700

Ser Gly Gln Phe Ser Met Lys Asn His Asp Thr Ala Ile Ser Ser His
705                 710                 715                 720

Thr Val Lys Ser Val Leu Gly Gln Asn Ser Lys Leu Ala Glu Pro Leu
                725                 730                 735

Arg Lys Ser Leu Ser Asn Pro Thr Pro Asp Tyr Cys His Asp Lys Met
            740                 745                 750

Ile Ile Cys Ser Glu Glu Gln Asn Met Asp Leu Thr Lys Ser His
            755                 760                 765

Thr Val Val Ile Gly Phe Gly Pro Ser Glu Leu Gln Glu Leu Gly Lys
        770                 775                 780

Thr Asn Leu Glu His Thr Thr Gly Gln Leu Thr Thr Met Asn Arg Gln
785                 790                 795                 800

Ile Ala Val Lys Val Glu Lys Cys Gly Lys Ser Pro Ile Glu Lys Ser
                805                 810                 815

Gly Val Leu Lys Ser Asn Cys Ile Met Asp Val Leu Glu Asp Glu Ser
            820                 825                 830

Val Gln Lys Pro Lys Phe Pro Lys Glu Lys Gln Asn Val Lys Ile Trp
```

```
                835                 840                 845
Gly Arg Lys Ser Val Gly Pro Lys Ile Asp Lys Thr Ile Val Phe
    850                 855                 860
Ser Glu Asp Asp Lys Asn Asp Met Asp Ile Thr Lys Ser Tyr Thr Ile
865                 870                 875                 880
Glu Ile Asn His Arg Pro Leu Leu Glu Lys Arg Asp Cys His Leu Val
                885                 890                 895
Pro Leu Ala Gly Thr Ser Glu Thr Ile Leu Tyr Thr Cys Gly Gln Asp
            900                 905                 910
Asp Met Glu Ile Thr Arg Ser His Thr Thr Ala Leu Glu Cys Lys Thr
                915                 920                 925
Val Ser Pro Asp Glu Ile Thr Thr Arg Pro Met Asp Lys Thr Val Val
    930                 935                 940
Phe Val Asp Asn His Val Glu Leu Glu Met Thr Glu Ser His Thr Val
945                 950                 955                 960
Phe Ile Asp Tyr Gln Glu Lys Glu Arg Thr Asp Arg Pro Asn Phe Glu
                965                 970                 975
Leu Ser Gln Arg Lys Ser Leu Gly Pro Thr Val Ile Cys Thr Pro
                980                 985                 990
Thr Glu Glu Ser Val Phe Phe Pro  Gly Asn Gly Glu Ser  Asp Arg Leu
            995                 1000                1005
Val Ala Asn Asp Ser Gln Leu  Thr Pro Leu Glu Glu  Trp Ser Asn
    1010                1015                1020
Asn Arg Gly Pro Val Glu Val  Ala Asp Asn Met Glu  Leu Ser Lys
        1025                1030                1035
Ser Ala Thr Cys Lys Asn Ile  Lys Asp Val Gln Ser  Pro Gly Phe
        1040                1045                1050
Leu Asn Glu Pro Leu Ser Ser  Lys Ser Gln Arg Arg  Lys Ser Leu
        1055                1060                1065
Lys Leu Lys Asn Asp Lys Thr  Ile Val Phe Ser Glu  Asn His Lys
        1070                1075                1080
Asn Asp Met Asp Ile Thr Gln  Ser Cys Met Val Glu  Ile Asp Asn
        1085                1090                1095
Glu Ser Ala Leu Glu Asp Lys  Glu Asp Phe His Leu  Ala Gly Ala
        1100                1105                1110
Ser Lys Thr Ile Leu Tyr Ser  Cys Gly Gln Asp  Met Glu Ile
        1115                1120                1125
Thr Arg Ser His Thr Thr Ala  Leu Glu Cys Lys Thr  Leu Leu Pro
        1130                1135                1140
Asn Glu Ile Ala Ile Arg Pro  Met Asp Lys Thr Val  Leu Phe Thr
        1145                1150                1155
Asp Asn Tyr Ser Asp Leu Glu  Val Thr Asp Ser His  Thr Val Phe
        1160                1165                1170
Ile Asp Cys Gln Ala Thr Glu  Lys Ile Leu Glu Glu  Asn Pro Lys
        1175                1180                1185
Phe Gly Ile Gly Lys Gly Lys  Asn Leu Gly Val Ser  Phe Pro Lys
        1190                1195                1200
Asp Asn Ser Cys Val Gln Glu  Ile Ala Glu Lys Gln  Ala Leu Ala
        1205                1210                1215
Val Gly Asn Lys Ile Val Leu  His Thr Glu Gln Lys  Gln Gln Leu
        1220                1225                1230
Phe Ala Ala Thr Asn Arg Thr  Thr Asn Glu Ile Ile  Lys Phe His
        1235                1240                1245
```

```
Ser Ala Ala Met Asp Glu Lys Val Ile Gly Lys Val Val Asp Gln
    1250                1255                1260

Ala Cys Thr Leu Glu Lys Ala Gln Val Glu Ser Cys Gln Leu Asn
    1265                1270                1275

Asn Arg Asp Arg Arg Asn Val Asp Phe Thr Ser Ser His Ala Thr
    1280                1285                1290

Ala Val Cys Gly Ser Ser Asp Asn Tyr Ser Cys Leu Pro Asn Val
    1295                1300                1305

Ile Ser Cys Thr Asp Asn Leu Glu Gly Ser Ala Met Leu Leu Cys
    1310                1315                1320

Asp Lys Asp Glu Glu Lys Ala Asn Tyr Cys Pro Val Gln Asn Asp
    1325                1330                1335

Leu Ala Tyr Ala Asn Asp Phe Ala Ser Glu Tyr Tyr Leu Glu Ser
    1340                1345                1350

Glu Gly Gln Pro Leu Ser Ala Pro Cys Pro Leu Leu Glu Lys Glu
    1355                1360                1365

Glu Val Ile Gln Thr Ser Thr Lys Gly Gln Leu Asp Cys Val Ile
    1370                1375                1380

Thr Leu His Lys Asp Gln Asp Leu Ile Lys Asp Pro Arg Asn Leu
    1385                1390                1395

Leu Ala Asn Gln Thr Leu Val Tyr Ser Gln Asp Leu Gly Glu Met
    1400                1405                1410

Thr Lys Leu Asn Ser Lys Arg Val Ser Phe Lys Leu Pro Lys Asp
    1415                1420                1425

Gln Met Lys Val Tyr Val Asp Asp Ile Tyr Val Ile Pro Gln Pro
    1430                1435                1440

His Phe Ser Thr Asp Gln Pro Pro Leu Pro Lys Lys Gly Gln Ser
    1445                1450                1455

Ser Ile Asn Lys Glu Glu Val Ile Leu Ser Lys Ala Gly Asn Lys
    1460                1465                1470

Ser Leu Asn Ile Ile Glu Asn Ser Ser Ala Pro Ile Cys Glu Asn
    1475                1480                1485

Lys Pro Lys Ile Leu Asn Ser Glu Glu Trp Phe Ala Ala Ala Cys
    1490                1495                1500

Lys Lys Glu Leu Lys Glu Asn Ile Gln Thr Thr Asn Tyr Asn Thr
    1505                1510                1515

Ala Leu Asp Phe His Ser Asn Ser Asp Val Thr Lys Gln Val Ile
    1520                1525                1530

Gln Thr His Val Asn Ala Gly Glu Ala Pro Asp Pro Val Ile Thr
    1535                1540                1545

Ser Asn Val Pro Cys Phe His Ser Ile Lys Pro Asn Leu Asn Asn
    1550                1555                1560

Leu Asn Gly Lys Thr Gly Glu Phe Leu Ala Phe Gln Thr Val His
    1565                1570                1575

Leu Pro Pro Leu Pro Glu Gln Leu Leu Glu Leu Gly Asn Lys Ala
    1580                1585                1590

His Asn Asp Met His Ile Val Gln Ala Thr Glu Ile His Asn Ile
    1595                1600                1605

Asn Ile Ile Ser Ser Asn Ala Lys Asp Ser Arg Asp Glu Glu Asn
    1610                1615                1620

Lys Lys Ser His Asn Gly Ala Glu Thr Thr Ser Leu Pro Pro Lys
    1625                1630                1635
```

Thr Val Phe Lys Asp Lys Val Arg Arg Cys Ser Leu Gly Ile Phe
1640                1645                1650

Leu Pro Arg Leu Pro Asn Lys Arg Asn Cys Ser Val Thr Gly Ile
1655                1660                1665

Asp Asp Leu Glu Gln Ile Pro Ala Asp Thr Thr Asp Ile Asn His
1670                1675                1680

Leu Glu Thr Gln Pro Val Ser Ser Lys Asp Ser Gly Ile Gly Ser
1685                1690                1695

Val Ala Gly Lys Leu Asn Leu Ser Pro Ser Gln Tyr Ile Asn Glu
1700                1705                1710

Glu Asn Leu Pro Val Tyr Pro Asp Glu Ile Asn Ser Ser Asp Ser
1715                1720                1725

Ile Asn Ile Glu Thr Glu Glu Lys Ala Leu Ile Glu Thr Tyr Gln
1730                1735                1740

Lys Glu Ile Ser Pro Tyr Glu Asn Lys Met Gly Lys Thr Cys Asn
1745                1750                1755

Ser Gln Lys Arg Thr Trp Val Gln Glu Glu Glu Asp Ile His Lys
1760                1765                1770

Glu Lys Lys Ile Arg Lys Asn Glu Ile Lys Phe Ser Asp Thr Thr
1775                1780                1785

Gln Asp Arg Glu Val Ser Ser Val Leu Asn Gln Arg Met Phe Leu
1790                1795                1800

Asn Phe Gly Phe Cys Phe Val Phe Leu Asn Cys Gly Tyr Ser Gln
1805                1810                1815

Ile Leu Ile Leu Val Ser Gly Arg Gln Lys Ile Ile Ile Ser Thr
1820                1825                1830

<210> SEQ ID NO 37
<211> LENGTH: 2196
<212> TYPE: PRT
<213> ORGANISM: Homo sapiens

<400> SEQUENCE: 37

Met Asp Gly Val Ser Ser Glu Ala Asn Glu Glu Asn Asp Asn Ile Glu
1               5                   10                  15

Arg Pro Val Arg Arg His Ser Ser Ile Leu Lys Pro Pro Arg Ser
                20                  25                  30

Pro Leu Gln Asp Leu Arg Gly Gly Asn Glu Arg Val Gln Glu Ser Asn
                35                  40                  45

Ala Leu Arg Asn Lys Lys Asn Ser Arg Arg Val Ser Phe Ala Asp Thr
50                  55                  60

Ile Lys Val Phe Gln Thr Glu Ser His Met Lys Ile Val Arg Lys Ser
65                  70                  75                  80

Glu Met Glu Glu Thr Glu Thr Gly Glu Asn Leu Leu Leu Ile Gln Asn
                85                  90                  95

Lys Lys Leu Glu Asp Asn Tyr Cys Glu Ile Thr Gly Met Asn Thr Leu
                100                 105                 110

Leu Ser Ala Pro Ile His Thr Gln Met Gln Gln Lys Glu Phe Ser Ile
            115                 120                 125

Ile Glu His Thr Arg Glu Arg Lys His Ala Asn Asp Gln Thr Val Ile
            130                 135                 140

Phe Ser Asp Glu Asn Gln Met Asp Leu Thr Ser Ser His Thr Val Met
145                 150                 155                 160

Ile Thr Lys Gly Leu Leu Asp Asn Pro Ile Ser Glu Lys Ser Thr Lys
                165                 170                 175

```
Ile Asp Thr Thr Ser Phe Leu Ala Asn Leu Lys Leu His Thr Glu Asp
            180                 185                 190

Ser Arg Met Lys Lys Glu Val Asn Phe Ser Val Asp Gln Asn Thr Ser
            195                 200                 205

Ser Glu Asn Lys Ile Asp Phe Asn Asp Phe Ile Lys Arg Leu Lys Thr
            210                 215                 220

Gly Lys Cys Ser Ala Phe Pro Asp Val Pro Asp Lys Glu Asn Phe Glu
225                 230                 235                 240

Ile Pro Ile Tyr Ser Lys Glu Pro Asn Ser Ala Ser Ser Thr His Gln
            245                 250                 255

Met His Val Ser Leu Lys Glu Asp Glu Asn Asn Ser Asn Ile Thr Arg
            260                 265                 270

Leu Phe Arg Glu Lys Asp Asp Gly Met Asn Phe Thr Gln Cys His Thr
            275                 280                 285

Ala Asn Ile Gln Thr Leu Ile Pro Thr Ser Ser Glu Thr Asn Ser Arg
            290                 295                 300

Glu Ser Lys Gly Asn Asp Ile Thr Ile Tyr Gly Asn Asp Phe Met Asp
305                 310                 315                 320

Leu Thr Phe Asn His Thr Leu Gln Ile Leu Pro Ala Thr Gly Asn Phe
            325                 330                 335

Ser Glu Ile Glu Asn Gln Thr Gln Asn Ala Met Asp Val Thr Thr Gly
            340                 345                 350

Tyr Gly Thr Lys Ala Ser Gly Asn Lys Thr Val Phe Lys Ser Lys Gln
            355                 360                 365

Asn Thr Ala Phe Gln Asp Leu Ser Ile Asn Ser Ala Asp Lys Ile His
            370                 375                 380

Ile Thr Arg Ser His Ile Met Gly Ala Glu Thr His Ile Val Ser Gln
385                 390                 395                 400

Thr Cys Asn Gln Asp Ala Arg Ile Leu Ala Met Thr Pro Glu Ser Ile
            405                 410                 415

Tyr Ser Asn Pro Ser Ile Gln Gly Cys Lys Thr Val Phe Tyr Ser Ser
            420                 425                 430

Cys Asn Asp Ala Met Glu Met Thr Lys Cys Leu Ser Asn Met Arg Glu
            435                 440                 445

Glu Lys Asn Leu Leu Lys His Asp Ser Asn Tyr Ser Lys Met Tyr Cys
            450                 455                 460

Asn Pro Asp Ala Met Ser Ser Leu Thr Glu Lys Thr Ile Tyr Ser Gly
465                 470                 475                 480

Glu Glu Asn Met Asp Ile Thr Lys Ser His Thr Val Ala Ile Asp Asn
            485                 490                 495

Gln Ile Phe Lys Gln Asp Gln Ser Asn Val Gln Ile Ala Ala Ala Pro
            500                 505                 510

Thr Pro Glu Lys Glu Met Met Leu Gln Asn Leu Met Thr Thr Ser Glu
            515                 520                 525

Asp Gly Lys Met Asn Val Asn Cys Asn Ser Val Pro His Val Ser Lys
            530                 535                 540

Glu Arg Ile Gln Gln Ser Leu Ser Asn Pro Leu Ser Ile Ser Leu Thr
545                 550                 555                 560

Asp Arg Lys Thr Glu Leu Leu Ser Gly Glu Asn Met Asp Leu Thr Glu
            565                 570                 575

Ser His Thr Ser Asn Leu Gly Ser Gln Val Pro Leu Ala Ala Tyr Asn
            580                 585                 590
```

-continued

Leu Ala Pro Glu Ser Thr Ser Glu Ser His Ser Gln Ser Lys Ser Ser
            595                 600                 605

Ser Asp Glu Cys Glu Glu Ile Thr Lys Ser Arg Asn Glu Pro Phe Gln
610                 615                 620

Arg Ser Asp Ile Ile Ala Lys Asn Ser Leu Thr Asp Thr Trp Asn Lys
625                 630                 635                 640

Asp Lys Asp Trp Val Leu Lys Ile Leu Pro Tyr Leu Asp Lys Asp Ser
            645                 650                 655

Pro Gln Ser Ala Asp Cys Asn Gln Glu Ile Ala Thr Ser His Asn Ile
            660                 665                 670

Val Tyr Cys Gly Gly Val Leu Asp Lys Gln Ile Thr Asn Arg Asn Thr
            675                 680                 685

Val Ser Trp Glu Gln Ser Leu Phe Ser Thr Lys Pro Leu Phe Ser
            690                 695                 700

Ser Gly Gln Phe Ser Met Lys Asn His Asp Thr Ala Ile Ser Ser His
705                 710                 715                 720

Thr Val Lys Ser Val Leu Gly Gln Asn Ser Lys Leu Ala Glu Pro Leu
                725                 730                 735

Arg Lys Ser Leu Ser Asn Pro Thr Pro Asp Tyr Cys His Asp Lys Met
                740                 745                 750

Ile Ile Cys Ser Glu Glu Gln Asn Met Asp Leu Thr Lys Ser His
            755                 760                 765

Thr Val Val Ile Gly Phe Gly Pro Ser Glu Leu Gln Glu Leu Gly Lys
            770                 775                 780

Thr Asn Leu Glu His Thr Thr Gly Gln Leu Thr Thr Met Asn Arg Gln
785                 790                 795                 800

Ile Ala Val Lys Val Glu Lys Cys Gly Lys Ser Pro Ile Glu Lys Ser
                805                 810                 815

Gly Val Leu Lys Ser Asn Cys Ile Met Asp Val Leu Glu Asp Glu Ser
            820                 825                 830

Val Gln Lys Pro Lys Phe Pro Lys Glu Lys Gln Asn Val Lys Ile Trp
            835                 840                 845

Gly Arg Lys Ser Val Gly Gly Pro Lys Ile Asp Lys Thr Ile Val Phe
850                 855                 860

Ser Glu Asp Asp Lys Asn Asp Met Asp Ile Thr Lys Ser Tyr Thr Ile
865                 870                 875                 880

Glu Ile Asn His Arg Pro Leu Leu Glu Lys Arg Asp Cys His Leu Val
                885                 890                 895

Pro Leu Ala Gly Thr Ser Glu Thr Ile Leu Tyr Thr Cys Gly Gln Asp
            900                 905                 910

Asp Met Glu Ile Thr Arg Ser His Thr Thr Ala Leu Glu Cys Lys Thr
            915                 920                 925

Val Ser Pro Asp Glu Ile Thr Thr Arg Pro Met Asp Lys Thr Val Val
            930                 935                 940

Phe Val Asp Asn His Val Glu Leu Glu Met Thr Glu Ser His Thr Val
945                 950                 955                 960

Phe Ile Asp Tyr Gln Glu Lys Glu Arg Thr Asp Arg Pro Asn Phe Glu
                965                 970                 975

Leu Ser Gln Arg Lys Ser Leu Gly Thr Pro Val Ile Cys Thr Pro
                980                 985                 990

Thr Glu Glu Ser Val Phe Phe Pro Gly Asn Gly Glu Ser Asp Arg Leu
            995                 1000                1005

Val Ala Asn Asp Ser Gln Leu Thr Pro Leu Glu Glu Trp Ser Asn

-continued

```
                1010                1015                1020

Asn Arg Gly Pro Val Glu Val Ala Asp Asn Met Glu Leu Ser Lys
        1025                1030                1035

Ser Ala Thr Cys Lys Asn Ile Lys Asp Val Gln Ser Pro Gly Phe
        1040                1045                1050

Leu Asn Glu Pro Leu Ser Ser Lys Ser Gln Arg Arg Lys Ser Leu
        1055                1060                1065

Lys Leu Lys Asn Asp Lys Thr Ile Val Phe Ser Glu Asn His Lys
        1070                1075                1080

Asn Asp Met Asp Ile Thr Gln Ser Cys Met Val Glu Ile Asp Asn
        1085                1090                1095

Glu Ser Ala Leu Glu Asp Lys Glu Asp Phe His Leu Ala Gly Ala
        1100                1105                1110

Ser Lys Thr Ile Leu Tyr Ser Cys Gly Gln Asp Met Glu Ile
        1115                1120                1125

Thr Arg Ser His Thr Thr Ala Leu Glu Cys Lys Thr Leu Leu Pro
        1130                1135                1140

Asn Glu Ile Ala Ile Arg Pro Met Asp Lys Thr Val Leu Phe Thr
        1145                1150                1155

Asp Asn Tyr Ser Asp Leu Glu Val Thr Asp Ser His Thr Val Phe
        1160                1165                1170

Ile Asp Cys Gln Ala Thr Glu Lys Ile Leu Glu Glu Asn Pro Lys
        1175                1180                1185

Phe Gly Ile Gly Lys Gly Lys Asn Leu Gly Val Ser Phe Pro Lys
        1190                1195                1200

Asp Asn Ser Cys Val Gln Glu Ile Ala Glu Lys Gln Ala Leu Ala
        1205                1210                1215

Val Gly Asn Lys Ile Val Leu His Thr Glu Gln Lys Gln Gln Leu
        1220                1225                1230

Phe Ala Ala Thr Asn Arg Thr Thr Asn Glu Ile Ile Lys Phe His
        1235                1240                1245

Ser Ala Ala Met Asp Glu Lys Val Ile Gly Lys Val Val Asp Gln
        1250                1255                1260

Ala Cys Thr Leu Glu Lys Ala Gln Val Glu Ser Cys Gln Leu Asn
        1265                1270                1275

Asn Arg Asp Arg Arg Asn Val Asp Phe Thr Ser Ser His Ala Thr
        1280                1285                1290

Ala Val Cys Gly Ser Ser Asp Asn Tyr Ser Cys Leu Pro Asn Val
        1295                1300                1305

Ile Ser Cys Thr Asp Asn Leu Glu Gly Ser Ala Met Leu Leu Cys
        1310                1315                1320

Asp Lys Asp Glu Glu Lys Ala Asn Tyr Cys Pro Val Gln Asn Asp
        1325                1330                1335

Leu Ala Tyr Ala Asn Asp Phe Ala Ser Glu Tyr Tyr Leu Glu Ser
        1340                1345                1350

Glu Gly Gln Pro Leu Ser Ala Pro Cys Pro Leu Leu Glu Lys Glu
        1355                1360                1365

Glu Val Ile Gln Thr Ser Thr Lys Gly Gln Leu Asp Cys Val Ile
        1370                1375                1380

Thr Leu His Lys Asp Gln Asp Leu Ile Lys Asp Pro Arg Asn Leu
        1385                1390                1395

Leu Ala Asn Gln Thr Leu Val Tyr Ser Gln Asp Leu Gly Glu Met
        1400                1405                1410
```

```
Thr Lys Leu Asn Ser Lys Arg Val Ser Phe Lys Leu Pro Lys Asp
1415                1420                1425

Gln Met Lys Val Tyr Val Asp Asp Ile Tyr Val Ile Pro Gln Pro
1430                1435                1440

His Phe Ser Thr Asp Gln Pro Pro Leu Pro Lys Lys Gly Gln Ser
1445                1450                1455

Ser Ile Asn Lys Glu Glu Val Ile Leu Ser Lys Ala Gly Asn Lys
1460                1465                1470

Ser Leu Asn Ile Ile Glu Asn Ser Ser Ala Pro Ile Cys Glu Asn
1475                1480                1485

Lys Pro Lys Ile Leu Asn Ser Glu Glu Trp Phe Ala Ala Ala Cys
1490                1495                1500

Lys Lys Glu Leu Lys Glu Asn Ile Gln Thr Thr Asn Tyr Asn Thr
1505                1510                1515

Ala Leu Asp Phe His Ser Asn Ser Asp Val Thr Lys Gln Val Ile
1520                1525                1530

Gln Thr His Val Asn Ala Gly Glu Ala Pro Asp Pro Val Ile Thr
1535                1540                1545

Ser Asn Val Pro Cys Phe His Ser Ile Lys Pro Asn Leu Asn Asn
1550                1555                1560

Leu Asn Gly Lys Thr Gly Glu Phe Leu Ala Phe Gln Thr Val His
1565                1570                1575

Leu Pro Pro Leu Pro Glu Gln Leu Leu Glu Leu Gly Asn Lys Ala
1580                1585                1590

His Asn Asp Met His Ile Val Gln Ala Thr Glu Ile His Asn Ile
1595                1600                1605

Asn Ile Ile Ser Ser Asn Ala Lys Asp Ser Arg Asp Glu Glu Asn
1610                1615                1620

Lys Lys Ser His Asn Gly Ala Glu Thr Thr Ser Leu Pro Pro Lys
1625                1630                1635

Thr Val Phe Lys Asp Lys Val Arg Arg Cys Ser Leu Gly Ile Phe
1640                1645                1650

Leu Pro Arg Leu Pro Asn Lys Arg Asn Cys Ser Val Thr Gly Ile
1655                1660                1665

Asp Asp Leu Glu Gln Ile Pro Ala Asp Thr Thr Asp Ile Asn His
1670                1675                1680

Leu Glu Thr Gln Pro Val Ser Ser Lys Asp Ser Gly Ile Gly Ser
1685                1690                1695

Val Ala Gly Lys Leu Asn Leu Ser Pro Ser Gln Tyr Ile Asn Glu
1700                1705                1710

Glu Asn Leu Pro Val Tyr Pro Asp Glu Ile Asn Ser Ser Asp Ser
1715                1720                1725

Ile Asn Ile Glu Thr Glu Glu Lys Ala Leu Ile Glu Thr Tyr Gln
1730                1735                1740

Lys Glu Ile Ser Pro Tyr Glu Asn Lys Met Gly Lys Thr Cys Asn
1745                1750                1755

Ser Gln Lys Arg Thr Trp Val Gln Glu Glu Glu Asp Ile His Lys
1760                1765                1770

Glu Lys Lys Ile Arg Lys Asn Glu Ile Lys Phe Ser Asp Thr Thr
1775                1780                1785

Gln Asp Arg Glu Ile Phe Asp His His Thr Glu Glu Asp Ile Asp
1790                1795                1800
```

-continued

```
Lys Ser Ala Asn Ser Val Leu Ile Lys Asn Leu Ser Arg Thr Pro
1805                1810                1815

Ser Ser Cys Ser Ser Ser Leu Asp Ser Ile Lys Ala Asp Gly Thr
1820                1825                1830

Ser Leu Asp Phe Ser Thr Tyr Arg Ser Ser Gln Met Glu Ser Gln
1835                1840                1845

Phe Leu Arg Asp Thr Ile Cys Glu Glu Ser Leu Arg Glu Lys Leu
1850                1855                1860

Gln Asp Gly Arg Ile Thr Ile Arg Glu Phe Phe Ile Leu Leu Gln
1865                1870                1875

Val His Ile Leu Ile Gln Lys Pro Arg Gln Ser Asn Leu Pro Gly
1880                1885                1890

Asn Phe Thr Val Asn Thr Pro Pro Thr Pro Glu Asp Leu Met Leu
1895                1900                1905

Ser Gln Tyr Val Tyr Arg Pro Lys Ile Gln Ile Tyr Arg Glu Asp
1910                1915                1920

Cys Glu Ala Arg Arg Gln Lys Ile Glu Glu Leu Lys Leu Ser Ala
1925                1930                1935

Ser Asn Gln Asp Lys Leu Leu Val Asp Ile Asn Lys Asn Leu Trp
1940                1945                1950

Glu Lys Met Arg His Cys Ser Asp Lys Glu Leu Lys Ala Phe Gly
1955                1960                1965

Ile Tyr Leu Asn Lys Ile Lys Ser Cys Phe Thr Lys Met Thr Lys
1970                1975                1980

Val Phe Thr His Gln Gly Lys Val Ala Leu Tyr Gly Lys Leu Val
1985                1990                1995

Gln Ser Ala Gln Asn Glu Arg Glu Lys Leu Gln Ile Lys Ile Asp
2000                2005                2010

Glu Met Asp Lys Ile Leu Lys Lys Ile Asp Asn Cys Leu Thr Glu
2015                2020                2025

Met Glu Thr Glu Thr Lys Asn Leu Glu Asp Glu Glu Lys Asn Asn
2030                2035                2040

Pro Val Glu Glu Trp Asp Ser Glu Met Arg Ala Ala Glu Lys Glu
2045                2050                2055

Leu Glu Gln Leu Lys Thr Glu Glu Glu Leu Gln Arg Asn Leu
2060                2065                2070

Leu Glu Leu Glu Val Gln Lys Glu Gln Thr Leu Ala Gln Ile Asp
2075                2080                2085

Phe Met Gln Lys Gln Arg Asn Arg Thr Glu Glu Leu Leu Asp Gln
2090                2095                2100

Leu Ser Leu Ser Glu Trp Asp Val Val Glu Trp Ser Asp Asp Gln
2105                2110                2115

Ala Val Phe Thr Phe Val Tyr Asp Thr Ile Gln Leu Thr Ile Thr
2120                2125                2130

Phe Glu Glu Ser Val Val Gly Phe Pro Phe Leu Asp Lys Arg Tyr
2135                2140                2145

Arg Lys Ile Val Asp Val Asn Phe Gln Ser Leu Leu Asp Glu Asp
2150                2155                2160

Gln Ala Pro Pro Ser Ser Leu Leu Val His Lys Leu Ile Phe Gln
2165                2170                2175

Tyr Val Glu Glu Lys Glu Ser Trp Lys Lys Thr Cys Thr Thr Gln
2180                2185                2190

His Gln Leu
```

2195

<210> SEQ ID NO 38
<211> LENGTH: 281
<212> TYPE: PRT
<213> ORGANISM: Homo sapiens

<400> SEQUENCE: 38

```
Met Ala Gly Ser Pro Glu Leu Val Val Leu Asp Pro Trp Asp Lys
1               5                   10                  15

Glu Leu Ala Ala Gly Thr Glu Ser Gln Ala Leu Val Ser Ala Thr Pro
                20                  25                  30

Arg Glu Asp Phe Arg Val Arg Cys Thr Ser Lys Arg Ala Val Thr Glu
            35                  40                  45

Met Leu Gln Leu Cys Gly Arg Phe Val Gln Lys Leu Gly Asp Ala Leu
        50                  55                  60

Pro Glu Glu Ile Arg Glu Pro Ala Leu Arg Asp Ala Gln Trp Thr Phe
65                  70                  75                  80

Glu Ser Ala Val Gln Glu Asn Ile Ser Ile Asn Gly Gln Ala Trp Gln
                85                  90                  95

Glu Ala Ser Asp Asn Cys Phe Met Asp Ser Ile Lys Val Leu Glu
            100                 105                 110

Asp Gln Phe Asp Glu Ile Ile Val Asp Ile Ala Thr Lys Arg Lys Gln
        115                 120                 125

Tyr Pro Arg Lys Ile Leu Glu Cys Val Ile Lys Thr Ile Lys Ala Lys
    130                 135                 140

Gln Glu Ile Leu Lys Gln Tyr His Pro Val Val His Pro Leu Asp Leu
145                 150                 155                 160

Lys Tyr Asp Pro Asp Pro Ala Pro His Met Glu Asn Leu Lys Cys Arg
                165                 170                 175

Gly Glu Thr Val Ala Lys Glu Ile Ser Glu Ala Met Lys Ser Leu Pro
            180                 185                 190

Ala Leu Ile Glu Gln Gly Glu Gly Phe Ser Gln Val Leu Arg Met Gln
        195                 200                 205

Pro Val Ile His Leu Gln Arg Ile His Gln Glu Val Phe Ser Ser Cys
    210                 215                 220

His Arg Lys Pro Asp Ala Lys Pro Glu Asn Phe Ile Thr Gln Ile Glu
225                 230                 235                 240

Thr Thr Pro Thr Glu Thr Ala Ser Arg Lys Thr Ser Asp Met Val Leu
                245                 250                 255

Lys Arg Lys Gln Thr Lys Asp Cys Pro Gln Arg Lys Trp Tyr Pro Leu
            260                 265                 270

Arg Pro Lys Lys Ile Asn Leu Asp Thr
        275                 280
```

<210> SEQ ID NO 39
<211> LENGTH: 213
<212> TYPE: PRT
<213> ORGANISM: Homo sapiens

<400> SEQUENCE: 39

```
Met Ala Gly Ser Pro Glu Leu Val Val Leu Asp Pro Trp Asp Lys
1               5                   10                  15

Glu Leu Ala Ala Gly Thr Glu Ser Gln Ala Leu Val Ser Ala Thr Pro
                20                  25                  30

Arg Glu Asp Phe Arg Val Arg Cys Thr Ser Lys Arg Ala Val Thr Glu
```

```
                35                  40                  45
Met Leu Gln Leu Cys Gly Arg Phe Val Gln Lys Leu Gly Asp Ala Leu
 50                  55                  60

Pro Glu Glu Ile Arg Glu Pro Ala Leu Arg Asp Ala Gln Trp Thr Phe
 65                  70                  75                  80

Glu Ser Ala Val Gln Glu Asn Ile Ser Ile Asn Gly Gln Ala Trp Gln
                 85                  90                  95

Glu Ala Ser Asp Asn Cys Phe Met Asp Ser Asp Ile Lys Val Leu Glu
                100                 105                 110

Asp Gln Phe Asp Glu Ile Ile Val Asp Ile Ala Thr Lys Arg Lys Gln
                115                 120                 125

Tyr Pro Arg Lys Ile Leu Glu Cys Val Ile Lys Thr Ile Lys Ala Lys
                130                 135                 140

Gln Glu Ile Leu Lys Gln Tyr His Pro Val Val His Pro Leu Asp Leu
145                 150                 155                 160

Lys Tyr Asp Pro Asp Pro Val Leu Asn Gly Asn Ala Phe Asn Phe Ser
                165                 170                 175

Pro Phe Asn Met Met Leu Ala Val Asp Leu Ser Tyr Met Val Phe Ile
                180                 185                 190

Thr Ser Ser Pro Ser Tyr Gly Lys Phe Glu Met Gln Arg Gly Asn Ser
                195                 200                 205

Ser Lys Gly Asp Gln
                210

<210> SEQ ID NO 40
<211> LENGTH: 356
<212> TYPE: PRT
<213> ORGANISM: Homo sapiens

<400> SEQUENCE: 40

Met Thr Ser Val Thr Arg Ser Glu Ile Ile Asp Glu Lys Gly Pro Val
  1               5                  10                  15

Met Ser Lys Thr His Asp His Gln Leu Glu Ser Ser Leu Ser Pro Val
                 20                  25                  30

Glu Val Phe Ala Lys Thr Ser Ala Ser Leu Glu Met Asn Gln Gly Val
                 35                  40                  45

Ser Glu Glu Arg Ile His Leu Gly Ser Ser Pro Lys Lys Gly Gly Asn
                 50                  55                  60

Cys Asp Leu Ser His Gln Glu Arg Leu Gln Ser Lys Ser Leu His Leu
 65                  70                  75                  80

Ser Pro Gln Glu Gln Ser Ala Ser Tyr Gln Asp Arg Arg Gln Ser Trp
                 85                  90                  95

Arg Arg Ala Ser Met Lys Glu Thr Asn Arg Arg Lys Ser Leu His Pro
                100                 105                 110

Ile His Gln Gly Ile Thr Glu Leu Ser Arg Ser Ile Ser Val Asp Leu
                115                 120                 125

Ala Glu Ser Lys Arg Leu Gly Cys Leu Leu Leu Ser Ser Phe Gln Phe
                130                 135                 140

Ser Ile Gln Lys Leu Glu Pro Phe Leu Arg Asp Thr Lys Gly Phe Ser
145                 150                 155                 160

Leu Glu Ser Phe Arg Ala Lys Ala Ser Ser Leu Ser Glu Glu Leu Lys
                165                 170                 175

His Phe Ala Asp Gly Leu Glu Thr Asp Gly Thr Leu Gln Lys Cys Phe
                180                 185                 190
```

-continued

Glu Asp Ser Asn Gly Lys Ala Ser Asp Phe Ser Leu Glu Ala Ser Val
            195                 200                 205

Ala Glu Met Lys Glu Tyr Ile Thr Lys Phe Ser Leu Glu Arg Gln Thr
    210                 215                 220

Trp Asp Gln Leu Leu Leu His Tyr Gln Gln Glu Ala Lys Glu Ile Leu
225                 230                 235                 240

Ser Arg Gly Ser Thr Glu Ala Lys Ile Thr Glu Val Lys Val Glu Pro
                245                 250                 255

Met Thr Tyr Leu Gly Ser Ser Gln Asn Glu Val Leu Asn Thr Lys Pro
                260                 265                 270

Asp Tyr Gln Lys Ile Leu Gln Asn Gln Ser Lys Val Phe Asp Cys Met
            275                 280                 285

Glu Leu Val Met Asp Glu Leu Gln Gly Ser Val Lys Gln Leu Gln Ala
        290                 295                 300

Phe Met Asp Glu Ser Thr Gln Cys Phe Gln Lys Val Ser Val Gln Leu
305                 310                 315                 320

Gly Lys Arg Ser Met Gln Gln Leu Asp Pro Ser Pro Ala Arg Lys Leu
                325                 330                 335

Leu Lys Leu Gln Leu Gln Asn Pro Pro Ala Ile His Gly Ser Gly Ser
            340                 345                 350

Gly Ser Cys Gln
        355

<210> SEQ ID NO 41
<211> LENGTH: 340
<212> TYPE: PRT
<213> ORGANISM: Homo sapiens

<400> SEQUENCE: 41

Met Ser Lys Thr His Asp His Gln Leu Glu Ser Ser Leu Ser Pro Val
1               5                   10                  15

Glu Val Phe Ala Lys Thr Ser Ala Ser Leu Glu Met Asn Gln Gly Val
            20                  25                  30

Ser Glu Glu Arg Ile His Leu Gly Ser Ser Pro Lys Lys Gly Gly Asn
        35                  40                  45

Cys Asp Leu Ser His Gln Glu Arg Leu Gln Ser Lys Ser Leu His Leu
    50                  55                  60

Ser Pro Gln Glu Gln Ser Ala Ser Tyr Gln Asp Arg Arg Gln Ser Trp
65                  70                  75                  80

Arg Arg Ala Ser Met Lys Glu Thr Asn Arg Arg Lys Ser Leu His Pro
                85                  90                  95

Ile His Gln Gly Ile Thr Glu Leu Ser Arg Ser Ile Ser Val Asp Leu
            100                 105                 110

Ala Glu Ser Lys Arg Leu Gly Cys Leu Leu Ser Ser Phe Gln Phe
        115                 120                 125

Ser Ile Gln Lys Leu Glu Pro Phe Leu Arg Asp Thr Lys Gly Phe Ser
    130                 135                 140

Leu Glu Ser Phe Arg Ala Lys Ala Ser Ser Leu Ser Glu Glu Leu Lys
145                 150                 155                 160

His Phe Ala Asp Gly Leu Glu Thr Asp Gly Thr Leu Gln Lys Cys Phe
                165                 170                 175

Glu Asp Ser Asn Gly Lys Ala Ser Asp Phe Ser Leu Glu Ala Ser Val
            180                 185                 190

Ala Glu Met Lys Glu Tyr Ile Thr Lys Phe Ser Leu Glu Arg Gln Thr
        195                 200                 205

```
Trp Asp Gln Leu Leu His Tyr Gln Gln Glu Ala Lys Glu Ile Leu
    210                 215                 220

Ser Arg Gly Ser Thr Glu Ala Lys Ile Thr Glu Val Lys Val Glu Pro
225                 230                 235                 240

Met Thr Tyr Leu Gly Ser Ser Gln Asn Glu Val Leu Asn Thr Lys Pro
                245                 250                 255

Asp Tyr Gln Lys Ile Leu Gln Asn Gln Ser Lys Val Phe Asp Cys Met
                260                 265                 270

Glu Leu Val Met Asp Glu Leu Gln Gly Ser Val Lys Gln Leu Gln Ala
            275                 280                 285

Phe Met Asp Glu Ser Thr Gln Cys Phe Gln Lys Val Ser Val Gln Leu
        290                 295                 300

Gly Lys Arg Ser Met Gln Gln Leu Asp Pro Ser Pro Ala Arg Lys Leu
305                 310                 315                 320

Leu Lys Leu Gln Leu Gln Asn Pro Pro Ala Ile His Gly Ser Gly Ser
                325                 330                 335

Gly Ser Cys Gln
            340

<210> SEQ ID NO 42
<211> LENGTH: 249
<212> TYPE: PRT
<213> ORGANISM: Homo sapiens

<400> SEQUENCE: 42

Met Thr Ser Val Thr Arg Ser Glu Ile Ile Asp Glu Leu Ser Arg Ser
1               5                   10                  15

Ile Ser Val Asp Leu Ala Glu Ser Lys Arg Leu Gly Cys Leu Leu Leu
            20                  25                  30

Ser Ser Phe Gln Phe Ser Ile Gln Lys Leu Glu Pro Phe Leu Arg Asp
        35                  40                  45

Thr Lys Gly Phe Ser Leu Glu Ser Phe Arg Ala Lys Ala Ser Ser Leu
    50                  55                  60

Ser Glu Glu Leu Lys His Phe Ala Asp Gly Leu Glu Thr Asp Gly Thr
65                  70                  75                  80

Leu Gln Lys Cys Phe Glu Asp Ser Asn Gly Lys Ala Ser Asp Phe Ser
                85                  90                  95

Leu Glu Ala Ser Val Ala Glu Met Lys Glu Tyr Ile Thr Lys Phe Ser
            100                 105                 110

Leu Glu Arg Gln Thr Trp Asp Gln Leu Leu His Tyr Gln Gln Glu
        115                 120                 125

Ala Lys Glu Ile Leu Ser Arg Gly Ser Thr Glu Ala Lys Ile Thr Glu
    130                 135                 140

Val Lys Val Glu Pro Met Thr Tyr Leu Gly Ser Ser Gln Asn Glu Val
145                 150                 155                 160

Leu Asn Thr Lys Pro Asp Tyr Gln Lys Ile Leu Gln Asn Gln Ser Lys
                165                 170                 175

Val Phe Asp Cys Met Glu Leu Val Met Asp Glu Leu Gln Gly Ser Val
            180                 185                 190

Lys Gln Leu Gln Ala Phe Met Asp Glu Ser Thr Gln Cys Phe Gln Lys
        195                 200                 205

Val Ser Val Gln Leu Gly Lys Arg Ser Met Gln Gln Leu Asp Pro Ser
    210                 215                 220

Pro Ala Arg Lys Leu Leu Lys Leu Gln Leu Gln Asn Pro Pro Ala Ile
```

```
                225                 230                 235                 240

His Gly Ser Gly Ser Gly Ser Cys Gln
                245

<210> SEQ ID NO 43
<211> LENGTH: 642
<212> TYPE: PRT
<213> ORGANISM: Homo sapiens

<400> SEQUENCE: 43

Met Lys Arg Ser Ser Val Ser Gly Gly Ala Gly Arg Leu Ser Met
1               5                   10                  15

Gln Glu Leu Arg Ser Gln Asp Val Asn Lys Gln Gly Leu Tyr Thr Pro
                20                  25                  30

Gln Thr Lys Glu Lys Pro Thr Phe Gly Lys Leu Ser Ile Asn Lys Pro
            35                  40                  45

Thr Ser Glu Arg Lys Val Ser Leu Phe Gly Lys Arg Thr Ser Gly His
        50                  55                  60

Gly Ser Arg Asn Ser Gln Leu Gly Ile Phe Ser Ser Glu Lys Ile
65                  70                  75                  80

Lys Asp Pro Arg Pro Leu Asn Asp Lys Ala Phe Ile Gln Gln Cys Ile
                85                  90                  95

Arg Gln Leu Cys Glu Phe Leu Thr Glu Asn Gly Tyr Ala His Asn Val
            100                 105                 110

Ser Met Lys Ser Leu Gln Ala Pro Ser Val Lys Asp Phe Leu Lys Ile
        115                 120                 125

Phe Thr Phe Leu Tyr Gly Phe Leu Cys Pro Ser Tyr Glu Leu Pro Asp
130                 135                 140

Thr Lys Phe Glu Glu Val Pro Arg Ile Phe Lys Asp Leu Gly Tyr
145                 150                 155                 160

Pro Phe Ala Leu Ser Lys Ser Ser Met Tyr Thr Val Gly Ala Pro His
                165                 170                 175

Thr Trp Pro His Ile Val Ala Ala Leu Val Trp Leu Ile Asp Cys Ile
            180                 185                 190

Lys Ile His Thr Ala Met Lys Glu Ser Ser Pro Leu Phe Asp Asp Gly
        195                 200                 205

Gln Pro Trp Gly Glu Glu Thr Glu Asp Gly Ile Met His Asn Lys Leu
    210                 215                 220

Phe Leu Asp Tyr Thr Ile Lys Cys Tyr Glu Ser Phe Met Ser Gly Ala
225                 230                 235                 240

Asp Ser Phe Asp Glu Met Asn Ala Glu Leu Gln Ser Lys Leu Lys Asp
                245                 250                 255

Leu Phe Asn Val Asp Ala Phe Lys Leu Glu Ser Leu Glu Ala Lys Asn
            260                 265                 270

Arg Ala Leu Asn Glu Gln Ile Ala Arg Leu Glu Gln Glu Arg Glu Lys
        275                 280                 285

Glu Pro Asn Arg Leu Glu Ser Leu Arg Lys Leu Ala Ser Leu Gln
    290                 295                 300

Gly Asp Val Gln Lys Tyr Gln Ala Tyr Met Ser Asn Leu Glu Ser His
305                 310                 315                 320

Ser Ala Ile Leu Asp Gln Lys Leu Asn Gly Leu Asn Glu Glu Ile Ala
                325                 330                 335

Arg Val Glu Leu Glu Cys Glu Thr Ile Lys Gln Glu Asn Thr Arg Leu
            340                 345                 350
```

Gln Asn Ile Ile Asp Asn Gln Lys Tyr Ser Val Ala Asp Ile Glu Arg
            355                 360                 365

Ile Asn His Glu Arg Asn Glu Leu Gln Gln Thr Ile Asn Lys Leu Thr
    370                 375                 380

Lys Asp Leu Glu Ala Glu Gln Gln Lys Leu Trp Asn Glu Leu Lys
385                 390                 395                 400

Tyr Ala Arg Gly Lys Glu Ala Ile Glu Thr Gln Leu Ala Glu Tyr His
                405                 410                 415

Lys Leu Ala Arg Lys Leu Lys Leu Ile Pro Lys Gly Ala Glu Asn Ser
                420                 425                 430

Lys Gly Tyr Asp Phe Glu Ile Lys Phe Asn Pro Glu Ala Gly Ala Asn
            435                 440                 445

Cys Leu Val Lys Tyr Arg Ala Gln Val Tyr Val Pro Leu Lys Glu Leu
    450                 455                 460

Leu Asn Glu Thr Glu Glu Ile Asn Lys Ala Leu Asn Lys Lys Met
465                 470                 475                 480

Gly Leu Glu Asp Thr Leu Glu Gln Leu Asn Ala Met Ile Thr Glu Ser
                485                 490                 495

Lys Arg Ser Val Arg Thr Leu Lys Glu Glu Val Gln Lys Leu Asp Asp
            500                 505                 510

Leu Tyr Gln Gln Lys Ile Lys Glu Ala Glu Glu Asp Glu Lys Cys
    515                 520                 525

Ala Ser Glu Leu Glu Ser Leu Glu Lys His Lys His Leu Leu Glu Ser
530                 535                 540

Thr Val Asn Gln Gly Leu Ser Glu Ala Met Asn Glu Leu Asp Ala Val
545                 550                 555                 560

Gln Arg Glu Tyr Gln Leu Val Val Gln Thr Thr Thr Glu Glu Arg Arg
                565                 570                 575

Lys Val Gly Asn Asn Leu Gln Arg Leu Leu Glu Met Val Ala Thr His
                580                 585                 590

Val Gly Ser Val Glu Lys His Leu Glu Glu Gln Ile Ala Lys Val Asp
            595                 600                 605

Arg Glu Tyr Glu Glu Cys Met Ser Glu Asp Leu Ser Glu Asn Ile Lys
    610                 615                 620

Glu Ile Arg Asp Lys Tyr Glu Lys Lys Ala Thr Leu Ile Lys Ser Ser
625                 630                 635                 640

Glu Glu

<210> SEQ ID NO 44
<211> LENGTH: 197
<212> TYPE: PRT
<213> ORGANISM: Homo sapiens

<400> SEQUENCE: 44

Met Ala Ala Phe Arg Asp Ile Glu Glu Val Ser Gln Gly Leu Leu Ser
1               5                   10                  15

Leu Leu Gly Ala Asn Arg Ala Glu Ala Gln Gln Arg Arg Leu Leu Gly
            20                  25                  30

Arg His Glu Gln Val Val Glu Arg Leu Leu Glu Thr Gln Asp Gly Ala
        35                  40                  45

Glu Lys Gln Leu Arg Glu Ile Leu Thr Met Glu Lys Glu Val Ala Gln
    50                  55                  60

Ser Leu Leu Asn Ala Lys Glu Gln Val His Gln Gly Gly Val Glu Leu
65                  70                  75                  80

```
Gln Gln Leu Glu Ala Gly Leu Gln Glu Ala Gly Glu Glu Asp Thr Arg
                85                  90                  95
Leu Lys Ala Ser Leu Leu Gln Leu Thr Arg Glu Leu Glu Leu Lys
            100                 105                 110
Glu Ile Glu Ala Asp Leu Glu Arg Gln Glu Lys Glu Val Asp Glu Asp
            115                 120                 125
Thr Thr Val Thr Ile Pro Ser Ala Val Tyr Val Ala Gln Leu Tyr His
        130                 135                 140
Gln Val Ser Lys Ile Glu Trp Asp Tyr Glu Cys Glu Pro Gly Met Val
145                 150                 155                 160
Lys Gly Ile His His Gly Pro Ser Val Ala Gln Pro Ile His Leu Asp
                165                 170                 175
Ser Thr Gln Leu Ser Arg Lys Phe Ile Ser Asp Tyr Leu Trp Ser Leu
            180                 185                 190
Val Asp Thr Glu Trp
        195

<210> SEQ ID NO 45
<211> LENGTH: 224
<212> TYPE: PRT
<213> ORGANISM: Homo sapiens

<400> SEQUENCE: 45

Met Val Glu Asp Glu Leu Ala Leu Phe Asp Lys Ser Ile Asn Glu Phe
1               5                   10                  15
Trp Asn Lys Phe Lys Ser Thr Asp Thr Ser Cys Gln Met Ala Gly Leu
                20                  25                  30
Arg Asp Thr Tyr Lys Asp Ser Ile Lys Ala Phe Ala Glu Lys Leu Ser
            35                  40                  45
Val Lys Leu Lys Glu Glu Glu Arg Met Val Glu Met Phe Leu Glu Tyr
        50                  55                  60
Gln Asn Gln Ile Ser Arg Gln Asn Lys Leu Ile Gln Glu Lys Lys Asp
65                  70                  75                  80
Asn Leu Leu Lys Leu Ile Ala Glu Val Lys Gly Lys Gln Glu Leu
                85                  90                  95
Glu Val Leu Thr Ala Asn Ile Gln Asp Leu Lys Glu Glu Tyr Ser Arg
            100                 105                 110
Lys Lys Glu Thr Ile Ser Thr Ala Asn Lys Ala Asn Ala Glu Arg Leu
        115                 120                 125
Lys Arg Leu Gln Lys Ser Ala Asp Leu Tyr Lys Asp Arg Leu Gly Leu
    130                 135                 140
Glu Ile Arg Lys Ile Tyr Gly Glu Lys Leu Gln Phe Ile Phe Thr Asn
145                 150                 155                 160
Ile Asp Pro Lys Asn Pro Glu Ser Pro Phe Met Phe Ser Leu His Leu
                165                 170                 175
Asn Glu Ala Arg Asp Tyr Glu Val Ser Asp Ser Ala Pro His Leu Glu
            180                 185                 190
Gly Leu Ala Glu Phe Gln Glu Asn Val Arg Lys Thr Asn Asn Phe Ser
        195                 200                 205
Ala Phe Leu Ala Asn Val Arg Lys Ala Phe Thr Ala Thr Val Tyr Asn
    210                 215                 220

<210> SEQ ID NO 46
<211> LENGTH: 464
<212> TYPE: PRT
<213> ORGANISM: Homo sapiens
```

<400> SEQUENCE: 46

```
Met Glu Thr Leu Ser Phe Pro Arg Tyr Asn Val Ala Glu Ile Val Ile
1               5                   10                  15

His Ile Arg Asn Lys Ile Leu Thr Gly Ala Asp Gly Lys Asn Leu Thr
            20                  25                  30

Lys Asn Asp Leu Tyr Pro Asn Pro Lys Pro Glu Val Leu His Met Ile
        35                  40                  45

Tyr Met Arg Ala Leu Gln Ile Val Tyr Gly Ile Arg Leu Glu His Phe
50                  55                  60

Tyr Met Met Pro Val Asn Ser Glu Val Met Tyr Pro His Leu Met Glu
65                  70                  75                  80

Gly Phe Leu Pro Phe Ser Asn Leu Val Thr His Leu Asp Ser Phe Leu
                85                  90                  95

Pro Ile Cys Arg Val Asn Asp Phe Glu Thr Ala Asp Ile Leu Cys Pro
            100                 105                 110

Lys Ala Lys Arg Thr Ser Arg Phe Leu Ser Gly Ile Ile Asn Phe Ile
        115                 120                 125

His Phe Arg Glu Ala Cys Arg Glu Thr Tyr Met Glu Phe Leu Trp Gln
130                 135                 140

Tyr Lys Ser Ser Ala Asp Lys Met Gln Gln Leu Asn Ala Ala His Gln
145                 150                 155                 160

Glu Ala Leu Met Lys Leu Glu Arg Leu Asp Ser Val Pro Val Glu Glu
                165                 170                 175

Gln Glu Glu Phe Lys Gln Leu Ser Asp Gly Ile Gln Glu Leu Gln Gln
            180                 185                 190

Ser Leu Asn Gln Asp Phe His Gln Lys Thr Ile Val Leu Gln Glu Gly
        195                 200                 205

Asn Ser Gln Lys Lys Ser Asn Ile Ser Glu Lys Thr Lys Arg Leu Asn
210                 215                 220

Glu Leu Lys Leu Ser Val Val Ser Leu Lys Ile Gln Glu Ser Leu
225                 230                 235                 240

Lys Thr Lys Ile Val Asp Ser Pro Glu Lys Leu Lys Asn Tyr Lys Glu
                245                 250                 255

Lys Met Lys Asp Thr Val Gln Lys Leu Lys Asn Ala Arg Gln Glu Val
            260                 265                 270

Val Glu Lys Tyr Glu Ile Tyr Gly Asp Ser Val Asp Cys Leu Pro Ser
        275                 280                 285

Cys Gln Leu Glu Val Gln Leu Tyr Gln Lys Ile Gln Asp Leu Ser
290                 295                 300

Asp Asn Arg Glu Lys Leu Ala Ser Ile Leu Lys Glu Ser Leu Asn Leu
305                 310                 315                 320

Glu Asp Gln Ile Glu Ser Asp Glu Ser Glu Leu Lys Lys Leu Lys Thr
                325                 330                 335

Glu Glu Asn Ser Phe Lys Arg Leu Met Ile Val Lys Lys Glu Lys Leu
            340                 345                 350

Ala Thr Ala Gln Phe Lys Ile Asn Lys Lys His Glu Asp Val Lys Gln
        355                 360                 365

Tyr Lys Arg Thr Val Ile Glu Asp Cys Asn Lys Val Gln Glu Lys Arg
370                 375                 380

Gly Ala Val Tyr Glu Arg Val Thr Thr Ile Asn Gln Glu Ile Gln Lys
385                 390                 395                 400

Ile Lys Leu Gly Ile Gln Gln Leu Lys Asp Ala Ala Glu Arg Glu Lys
```

```
                        405                 410                 415
Leu Lys Ser Gln Glu Ile Phe Leu Asn Leu Lys Thr Ala Leu Glu Lys
            420                 425                 430

Tyr His Asp Gly Ile Glu Lys Ala Ala Glu Asp Ser Tyr Ala Lys Ile
        435                 440                 445

Asp Glu Lys Thr Ala Glu Leu Lys Arg Lys Met Phe Lys Met Ser Thr
    450                 455                 460
```